(12) United States Patent
Deryan et al.

(10) Patent No.: US 6,683,189 B1
(45) Date of Patent: *Jan. 27, 2004

(54) METHOD FOR THE SYNTHESIS OF PYRROLE AND IMIDAZOLE CARBOXAMIDES ON A SOLID SUPPORT

(75) Inventors: Peter B. Deryan, San Marino, CA (US); Eldon Baird, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/360,344

(22) Filed: Jul. 22, 1999

Related U.S. Application Data

(63) Continuation of application No. 08/607,078, filed on Feb. 26, 1996, now Pat. No. 6,090,947.

(51) Int. Cl.$^7$ ............................................. C07D 231/02
(52) U.S. Cl. .............................. 548/312.2; 548/312.11; 548/312.7; 548/313.1; 548/314.7; 548/334.5; 548/557
(58) Field of Search ........................... 548/312.2, 312.4, 548/312, 313.1, 314.7, 557, 334.5

(56) References Cited

U.S. PATENT DOCUMENTS

| | | | |
|---|---|---|---|
| 4,795,700 A | 1/1989 | Dervan et al. ................. | 435/5 |
| 5,539,083 A | 7/1996 | Cook et al. ................. | 530/333 |
| 5,578,444 A | 11/1996 | Edwards et al. ............... | 435/6 |
| 5,693,463 A | 12/1997 | Edwards et al. ............... | 435/6 |
| 5,726,014 A | 3/1998 | Edwards et al. ............... | 435/6 |
| 5,738,990 A | 4/1998 | Edwards et al. ............... | 435/6 |
| 6,090,947 A | 7/2000 | Dervan et al. ........... | 548/312.4 |

FOREIGN PATENT DOCUMENTS

| | | |
|---|---|---|
| DE | 43 31 012 A1 | 3/1995 |
| EP | 0 246 868 A1 | 11/1987 |
| EP | 0 388 948 A1 | 9/1990 |
| GB | 2 261 661 A | 5/1993 |
| WO | 92/09574 | 6/1992 |
| WO | 92/13838 | 8/1992 |
| WO | 92/14707 | 9/1992 |
| WO | 93/00446 | 1/1993 |
| WO | 94/03434 | 2/1994 |
| WO | 94/14980 | 7/1994 |
| WO | 94/20463 | 9/1994 |
| WO | 94/25436 | 11/1994 |
| WO | 95/04732 | 2/1995 |
| WO | 96/05196 | 2/1996 |
| WO | 96/32496 | 10/1996 |

OTHER PUBLICATIONS

Feng, et al., "Hin Recombinase Bound to DNA: The Origin of Specificity in Major and Minor Groove Interactions," *Science* (1994).

Seeman, et al., "Sequence Specific Recognition of Double Helical Nucleic Acids by Proteins," *Proc. Natl. Acad. Sci. USA* 73:804–808 (1976).

Wasserman, et al., "Intramolecular Alkylation of 3–Hydroxypyrrole–2–Carboxylates. The formation of 5/5, 5/6, and 5/7 Ring Systems, Related to Pyrrolidine Alkaloids," *Tetrahedron Letters* 31 (34) 4945–4948 (1990).

Wasserman, et al., "The Chemistry of Vicinal Tricarbonyl Esters in the Formation of 3–Hydroxypyrrole–2–Carboxylates," *Tetrahedron Letters* 30:1721–1724 (1989).

Wemmer, et al., "Minor Groove Recognition of DNA by Distamycin and its Analogs," *Structural Biology* 301–323 (1993).

Abu–Daya et al., "DNA sequence preferences of several AT–selective minor groove binding ligands," *Nucleic Acids Research* 23:3385–3392 (1995).

Abu–Daya et al., "Interaction of minor groove binding ligands with long AT tracts," *Nucleic Acids Research* 25:4962–4969 (1977).

Aleman et al., "Toward an Understanding of the Drug–DNA Recognition Mechanism. Hydrogen–Bond Strength in Netropsin–DNA Complexes," *J. Phys. Chem.* 100:11480–11487 (1996).

Al–Said et al., "A convenient synthesis of cross–linked homodimeric bis–lexitropsins," *Synth. Commun.* 25(7):1059–1070 (1995).

Al–Said et al., "Synthesis of novel cross–linked bis–lexitropsins," *Tetrahedron Lett.* 35(41):7577–7580 (1994).

Andronikashvili et al., "Spectral Manifestations of the Action of $Zn^{2+}$ Ions on DNA Complexes with Distamycin," *Biophysics* 33:824–829 (1988).

Arcamone et al., "Distamicina A. Nota I. Isolamento e struttura dell'agente antivirale distamicinia A," pp. 1097–1109 (In Spanish With English Abstract).

Arcamone et al., "Structure and synthesis of Distamycin A," *Nature* 203:1064–1065 (1964).

(List continued on next page.)

*Primary Examiner*—Robert Gerstl
(74) *Attorney, Agent, or Firm*—Foley & Lardner; Richard J. Warburg

(57) ABSTRACT

The present invention describes a novel method for the solid phase synthesis of polyamides containing imidazole and pyrrole carboxamides. The polyamides are prepared on a solid support from aromatic carboxylic acids and aromatic amines with high stepwise coupling yields (>99%), providing milligram quantities of highly pure polyamides. The present invention also describes the synthesis of analogs of the natural products Netropsin and Distamycin A, two antiviral antibiotics. The present invention also describes a novel method for the solid phase synthesis of imidazole and pyrrole carboxamide polyamide-oligonucleotide conjugates. This methodology will greatly increase both the complexity and quantity of minor-groove binding polyamides and minor-groove binding polyamide-oligonucleotide conjugates which can be synthesized and tested.

25 Claims, 41 Drawing Sheets

OTHER PUBLICATIONS

Arcamone et al., "Synthesis, DNA binding and antiviral activity of distamycin analogues containing different heterocyclic moieties," *Anti–Cancer Drug Design* 1:235–244 (1986).

Bailey et al., "Ethyl pyrrole–2–carboxylate," *Org. Syn.* pp. 100–102 (1971).

Bailly et al., "Depsipeptide Analogs of the Antitumor Drug Distamycin Containing Thiazole Amino Acids Residues," *Tetrahedron* 44:5833–5843 (1988).

Bailly et al., "Design, Synthesis, DNA Binding, and Biological Activity of a Series of DNA Minor–Groove–Binding Intercalating Drugs," *Journal of Pharmaceutical Sciences* 78:910–917 (1989).

Bailly et al., "Subcellular Distribution of a Nitroxide Spin–Labeled Netropsin in Living KB Cells," *Biochemical Pharmacology* 38:1625–1630 (1989).

Baird and Dervan, "Solid Phase Synthesis of Polyamdies Containing Imidazole and Pyrrole Amino Acids," *J. Am. Chem .Soc.* 118:6141–6146 (1996).

Baker and Dervan, "70. Sequence Specific Cleavage or Double Helical DNA. N–Bromoacetyldistamycin" (Abstract).

Baker and Dervan, "Sequence–Specific Cleavage of DNA by N–Bromoacetyldistamycin. Product and Kinetic Analyses," *J. Am. Chem. Soc.* 111:2700–2712 (1989).

Baker and Dervan, "Sequence–Specific Cleavage of Double–Helix DNA. N–Bromoacetyldistamycin," *J. Am. Chem. Soc.* 107:8266–8268 (1985).

Baliga et al., "RecA•oligonucleotide filaments bind in the minor groove of double–stranded DNA," *Proc. Natl. Acad. Sci. USA* 92:10393–10397 (1995).

Beal and Dervan, "Recognition of Double Helical DNA by Alternate Strand Triple Helix Formation,"*J. Am. Chem. Soc.* 114:4976–4982 (1992).

Beal et al., "Second Structural Motif Recognition of DNA by Oligonucleotide–Directed Triple Helix Formation" *Science* 251:1360–1363 (1991).

Beal et al., "The influence of single base triplet changes on the stability of a Pur•Pur•Pyr triple helix determined by affinity cleaving" *Nucleic Acid Res.* 20(11):2733–2776 (1992).

Best and Dervan, "Energetics of Formation of Sixteen Triple Helical Complexes Which Vary at a Single Position within a Pyrimidine Motif," *J. Am. Chem Soc.* 117:1187–1193 (1995).

Bianchi et al., "Alteration of the Expression of Human Estrogen Receptor Gene by Distamycin," *J. Steroid Biochem. Molec. Biol.* 54:211–215 (1995).

Borodulin et al., "Interaction of Ligand of the bis–Netropsin Type with Poly(dA)•Poly(dT). Optical, Structural, and Energetic Characteristics of AT–Specific Binding," *Institute of Molecular Biology*, Academy of Sciences of USSR, pp. 929–934 (1987) translated from *Molekulyarnaya Biologiya* 20(4):1144–1149 (1986).

Borodulin et al., "New Modes of Ligand Interaction with DNA: A Trimeric bis–Netropsin Complex with Poly-(dA–dT)," *Molecular Biology* 30:661–665 (1996).

Botella and Nieto, "The C–terminal DNA–binding domain of Chironomus BR gene products shows preferentially affinity for (dA•dT)–rich sequences," *Mol Gen Genet* 251:422–427 (1996).

Brabec and Balcarova, "459—The Effect of Netropsin on the Electrochemical Oxidation of DNA at a Graphite Electrode," *Bioelectrochemistry & Bioenergetics* 9:245–252 (1982).

Braun et al., "Stereoselective Aldol Reactions with ®– and (S)–2–Hydroxy–1,2,2–triphyenylethyl Acetate ("HYTRA")" (Abstract).

Brenowitz et al., "Footprint" titrations yield valid thermodynamic isotherms *Proc. Natl. Acad. Sci. USA* 83:8462–8466 (1986).

Brenowitz et al., "Quantitative Dnase Footprint Titration: A Method for Studying Protein–DNA Interactions" *Methods Enzymol.* 130:132–181 (1986).

Broeker et al., "The Mixed Lineage Leukemia (MLL) Protein Involved in 11q23 Translocations Contains a Domain that Binds Cruciform DNA and Scaffold Attachment Region (SAR) DNA," pp. 259–268.

Broggini et al., "Modulations of transcription factor–DNA interactions by anticancer drugs,"*Anti–Cancer Drug Design* 9:373–387 (1994).

Bruice et al., "Rational design of substituted tripyrrole peptides that complex with DNA by both selective minor–groove binding and electrostatic interaction with the phosphate backbone," *Proc. Natl. Acad. Sci. USA* 89:1700–1704 (1992).

Bruzik et al., "Specific Activation of Transcription Initiation by the Sequence–Specific DNA–Binding Agents Distamycin A and Netropsin," *Biochemistry* 26:950–956 (1987).

Burckhardt et al., "Reversal of the Z– to B–Conformation of Poly(dA–dT)•Poly(dA–dT) Induced by Netropsin and Distamycin A," *Journal of Biomolecular Structure & Dynamics* 13:671–676 (1996).

Burckhardt et al., "Two Binding Modes of Netropsin are Involved in the Complex Formation with Poly(dA–dT)•Poly(dA–dT) and other Alternating DNA Duplex Polymers," *Journal of Biomolecular Structure and Dynamics* 2:721–736 (1985).

Burckhardt et al., "Variation of DNA sequence specificity of DNA–oligopeptide binding ligands related to netropsin: imidazole–containing lexotropsins," *Biochimica et Biophysica Acta* 1009:11–18 (1989).

Burridge et al., "Electrostatic potential and binding of drugs to the minor groove of DNA," 5(3):165–166 (Sep. 1987).

Cartwright et al., "Cleavage of chromatin with methidiumpropyl–EDTA•iron(II)," *Proc. Natl. Acad. Sci. USA* 80:3213–3217 (1983).

Chai and Alonso, "Distamycin–induced inhibition of formation of a nucleoprotein complex between the terminase small subunit of G1P and the non–encapsidated end (pacL site) of *Bacillus subtilis* bacteriophage SPP1," *Nucleic Acids Research* 24:282–288 (1996).

Chaloupka and Kucerova, "Netropsin increases formation of mRNA coding for a netural metalloproteinase in *Bacillus megaterium,"* *J. Basic Microbiol.* 28:11–16 (1988).

Chandra et al., "Some Structural Requirements for the Antibiotic Action of Distamycins," *FEBS Letters* 16:249–252 (1971).

Chang et al., "On the importance of van der Waals interaction in the groove binding of DNA with ligands: restrained molecular dynamics study," International Journal of Biological Macromolecules 19:279–285 (1996).

Chen et al., "Binding of two distamycin A molecules in the minor groove of an alternating B–DNA duplex" *M. Struct. Biol. Nat.* 1(3):169–175 (1994).

Chen et al., "Design of Distamicin Analogues to Probe the Physical Origin of the Antiparallel Side by Side Oligopeptide Binding Motif in DNA Minor Groove Recognition," *Biochemical and Biophysical Research Communications* 220:213–218 (1996).

Chen et al., "Only one of the two DNA–bound orientations of AP–1 found in solution cooperates with NFATp," *Current Biology* 5:882–889 (1995).

Chen et al., "Optimization of Cross–Linked Lexitropsins," *Journal of Biomolecular Structure & Dynamics* 14:341–355 (1996).

Chen et al., "A new DNA minor groove binding motif: Cross–linked lexotropsins," *J. Am. Chem. Soc.* 116(16):6995–7005 (1994).

Chen et al., "Design and synthesis of sequence–specific DNA minor groove recognizing ligands of the cross–linked lexitropsin class," *Heterocycles* 41(8):1691–1707 (1995).

Chen et al., "DNA minor groove binding of cross–linked lexitropsins: Experimental conditions required to observe the covalently linked WPPW (Groove wall peptide–peptide–groove wall)motif," *Biophys. J.* 68(5):2041–2048 (1995).

Chen, "Design, synthesis and evaluation of novel bismustard cross–linked lexitropsins," *Bioorg. Med. Chem. Lett.* 5(19):2223–2228 (1995).

Chiang et al., "Effect of DNA–binding Drugs on Early Growth Response Factor–I and TATA Box–binding Protein Complex Formation with the Herpes Simplex Virus Latency Promoter," *J. Biol Chem.* 271:23999–24004 (1996).

Cho et al., "Cyclic polyamides for recognition in the minor groove of DNA," *Proc. Natl. Acad. Sci USA* 92:10389–10392 (1995).

Colocci and Dervan, "Cooperative Binding of 8–mer Oligonucleotides Containing 5–(1–Propynyl)–2'–deoxyuridine to Adjacent DNA Sites by Triple–Helix Formation," *J. Am. Chem. Soc.* 116:785–786 (1994).

Colocci and Dervan, "Cooperative Triple–Helix Formation at Adjacent DNA Sites: Sequence Composition Dependence at the Junction," *J. Am. Chem. Soc.* 117:4781–4787 (1995).

Colocci et al., "Cooperative Oligonucleotide–Directed Triple Helix Formation at Adjacent DNA Sites," *J. Am. Chem.Soc.* 115:4468–4473 (1993).

Colson et al., "Electric linear dichroism as a new tool to study sequence preference in drug binding to DNA," *Biophysical Chemistry* 58:125–140 (1996).

Connolly et al., "Chemical synthesis of oligonucleotides containing a free sulphydryl group and subsequent attachment of thiol specific probes" *Nucleic Acids Res.* 13(12):4485–4502 (1985).

Corwin et al., "Studies in the Pyrrole Series—The Preparation of Certain N–Methyl Pyrroles[1,]" *Am. Chem. Soc.* 58:1081–1085 (1936).

Costa et al., "A BGO–$C_sI$(TI) Phoswich: A New Detector for X– and γ–Ray Astronomy" *Nucl Inst. Meth. Phys. Res.* A246:572–578 (1986).

Dasgupta et al., "DNA–Binding Characteristics of a Synthetic Analogue of Distamycin," *Biochemical and Biophysical Research Communications* 140:626–631 (1986).

Dasgupta et al., "Interaction of Synthetic Analogues of Distamycin with Poly(dA–dT): Role of the Conjugated N–Methylpyrrole System," *Biochemistry* 26:6381–6386 (1987).

Debart et al., "Synthesis, DNA Binding, and Biological Evaluation of Synthetic Precursors and Novel Analogues of Netropsin," *J. Med. Chem.* 32:1074–1083 (1989).

Dervan and Baker, "Design of Sequence–Specific DNA Cleaving Molecules," *Annals of the New York Academy of Sciences* pp. 51–59.

Dervan, "113. A Chemical Approach to the Single Site Cleavage of Human Chromosomes," *Abstracts, Division of Biological Chemistry* 31:2209 (1992).

Dervan, "117. A Chemical Approach to the Single Site Cleavage of Human Chromosomes" (Abstracts).

Dervan, "122. Design of Sequence Specific DNA Binding Molecules" (Abstract).

Dervan, "7. Design of Sequence Specific DNA Cleaving Molecules" (Abstract).

Dervan, "83. Design of Sequence Specific DNA Cleaving Molecules" (Abstract).

Dervan, "83. Synthetic Sequence Specific DNA Binding Molecules" (Abstract).

Dervan, "83. Synthetic Sequence Specific DNA Binding Molecules" *Abstracts, Division of Biological Chemistry* 26:4171 (1987).

Dervan, "Design of Sequence–Specific DNA–Binding Molecules," *Science* 232:464–471 (1986).

Dervan, "Reagents for the site–specific cleavage of megabase DNA," *Nature* 359:87–88 (1992).

Di Marco et al., "Experimental Studies on Distamycin A—A New Antibiotic with Cytotoxic Activity," *Cancer Chemotherapy Reports* 18:15–19 (1962).

Di Marco et al., "Selective Inhibition of the Multiplication of Phage T1 in *E. coli* K12," *Experientia* 19:134–136 (1963).

Di Marco et al., "The Antimitotic Activity of Antibiotic Distamycin A," pp. 423–426.

Di Pietro et al., "N–Formimidoyl analogues of distamycin," *J. Chem. Soc., Perkin Trans. 1*, pp. 1333–1335 (1996).

Diana et al., "Synthesis and Antiviral Activity of Homologs of Noformycin" *J. Med. Chem.* 16(9):1050–1053 (1973).

Diana, "A Synthesis of Noformycin," *Med Chem.* 16(7):857–859 (1973).

D'Incalci et al., "Studies on the Mode of Action of FCE 24517, a New Distamycin A Derivative," *Proceedings of AACR* 29:329 at abstract No. 1310 (1988).

Ding et al., "Synthesis and antiviral activity of three pyrazole analogues of distamycin A," Acta Chemica Scandinavica 48:498–505 (1994).

Ding et al., "The preparation of partially protected 3–amino–1–methylpyrazole–5–carboxylic acids to be used as intermediates in the synthesis of analogs of distamycin–A," Acta Chemica Scandivavica 44(1):75–81 (1990).

Distefano and Dervan, "Energetics of cooperative binding olgionucleotides with discrete dimerization domains to DNA by triple helix formation," *Proc. Natl. Acad. Sci. USA* 90:1179–1183 (1993).

Distefano and Dervan, "Ligand–Promoted Dimerization of Oligonucleotides Binding Cooperatively to DNA," *J. Am. Chem. Soc.* 114:11006–11007 (1992).

Dorn et al., "Dystamycin–induced inhibitor of homeodomain DNA complexes," EMBO Journal 11:279–286 (1992).

Dreyer and Dervan, "Sequence–specific cleavage of single–stranded DNA: Oligonucleotide–EDTA•Fe(II)," *Proc. Natl. Acad. Sci. USA* 82:968–972 (1985).

Dunner et al., "Enhancement of a Fra(16)(q22) with Distamycin A: A Family Ascertained Through an Abnormal Proposita," *American Journal of Medical Genetics* 16:277–284 (1983).

Durand and Maurizot, "Distamycin A Complexation with a Nucleic Acid Triple Helix," *Biochemistry* 35:9133–9139 (1986).

Durland et al., "Binding of Triple Helix Forming Oligonucleotides to Sites in Gene Promoters," *Biochemistry* 30:9246–9255 (1991).

Dwyer et al., "Structural Analysis of Covalent Peptide Dimers, Bis(pyridine–2–carboxamidonetropsin)($CH_2$)$_{3-6}$, in Complex with 5'TGACT–3' Sites by Two–Dimensional NMR," *J. Am. Chem. Soc.* 115:9900–9906 (1993).

Eliadis et al., "The Synthesis and DNA Footprinting of Acridine–linked Netropsin and Distamycin Bifunctional Mixed Ligands," *J.Chem. Soc. Chem. Commun.* 1049–1052 (1988).

Fanta, "Sodium Nitromalonaldehyde Monohydrate" *Org. Syn. Coll.* 4:844–845 (1966).

Felsenfeld et al., "Formation of a Three–Stranded Polynucleotide Molecule" *J. Am. Chem. Soc.* 79:2023–2024 (1957).

Feng et al., "Crystallization and preliminary X–ray analysis of the DNA binding domain of the Hin recombinase with its DNA binding site," *J. Mol. Biol.* 232:982–986 (1993).

Fesen and Pommier, "Topoisomerase Inhibition by Anticancer Drugs is Antagonized by Distamycin," *Proceedings of AACR* 29:276 at abstract No. 1095 (1988).

Filipowsky et al., "Linked lexitropsins and the in vitro inhibition of HIV–1 reverse transcriptase RNA–directed DNA polymerization: A novel induced–fit of 3,5 m–pyridyl bisdistamycin to enzyme–associated template primer," *Biochemistry* 35(48)15397–15410 (1996).

Fish et al., "Determination of Equilibrium Binding Affinity of Distamycin and Netropsin to the Synthetic Deoxyoligonucleotide Sequence d(GGTATACC)$_2$ by Quantitative Dnase 1 Footprinting," *Biochemistry* 27:6026–6032 (1988).

Fox and Waring, "DNA structural variations produced by actinomycin and distamycin as revealed by DNAse I footprinting," *Nucleic Acids Research* 12:9271–9285 (1984).

Fransson et al., "High–performance liquid chromatography of distamycin A and its primary decomposition products as well as some synthetic analogues," *Journal of Chromatography* 268:347–351 (1983).

Fregeau et al., "Characterization of a CPI–lexitropsin conjugate–oligonucleotide covalent complex by 1H NMR and restrained molecular dynamics simulations," *J. Am. Chem. Soc.* 117(35):8917–8925.

Frigerio et al., "Determination of FCE 2664, a new polysulphonated derivative of distamycin A, in monkey plasma by reversed–phase ion–pair high–performance liquid chromatography with ultraviolet detection," *Journal of Chromatography A* 729:237–242 (1996).

Galas et al., "DNAase footprinting a simple method for the detection of protein–DNA binding specificity," *Nucleic Acids Res.* 5(9):3157–3170 (1978).

Gao et al., "Comparative NMR Studies of Oligo–N–Methylpyrrolecarboxamide d[CGAAATTTCG] Complexes" (Abstract).

Geierstanger et al., "Design of a G•C—Specific DNA Minor Groove–Binding Peptide," *Science* 266:646–650 (1994).

Geierstanger et al., "Extending the recognition site of designed minor groove binding molecules," *Nature Structural Biology* 3:321–324 (1996).

Geierstanger et al., "Structural and Dynamic Characterization of the Heterodimeric and Homodimeric Complexes of Distamycin and 1–Methylimidazole–2–carboxamide–Netropsin Bound to the Minor Groove of DNA," *Biochemistry* 33:3055–3062 (1994).

Geierstanger, Bernhard Hubert, , PhD Thesis entitled *NMR Studies of Peptides, Distamycin and its Analogs Bound to the Minor Groove of DNA*, University of California, Berkeley (1994).

Genelabs, PCR Newswire—"Genelabs Receives Seven Patent Allowances for Its DNA–Binding Technology" (1987—exact date unknown).

Germann et al., "Relative Stability of Parallel– and Antiparallel–Stranded Duplex DNA," *Biochemistry* 27:8302–8306 (1988).

Gisin, "The monitoring of reactions in solid–phase peptide synthesis with picric acid" *Anal. Chem. Acta.* 58:248–249 (1972).

Giuliani et al., "Distamycin A derivatives: in vitro and in vivo activity of a new class of antitumor agents," *Proceedings of AACR* 29:330 at abstract No. 1311 (1988).

Goodsell et al., "Structure of dicationic monoimidazole lexitropsin bound to DNA," *Biochemistry* 34(51):16654–16661 (1995).

Greenberg et al., "Energetics of Formation of Sixteen Triple Helical Complexes Which Vary at a Single Position within a Purine Motif," *J. Am. Chem. Soc.* 117:5016–5022 (1995).

Grehn et al. "Synthesis and Antiviral Activity of Distamycin A Analogues: Substitutions on the Different Pyrrole Nitrogens and in the Amidine Function," *J. Med. Chem.* 26:1042–1049 (1983).

Grehn et al., "A convenient method for the preparation of 1% Tert–butyloxycarbonyl <Pyrroles," Angewandte Chemie International Edition in English v23(4)296 (1984).

Grehn et al., "Novel efficient total synthesis of antiviral antibiotic distamycin A," *Journal of Organic Chemistry* 46:3492–3497 (1981).

Grehn et al., "Removal of formyl, acetly, and benzoyl groups from amides with conversion into the corresponding tert–butyl carbamates," Journal of the Chemical Society Chemical Communications 19(2):1317–1318 (1985).

Grehn et al., "Structure–activity–relationships in distamycin–A analogs–effect of alkyl groups on the pyrrole nitrogen at the non–amidine end of the molecule combined with methylelimination in the following ring," *Acta Chemica Scandivavica* 40(2):145–151 (1986).

Grehn et al., "The preparation and properties of partially protected 4–amino–1–methylimidazole–2–carboxylic acids to be used as intermediates in the synthesis of analogs of dystamycin–A," *Acta Chemica Scandivavica* 44(1):67–74 (1990).

Grehn, "Preparative Aspects of the Nitration of 1–methylpyrrole Derivatives. $^{13}C$ NMR of some Nitropyrroles" *Chim. Scripta* 13:67–77 (1978).

Griffin and Dervan, "207. Sequence Specific Recognition of DNA by Chiral (Bis(Netropsin)s" (Abstract).

Griffin and Dervan, "98. Designed, Synthetic, Metalloregulatory DNA Binding Molecules" (Abstract).

Griffin and Dervan, "Recognition of Thymine•Adenine Base Pairs by Guanine in a Pyrimidine Triple Helix Motif," *Science* 245:967–971 (1989).

Griffin and Dervan, "Sequence–Specific Chiral Recognition of Right–Handed Double–Helical DNA by (2S,3S)– and (2R, 3R)–Dihydroxybis(netropsin)succinamide," *J. Am. Soc. Chem.* 108:5008–5009 (1986).

Griffin, Dreyer and Dervan, "68. Sequence Specific Cleavage of Single Stranded DNA: Oligodeoxynucleotide–EDTA–FE(II)" (Abstract).

Griffin, John Hampton, PhD Thesis entitled *Structure–, Stereochemistry–, and Metal–Regulated DNA Binding/Cleaving Molecules,* California Institute of Technology, Pasadena, California (Submitted Jul. 11, 1989).

Grygon and Spiro, "Ultraviolet Resonance Raman Spectroscopy of Distamycin Complexes with Poly(dA)–(dT) and Poly(dA–dT): Role of H–Bonding," *Biochemistry* 28:4397–4402 (1989).

Guo et al., "DNA sequence–selective binding of head–to–tail linked bis–lexitropsins: relation of phasing to cytotoxic potency," *Anti–Cancer Drug Des.* 8(5):369–397 (1993).

Gupta et al., "Design, synthesis and topoisomerase II inhibiton activity of 4'–demethylepipodo–phyllotoxin–lexitropsin conjugates," *Anti–Cancer Drug Design* 11:325–338 (1996).

Gupta et al., "Hybrid molecules containing propargylic sulfones and DNA minor groove–binding leixtropsins: Synthesis, sequences specificity of reaction with DNA and biological evaluation," *Gene* 149(1):81–90 (1994).

Gupta et al., "Novel DNA–directed alkylating agents consisting of naphthalmide, nitrogen mustard and lexitropsin moieties: synthesis, DNA sequence specificity and biological evaluation," *Anti–Cancer Drug Des.* 11:581–596 (1996).

Hacia et al., "Inhibition of Klenow Fragment DNA Polymerase on Double–Helical Templates by Oligonucleotide–Directed Triple–Helix Formation," *Biochemistry* 33:6192–6200 (1994).

Hacia et al., "Phosphorothioate Oligonucleotide–Directed Triple Helix Formation," *Biochemistry* 33:5367–5369 (1994).

Han and Dervan, "Different conformational families of pyrimidine•purine•pyrimidine triple helices depending on backbone composition," *Nucleic Acids Research* 22:2837–2844 (1994).

Han and Dervan "Sequence–specific recognition of double helical RNA and RNA•DNA by triple helix formation," *Proc. Natl. Acad. Sci USA* 90:3806–3810 (1993).

Han and Dervan, "Visulation of RNA tertiary structure by RNA–EDTA•FE(II) autocleavage: Analysis of tRNA$^{Phe}$ with uridine–EDTA•Fe(II) at position 47," *Proc. Natl. Acad. Sci. USA* 91:4955–4959 (1994).

Han et al., "Mapping RNA Regions in Eukaryotic Ribosomes That Are Accessible to Methidiumpropyl–EDTA•Fe(II) and EDTA•Fe(II)," *Biochemistry* 33:9831–9844 (1994).

Harapanhalli et al., "[$^{125}$I/$^{127}$I]IodoHoechst 33342: Synthesis, DNA Binding and Biodistribution, *J. Med. Chem.* 39:4804–4809 (1996).

Harshman and Dervan, "Molecular recognition of B–DNA by Hoechst 33258," *Nucleic Acids Research* 13:4825–4835 (1985).

Hertzberg and Dervan, "Cleavage of DNA with Methidiumpropyl–EDTA–Iron(II): Reaction Conditions and Product Analyses," *Biochemistry* 23:3934–3945 (1984).

Hinsberg et al., "Direct Studies of 1,1–Diazenes. Syntheses, Infrared and Electronic Spectra, and Kinetics of the Thermal Decomposition of N–(2,2,6,6–Tetramethylpiperidyl)nitrene and N–(2,2,5,5–Tetramethylpyrrolidyl)nitrene," *J. Amer. Chem. Soc.* 104:766–773 (1982).

Howard et al., "Infrared Demonstration of Two—and Three–Strand Helix Formation between Poly C and Guanosine Mononucleotides and Oligionucleotides", *Biochem & Biophys. Res. Commun.* 17(1):93–102 (1964).

Huang et al., "Design of DNA–cleaving molecules which incorporate a simplified metal–complexing moiety of bleomycin and lexitropsin carriers," *Bioorg. Med. Chem. Lett.* 3(8):1751–1756 (1993).

Huang et al., "Design, synthesis, and sequence selective DNA cleavage of functional models of bleomycin. 1. Hybrids incorporating a sample metal–complexing moiety of bleomycin and lexitropsin carriers," *Biocojugate Chem.* 6(1):21–33 (1995).

Huang et al., "Synthesis of designed functional models of bleomycin incorporating imidazole– containing lexitropsins as novel DNA recognition sites," *Heterocycles* 41(6):1181–1196 (1995).

Huntingon's Disease Collaborative Research Group, "A Novel Gene Containing a Trinucleotide Repeat That is Expanded and Unstable on Huntington's Disease Chromosomes," *Cell* 72:971–983 (1993).

Hunziker et al., "Design of an N$^7$–Glycosylated Purine Nucleoside for Recognition of GC Base Pairs by Triple Helix Formation," *J. Am. Chem. Soc.* 117:2661–2662 (1995).

Ikeda and Dervan, "Sequence–Selective Inhibition of Restriction Endonucleases by the Polyintercalator Bis(methidium)spermine," *J. Am. Chem. Soc.* 104:296–297 (1982).

Iverson and Dervan, "69. Cleavage of Complementary Strands of Nucleic Acids with Single Base Specificity. Enzymatic Incorporation of Modified Uridine Triphosphates" (Abstract).

Iverson and Dervan, "Adenine–Specific DNA Chemical Sequencing Reaction," *Methods in Enzymology* 218:222–227 (1993).

Iverson and Dervan, "Piperdine specific DNA chemical sequencing reaction," *Nucleic Acids Research* 14:7823–7830 (1987).

Jensen and Lysek, "Differences in the mycelial growth rhythms in a population of *Sclerotinia fructigena* (Pers.) Schroter," *Experientia* 39:1401–1402 (1983).

Johnston et al., "Autoradiography using storage phosphor technology," *Electrophoresis* 11:355–360 (1990).

Jotterand–Bellomo, "The effects of distamycin A on cultured amniotic fluid cells," *Ann. Genet.* 26:27–30 (1983) (In French with English Abstract).

Juby et al., "Facile Preparation of 3'Oligonucleotide–Peptide Conjugates" *Tet. Lett.* 32(7):879–882 (1991).

Kent, "Chemical Synthesis of Peptides and Proteins" *Ann. Rev. Biochem.* 57:957–89 (1988).

Kharatishvili et al., "Formation of the Left Helix On Simultaneous Exposure to Poly [d(GC)]bis–Netropsin and Zn(II) Ions," *Biophysics* 30:764–766 (1985).

Kiessling et al., "Flanking Sequence Effects within the Pyrimidine Triple–Helix Motif Characterized by Affinity Cleaving," *Biochemistry* 31:2829–2834 (1992).

Kissinger et al., "Molecular Recognition between Oligopeptides and Nucleic Acids, Monocationic Imidazole Lexitropsins that display Enhanced GC Sequence Dependnet DNA Binding," *Biochemistry* 26:5590–5595 (1987).

Koh and Dervan, "Design of a Nonnatural Deoxyribonucleoside for Recognition of GC Base Pairs by Oligonucleotice–Directed Triple Helix Formation," *J. Am. Chem. Soc.* 114:1470–1478 (1992).

Kopka et al., "Binding of an Antitumor Drug to DNA" *J. Mol. Biol.* 183:553–563 (1985).

Kopka et al., "The molecular origin of DNA–drug specificity in netropsin and distamycin," *Proc. Natl. Acad. Sci.* 82:1376–1380 (1985).

Koppel et al., "Basicity of 3–Aminopropionamidine Derivatives in Water and Dimethyl Sulphoxide, Implication for a Pivotal Step in the Synthesis of Distamycin A Analogues," *Journal of Physical Organic Chemistry* 9:265–268 (1996).

Koshlap et al., "Nonnatural Deoxyribonucleoside $D_3$ Incorporated in an Intramolecular DNA Triplex Binds Sequence–Specifically by Intercalation," *J. Am. Chem. Soc.* 115:7908–7909 (1993).

Kothekar et al., "Influence of Local Excitations in DNA Conformation on Binding of Nonintercalating Antitumor Antibiotic in the Minor Groove," *International Journal of Quantum Chemistry: Quantum Biology Symposium* 13:175–183 (1986).

Krauch et al., "New Base Pairs for DNA and RNA" (abstract).

Krowicki and Lown, "Synthesis of Novel Imidazole–Containing DNA Minor Groove Binding Oligopeptides Related to the Antiviral Antibiotic Netropsin," *J. Org. Chem.* 52:3493–3501 (1987).

Krugh, "Drug–DNA interactions," *Curr. Opin Struct.* 4:351–364 (1994).

Kucerova et al., "Netropsin stimulates the formation of extracellular proteinase and suppresses protein turnover in sporulating Bacillus megaterium," *FEMS Microbiology Letters* 34:21–26 (1986).

Kumar et al., "Molecular recognition and binding of a GC site–avoiding thiazole–lexitropsin to the decadeoxyribonucleotide d–[CGCAATTCGC]$_2$: An H–NMR evidence for thiazole intercalation," *J. Biomol. Struct. Dyn.* 8(1):99–121 (1990).

Kumar et al., "Structural and dynamic aspects of non–intercalative (1:1) binding of a thiazole–lexitropsin to the decadeoxyribonucleotide d–[CGCAATTCGC]$_2$: An H–NMR and molecular modeling study," *J. Biomol. Struct. Dyn.* 9(1):1–21 (1991).

Kuroda et al., "Intelligent compounds which read DNA base sequences," *Supramolecular Chemistry* 6:95–102 (1995).

Kurreck et al., "ENDOR spectroscopy—A promising technique for investigating the structure of organic radicals," *Angew. Chem. Int. Ed. Engl.* 23:173–194 (1984).

Lane et al., "Sequence specificity of actinomycin D and Netropsin binding to pBR322 DNA analyzed by protection from Dnase I," *Proc. Natl. Acad. Sci USA* 80:3260–3264 (1983).

Larsen and Dickerson, "As the Helix Turns, or, Rational Design of Sequence Specific DNA Minor Groove Binding Drugs," *J. Mol. Graphics* 6:211 (1988).

Lazzari et al., EPO Patent Application No. 0 246 868 A1 published Nov. 25, 1987 for "Site Specific Alkylating Agents".

Le Doan et al., "Sequence–specific recognition, photo-crosslinking and cleavage of the DNA double helix by an oligo–[α]–thymidylate covalently linked to an azidoproflavine derivative," *Nucleic Acids Res.* 15:7749–7760 (1987).

Lee and Walker, "Ch. 3—Sequence–Selective Binding of DNA by Oligopeptides as a Novel Approach to Drug Design," in *Polymeric Drugs and Drug Administration,* American Chemical Society, pp. 29–46 (1994).

Lee et al., "GC Base Sequence Recognition by Oligo (imidazolecarboxamide) and C–Terminus Modified Analogues of Distamycin Deduced from Circular Dichroism, Proton Nuclear Magnetic Resonance, and Methidiumpropy-lethylenediaminetetraacetate–Iron (II) Footprinting Studies," *Biochemistry* 32:32:4237–4245 (1993).

Lee et al., "Structural and Dynamic Aspects of Binding of a Prototype Lexitropsin to the Decadeoxyribonucleotide d(CGCAATTGCG)$_2$ Deduced from High–Resolution $^1$H NMR Studies," *Biochemistry* 27:445–455 (1987).

Lee et al., "Structural and Dynamic Aspects of the Sequence Specific Binding of Netropsin and its Bis–Imidazole Analogue on the Decadeoxyribonucleotide d–[CGCAATT GCG]$_2$," *Journal of Biomolecular Structure & Dynanmics* 5:939–949.

Lee et al., "Molecular recognition between oligopeptides and nucleic acids. Specificity of binding of a monocationic bis–furan lexitropsin to DNA deduced from footprinting and H NMR studies," *J. Mol. Recognit.* 2(2):84–93 (1989).

Lee et al., "Sequence specific molecular recognition and binding of a monocationic bis–imidazole lexitropsin to the decadeoxyribonucleotide d–[(GATCCGTATG) (CATACG-GATC)]: structural and dynamic aspects of intermolecular exchange studies by H–NMR," *J. Biomol. Struct. Dyn.* 5(5):1059–1087 (1988).

Leinsoo et al., "Attachment of Trivaline to a Netropsin Analog Changes the Specificity of its Binding to DNA," *Institute of Molecular Biology,* Academy of Sciences of USSR, pp. 134–148 (1988) translated from *Molekulyarnaya Biologiya* 22(1):159–175 (1988).

Levina et al., "Conjugates of Minor Groove DNA Binders with Oligodeoxynucleotides: Synthesis and Properties," *Antisense & Nucleic Acid Drug Development* 6:75–85 (1996).

Liquier et al., "FTIR Study of Netropsin Binding to Poly d(A–T) and Poly dA•Poly dT," *J. Biomolecular Structure & Dynamics* 7:119–126 (1989).

Lombardi and Crisanti, "Antimalarial Activity of Synthetic Analogues of Distamycin," *Pharmacol. Ther.* 76:125–133 (1977).

Lown and Krowicki, "Efficient Total Syntheses of the Oligopeptide Antibiotics Netropsin and Distamaycin," *J. Org. Chem.* 50:3774–3779 (1985).

Lown et al., "Molecular Recognition between Oligopeptides and Nucleic Acids: Novel Imidazole–Containing Oligopeptides Related to Netropsin That Exhibit Altered DNA Sequence Specificity," *Biochemistry* 25:7408–7416 (1986).

Lown et al., "Novel Linked Antiviral and Antitumor Agents Related to Netropsin and Distamycin: Synthesis and Biological Evaluation," *J. Med. Chem.* 32:2368–2375.

Lown et al., "Structure–Activity Relationship of Novel Oligopeptide Antiviral and Antitumor Agents Related to Netropsin and Distamycin," *J. Med. Chem.* 29:1210–1214 (1986).

Lown, "Design and Development of Sequence Selective Lexitropsin DNA Minor Groove Binders," *Drug Development Research* 34:145–183 (1995).

Lown, "Design of sequence–specific agents: Lexitropsins," *Mol. Aspects Anticancer Drug– DNA Interact* Ch. 11:322–355 (1993).

Lown, "DNA recognition by lexitropsins, minor groove binding agents," *J. Mol. Recognit.* 7(2):79–88 (1994).

Lown, "Lexitropsins in antiviral drug development," *Antiviral Res.* 17(3):179–196 (1992).

Lown, "Synthetic chemistry of naturally occurring oligopeptide antibiotics and related lexitropsins," *Org. Prep. Proced. Int.* 21(1):1–46 (1989).

Lu–D et al., "Synthesis and antiviral activity of 3 pyrazole analogs of distamycin–A," *Acta Chemica Scandivavica* v48(6):498–505 (1994).

Luebke and Dervan, "Nonenzymatic Ligation of Oligodeoxyribonucleotides on a Duplex DNA Template by Triple–Helix Formation," *J. Am. Chem. Soc.* 11:8733–8735 (1989).

Lundt et al., "Removal of t–Butoxycarbonyl protecting groups with Trifluoroacetic Acid" *Int. J. Pep. Prot. Res.* 12:258–268 (1978).

Lythgoe and Ramsden, "4–Unsubstituted, 5–Amino and 5–Unsubstituted, 4–Aminoimidazoles," *Advances in Heterocyclic Chemistry* 61:1–58 (1994).

Mack and Dervan, "Sequence–Specific Oxidative Cleavage of DNA by a Designed Metalloprotein, Ni(II)•GGH(Hin139–190)," *Biochemistry* 31:9399–9405 (1992).

Maher et al., "Analysis of Promoter–Specific Repression by Triple–Helical DNA Complexes in a Eukaryotic Cell–Free Transcription System," *Biochemistry* 31:70–81 (1992).

Maher et al., "Inhibition of DNA Binding Proteins by Oligonucleotide–Directed Triple Helix Formation," *Science* 245:725–730 (1989).

Malcolm and Snounou, "Netropsin Increases the Linking Number of DNA," pp. 323–326.

Marck et al., "Specific interaction of netropsin, distamycin–3 and analogs with I.C duplexes: reversion towards the B form of the 2–deoxy–, 2'–deoxy-2'–fluoro– hybrid duplexes upon specific interactions with netropsin, distamycin–3 and analogs," *Nucleic Acids Research* 10:6147–6161 (1982).

Marky et al., "Calorimetric and spectroscopic investigation of drug–DNA interactions. I. The binding of netropsin to poly d(AT)," *Nucleic Acids Research* 11:2857–2871 (1983).

Marky, "Interaction of a Non–Intergalative Drug with DNA: Netropsin," pp. 417–418.

Martello et al., "Specific Activation of Open Complex Formation at an *Escherichia coli* Promoter by Oligo(N–methylpyrrolecarboxamide)s: Effects of Peptide Length and Identification of DNA Target Sites," *Biochemistry* 28:4455–4461 (1989).

Martinson et al., "1,3,5–Tripivaloylbenzene" *Acta. Chem. Scan.* 23:751–764 (1963).

Matyasek et al., "Evidence for a sequence–directed conformation perodicity in the genomic highly repetitive DNA detectable with single–strand–specific chemical probe potassium permangante," *Chromosome Research* 4:340–349 (1996).

Mazurek et al., "The binding of prototype lexitropsins to the minor groove of DNA: Quantum chemical studies," *J. Biomol. Struct. Dyn.* 9(2)299–313 (1991).

Milton et al., "Total chemical synthesis of a D–enzyme: The enantiomers of HIV–1 protease show demonstration of reciprocal chiral substrate specificity," *Science* 256:1445–1448 (1992).

Mitchell and Dervan, "Interhelical DNA–DNA Cross–linking. Bis(monoazidoemthidium) octaoxahexacosanediamine: A Probe of Packaged Nucleic Acid," *J. Am. Chem. Soc.* 104:4265–4266 (1982).

Mitchell and Dervan, "Interhelical DNA–DNA Cross–Linking. Bis(monoazidomethidium) octaoxahexacosanediamine: A Probe of Packaged Nucleic Acid," *J. Am. Chem. Soc.* 104:4265–4266 (1982).

Momose et al., "3–hydroxypyrroles. I. A general synthetic route to 4,5–unsubstituted alkyl 3–hydroxypyrrole–2–carboxylates," *Chemical Pharmacology Bulletin* 26:2224–2232 (1978).

Momose et al., "3–hydroxypyrroles. II. The reaction of 4,5–unsubstituted alkyl 3–hydroxypyrrole–2–carboxylates with some electrophiles," *Chemical Pharmacology Bulletin* 26:3521–3529 (1978).

Morgan et al., "The Preparation and Properties of 2– and 3–Nitropyrrole," *Tetrahedron* 22:57–62 (1966).

Moser and Dervan, "Sequence–Specific Cleavage of Double Helical DNA by Triple Helix Formation," *Science* 238:645–650 (1987).

Mosher et al., "Synthesis of N–Methyl–2–trichloroacetylpyrrole—A Key Building Block in Peptides that Bind DNA: Micro–, Semimicro–, and Macro–Scale Organic Lab Experiments," *Journal of Chemical Education* 73:1036–1039 (1996).

Mrksich and Dervan, "Antiparallel Side–by–Side Heterodimer for Sequence–Specific Recognition in the Minor Groove of DNA by a Distamycin/1–Methylimidazole–2–carboxamide–netropsin Pair," *J. Am. Chem. Soc.* 115:2572–2576 (1993).

Mrksich and Dervan, "Design of a Covalent Peptide Heterodimer of Sequence–Specific Recognition in the Minor Groove of Double–Helix DNA," *J. Am. Chem. Soc.* 116:3663–3664 (1994).

Mrksich and Dervan, "Enhanced Sequence Specific Recognition in the Minor Groove of DNA by Covalent Peptide Dimers: Bis(pyridine–2–carboxamidonetropsin)(CH$_2$)$_{3-6}$," *J. Am. Chem. Soc.* 115:9892–9899 (1993).

Mrksich and Dervan, "Recognition in the Minor Groove of DNA at 5'–(A,T)GCGC(A,T)–3' by a Four Ring Tripeptide Dimer. Reversal of the Specificity of the Natural Product Distamycin," *J. Am. Chem. Soc.* 117:3325–3332 (1995).

Mrksich et al., "Antiparallel side–by–side dimeric motif for sequence–specific recognition in the minor groove of DNA by the designed peptide 1–methylimidazole–2–carboxamide netropsin," *Proc. Natl. Acad. Sci. USA* 89:7586–7590 (1992).

Mrksich et al., "Hairpin Peptide Motif. A New Class of Oligopeptides for Sequence–Specific Recognition in the Minor Groove of Double–Helical DNA," *J. Am. Chem. Soc.* 116:7983–7988 (1994).

Mrksich et al., "Design of a covalent peptide heterodimer for sequence–specific recognition in the minor groove of double–helical DNA," *J. Am. Chem. Soc.* 116:3633–1664 (1994).

Mrksich et al., Abstracts of the American Chemical Society 206 part 2:413 (1993).

Mrksich Milan, phD Thesis entitled *Design of Peptides for Sequence–Specific Recognition of the Minor Groove of DNA,* California Institute of Technology, Pasadena, California (submitted Mar. 8, 1994).

Nechipurenko et al., "Cooperative Interactions Between Analogs of Distamycin A, Adsorbed on DNA," *Institute of Molecular Biology,* Academy of Sciences of USSR, pp. 263–272 (1984) translated from *Molekulyarnaya Biologiya* 18(2):332–342 (1984).

Nikolaev et al., "Design of Sequence–Specific DNA Binding Ligands That Use a Two–Stranded Peptide Motif for DNA Sequence Recognition," *Journal of Biomolecular Structure & Dynamics* 14:31–47 (1996).

Nilsson et al., "Structure at restriction endonuclease MboI cleavage sites protected by actinomycin D or distamycin A," *FEBS Letters* 145:360–364 (1982).

Nishiwaki et al., "Efficient Synthesis of Oligo–N–Methylpyrrolecarboxamides and Related Compounds," *Heterocycles* 27:1945–1952 (1988).

Oakley et al., "Structural Motif of the GCN4 DNA Binding Domain Characterized by Affinity Cleaving," *Science* 248:847–850 (1989).

Oakley et al., "Synthesis of a Hybrid Protein Containing the Iron–Binding Ligand of Bleomycin and the DNA–Binding Domain of Hin," *Bioconjugate Chem.* 5:242–247 (1994).

Oakley et al., "Evidence that a major groove– binding peptide can simultaneously occupy a common site on DNA," *Biochemistry* 31:10969–10975 (1992).

Oakley, thesis entitled "Design, Synthesis and characterization of sequence–specific DNA, cleaning metallophoteths," California Institute of Technology, Pasadena, California Submitted Nov. 8, 1993.

Ochi et al., "New Heritable Fragile Site on Chromosome 8 Induced by Distamycin A," *Jpn. J. Cancer Res.* 79:145–147 (1988).

Parks et al., "Optimization of the Hairpin Polyamide Design for Recognition of the Minor Groove of DNA," *J. Am. Chem. Soc.* 118:6147–6152 (1996).

Parks et al., "Recognition of 5'–(A,T)GG(A,T)$_2$–3' Sequences in the Minor Groove of DNA by Hairpin Polyamides," *J. Am. Chem. Soc.* 118:6153–6159 (1996).

Parrack et al., "Interaction of synthetic analogs of distamycin with DNA: Role of the conjugated N–methylpyrrole system in specificity of binding," *FEBS Letters* 212:297–301 (1987).

Pelton and Wemmer, "Binding Modes of Distamycin A with D(CGCAAATTTGCG)$_2$ Determined by Two–Dimensional NMR," *J. Am. Chem. Soc.* 112:1393–1399 (1990).

Pelton, "Structural characterization of a 2:1 distamycin A•d (CGCAAATTGGC) complex by two–dimensional NMR," *Proc. Natl. Acad. Sci.* 86:5723–5727 (1989).

Pilch et al., "Structure, Stability, and Thermodynamics of a Short Intermolecular Purine–Purine–Pyrimidine Triple Helix," *Biochemistry* 30(25):6081–6087 (1991).

Portugal and Waring, "Comparison of binding sites in DNA for berenil, netropsin and distamycin: A footprinting study," *Eur. J. Biochem.* 167:281–289 (1987).

Portugal and Waring, "Hydroxyl radical footprinting of the sequence–selective binding of netropsin and distamycin to DNA," *Febs Letters* 225:195–200 (1987).

Portugal and Waring, "Interaction of nucleosome core particles with distamycin and echinomycin: analysis of the effect of DNA sequences," *Nucleic Aicds Research* 15:885–903 (1987).

Povsic and Dervan, "Triple Helix Formation by Oligonucleotides on DNA Extended to the Physiological pH Range," *J. Am. Chem. Soc.* 111:3059–3061 (1989).

Priestley and Dervan, "Sequence Composition Effects on the Energetics of Triple Helix Formation by Oligonucleotides Containing a Designed Mimic of Protonated Cytosine," *J. Am. Chem. Soc.* 117:4761–4765 (1995).

Probst et al., "Anthelvencins, New Antibiotics with Anthelmintic Properties," *Antimicrob. Agents Chemother.* 789–795 (1965).

Radhakrishnan and Patel, "NMR Structural Studies on a Nonnatural Deoxyribonucleoside Which Mediates Recognition of GC Base Pairs in Pyrimidine•Purine•Pyrimidine DNA Triplexes," *Biochemistry* 32:11228–11234 (1993).

Radhakrishnan et al., "Nuclear Magnetic Resonance Structural Studies of Intramolecular Purine–Purine–Pyrimidine DNA Triplexes in Solution" *J. Mol. Biol.* 221:1403–1418 (1991).

Radhakrishnan et al., "NMR Structural Studies of Intramolecular $(Y+)_n$•$(R+)_n(Y-)_n$ DNA Triplexes in Solution: Imino and Amino Proton and Nitrogen Markers of G•TA Base Triple Formation," *Biochemistry* 30:9022–9030 (1991).

Rajagopal et al., "Triple–strand formation in the homopurine: homopyrimidine DNA oligonucleotides (d(G–A)$_4$ and d(T–C)$_4$," *Nature* 339:637–640 (1989).

Rajagopalan et al., "Interaction of non–intercalative drugs with DNA: Distamycin analogues," *J. Biosci.* 7:27–32 (1985).

Rajagopalan et al., "Synthesis of a Distamycin Analogue: Tris(m–benzamido) Compound," *Indian Journal of Chemistry* 26B:1021–1024 (1987).

Rao et al., "Interaction of Synthetic Analogues of Distamycin and Netropsin with Nucleic Acids. Does Curvature of Ligand Play a Role in Distamycin–DNA Interactions?" *Biochemistry* 27:3018–3024 (1988).

Rao et al., "Molecular recognition between ligands and nucleic acids: Sequence preferences and binding of Pyrrolo [3,2–d] and [2,3–d]thiazole–containing lexitropsins deduced from MPE–Fe(II) footprinting," *Actual. Chim. Ther.* 20:159–188 (1993).

Rao et al., "Molecular recognition between oligopeptides and nucleic acids: DNA binding selectivity of a series of 1,2,4–triazole–containing lexitropsins," *Chem. Res. Toxicol.* 4(2):241–252 (1991).

Rao et al., "Psoralen–lexitropsin hybrids: DNA sequence selectivity of photoinduced cross–linking from MPE footprinting and exonuclease III stop assay, and mode of binding from electric linear dichroism," *Anti–Cancer Drug Des.* 9(3):221–237 (1994).

Rao et al., "Sequence–selective DNA binding by linked Bis–N–methylpyrrole dipeptides: an analysis by MPE footprinting and force field calculations," *J. Org. Chem.* 56(2):786–797 (1991).

Reinert et al., "Deformyldistamycin–DNA Interaction; DNA Conformational Changes as Revealed by Titration Rotational Viscometry," *J. Biomolecular Structure & Dynamics* 14(2):245–253 (1996).

Reinert et al., "DNA interaction of the imidazole–containing lexitropsin ImPy: Titration viscometric study in comparison to Netropsin," *J. Biomol. Struct. Dyn.* 12(4):847–855 (1995).

Ronne et al., "The effect of in vitro distamycin A exposure on metaphase chromosome structure," *Hereditas* 96:269–277 (1982).

Royyuru et al., "Theoretical Study of Conformational Flexibility of Distamycin–A Analog and its Binding to DNA," *Current Science* 56:581–584 (1987).

Rubin et al., "An unexpected major groove binding of netropsin and distamycin A to tRNA$^{phe}$," *Journal of Biomolecular Structure and Dynamics* 2:165–174 (1984).

Sakaguchi et al., "Effect of entropsin on plasmid DNA cleavage by BAL 31 nuclease," *FEBS Letters* 191:59–62 (1985).

Salmanova et al., "Interaction of DNA with Synthetic Ligands Containing N,4–Disubstituted Mono– and Diphthalimides," *Molecular Biology* 29:491–498 (1995).

Sanfilippo et al., "Activity of the Distamycin A on the Induction of Adaptive Enzymes in *Escherichia coli*," *J. Gen. Microbiol.* 43:369–374 (1966).

Sarin et al., "Quantitative Monitoring of Solid–Phase Peptide Synthesis by the Ninhydrin Reaction[1]," *Anal. Biochem.* 117:147–157 (1981).

Sarma et al., "Structure of Poly(dA)•Poly(dT) is not Identical to the AT Rich Regions of the Single Crystal Structure of CGCGAATT$^{Br}$CGCG. The Consequence of this to Netropsin Binding to Poly(dA)•Poly(dT)," *J. Biomolecular Structure & Dynamics* 3(3):433–436 (1985).

Schabel et al., "Observations on Antiviral Activity of Netropsin," *Proceedings of the Society for Experimental Biology and Medicine* 83:1–3 (1953).

Schmid et al., "Characterization of a Y/15 translocation by banding methods, distamycin A treatment of lymphocytes and DNA restriction endonuclease analysis," *Clinical Genetics* 24:234–239 (1983).

Schmid et al., "The use of distamycin A in human lymphocyte cultures," *Human Genet* 65:377–384 (1984).

Schuhmann et al., "Wirkung von Distamycin A und Netropsin auf normale und zellwandlose Zellen von *Escherichia coli* W 1655F$^+$," *Zeitschrift fur Allg. Mikrobiologie* 14:321–327 (1974) (In German with English Abstract).

Schultz and Dervan, "Distamycin and Penta–N–Methylpyrrolecarboxamide Binding Sites on Native DNA—A Comparison of Methidiumpropyl–EDTA–Fe(II) Footprinting and DNA Affinity Cleaving," *J. Biomolecular Structure & Dynamics* 1:1133–1147 (1984).

Schultz and Dervan, "Sequence–specific double–strand cleavage of DNA by penta–N–methylpyrrolecarboxamide–EDTA•FE(II)," *Proc. Natl. Acad. Sci. USA* 80:6834–6837 (1983).

Schultz, "141. Design and Synthesis of Sequence Specific DNA Cleaving Molecules" (Abstract).

Schultz, thesis entitled "I. Ground and excited state studies of persistent 1,1–diazenes," and "II. Design of sequence specific DNA cleaving molecules," California Institute of Technology, Pasadena, California Submitted Feb. 2, 1989.

Schulz and Dervan, "Sequence–Specific Double–Strand Cleavage of DNA by Bis(EDTA–distamycin–Fe$^{II}$) and EDTA–Bis(distamycin)•Fe$^{II}$," *J. Am. Chem. Soc.* 105:7748–7750 (1983).

Senear et al., "Energetics of Cooperative Protein–DNA Interactions: Comparison between Quantitative Deoxyribonuclease Footprint Titration and Filter Binding," *Biochemistry* 25:7344–7354 (1986).

Sengupta et al., "A Microgonotropen Pentaaza Pentabutylamine and its Interactions with DNA," *Bioorganic & Medicinal Chemistry* 4:803–813 (1996).

Shabtai et al., "Familial fragile site found at the cancer breakpoint (1)(q32): Inducibility by distamycin A, concomitance with gragile (16)(q22)," *Hum Genet* 73:232–234 (1986).

Shabtai et al., "Familial Fragility on Chromosome 16 (Fra 16q22) Enhanced by Both Interferon and Distamycin A," *Hum Genet* 63:341–344 (1983).

Shin, Sluka, Horvath, Simon and Dervan, "99. Synthetic DNA–Cleaving Proteins" (Abstract).

Shishido et al., "Enhancement of S1 Nuclease–Susceptibility of Negatively Superhelical DNA by Netropsin," *Biochemical & Biophysical Research Communications* 124:388–392 (1984).

Sidorova et al., "Competition between Netropsin and Restriction Nuclease EcoRI for DNA Binding," *J. Biomolecular Structure & Dynamics* 13(2):367–385 (1995).

Singh et al., "Isohelicity and Strand Selectivity in the Minor Groove Binding of Chiral (1R,2R)– and (1S,2S)–Bis(netropsin)–1,2–cyclopropanedicarboxamide Ligands to Duplex DNA," *J. Am. Chem. Soc.* 116:7006–7020 (1994).

Singh et al., "A H–NMR study of the DNA binding characteristics of thioformyldistamycin an amide isosteric lexitropsin," *Biochemistry* 31(28):6453–6461 (1992).

Singh et al., "Structural characterization of side–by side binding for a cross–linked lexitropsin dimer designed to target G–C base pairs in the DNA minor groove," *Magn. Reson. Chem.* 34:S55–S66 (1996).

Singleton and Dervan, "Equilibrium Association Constants for Oligonuclotide–Directed Triple Helix Formation at Single DNA Sites: Linkage to Cation Valence and Concentration," *Biochemistry* 32:13171–13179 (1993).

Singleton and Dervan, "Influence of ph on the Equilibrium Association Constants for Oligodeoxyribonucleotide–Directed Triple Helix Formation at Single DNA Sites," *Biochemistry* 31:10995–11003 (1992).

Singleton and Dervan, "Temperature Dependence of the Energetics of Oligonucleotide–Directed Triple–Helix Formation at a Single DNA Site," *J. Am. Chem. Soc.* 116:10376–10382 (1994).

Skamrov et al., "Specific Protection of DNA from the Action of Dnase I by Distamycin A, Netropsin, and Bis–Netropsins," *Institute of Molecular Biology,* Academy of Sciences of USSR, pp. 153–167 (1985) translated from *Molekulyarnaya Biologiya* 19(1):177–195 (1985).

Sluka et al., "Synthesis of a Sequence–Specific DNA––Cleaving Peptide," *Science* 238:1129–1132 (1987).

Smith et al., "The synthesis of oligonucleotides containing an aliphatic amino group at the 5'terminus: synthesis of fluorescent DNA primers for use in DNA squence of fluorescent DNA primers for use in DNA sequence analysis" *Nucleic Acids Res.* 13(7):2399–2412 (1985).

Snounou and Malcolm, "Productin of Positively Supercoiled DNA by Netropsin," *J. Mol. Biol.* 167:211–216 (1983).

Soukchareun, "Preparation and characterization of antisense oligonucleotide–peptide hybrids containing viral fusion peptides," *J. Bioconj. Chem.* 61:43–53 (1995).

Sponar and Votavova, "Selective Binding of Synthetic Polypeptides to DNA of Varying Composition and Sequence: Effect of Minor Groove Binding Drugs," *J. Biomolecular Structure & Dynamics* 13(6):979–987 (1996).

Sproat et al., "The synthesis of protected 5'–mercapto–oligodeoyribonucleotides," *Nucleic Acids Res.* 15(12):4837–4848 (1987).

Stanchev et al., "Netropsin, Distamycin A, bis–Netropsins as Selective Inhibitors of the Effect of Restrictase and DNase I," *Institute of Molecular Biology,* Academy of Sciences of USSR, pp. 1324–1333 (1987) translated from *Molekulyarnaya Biologiya* 20(6):1614–1624 (1986).

Staubli and Dervan, "Sequence specificity of the non–natural pyrido[2,3–d]pyrimidine nucleoside in triple helix formation," *Nucleic Acids Research* 22:2637–2642 (1994).

Stilz and Dervan, "Specific Recognition of CG Base Pairs by 2–Deoxynebularine within the Purine•Purine•Pyrimidine Triple–Helix Motif," *Biochemistry* 32:2177–2185.

Strobel and Dervan, "Cooperative Site Specific Binding of Oligonucleotides to Duplex DNA," *J. Am. Chem. Soc.* 111:7286–7287 (1989).

Strobel and Dervan, "Triple Helix–Mediated Single–Site Enzymatic Cleavage of Megabase Genomic DNA," *Methods in Enzymology* 216:309–321 (1992).

Strobel et al., "Site–Specific Cleavage of Human Chromosome 4 Mediated by Triple–Helix Formation," *Science* 254:1639–1642 (1991).

Surovaya et al., "Construction of Peptide β–Hairpins Recognizing DNA Sequences," *Molecular Biology* 30:818–825 (1996).

Swalley et al., "Recognition of a 5'-(A,T)GGG(A,T)$_2$-3' Sequence in the Minor Groove of DNA by an Eight–Ring Hairpin Polyamide" *J. Am. Chem. Soc.* 118:8198–8206 (1996).

Takahashi et al., "82. Distamycin A–Induced Fragility on Chromosome 16, Fra(16)(q22), in a Japanese Population," *Proc. Japan Acad.* 61(B):299–302 (1985).

Takahashi et al., "A new rare distamycin A–inducible fragile site, fra(11)(p15.1), found in two acute nonlymphocytic leukemia (ANLL) patients with t(7;11)(p15–p13;p15)," *Hum Genet* 80:124–126 (1988).

Takaishi et al., "Structure of Kikumycin A and B," *Tetrahedron Lett.* 1873–1876 (1972).

Taylor et al., "DNA Affinity Cleaving—Sequence Specific Cleavage of DNA by Distamycin–EDTA•Fe(II) and EDTA–Distamycin•Fe(II)," *Tetrahedron* 40:457–465 (1984).

Tenette et al., "Force field development and conformational search strategy in the simulation of biomolecular recognition processes," *Biochemical Society Transactions* 24:268–274 (1996).

Tor and Dervan, "Site–Specific Enzymatic Incorporation of an Unnatural Base, $N^6$–(6–Aminohexyl)isoguanosine, into RNA," *J. Am. Chem. Soc.* 115:4461–4467 (1993).

Trauger et al., "Recognition of DNA by designed ligands at subnanomolar concentrations," *Nature* 382:559–561 (1996).

Turner et al., "The mutagenic propeties of DNA minor–groove binding ligands," *Mutation Research* 355:141–169 (1996).

Uchida et al., "High resolution footprinting of EcoRI and distamycin with Rh(phi)$_2$(bpy)$^{3+}$, a new photofootprinting reagent," *Nucleic Acids Research* 17:10259–10279 (1989).

Uggerud, "An Investigation of the Acidic Properties of the Methyl Cation and its possible role as a Hydrogen Bond Donor," *J. Am. Chem. Soc.* 116:6873–7988 (1994).

Van Dyke and Dervan, "Chromoycin, Mithramycin, and Olivomycin Binding Sites on Heterogeneous Deoxyribonucleic Acid. Footprinting with (Methidiumpropyl–EDTA) iron (II)," *Biochemistry* 22:2373–2377 (1983).

Van Dyke and Dervan, "Echinomycin Binding Sites on DNA," *Science* 225:1122–1127 (1984).

Van Dyke and Dervan, "Footprinting with MPE•Fe(II). Complementary–strand Analyses of Distamycin– and Actinomycin–binding Sites on Heterogenous DNA," pp. 347–353.

Van Dyke and Dervan, "Methidiumpropyl–EDTA•FE(II) and DNase I footprinting report different small molecule binding site sizes on DNA," *Nucleic Acids Research* 11:5555–5567 (1983).

Van Dyke et al., "Map of distamycin, netropsin, and actinomycin binding sites on heterogeneous DNA: DNA cleavage–inhibition patterns with methidiumpropyl–EDTA•FE(II)," *Proc. Natl. Acad. Sci. USA* 79:5470–5474 (1982).

Vigneswaran et al., "Influence of GC and AT Specific DNA Minor Groove Binding Drugs on Intermolecular Triplex Formation in the Human c–Ki–ras Promoter," *Biochemistry* 35:1106–1114 (1996).

Wade and Dervan, "Alteration of the Sequence Specificity of Distamycin on DNA by Replacement of an N–Methylpyrrolecarboxamide with Pyridine–2–carboxamide," *J. Am. Chem. Soc.* 109:1574–1575 (1987).

Wade et al., "Binding Affinities of Synthetic Peptides, Pyridine–2–carboxamidonetropsin and 1–Methylimidazole–2–carboxamidonetropsin, That Form 2:1 Complexes in the Minor Groove of Double–Helical DNA," *Biochemistry* 32:11385–11389 (1993).

Wade et al., "Design of Peptides That Bind in the Minor Groove of DNA at 5'-(A,T)G(A,T)C(A,T)-3' Sequences by a Dimeric Side–by–Side Motif," *J. Am. Chem. Soc.* 114:8783–8794 (1992).

Wade et al., "Recognition of G,C Base Pairs in the Minor Groove of DNA" (Abstract).

Wade, thesis entitled Sequence specific complexation of BDNA at sites containing G, C base pairs, California Institute of Technology, Pasadena, California Submitted Feb. 2, 1989.

Wang et al., "Interactions Between a Symmetrical Minor Groove Binding Compound and DNA Oligonucleotides: $^1$H and $^{19}$F NMR Studies," *J. Biomolecular Structure & Dynamics* 7:101–117 (1989).

Wang et al., "Anti HIV–I activity of linked lexitropsins," *J. Med. Chem.* 35(15):2890–2897 (1992).

Wang et al., "Convenient synthesis of pyrroloiminoquinone and its lexitropsin–linked derivative," *Tetrahedron Lett.* 35(24):4085–4086 (1994).

Wang et al., "Design, synthesis, cytotoxic properties and preliminary DNA sequencing evaluation of CPI–N–methylpyrrole hybrids. Enhancing effect of a trans double bond linker and role of the terminal amide functionality on cytotoxic potency," *Anti–Cancer Drug Des.* 11(1):15–34 (1996).

Ward et al., "Determination of Netropsin–DNA Binding Constants from Footprinting DATA," *Biochemistry* 27:1198–1205 (1988).

Ward et al., "Quantitative Footprinting Analysis of the Netropsin–DNA Interaction," *J. Biomolecular Structure & Dynamics* 4(5):685–695 (1987).

Wemmer et al., Abstracts of the American Chemical Society 208 Part 2:9 (1994).

Wiederholt et al., "DNA–Tethered Hoechst Groove–Binding Agents: Duplex Stabilization and Fluorescence Characteristics," *J. Amer. Chem. Soc.* 118:7055–7062 (1996).

Wilkins, "Selective binding of actinomycin D and distamycin A to DNA," *Nucleic Acids Research* 10:7273–7282 (1982).

Williamson et al., "Phase–Sensitive Heteronuclear Multiple– Bond Correlation in the Presence of Modes Homonuclear Coupling. Application to Distamycin A," *Journal of Magnetic Resonance* 82:605–612 (1989).

Wong and Bateman, "TBP–DNA interactions in the minor groove discriminate between A:T and T:A base pairs," *Nucleic Acids Research* 22:1890–51896 (1994).

Woynarowski et al., "DNA Minor–Groove Binding Agents Interefere with Topoisomerase II–Mediated Effects of VM–26 and m–AMSA," *Proceedings of AACR* 29:274 at abstract No. 1089 (1988).

Xie et al., "Synthesis and DNA cleaving properties of hybrid molecules containing propargylic sulfones and minor groove binding lexitropsins," *Bioorg. Med. Chem. Lett.* 3(8):1565–1570 (1993).

Yamamoto et al., "Synthesis and DNA Binding Properties of Amide Bond–Modified Analogues Related to Distamycin," *Tetrahedron Letters* 37:7801–7804 (1996).

Yang et al., "Studies on Cooperative Binding of an Extended Distamycin A Analogue in the Minor Groove of DNA by NMR Spectroscopy," *Biochemical and Biophysical Research Communications,* 222:764–769 (1996).

Youngquist and Dervan, "Sequence–specific recognition of B–DNA by oligo(N–methylpyrrolecarboxamide)s," *Proc. Natl. Acad. Sci. USA* 82:2565–2569 (1985).

Youngquist and Dervan, "Sequence–specific recognition of B–DNA by Bis(EDTA–distamycin)fumaramide," *J. Am. Chem. Soc.* 107:5528–5529 (1985).

Zakrzewska and Pullman, "Theoretical Study of the Sequence Selectivity of Isolexins, Isohelical DNA Groove Binding Ligands. Proposal for the GC Minor Groove Specific Compounds," *Journal of Biomolecular Structure & Development* 5(5):1043–1058 (1988).

Zakrzewska et al., "Drug Recognition of DNA. Proposal for GC Minor Groove Specific Ligands: Vinylexins," *Journal of Biomolecular Structure & Development* 6(2):331–334 (1988).

Zasedatelev et al., "Mono–, di– and trimeric binding of a bis–netropsin to DNA," *FEBS Letters* 375:304–306 (1995).

Zimmer and Wahnet, "Nonintercalating DNA–Binding Ligands: Specificity of the Interaction and Their Use as Tools in Biophysical, Biochemical and Biological Investigations of the Genetic Material," *Prog. Biophys. molec. Biol.* 47:31–112 (1986).

Zimmer et al., "Binding of Analogues of the Antibiotics Distamycin A and Netropsin to Native DNA," *Eur. J. Biochem.* 26:81–89 (1972).

Zimmer et al., "Chain Length–Dependent Association of Distamycin–Type Oligopeptides with A•T and G•C Pairs in Polydeoxynucleotide Duplexes," *Biochimica et Biophysica Acta* 741:15–22 (1983).

Zimmer et al., "Differential stabilization by netropsin of inducible B–like conformations in deoxyribo–, ribo– and 2'–deoxy–2'fluororibo–adenosine containing duplexes of $(dA)_n•(dT)_n$ and $(dA)_n•(dU)_n{}^a$," *Nucleic Acids Research* 10:1721–1732 (1982).

Zimmer et al., "Effects of the Antibiotics Netropsin and Distamycin A on the Structure and Function of Nucleic Acids," pp. 285–318.

Zimmer et al., "Z–DNA and other non–B–DNA structures are reversed to B–DNA by interaction with netropsin," *FEBS Letters* 154:156–160 (1983).

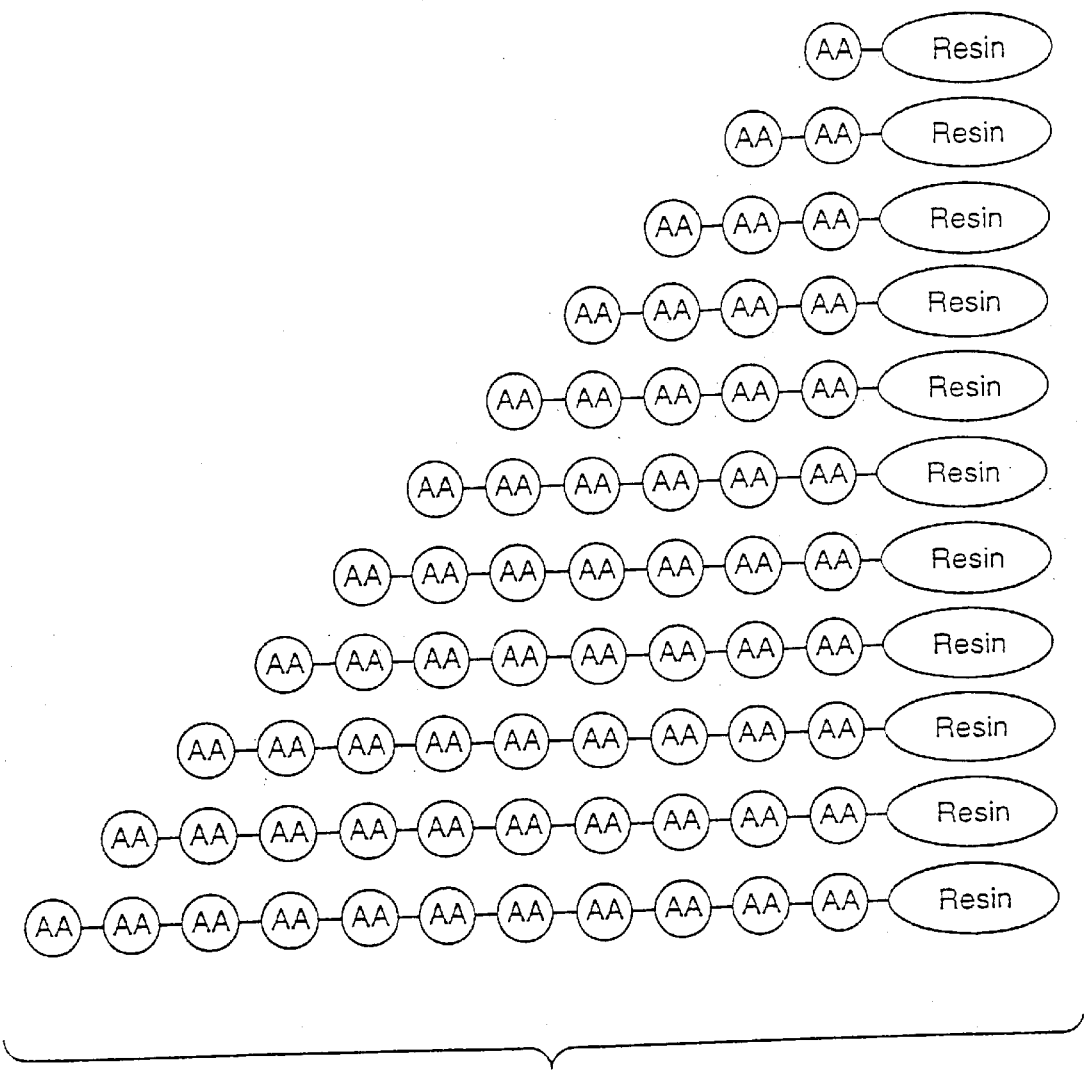
FIG._1

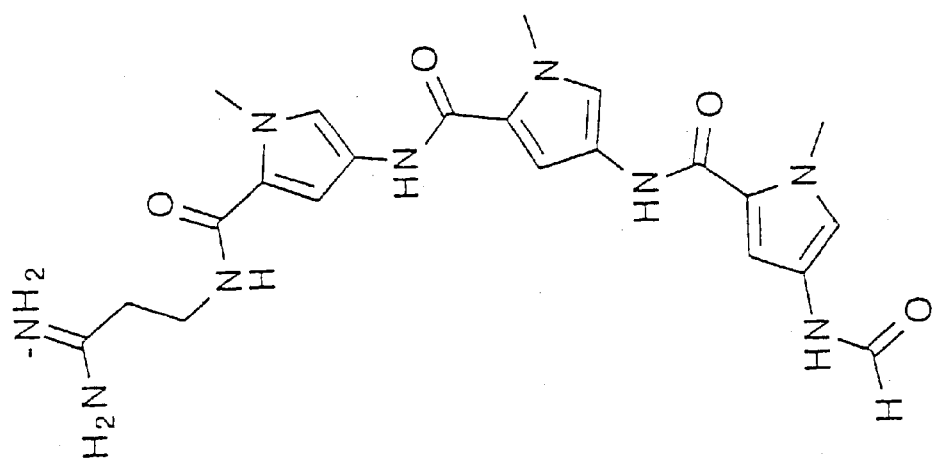
FIG._2B
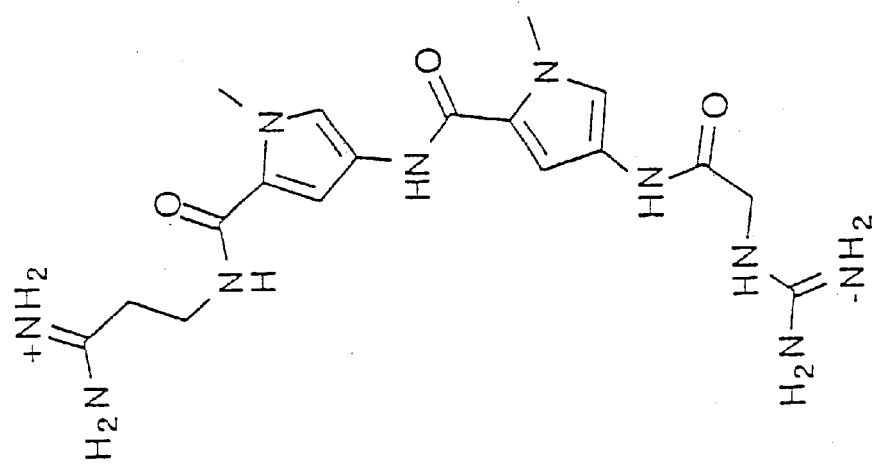
FIG._2A

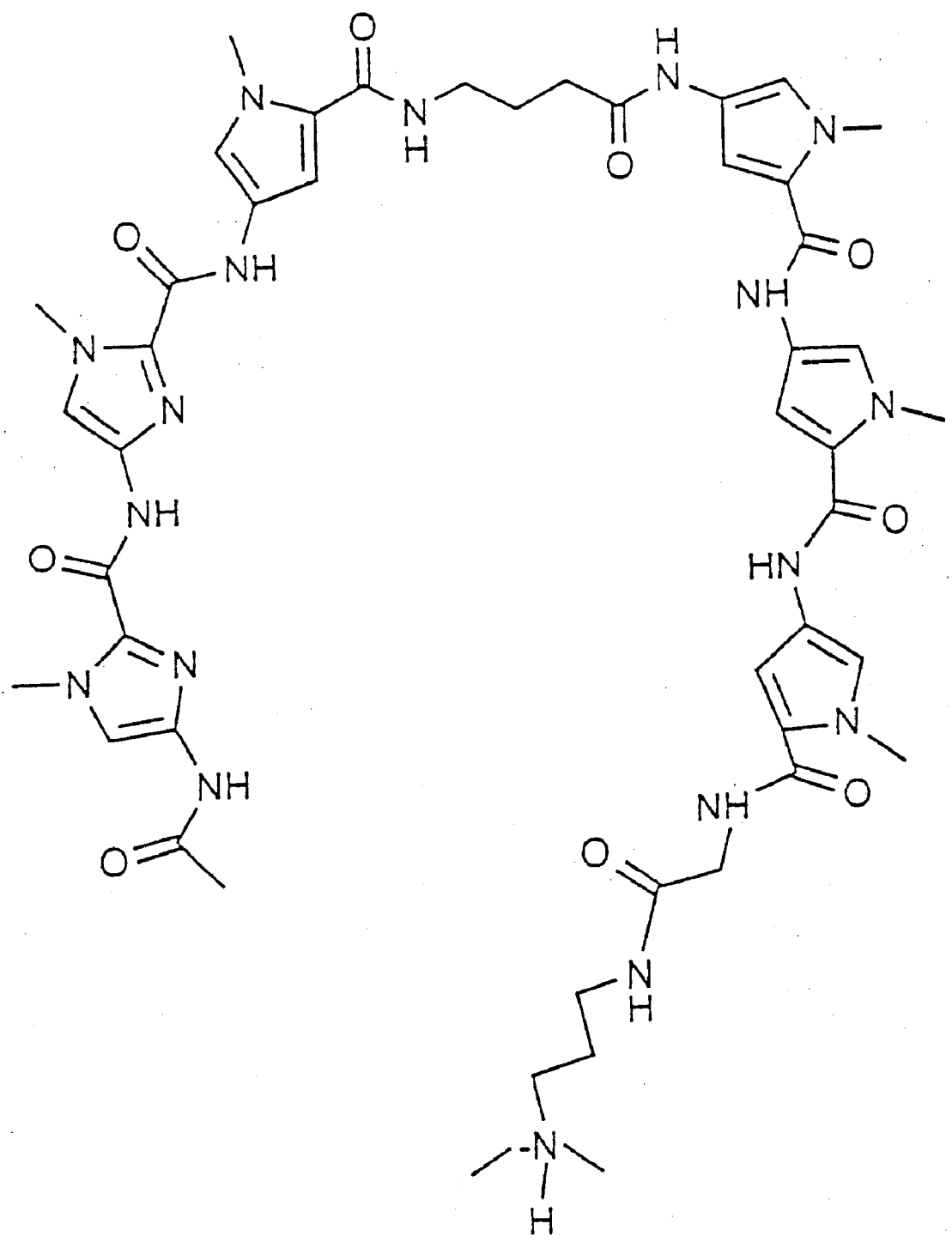
FIG._3A

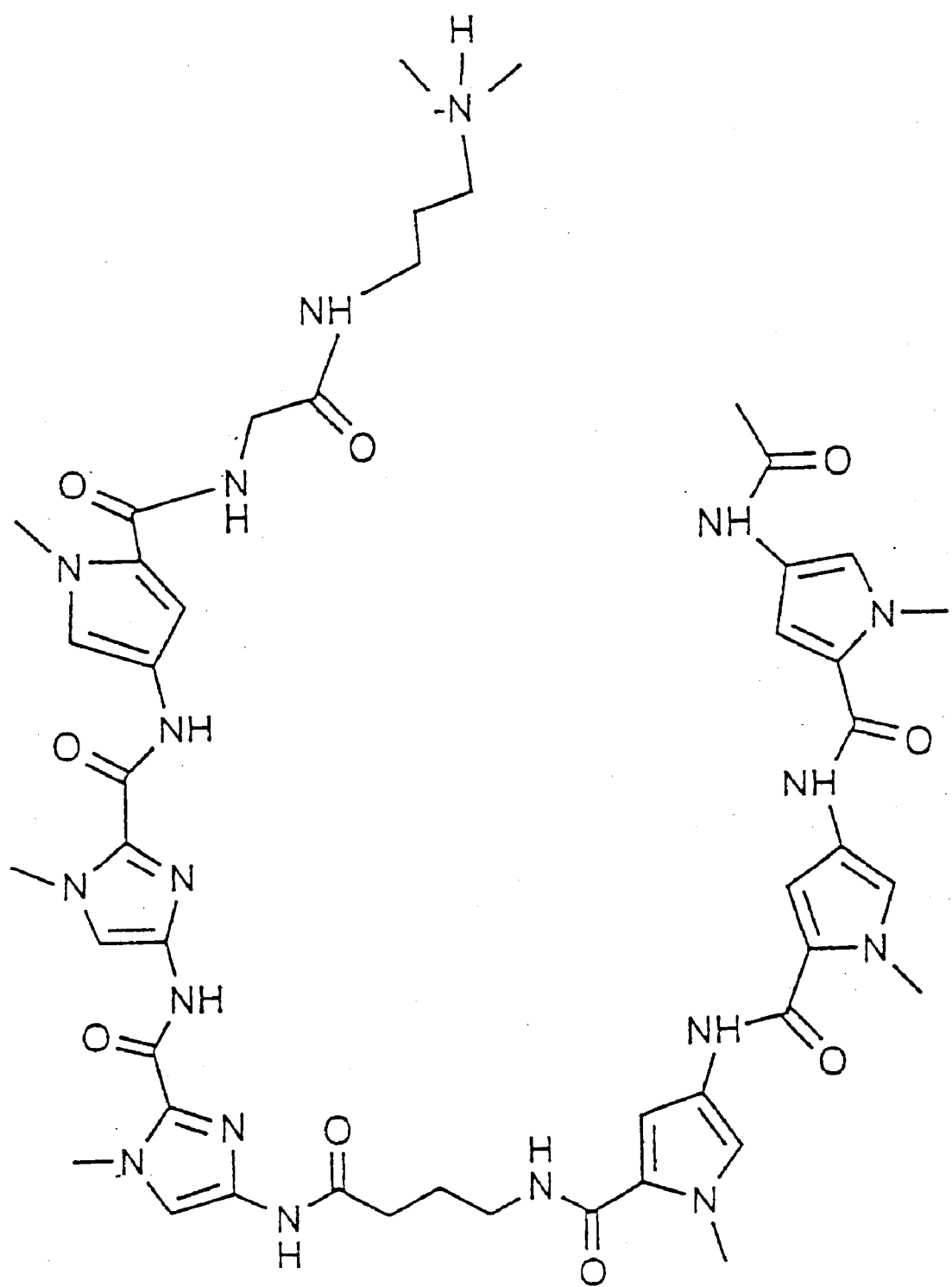
FIG._3B

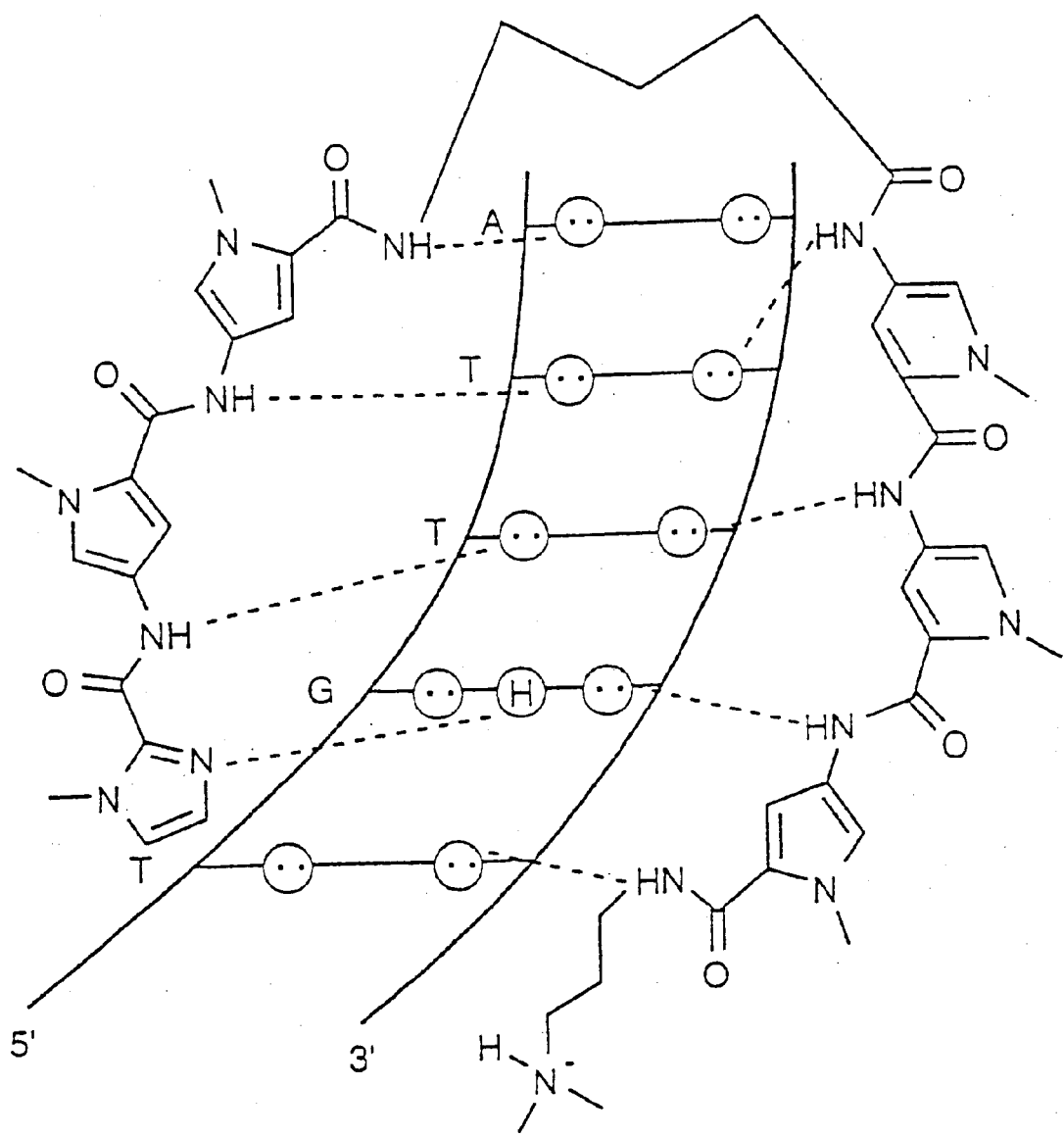
FIG._4A

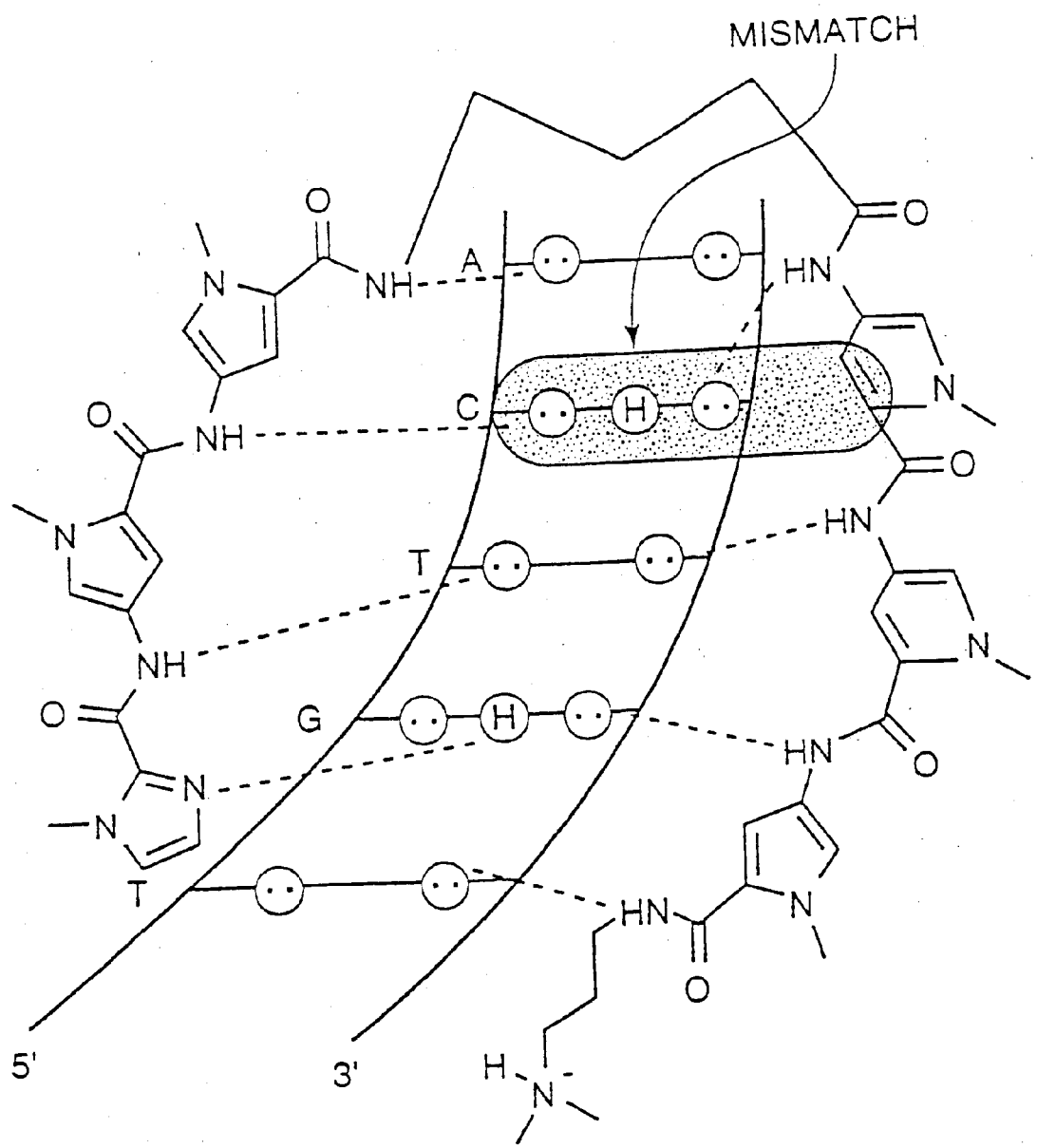
FIG._4B

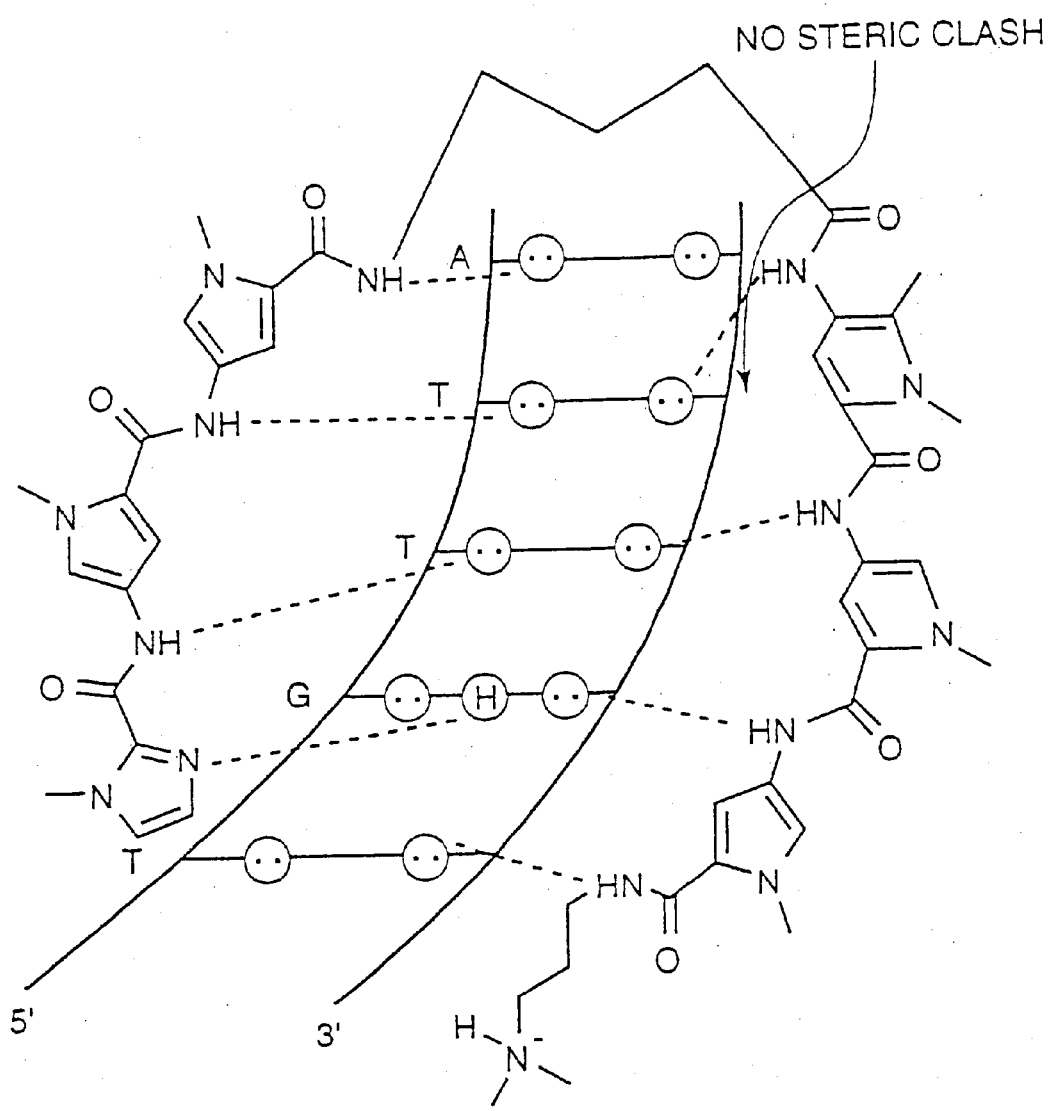
FIG._4C

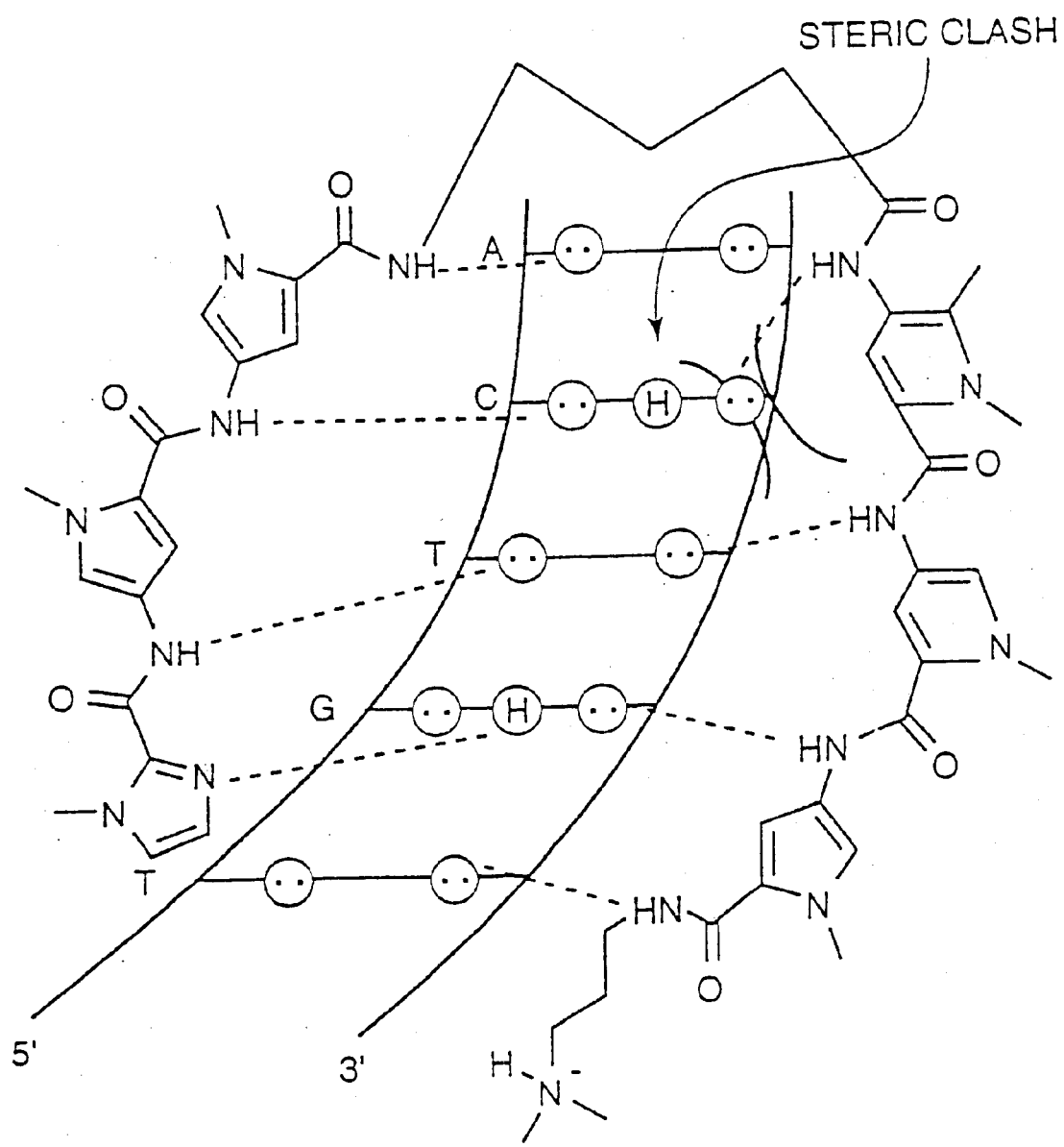
FIG._4D

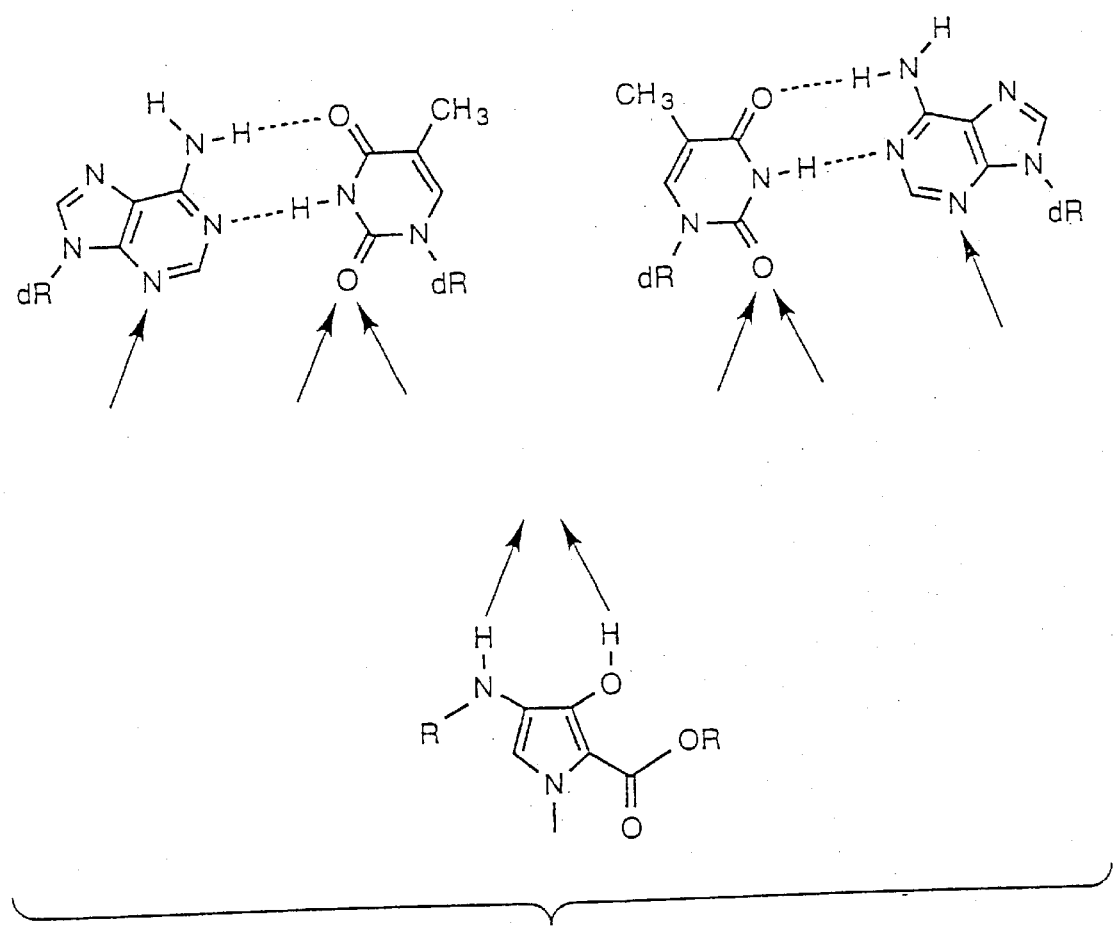
FIG._5

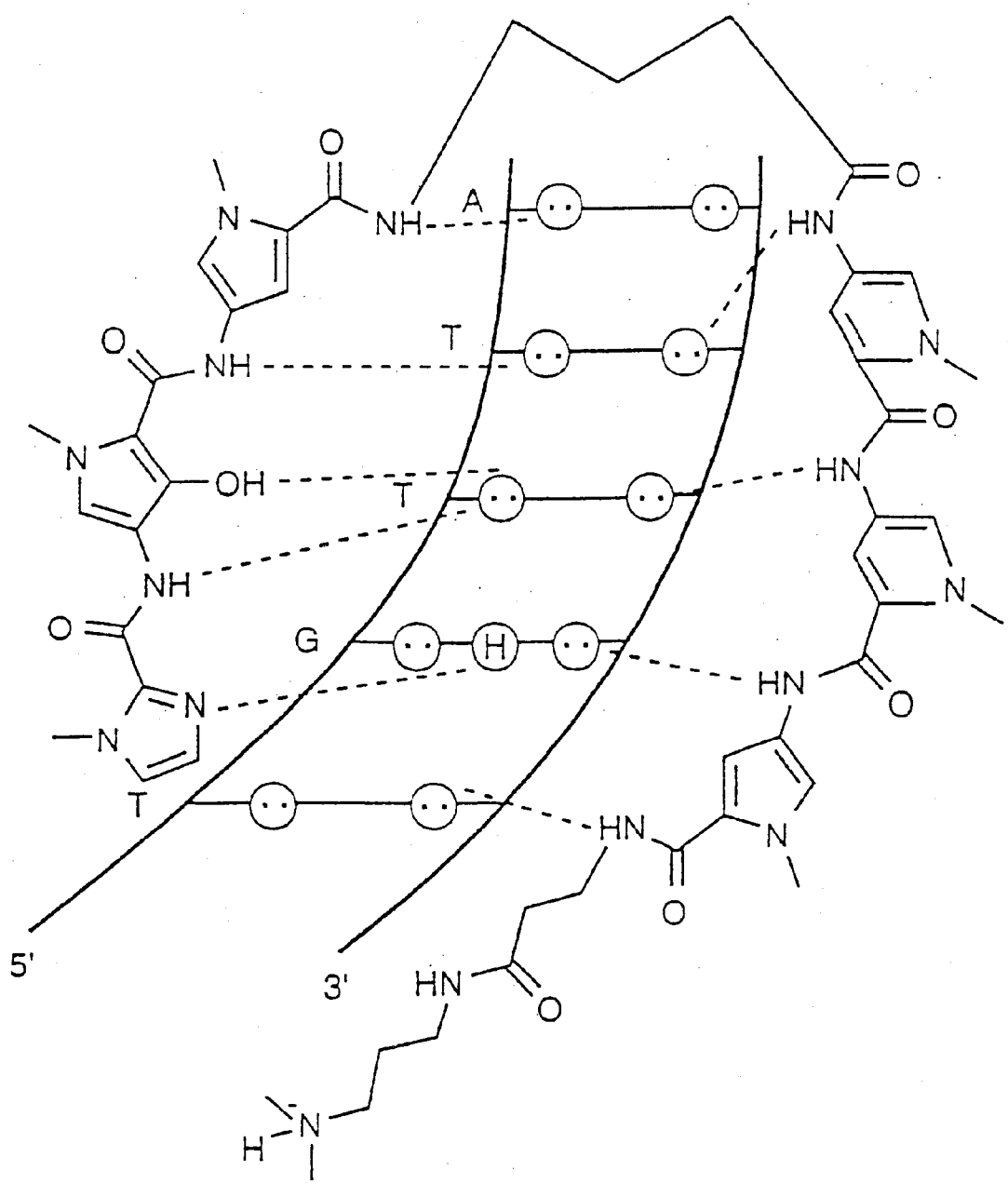
FIG._6A

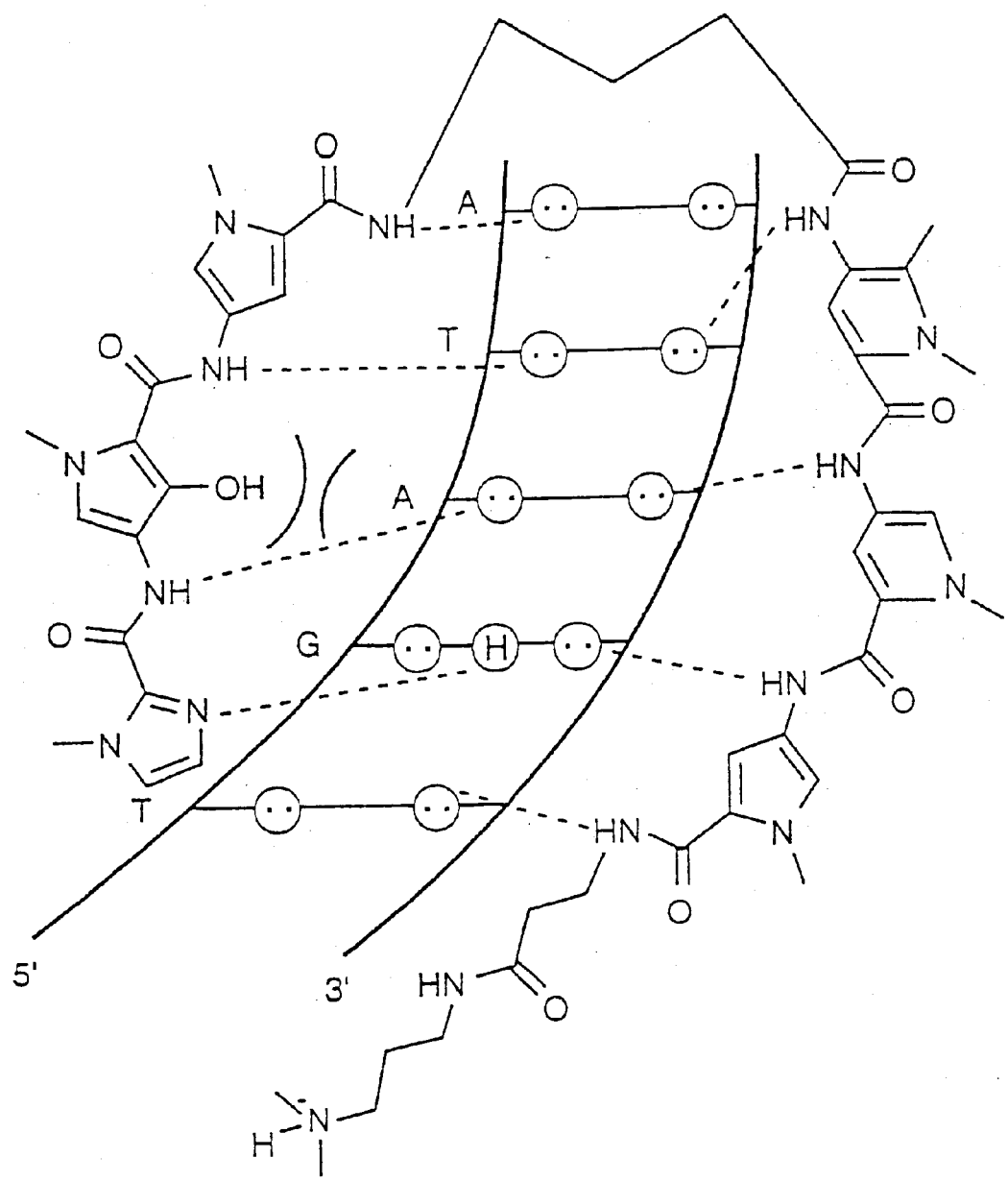
FIG._6B

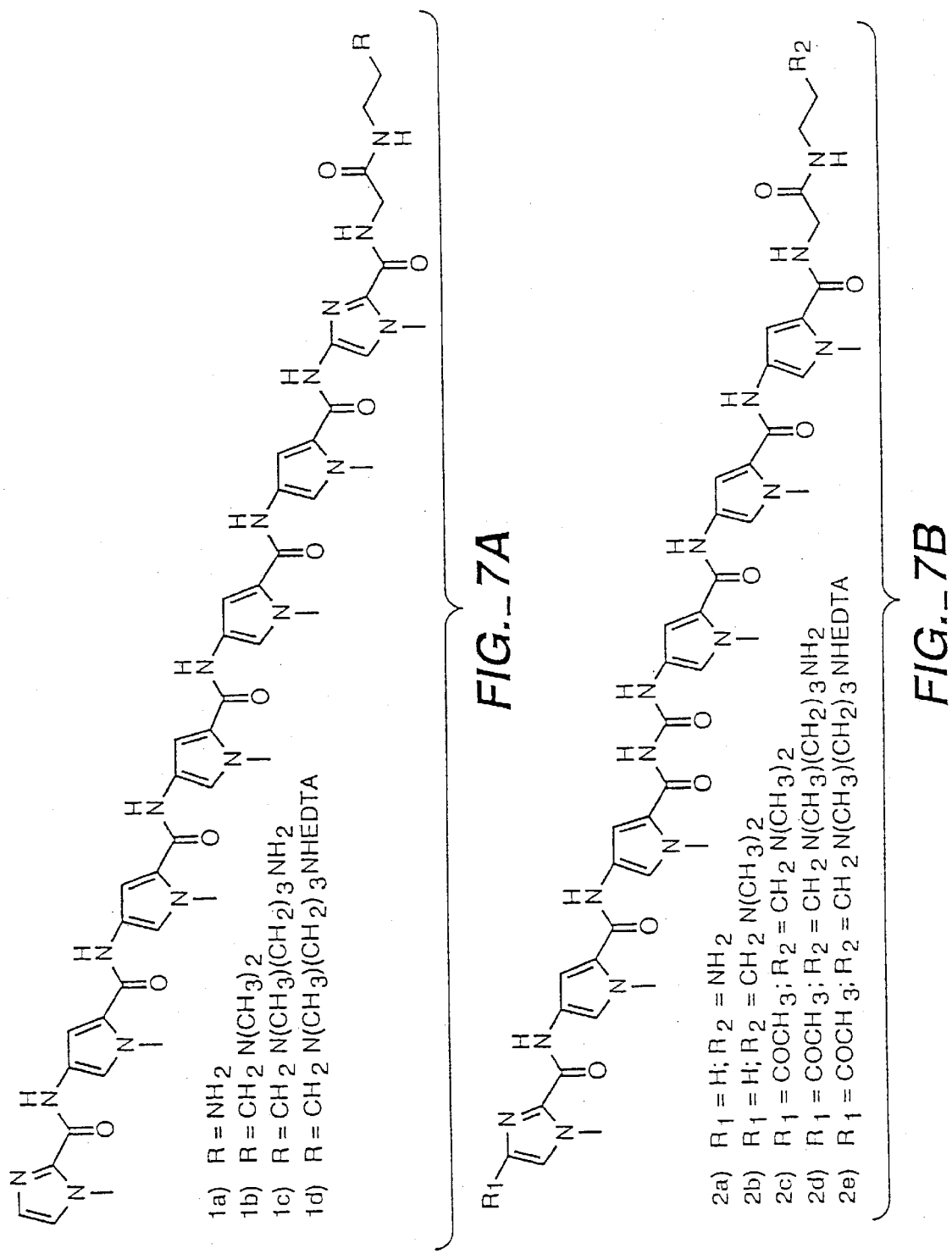
FIG._7A
FIG._7B

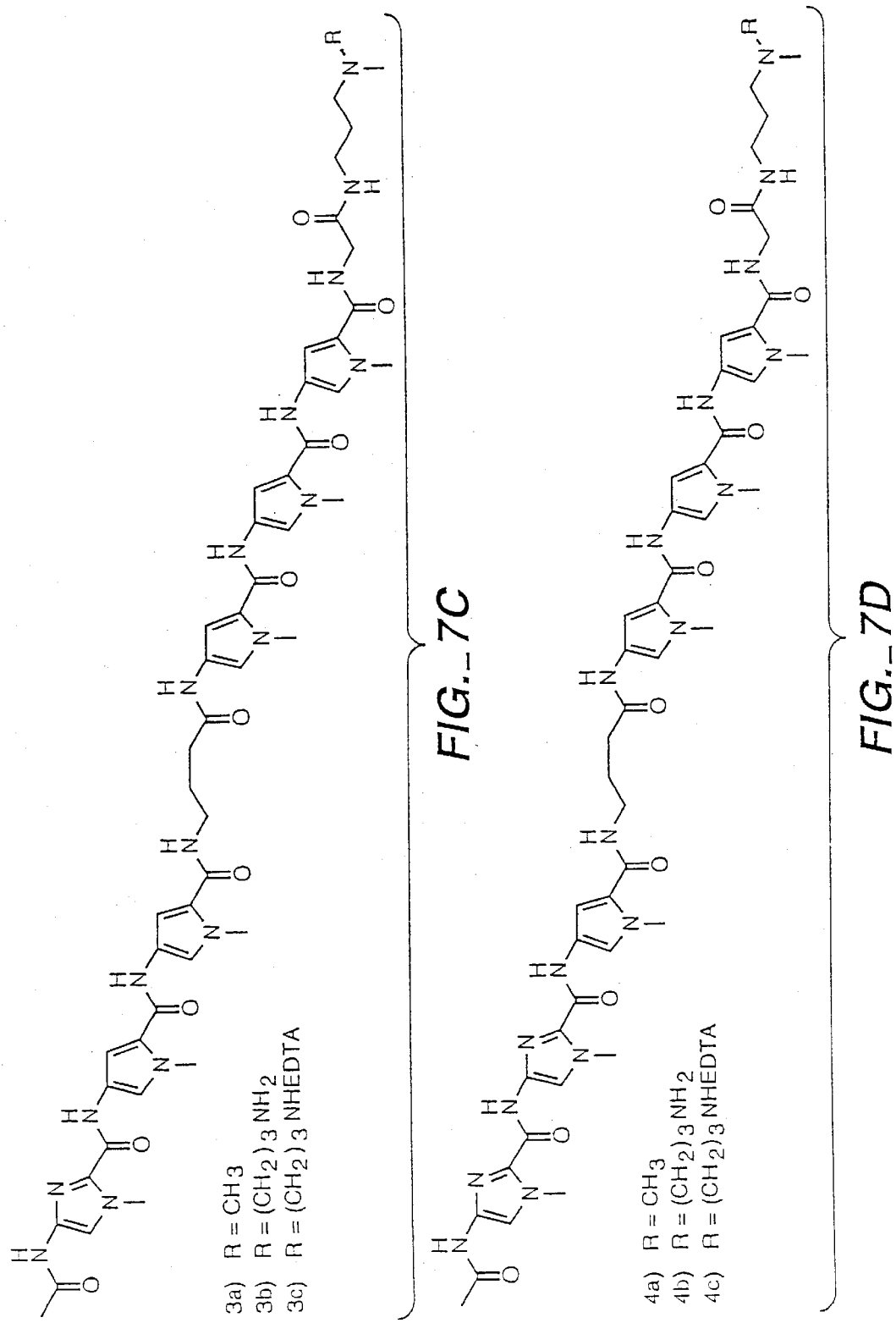
FIG._7C
FIG._7D

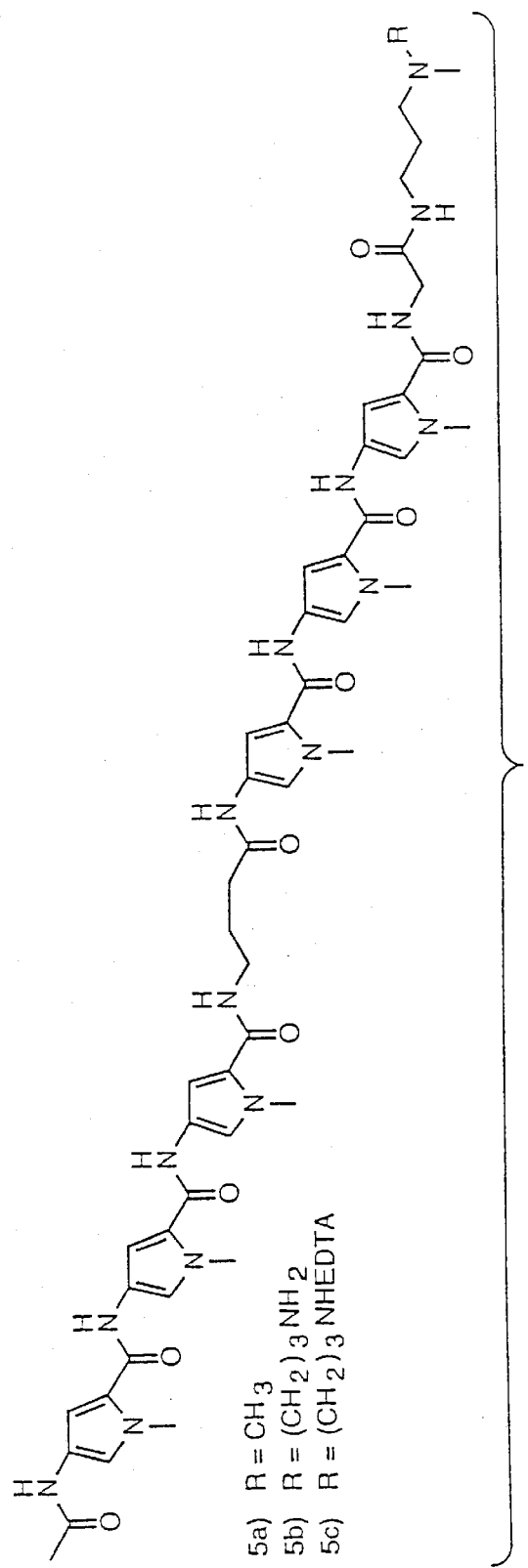
5a) R = CH$_3$
5b) R = (CH$_2$)$_3$NH$_2$
5c) R = (CH$_2$)$_3$NHEDTA
FIG._7E
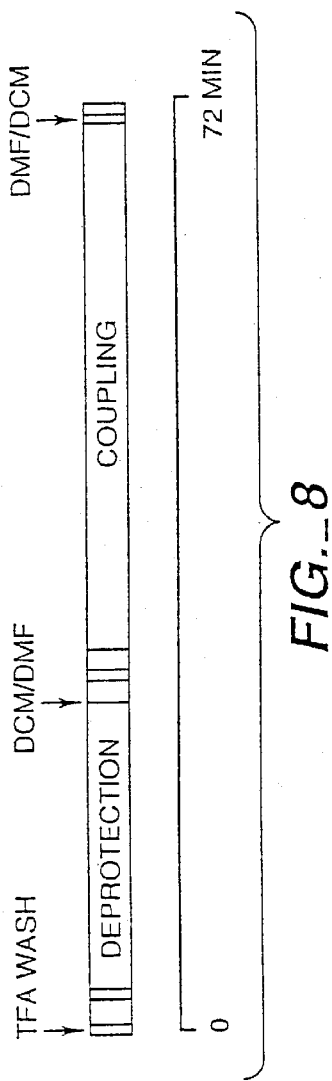
FIG._8

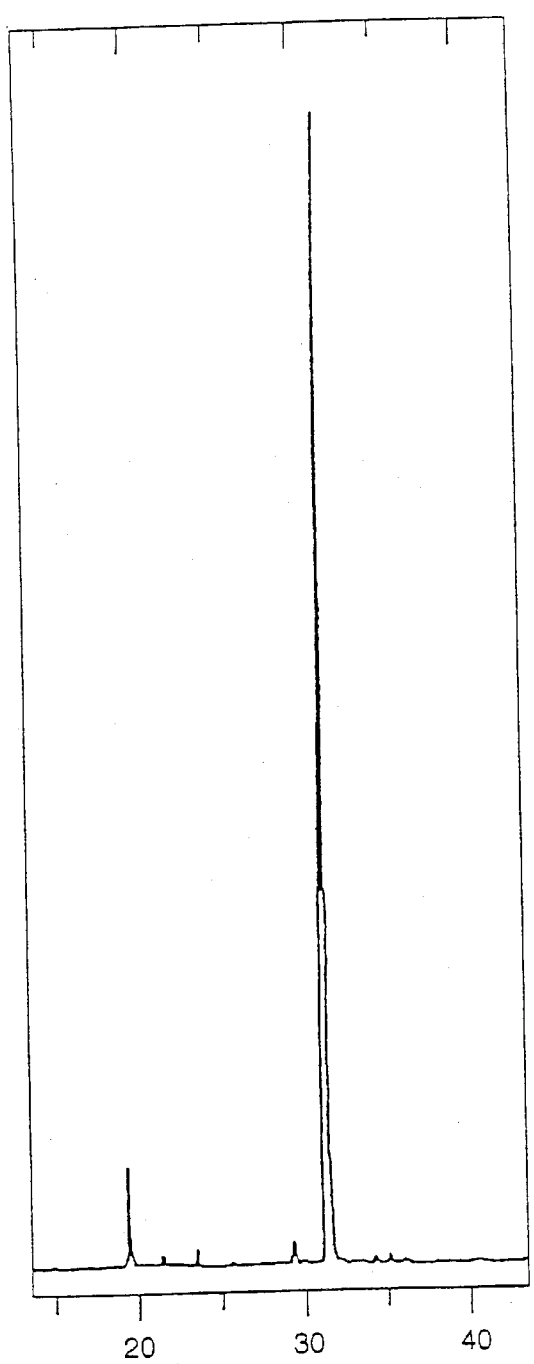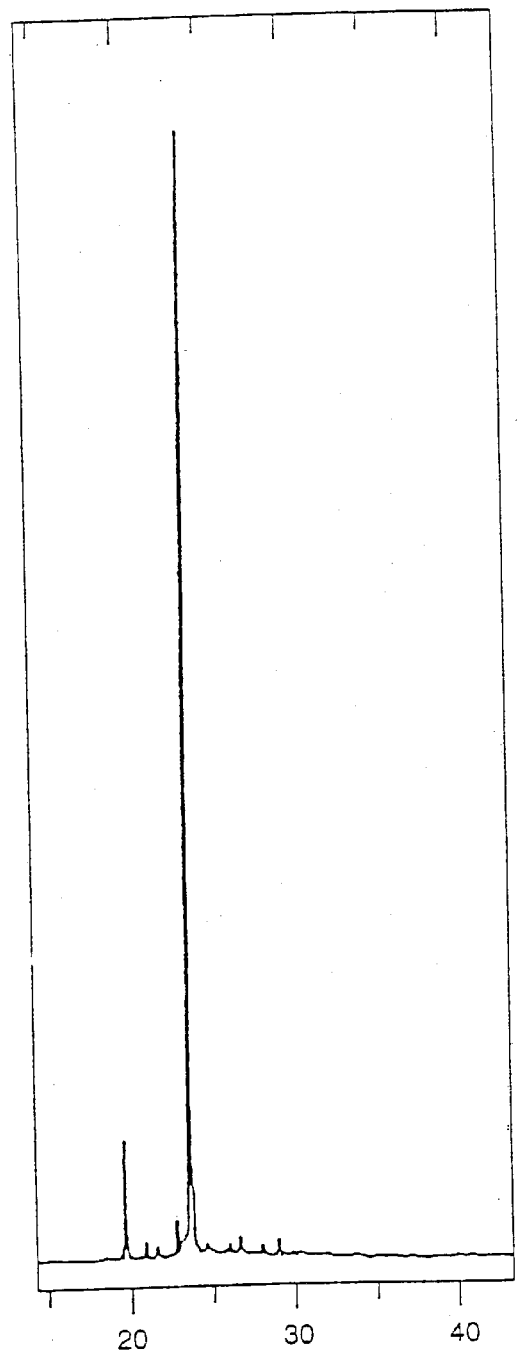
FIG._9A          FIG._9B

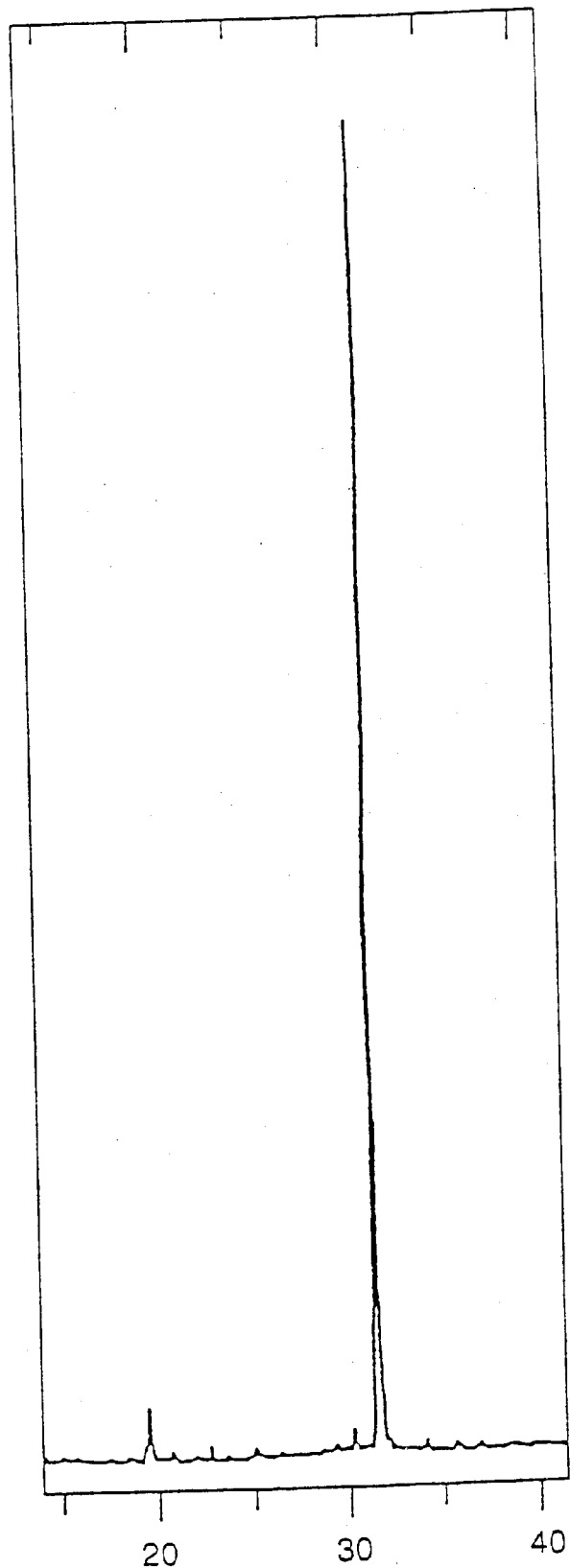
FIG._9C

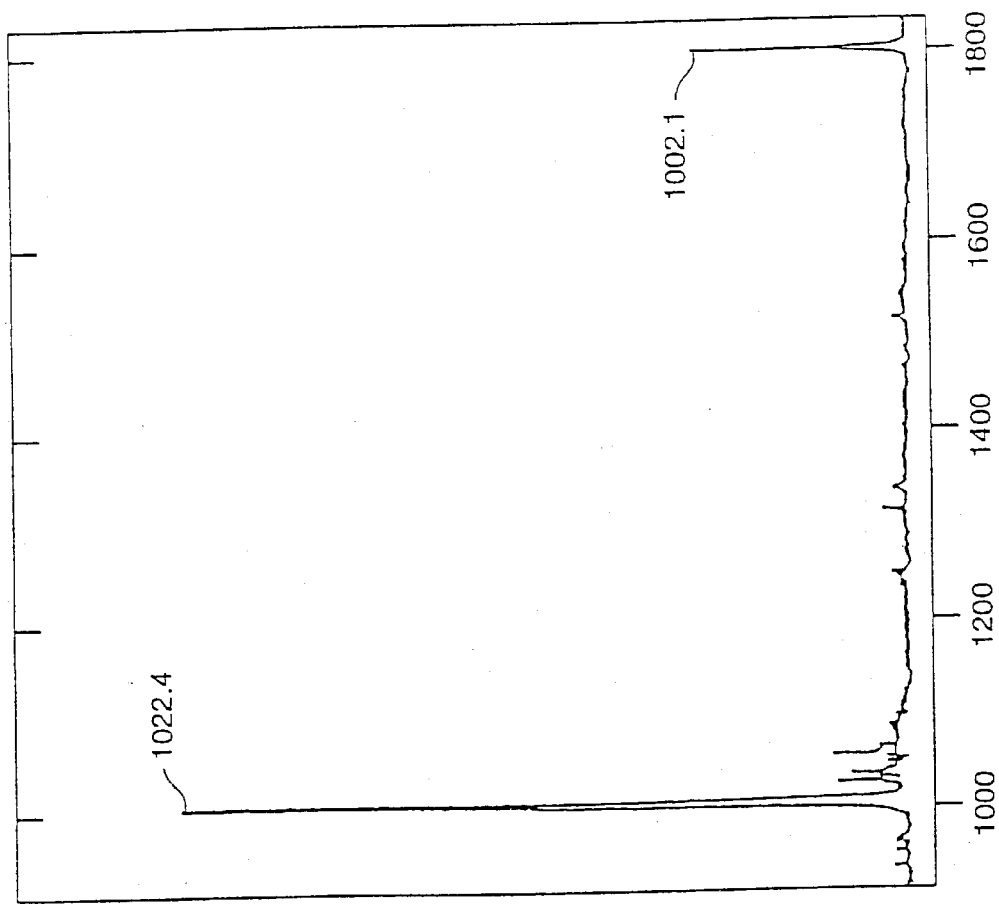
FIG._10B
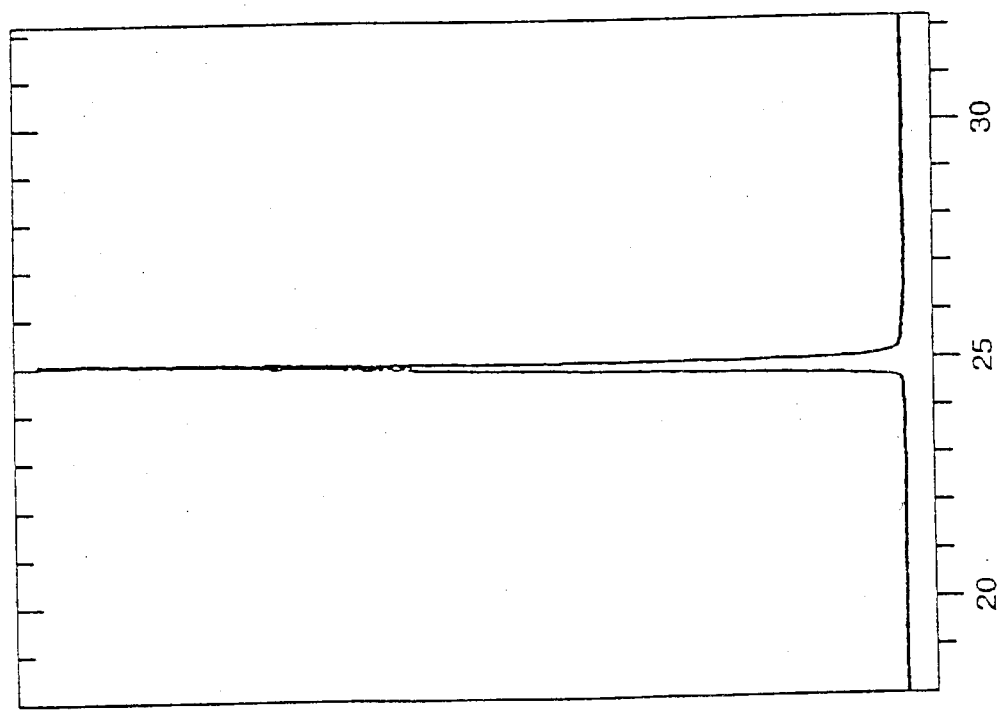
FIG._10A

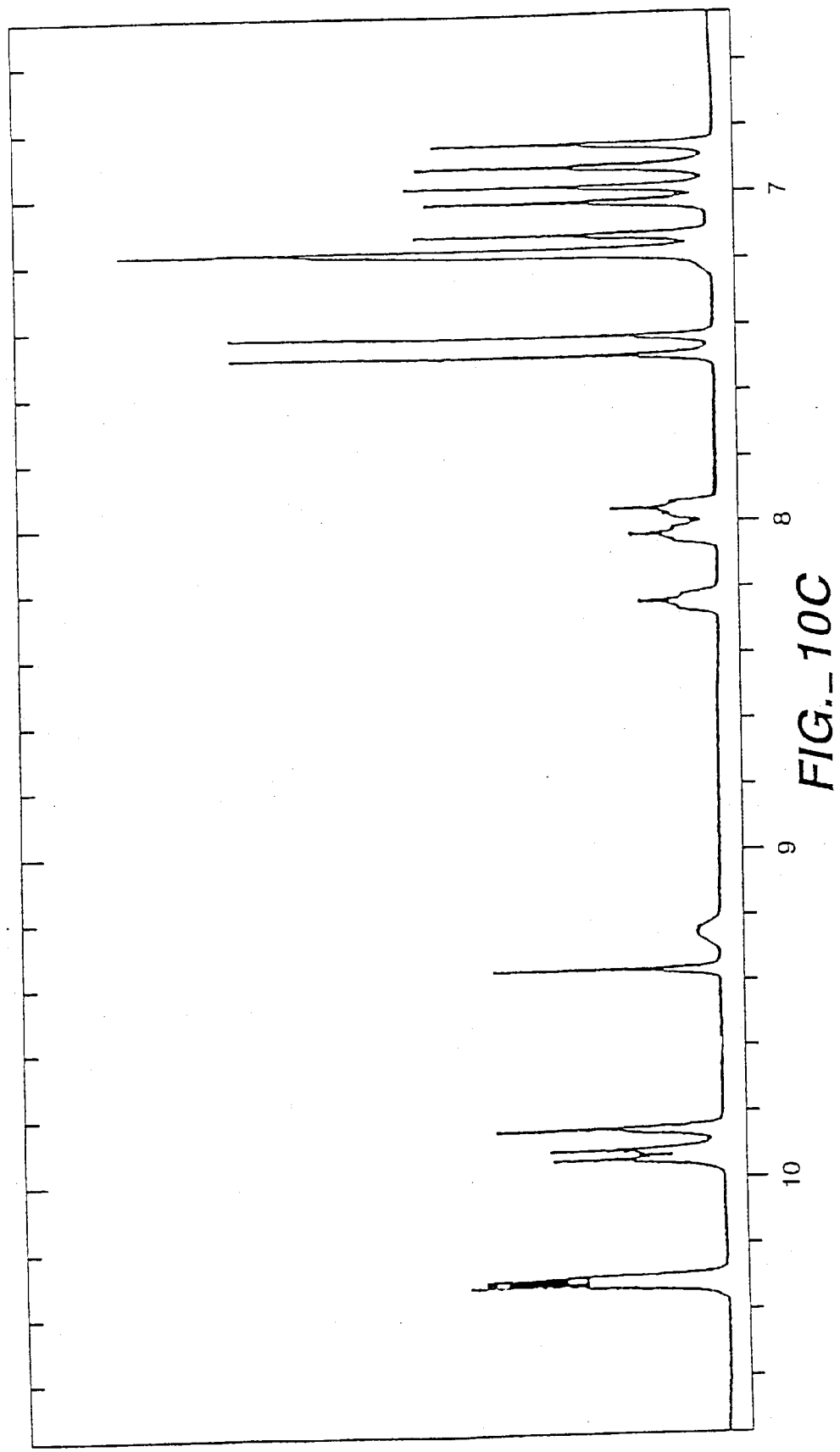
FIG._10C

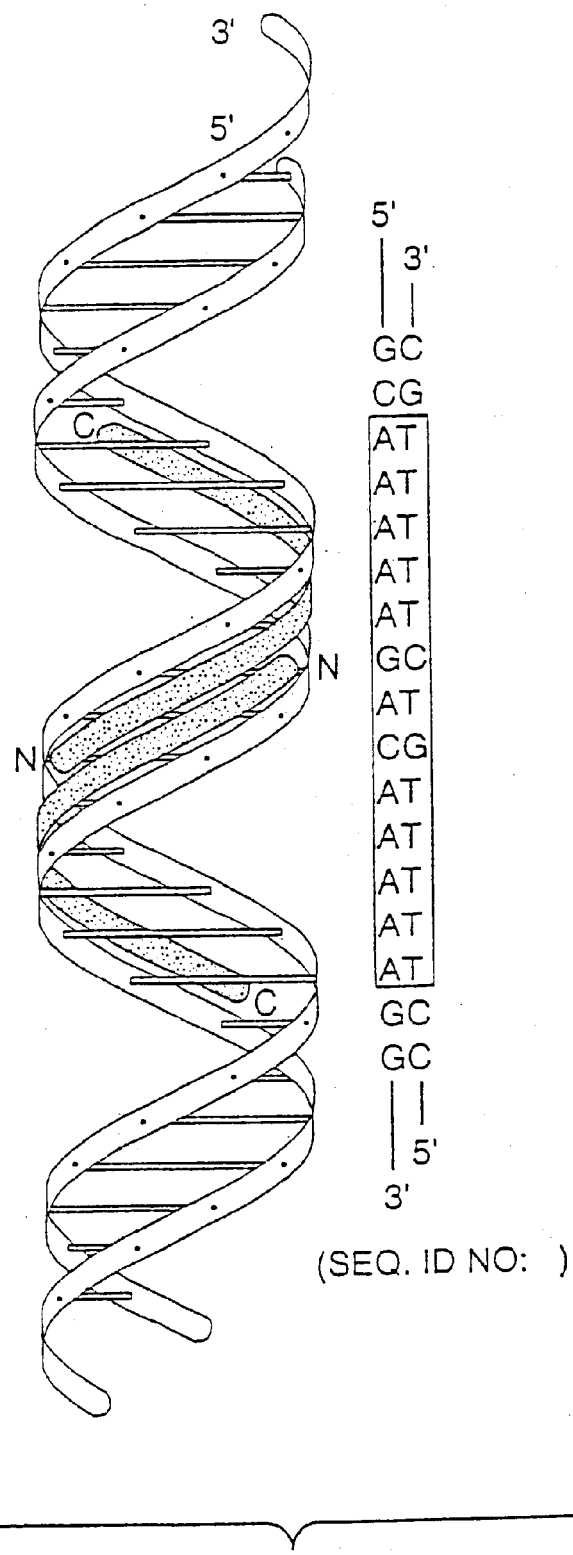
(SEQ. ID NO: )
FIG._11A

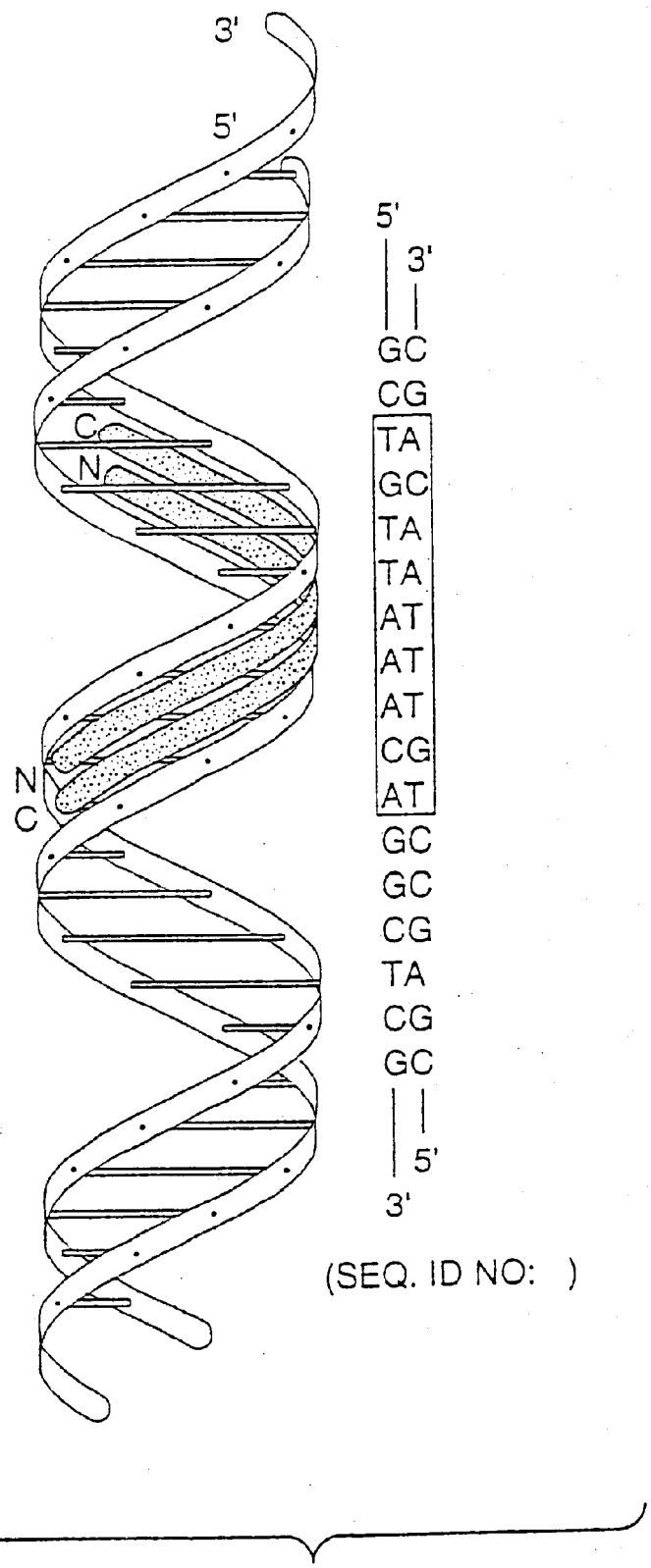
FIG._11B

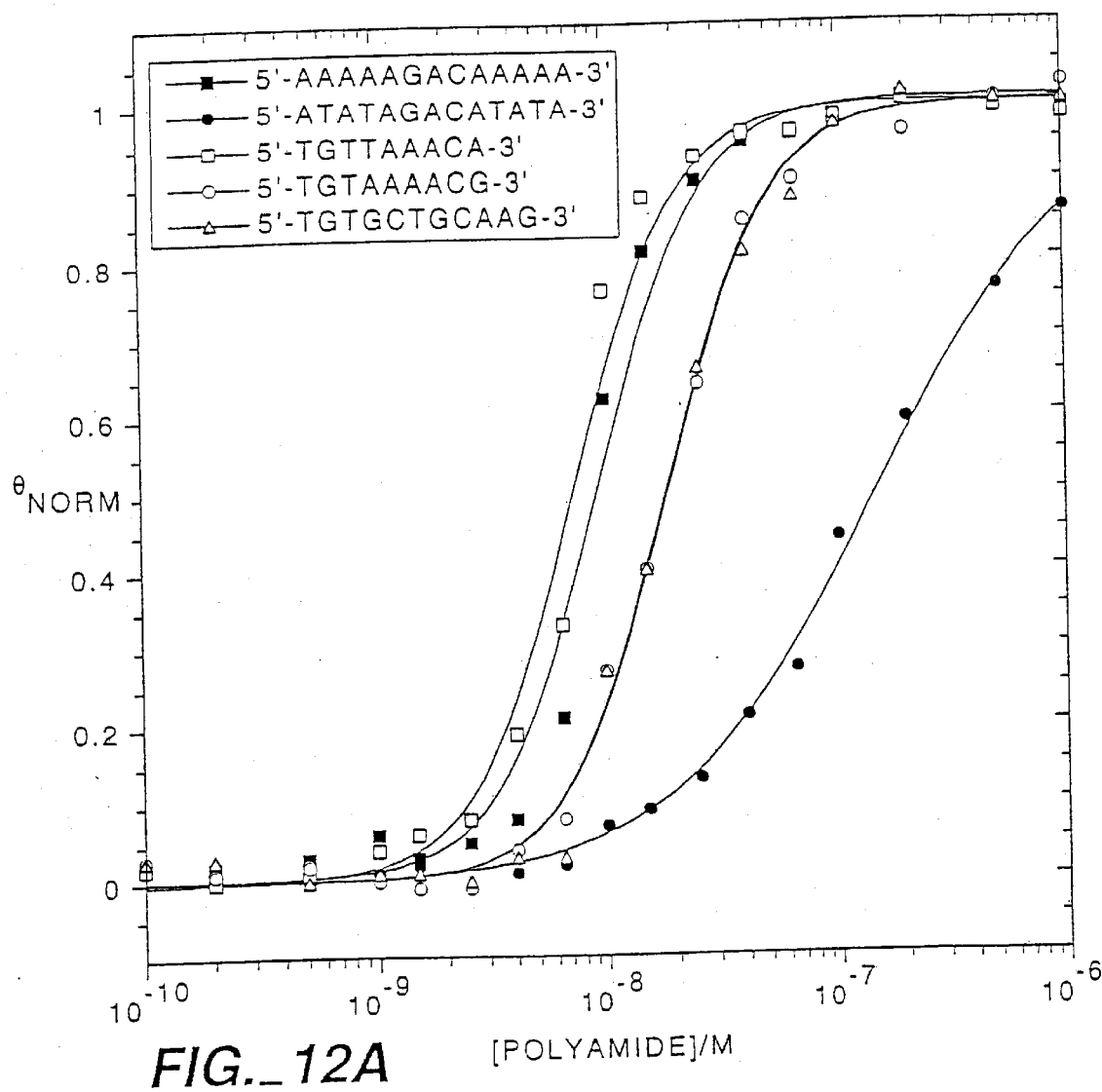
FIG._12A

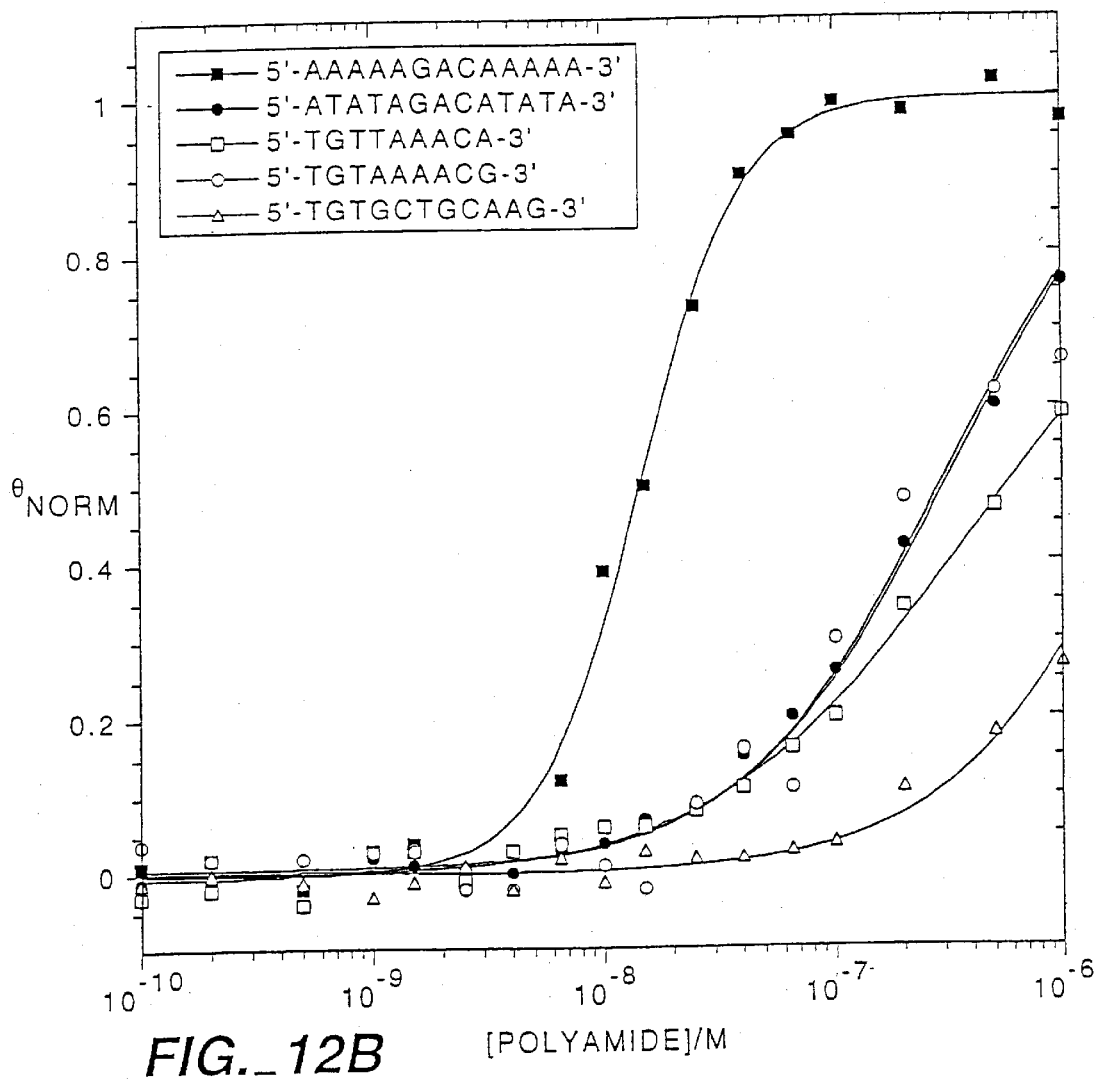
FIG._12B

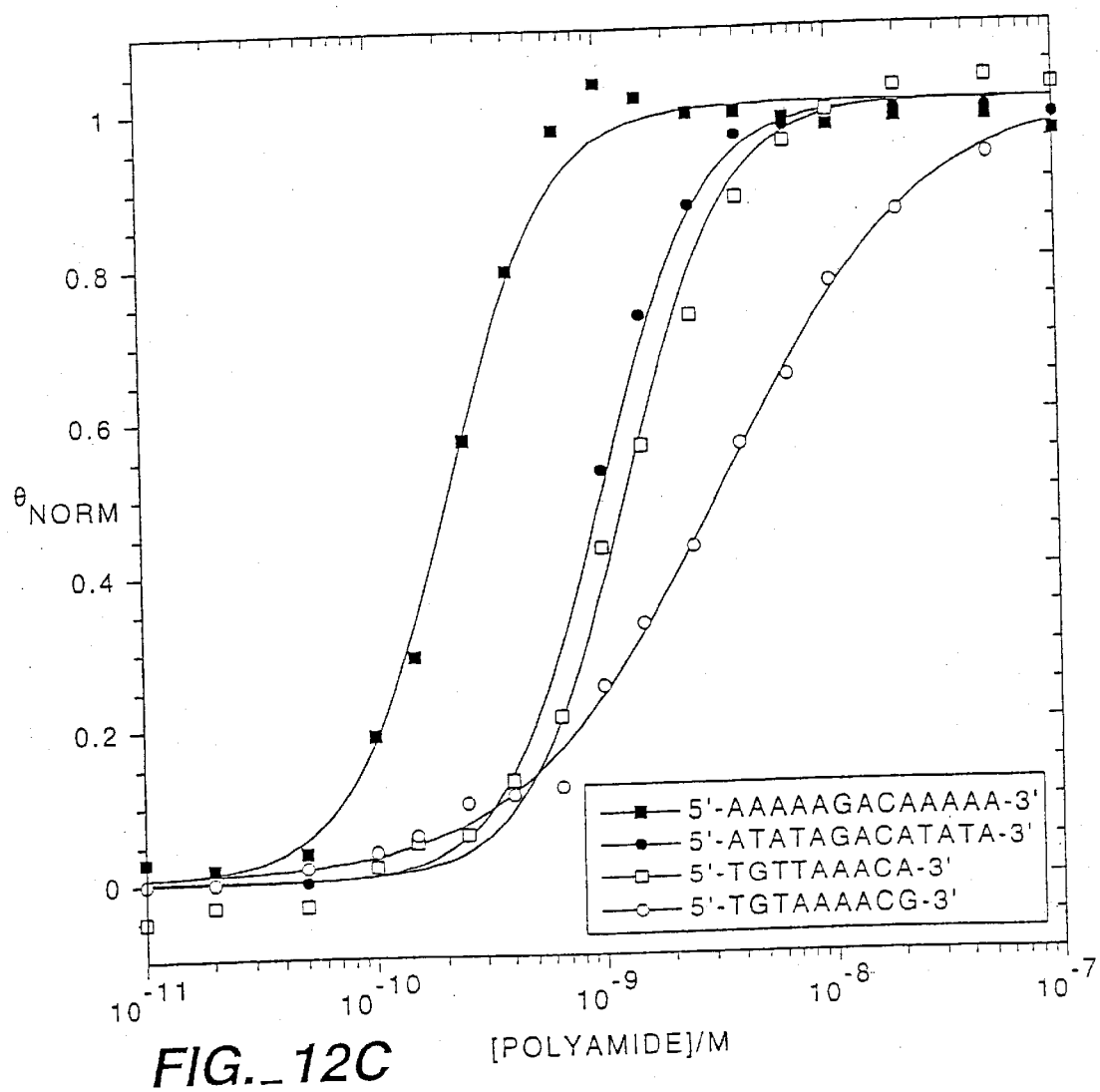
FIG._12C

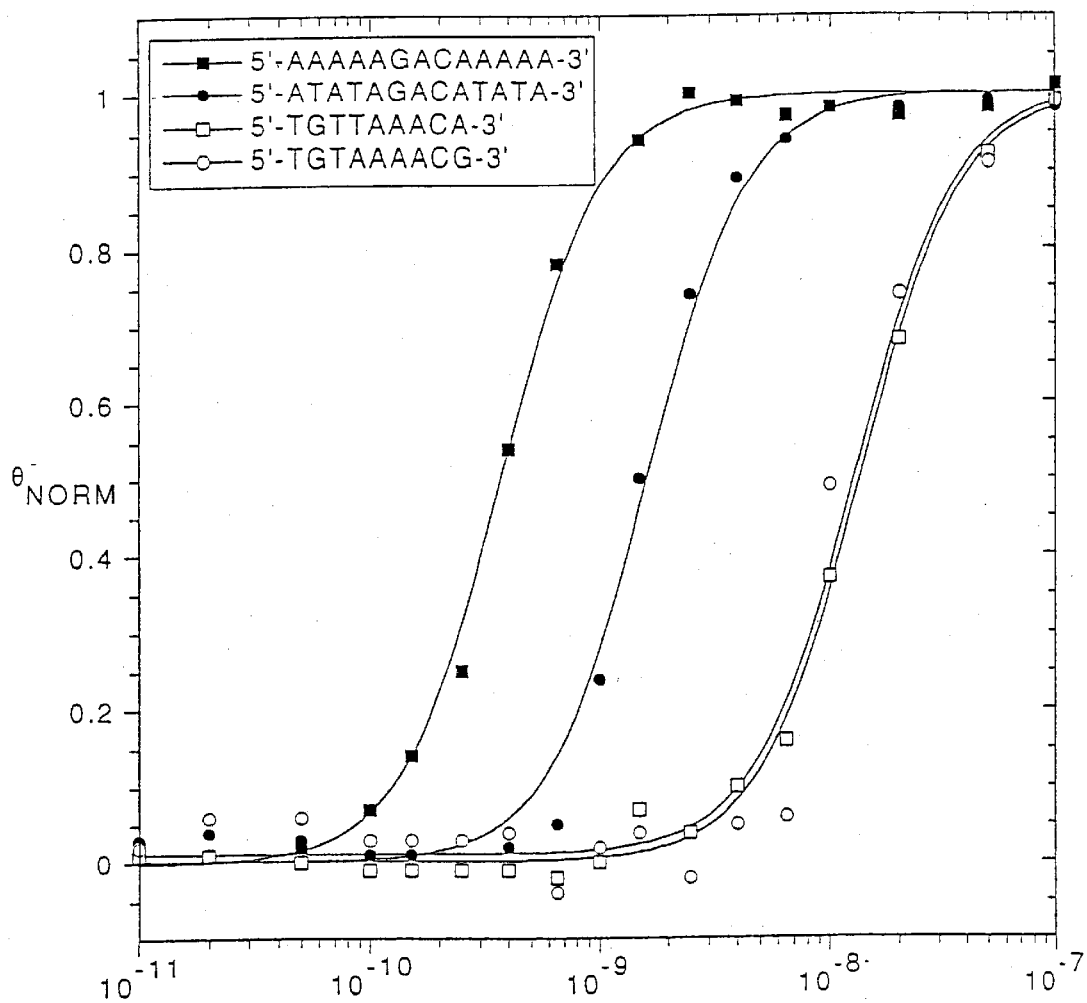
FIG._12D

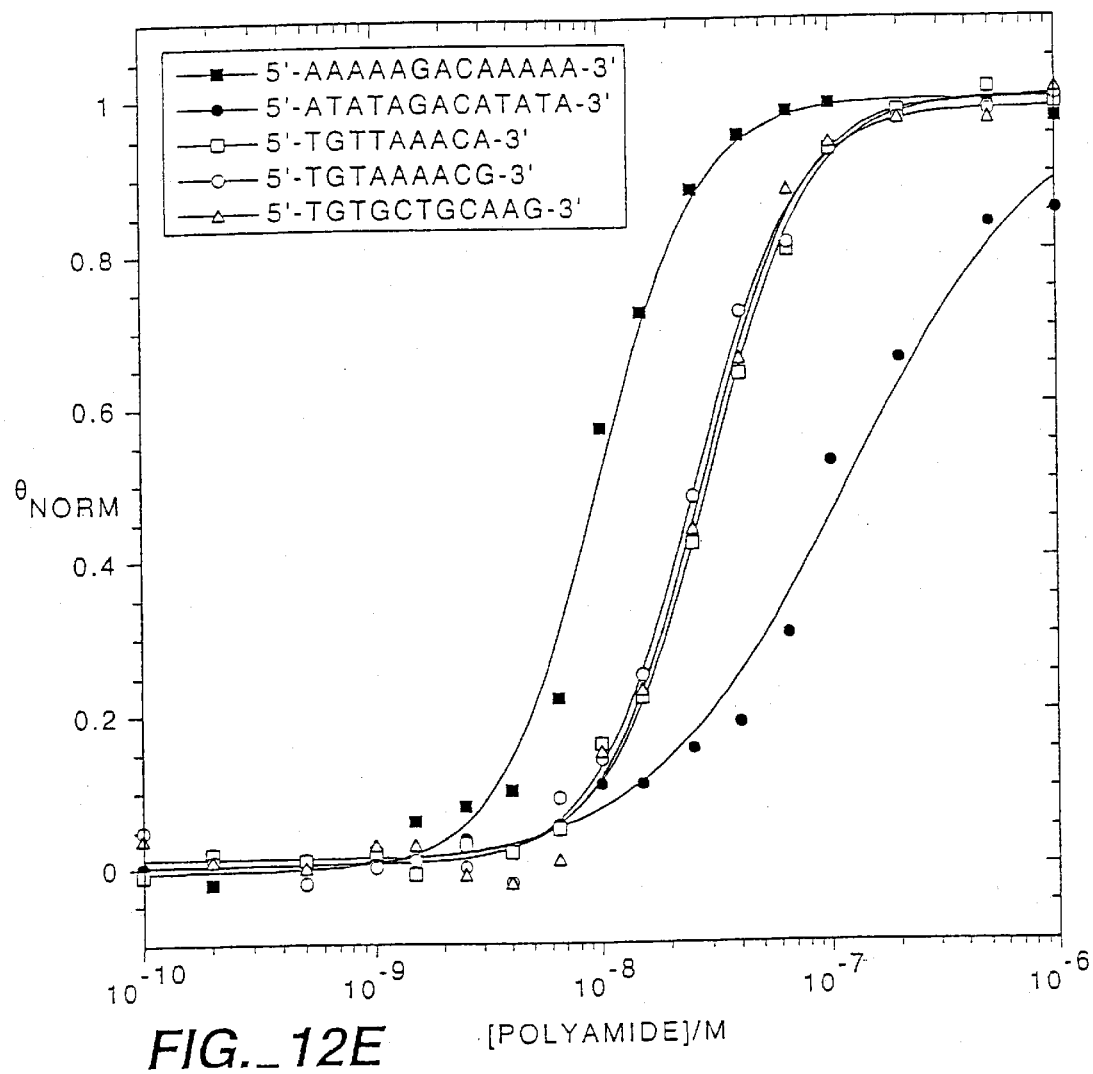
FIG._12E

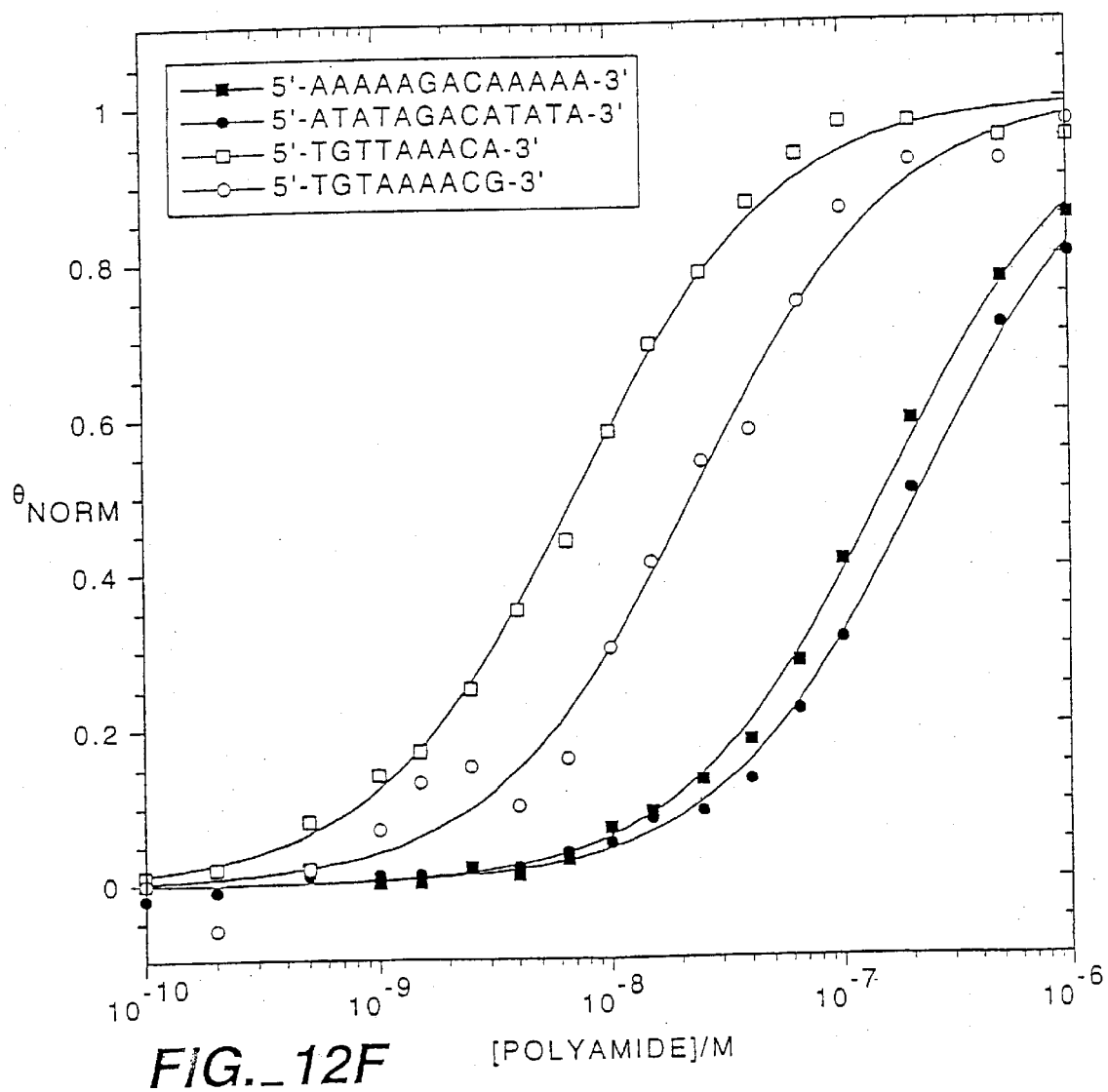
FIG._12F

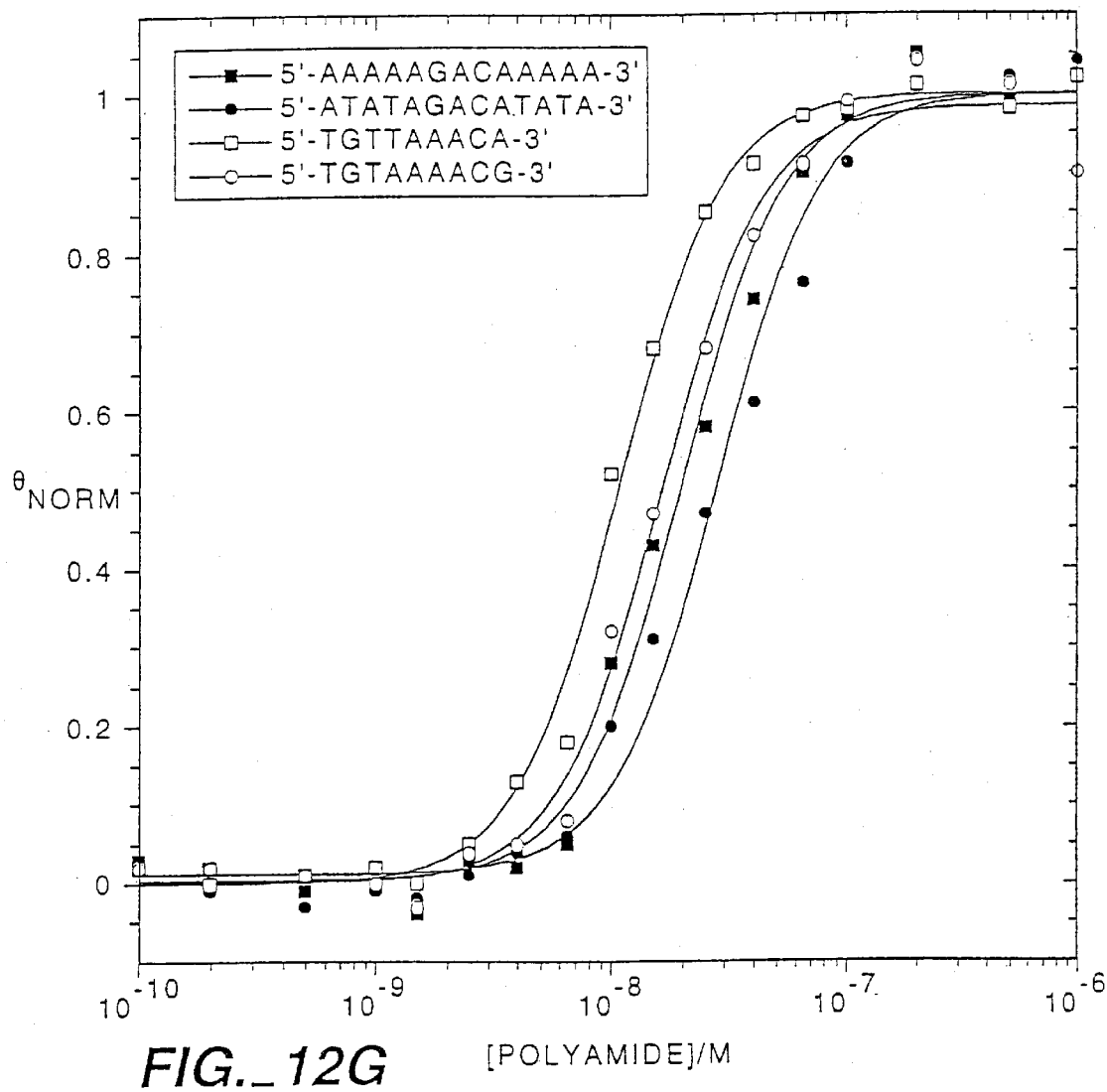
FIG._12G

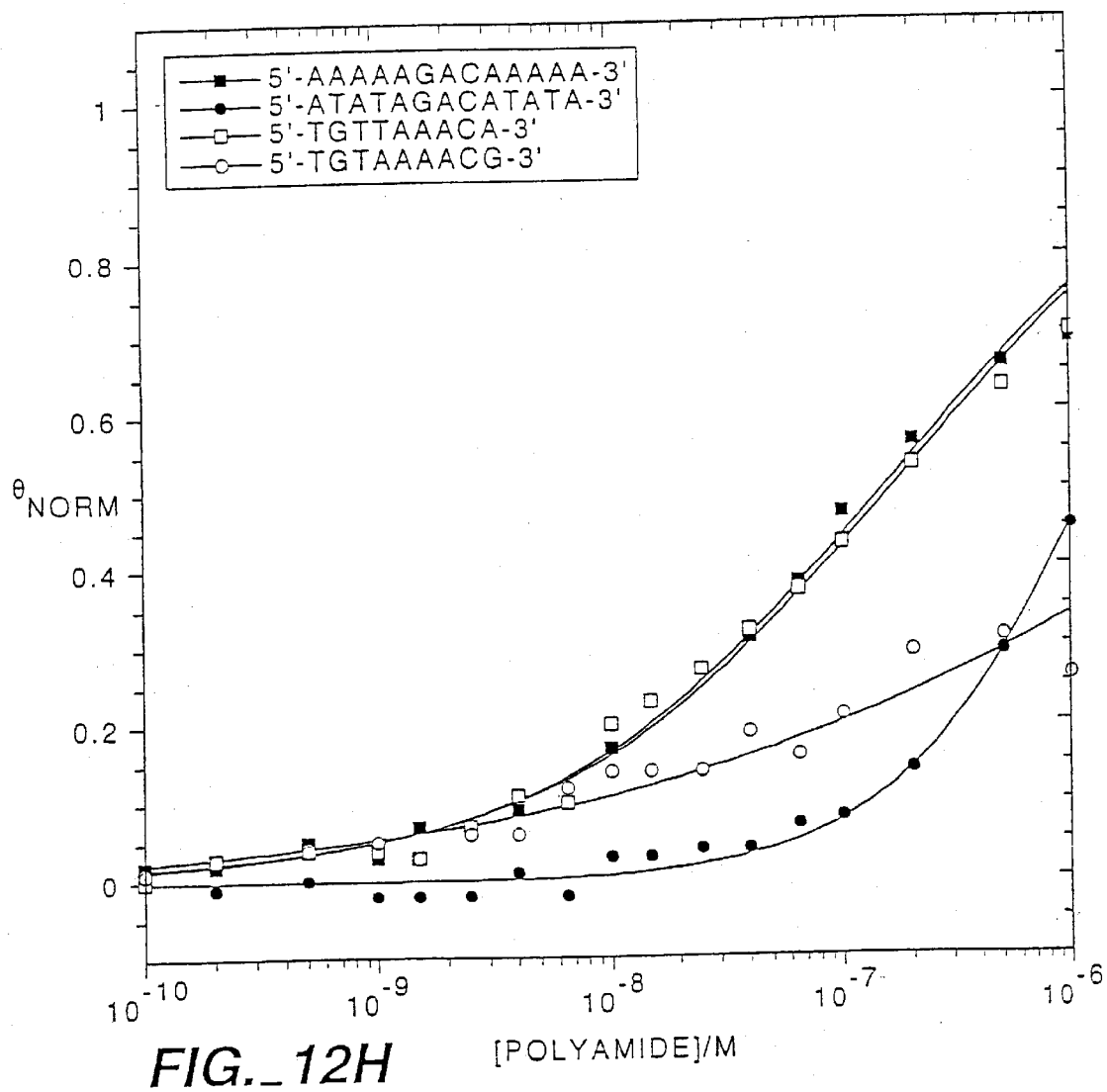
FIG._12H

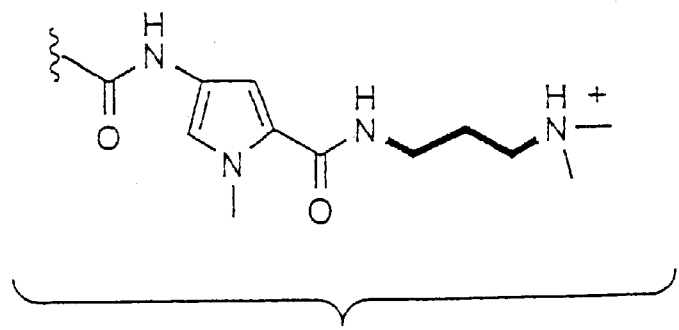
*FIG._13A*
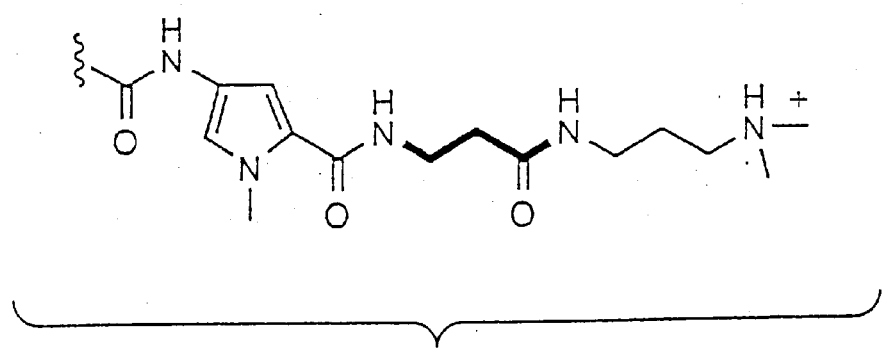
*FIG._13B*
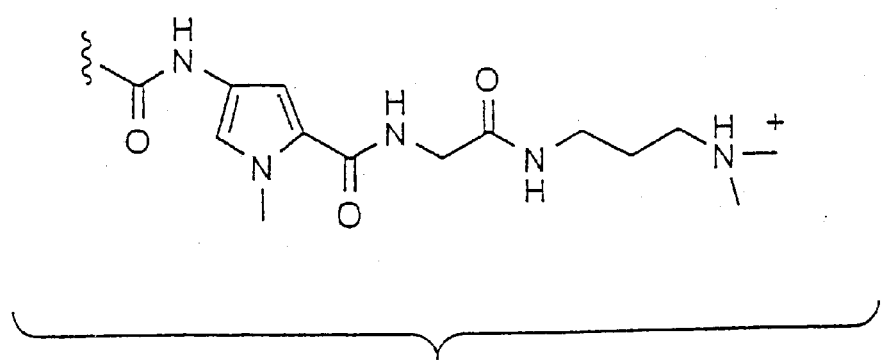
*FIG._13C*

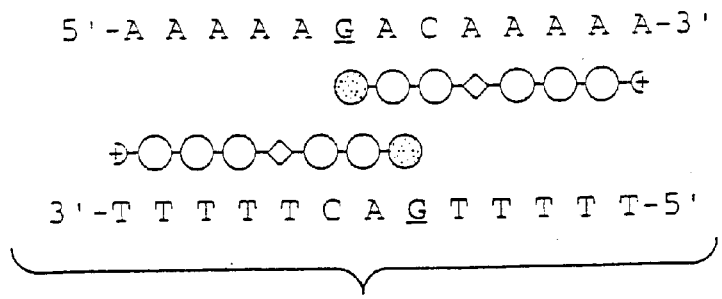
FIG._14A
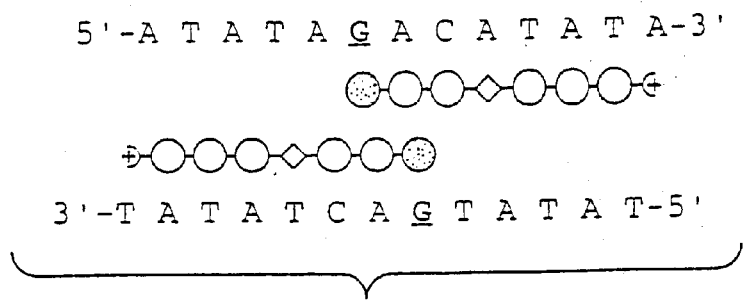
FIG._14B
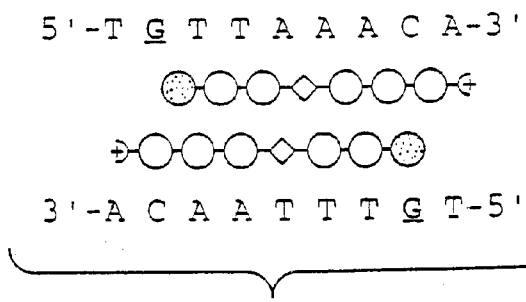
FIG._14C

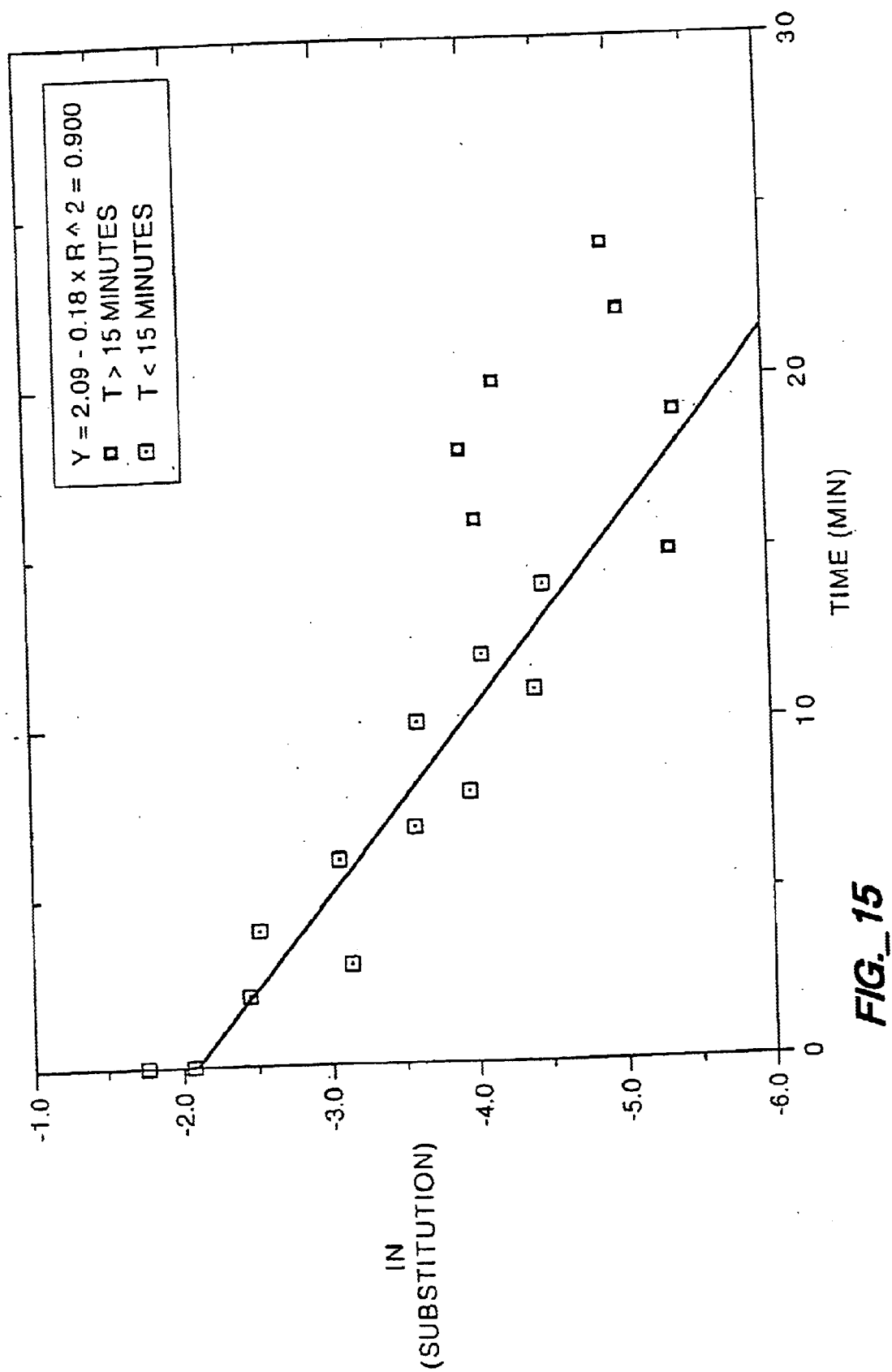
FIG._15

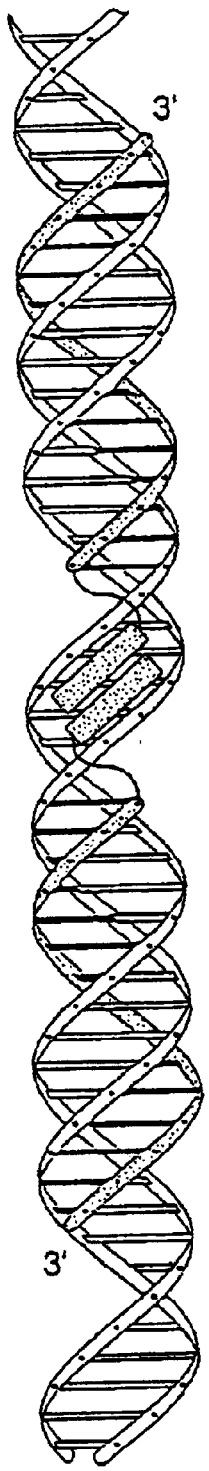
FIG._16A

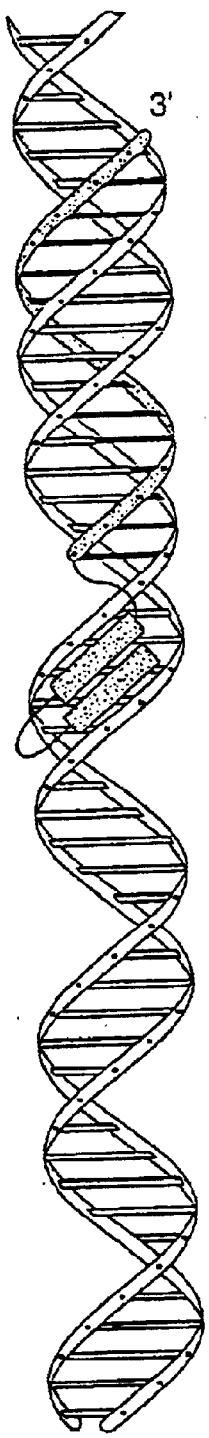
FIG._16B

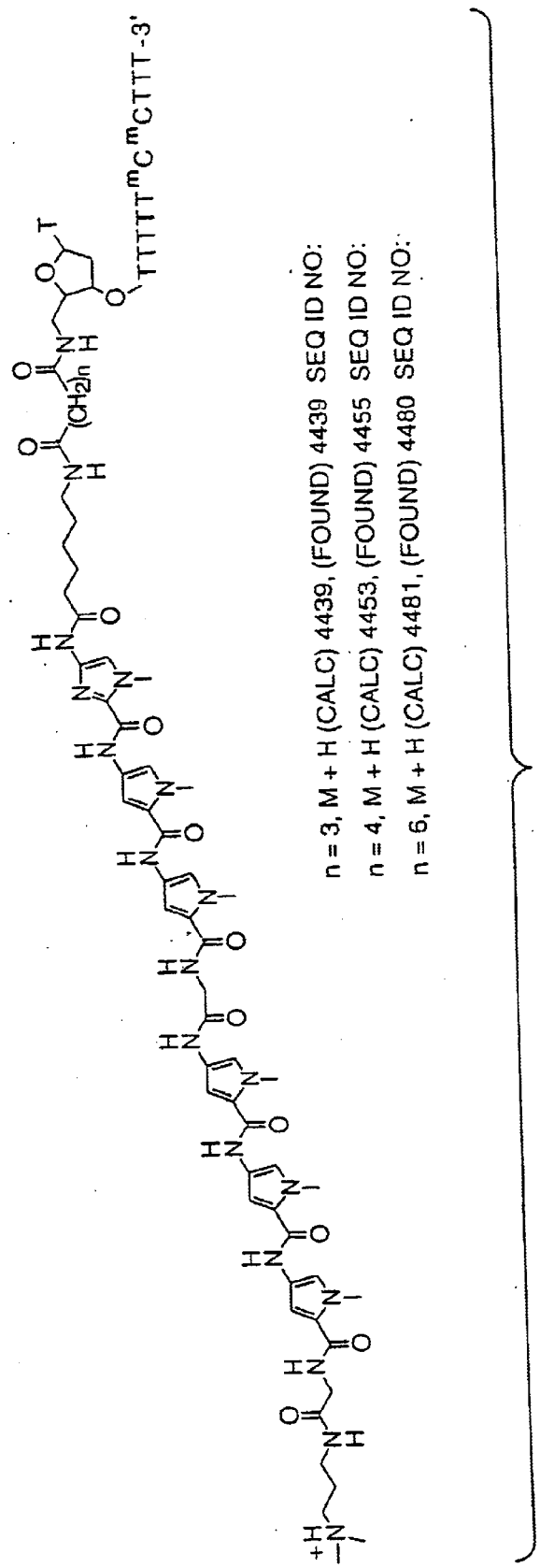
FIG._17A n = 3, M + H (CALC) 4444, (FOUND) 4440 SEQ ID NO:
n = 6, M + H (CALC) 4486, (FOUND) 4487 SEQ ID NO:

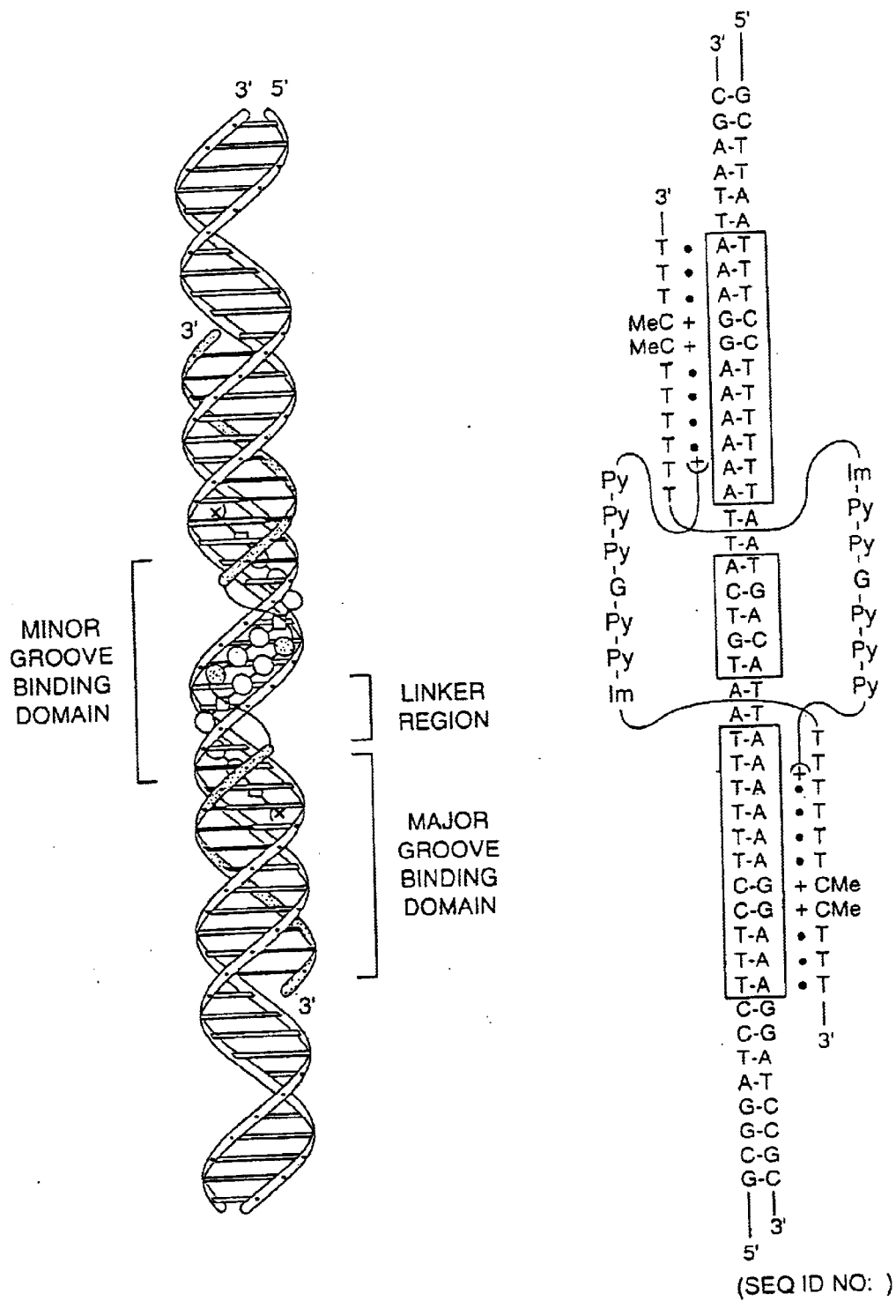
FIG._18

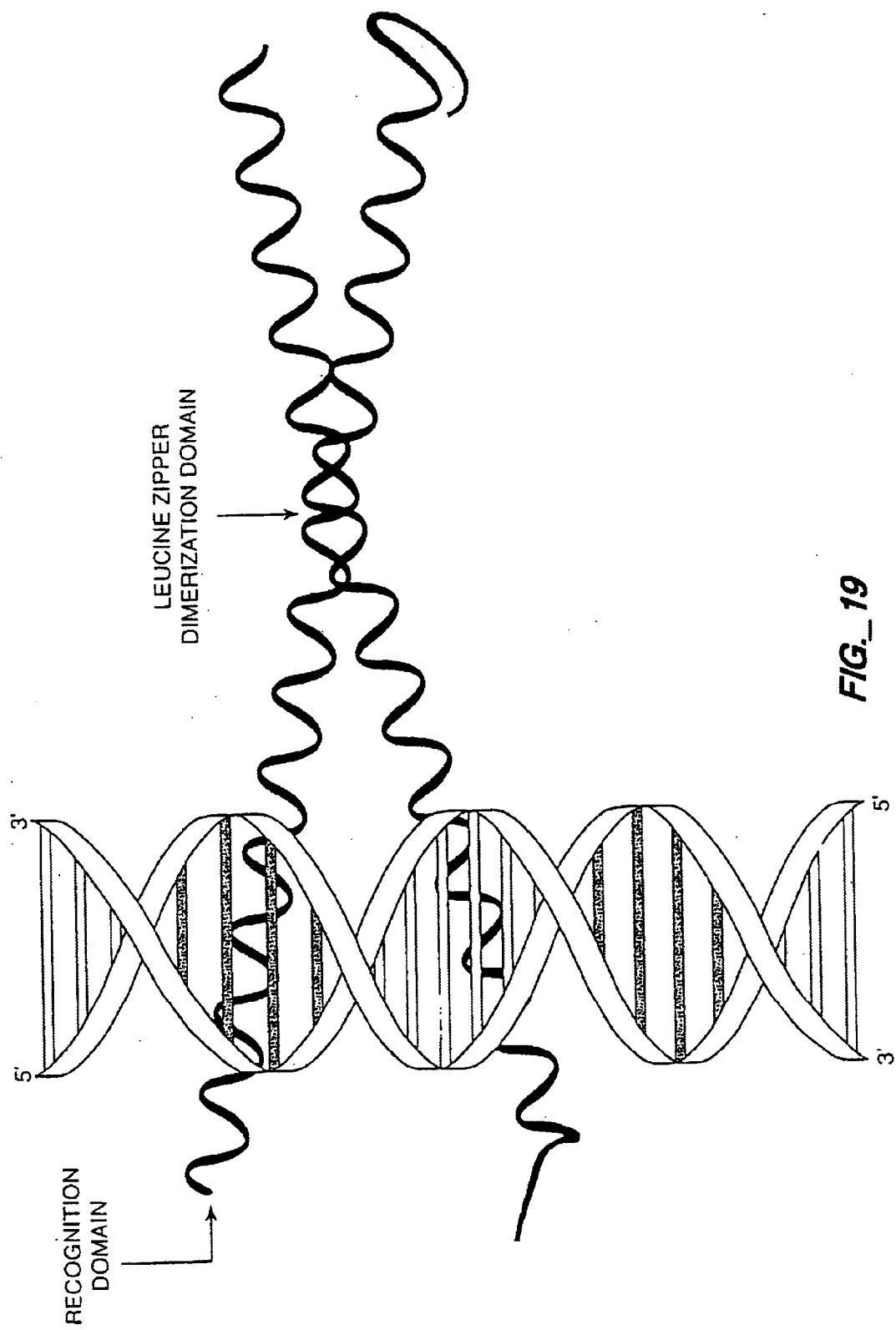
FIG._19

SEQUENCE LISTING

<160> NUMBER OF SEQ ID NOS: 31

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgcgaattcg cg                                                          12

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaagacaa aaa                                                         13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atatagacat ata                                                         13

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 tgttaaaca                                                               9

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggttagtac ct                                                          12

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtgctgcaa g                                                                                       11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal ImPyPy-CONH(CH2)6-P(O)4
<220> FEATURE:
<221> NAME/KEY: modified_base
<222> LOCATION: (7)..(8)
<223> OTHER INFORMATION: methylcytidine

<400> SEQUENCE: 7 tttttttnntt t                                                                                      11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal AcImPyPy-CONH(CH2)12-P(O)4
<220> FEATURE:
<221> NAME/KEY: modified_base
<222> LOCATION: (7)..(8)
<223> OTHER INFORMATION: methylcytidine

<400> SEQUENCE: 8 tttttttnntt t                                                                                      11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Boc-gamma-ImPyPy-CONH(CH2)12-P(O)4
<220> FEATURE:
<221> NAME/KEY: modified_base
<222> LOCATION: (7)..(8)
<223> OTHER INFORMATION: methylcytidine

<400> SEQUENCE: 9 tttttttnntt t                                                                                      11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal H2N-gamma-ImPyPy-CONH(CH2)12-P(O)4
<220> FEATURE:

```
<221> NAME/KEY: modified_base
<222> LOCATION: (7)..(8)
<223> OTHER INFORMATION: methylcytidine

<400> SEQUENCE: 10
tttttnnntt t                                                          11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal EDTA-gamma-ImPyPy-CONH(CH2)12-P(O)4
<220> FEATURE:
<221> NAME/KEY: modified_base
<222> LOCATION: (7)..(8)
<223> OTHER INFORMATION: methylcytidine

<400> SEQUENCE: 11
tttttnnntt t                                                          11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal ImPyPy-CONH(CH2)6-P(O)4
<220> FEATURE:
<221> NAME/KEY: modified_base
<222> LOCATION: (4)..(5)
<223> OTHER INFORMATION: methylcytidine

<400> SEQUENCE: 12
tttnnttttt t                                                          11

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal AcImPyPy-CONH(CH2)12-P(O)4
<220> FEATURE:
<221> NAME/KEY: modified_base
<222> LOCATION: (4)..(5)
<223> OTHER INFORMATION: methylcytidine

<400> SEQUENCE: 13
tttnnttttt t                                                          11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)
<223> OTHER INFORMATION: N-terminal H2N-gamma-ImPyPy-CONH(CH2)6-P(O)4
<220> FEATURE:
<221> NAME/KEY: modified_base
<222> LOCATION: (4)..(5)
<223> OTHER INFORMATION: methylcytidine

<400> SEQUENCE: 14
tttnnttttt t                                                            11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal H2N-gamma-ImPyPy-CONH(CH2)8-P(O)4
<220> FEATURE:
<221> NAME/KEY: modified_base
<222> LOCATION: (4)..(5)
<223> OTHER INFORMATION: methylcytidine

<400> SEQUENCE: 15
tttnnttttt t                                                            11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal H2N-gamma-ImPyPy-CONH(CH2)10-P(O)4
<220> FEATURE:
<221> NAME/KEY: modified_base
<222> LOCATION: (4)..(5)
<223> OTHER INFORMATION: methylcytidine

<400> SEQUENCE: 16
tttnnttttt t                                                            11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal H2N-gamma-ImPyPy-CONH(CH2)12-P(O)4
<220> FEATURE:
<221> NAME/KEY: modified_base
<222> LOCATION: (4)..(5)
<223> OTHER INFORMATION: methylcytidine

<400> SEQUENCE: 17
tttnnttttt t                                                            11

<210> SEQ ID NO 18
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal H2N-gamma-ImPyPy-CONH(CH2)6-
      P(O)4(CH2)8(NH)
<220> FEATURE:
<221> NAME/KEY: modified_base
<222> LOCATION: (4)..(5)
<223> OTHER INFORMATION: methylcytidine

<400> SEQUENCE: 18
tttnnttttt t                                                              11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Dp-G-PyPyPy-G-PyPyIm-epsilon-DSA-
      (NH)
<220> FEATURE:
<221> NAME/KEY: modified_base
<222> LOCATION: (4)..(5)
<223> OTHER INFORMATION: methylcytidine

<400> SEQUENCE: 19
tttnnttttt t                                                              11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Dp-G-PyPyPy-G-PyPyIm-epsilon-DSG-
      (NH)
<220> FEATURE:
<221> NAME/KEY: modified_base
<222> LOCATION: (4)..(5)
<223> OTHER INFORMATION: methylcytidine

<400> SEQUENCE: 20
tttnnttttt t                                                              11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Dp-G-PyPyPy-G-PyPyIm-epsilon-DSS-
      (NH)
<220> FEATURE:
<221> NAME/KEY: modified_base
<222> LOCATION: (4)..(5)
```

<223> OTHER INFORMATION: methylcytidine

<400> SEQUENCE: 21
tttnnttttt t                                                                                11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Dm-gamma-ImPyPy-gamma-ImPyPy-beta-
      ED-DSG-(NH)
<220> FEATURE:
<221> NAME/KEY: modified_base
<222> LOCATION: (4)..(5)
<223> OTHER INFORMATION: methylcytidine

<400> SEQUENCE: 22
tttnnttttt t                                                                                11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal DMgamma-ImPyPy-gamma-ImPyPy-beta-ED-
      DSA-(NH)
<220> FEATURE:
<221> NAME/KEY: modified_base
<222> LOCATION: (4)..(5)
<223> OTHER INFORMATION: methylcytidine

<400> SEQUENCE: 23
tttnnttttt t                                                                                11

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Gln Leu Glu Asp Lys Val Glu Glu Leu Leu Ser Lys Asn Tyr His
 1               5                  10                  15

Leu Glu Asn Glu Val Ala Arg Leu Lys Lys Leu Val Gly Glu Arg
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)
<223> OTHER INFORMATION: N-terminal H2N-beta-beta-ImPyPy-gamma-gamma -continued

<400> SEQUENCE: 25

Lys Gln Leu Glu Asp Lys Val Glu Glu Leu Leu Ser Lys Asn Tyr His
 1               5                  10                  15

Leu Glu Asn Glu Val Ala Arg Leu Lys Lys Leu Val Gly Glu Arg
            20                  25                  30

<210> SEQ ID NO 26
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 tgtaaaacg                                                              9

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcaaaaagac aaaaagg                                                    17

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgttaaac aggctcg                                                    17

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: N-terminal Dp-G-PyPyPy-G-PyPyIm-linker
<220> FEATURE:
<221> NAME/KEY: modified_base
<222> LOCATION: (7)..(8)
<223> OTHER INFORMATION: methylcytidine

<400> SEQUENCE: 29 tttttttnntt t                                                         11

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
gcttaatttc ctttttaat gacattaaaa aaggaaagga tccgc          45
```

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31

```
cctggttagt acctggatg                                      19
```

METHOD FOR THE SYNTHESIS OF PYRROLE AND IMIDAZOLE CARBOXAMIDES ON A SOLID SUPPORT

This is a continuation of application Ser. No. 08/607,078, filed on Feb. 26, 1996, which issued as U.S. Pat. No. 6,090,947 on Jul. 18, 2000.

This work as partially supported by the United States Government through the National Institute of Health under Grant No. GM 27681. The United States Government may have certain rights in this invention.

FIELD OF THE INVENTION

This invention relates to the field of peptide chemistry. Specifically, this invention relates to a novel process for preparing polyamides and polyamide conjugates containing imidazole and pyrrole carboxamides using solid state chemistry. Also included in this invention is a simple and effective method for preparing analogs of the antiviral antibiotics Netropsin and Distamycin A.

BACKGROUND OF THE INVENTION

Proteins and peptides play a critical role in virtually all biological processes, functioning as enzymes, hormones, antibodies, growth factors, ion carriers, antibiotics, toxins, and neuropeptides. Biologically active proteins and peptides, therefore, have been a major target for chemical synthesis. Chemical synthesis is used to verify structure and to study the relationship between structure and function, with the goal of designing novel compounds for potential therapeutic use. Thus, modified or novel peptides may be synthesized which have improved therapeutic activity and/or reduced side effects.

There are two basic methods for synthesizing proteins and peptides: the chemistry is either carried out in solution (solution phase) or on a solid support (solid phase). A major disadvantage of solution phase synthesis of peptides is the poor solubility of the protected peptide intermediates in organic solvents. Additionally, solution phase synthesis requires extensive experience on the part of the scientist and the purifications are difficult and time consuming. Solid phase synthesis overcomes these problems and thus, has become the method of choice in synthesizing peptides and proteins.

The basic approach for solid phase peptide synthesis is illustrated in FIG. 1. Briefly, the carboxy-terminal amino acid of the peptide to be synthesized is protected and covalently attached to a solid support, typically a resin. The subsequent amino acids (which have also been protected) are then sequentially added. When the synthesis is complete the peptide is deprotected, cleaved from the resin and purified. Because the molecules being synthesized are so large it is imperative that the steps proceed rapidly, in high yields and with minimal side reactions.

The most commonly used solid supports are cross-linked polystyrene and polydimethylacrylamide resins, which are both derivatives of polyethylene. In 1978, Merrifield and coworkers introduced the tert-butyloxycarbonylaminoacyl-4-(oxymethyl)phenyl-acetamidomethyl-resin (PAM resin), a novel polystyrene resin for solid phase peptide synthesis (Mitchell et al. (1978) J. Org. Chem. 43:2845–2852). PAM resin has a preformed resin ester linkage which is stable to trifluoroacetic acid and can be cleaved under a variety of conditions including, liquid hydrogen fluoride, aminolysis, hydrolysis, hydrazinolysis, catalytic hydrogenation, or lithium borohydride to give a peptide acid, amide, hydrazide, or primary alcohol (Stewart and Young (1984) in Solid Phase Peptide Synthesis, sec. ed., Pierce Chemical Company, Illinois pp. 88–95).

Netropsin and Distamycin A (FIGS. 2A and 2B) are heterocyclic polyamides, containing imidazole (Im) and pyrrole (Py) carboxamides. These compounds are isolated from Streptomyces distallicus and exhibit antibiotic, antiviral and antitumor activity. Other members of this family of antibiotics include noformycin (Diana (1973) J. Med. Chem. 16:3774–3779), kikumycin B (Takaishi et al. (1972) Tetrahedron Lett. 1873), and anthelvencin (Probst et al. (1965) Antimicrob. Agents Chemother. 789). Netropsin and Distamycin A are two examples of the many small molecules (MW<2 kD) as which can bind and/or cleave DNA with modest sequence specificity (Krugh (1994) Curr. Opin. Struct. 4:351–364). These drugs block template function by binding to specific nucleotides in the minor groove of double-stranded DNA.

Due to the pharmaceutical potential of this family of peptides a considerable amount of research has been devoted to the study of these compounds and their analogues. The x-ray crystal structure of a 1:1 complex of Netropsin with the B-DNA dodecamer 5'-CGCGAATTCGCG-3'(SEQ ID NO:1) provides an understanding of how the sequence specificity is achieved, revealing that the amide hydrogens of the N-methylpyrrolecarboxamides form bifurcated hydrogen bonds with adenine N3 and thymidine O2 atoms on the floor of the minor groove. (Koopka et al. (1985) Proc. Natl. Acad. Sci. 82:1376; Koopka et al. (1985) J. Mol. Biol. 183:553). The pyrrole rings completely fill the groove excluding the guanine amino group of a G, C base pair while making extensive van der Waals contacts with the walls of the groove, thereby affording specificity for A,T sequences. (Taylor et al. (1985) Tetrahedron 40:457; Schultz and Dervan (1984) J. Biomol. Struct. Dyn. 1:1133). Efforts to design ligands specific for G, C containing sequences, were largely unsuccessful (see e.g., Lown et al. (1986) Biochemistry 25:7408; Kssinger et al. (1987) Biochemistry 26:5590; Lee et al. (1987) Biochemistry 27:445; Lee et al. (1993) Biochemistry 32:4237), until the discovery that two polyamides combine side-by-side in the minor groove of DNA, forming a 2:1 complex with the DNA. (Pelton (1989) Proc. Natl. Acad. Sci., USA 86:5723–5727; Pelton (1990) J. Am. Chem. Soc. 112:1393–1399; Chen et al. (1994) M. Struct. Biol. Nat. 1:169–175; Wade et al. (1992) J. Am. Chem. Soc. 114:8783–8794; Mrksich et al. (1992) Proc. Natl. Acad. Sci., USA 89:7586–7590; Wade (1993) Biochemistry 32:11385–11389; Mrksich et al. (1994) J. Am. Chem. Soc. 116:7983–7988). Each ligand interacts with one of the DNA strands in the minor groove, with the imidazole nitrogen making specific hydrogen bonds with one guanine amino group. Thus, both Distamycin A and imidazole containing ligands such as the designed polyamide imidazole-pyrrole-pyrrole-dimethylaminoproplymine (ImPyPy-Dp), 1-methylimidazole-2-carboxamide Netropsin, bind specifically in the minor groove as 2:1 polyamide/DNA complexes recognizing G, C sequences.

From studies of the 2:1 model it is now known that the combination of imidazole/pyrrole carboxamide recognize a G, C base pair, and the combination of pyrrole carboxamide/imidazole recognizes a C, G base pair, the pyrrole carboxamide/pyrrole carboxamide combination is partially degenerate for T, A and A, T. The utility of the 2:1 model as an aid in designing ligands with sequence specificity for DNA is illustrated by the designed polyamide imidazole-pyrrole-imidazole-pyrrole-dimethylaminopropylamine (ImPyImPy-Dp) which binds a four base pair core sequence 5'-GCGC-3'. This is a complete reversal of the natural specificity of Netropsin and Distamycin A.

The literature contains a number of reports of the total synthesis of various members of this family of polyamides and their analogues. All of the reported syntheses have been performed in the solution phase. The amide bond unit in these polyamides is formed from an aromatic carboxylic acid and an aromatic amine, both of which have proven problematic for solution phase coupling reactions. The aromatic acids are often unstable resulting in decarboxylation and the aromatic amines have been found to be highly air and light sensitive (Lown and Krowicki (1985) J. Org. Chem. 50:3774–3779). It was believed that the variable coupling yields, long (often >24 hour) reaction, times, numerous side products, and wide scale use of acid chloride and trichloroketone intermediates in solution phase coupling reactions would make the synthesis of the aromatic carboxamides difficult, if not impossible by solid phase methods (He et al. (1993) J. Am. Chem. Soc. 115:7061–7071; Church et al. (1990) Biochemistry 29:6827–6838; Nishiwaki et al. (1988) Heterocycles 27:1945–1952). Thus, to date, there have been no reported attempts to synthesize this class of compounds using solid phase methodology.

The process of developing new ligands with novel sequence specificity generally involves four stages; design, synthesis, testing, and redesign of the model (Dervan (1986) Science 232:464). While exploring the limits of the 2:1 model, the synthetic portion of the process emerged as the major limiting factor, especially when confronted with expanding the 2:1 motif to include longer sequences recognized by increasingly larger polyamides. For example, the total synthesis of hairpin octa-amides such as AcImImPy-γ-PyPyPy-G-Dp and AcPyPyPy-γ-ImImPy-G-Dp (FIGS. 3A and 3B) is characterized by difficult purifications. (γ represents γ-aminobutyric acid and G represents guanine.) Each polyamide would likely require more than a months effort, even in the hands of a skilled researcher. Methods for expediting the synthesis of analogs of Distamycin A were investigated and the present invention describes a novel method for the synthesis of oligopeptides containing imidazole and pyrrole carboxamides on a solid support.

Oligonucleotide-directed triple helix formation is one of the most effective methods for accomplishing the sequence specific recognition of double helical DNA. (See e.g., Moser and Dervan (1987) Science 238:645; Le Doan et al. (1987) Nucleic Acids Res. 15:7749; Maher et al. (1989) Science 245:725; Beal and Dervan (1991) Science 251:1360; Strobel et al. (1991) Science 254:1639; Maher et al. (1992) Biochemistry 31:70). Triple helices form as the result of hydrogen bonding between bases in a third strand of DNA and duplex base pairs in the double stranded DNA, via Hoogstien base pairs. Pyrimidine rich oligonucleotides bind specifically to purine tracts in the major groove of double helical DNA parallel to the Watson-Crick (W-C) purine strand (Moser and Dervan (1987) Science 238:645). Specificity, is derived from thymine (T) recognition of adenine-thymine base pairs (T→AT) base triplets and protonated cytosine (C$^+$) recognition of guanine-cytosine base pairs (C$^+$→GC). (Felsenfeld et al. (1957) J. Am. Chem. Soc. 79:2023; Howard et al. (1964) Biochem. Biophys. Res. Commun. 17:93; Rajagopal and Feigon (1989) Nature 339:637; Radhakrishnan et al. (1991) Biochemistry 30:9022). Purine-rich oligonucleotides, on the other hand, bind in the major groove of purine rich tracts of double helical DNA antiparallel to the W-C purine strand. (Beal and Dervan (1991) Science 251:1360). Specificity is derived from guanine recognition of GC base pairs (G→GC base triplets) and adenine recognition of AT base pairs (A→AT base triplets). (Durland et al. (1991) Biochemistry 30:9246; Pilch et al (1991) Biochemistry 30:6081; Radhakrishnan et al. (1991) J. Mol. Biol. 221:1403; Beal and Dervan (1992) Nucleic Acids Res. 20: 2773). Oligonucleotide directed triple helix formation is therefore limited mainly to purine tracts.

A major challenge in the sequence specific recognition of duplex DNA by triple helix formation is designing oligonucleotides capable of binding all four base pairs. Efforts toward this goal have included the design of non-natural heterocycles for the completion of the triplex code and the design of oligonucleotides capable of binding alternate strands of duplex DNA by triple-helix formation. (Beal and Dervan (1992) J. Am. Chem. Soc. 114:4976–4982; Stiltz and Dervan (1992) Biochem. 9:2177–2185; Koshlap et al. (1993) J. Am. Chem. Soc. 115:7908–7909).

An increasingly versatile method for accomplishing the sequence specific recognition of DNA is the use of natural DNA binding molecules with altered sequence specificity. (Dervan (1986) Science 232:464). The construction of oligonucleotide-minor groove polyamide conjugates, using natural DNA binding molecules, such as Netropsin and Distamycin A, offers a promising method for expanding the number of sequences which can be targeted by oligonucleotide directed triple helix formation.

A number of methods have been reported for the synthesis of common oligonucleotide-polyamide conjugates, based on post-synthetic modification (Ede et al. (1994) Bioconj. Chem. 5:373–378; Haralambidis et al. (1993) Bioorg. and Med. Chem. Let. 4:1005–1010); assembly of a peptide on controlled pore glass followed by oligonucleotide synthesis (Haralambidis et al. (1990) Nuc. Acid. Res. 18:493–499; Haralambidis et al. (1987) Tet. Lett. 28:5199–5202; Tong et al. (1993) J. Org. Chem. 58:2923–2231; Tung et al. (1991) Bioconj. Chem. 2:464–465; Bongratz et al. (1994) Nuc. Acid. Res. 22:4681–4688; Zhu and Stein (1994) Bioconj. Chem. 5:312–315) and synthesis of amino modified oligonucleotides followed by solid phase synthesis of peptides.

There are a number of conceivable approaches to the design of oligonucleotide-polyamide conjugates capable of recognizing double helical DNA by triple helix formation. In one approach, the conjugate can be designed such that two minor-groove polyamide oligonucleotide conjugates bind antiparallel to a sequence of duplex DNA, with binding mediated by the dimerization of the individual polyamide moieties in the minor groove of DNA, FIG. 19A. In a second approach, the conjugate can be designed such that a single oligonucleotide head-to-tail hairpin polyamide dimer, binds a sequence of duplex DNA in the minor groove, with binding mediated by oligonucleotide directed triple helix formation in the major groove, FIG. 19B. In each of these designs specificity is derived from specific contacts in the major groove from the pyrimidine motif triple helix and in the minor groove from the 2:1 polyamide:DNA complex.

BRIEF SUMMARY OF THE INVENTION

The present invention describes a novel method for the preparation of acyclic polyamides containing imidazole and pyrrole carboxamides. The present invention also describes a novel method for the synthesis of cyclic polyamides containing imidazole and pyrrole carboxamides. Further included in the present invention is a novel method for the solid phase synthesis of imidazole and pyrrole polyamide-oligonucleotide and polyamide-protein conjugates capable of recognizing double stranded DNA.

Included in the present invention is the solid phase synthesis of analogs of the di- and tri-N-methylpyrrolecarboxamide antiviral antibiotics Netropsin and Distamycin A. (FIGS. 2B and 2B).

This invention includes reaction schemes for producing a wide variety of imidazole and pyrrole polyamides and imidazole and pyrrole polyamide-oligonucleotide and protein conjugates. A key element in the synthesis of these compounds is the use of a solid support in conjunction with Boc-(Boc=tert-butoxycarbonyl) and Fmoc-(Fmoc=9-fluorenylmethyl carbonyl) chemistry.

More specifically, the invention provides a method for the solid phase synthesis of imidazole and pyrrole polyamides comprising the steps of: preparing a solid support, preferably a polystyrene resin, for attachment of the polyamide to be synthesized; protecting and activating the appropriate amino acid monomers or dimers; sequentially adding the amino acid monomers or dimers to the solid support beginning with the carboxy terminal amino acid; deprotecting the amino acids after formation of the desired polyamide; cleaving the polyamide from the solid support and purifying the synthesized polyamide.

Further included in the present invention are novel amino acid monomers and dimers and novel methods for synthesizing the same.

BRIEF DESCRIPTION OF THE FIGURES

FIG. 1 illustrates the basic approach for solid phase peptide synthesis.

FIG. 2A depicts the di-N-methylpyrrole-carboxamide antibiotic Netropsin.

FIG. 2B depicts the tri-N-methylpyrrole-carboxamide antibiotic Distamycin A.

FIG. 3 depicts octapeptide hairpin dimers AcImImPy-γ-PyPyPy-G-Dp (FIG. 3A) and AcPyPyPy-γ-ImImPy-G-Dp (FIG. 3B), which are designed to bind the sites 5'-WGGWW-3' and 5'-WGGWW-3', respectively. W, is either an A,T or T,A base pair.

FIGS. 4A–4D illustrate C3-methyl pyrrole inhibition of pyrrole carboxamide-pyrrole carboxamide recognition of a GC base pair. The polyamide oligonucleotide complexes depicted in the Figures are ImPyPy-γ-PyPyPy-Dp.TGTTA and ImPyPy-γ-PyPyPy-Dp.TGTCA. In FIGS. 4A and 4B the polyamide is unmodified and in FIGS. 4C and 4D the third pyrrole of the polyamide has been modified by addition of a methyl group to the second carbon of the pyrrole ring.

FIG. 5 illustrates the potential for the formation of a bifurcated hydrogen bond between a 3-substituted hydroxypyrrole carboxamide and the carbonyl of thymine (dR represents deoxyribose).

FIG. 6A illustrates the additional hydrogen bond which can form between the hydroxyl group of a 3-substituted hydroxypyrrole carboxamide and the carbonyl of thymine.

FIG. 6B illustrates that adenine cannot form this additional hydrogen bond.

FIG. 7 depicts illustrative polyamides prepared by the method of this invention.

FIG. 8 illustrates a typical 72 minute solid phase synthesis cycle for minor groove polyamides according to one embodiment of this invention.

FIG. 9 illustrates three representative analytical high pressure liquid chromatography (HPLC) traces for stepwise monitoring of a solid phase polyamide synthesis cycle from the synthesis of AcImImPy-γ-PyPyPy-G-Dp (0.1% wt/v TFA, gradient elution 1.25% $CH_3CN$/min monitored at 254 nm). FIG. 9A depicts the HPLC spectrum of Boc-Py-γ-PyPyPy-G-Dp (Boc=tert-butoxycarbonyl) which elutes at 31.6 minutes. FIG. 9B depicts the spectrum of $H_2N$-Py-γ-PyPyPy-G-Dp which elutes at 24.3 minutes and FIG. 9C depicts the spectrum of Boc-ImPy-γ-PyPyPy-G-Dp which elutes at 31.8 minutes.

FIG. 10 illustrates various spectra of the HPLC purified polyamide, AcImImPy-γ-PyPyPy-G-Dp (4a) (Scheme 2). FIG. 10A depicts the HPLC spectrum (0.1% wt/v TFA, 1.25%. $CH_3CN$/min), monitored at 254 nm. FIG. 10B depicts the MALDI-TOF mass spectrum, internal standard at 1802.1 ($M^+H$ calculated for $C_{47}H_{60}N_{18}O_9$, 1022.1, found 1022.4). FIG. 10C depicts the $^1H$ NMR spectra recorded at 300 MHz in $d_6$-DMSO.

FIG. 11 depicts ribbon models of "slipped" 11A) and "overlapped" (11B) 2:1 polyamide:DNA complexes.

FIGS. 12A–12H depict graphically the data obtained from the quantitative DNase I footprint titration experiments. The ($\theta_{norm}$, $[L]_{tot}$) data points were obtained as described in Example 10.

FIG. 13 depicts the structures of the C-termini of various polyamides illustrating that polyamides with C-termini (a) Py-Dp and (b) Py-β-Dp (β=β-alanine) sequences present similar surfaces to the minor groove, while polyamides with C-termini (c) Py-G-Dp sequences present a different surface. In the case of (c) the glycine carbonyl group is directed to toward the minor groove.

FIG. 14 illustrates the predicted 2:1 complexes of ImPyPy-X-PyPyPy-G-Dp, where X=G, β or Py, with the targeted sites (a) 5'-AAAAAGACAAAAA-3'(SEQ ID NO:2), (b) 5'-ATATAGACATATA-3'(SEQ ID NO:3) (13 bp, "slipped") and (c) 5'-TGTTAAACA-3'(SEQ ID NO:4) (9 bp, "overlapped"). The shaded and light circles represent imidazole and pyrrole rings, respectively, and the diamond represents the internal amino acid X. The specifically targeted guanines are highlighted.

FIG. 15 depicts graphically the measurement of the time of the coupling of Boc-Py-OBt to $PyNH_2$ by picric acid titration. Samples were taken at one minute intervals.

FIG. 16 illustrates two ways in which double helical DNA can be recognized by an oligonucleotide-minor groove binding polyamide conjugate. In FIG. 16A oligonucleotide directed triple helix formation in the major groove is mediated by polyamide dimerization in the minor groove. In FIG. 16B directed binding of a head-to-tail polyamide dimer in the minor groove is mediated by oligonucleotide directed triple helix formation in the major groove.

FIG. 18 depicts a ribbon graphic illustrating how the oligonucleotide-polyamide conjugate Dp-G-PyPyPy-G-PyPyIm-linker-TTTTTT$^m$C$^m$CTTT might bind to double helical DNA.

FIG. 19 illustrates a ribbon model of the GCN-4 protein's coiled and DNA binding region binding to DNA.

DETAILED DESCRIPTION OF THE INVENTION

The present invention provides a method for the solid phase synthesis of straight chain and cyclic polyamides containing imidazole and pyrrole carboxamides. The present invention also provides a method for the solid phase synthesis of imidazole and pyrrole polyamide-oligonucleotide conjugates and imidazole and pyrrole polyamide-protein conjugates.

Included in the present invention is the solid phase synthesis of analogs of the di- and tri-N-methylpyrrolecarboxamide antibiotics Netropsin and Distamycin A (FIGS. 2A and 2B).

More specifically the present invention includes a method for the preparation and identification of pyrrole and imidazole carboxamide polyamides and polyamide-oligonucleotide and protein conjugates which recognize double stranded DNA by interaction with the minor groove of the DNA.

Figure 17B:
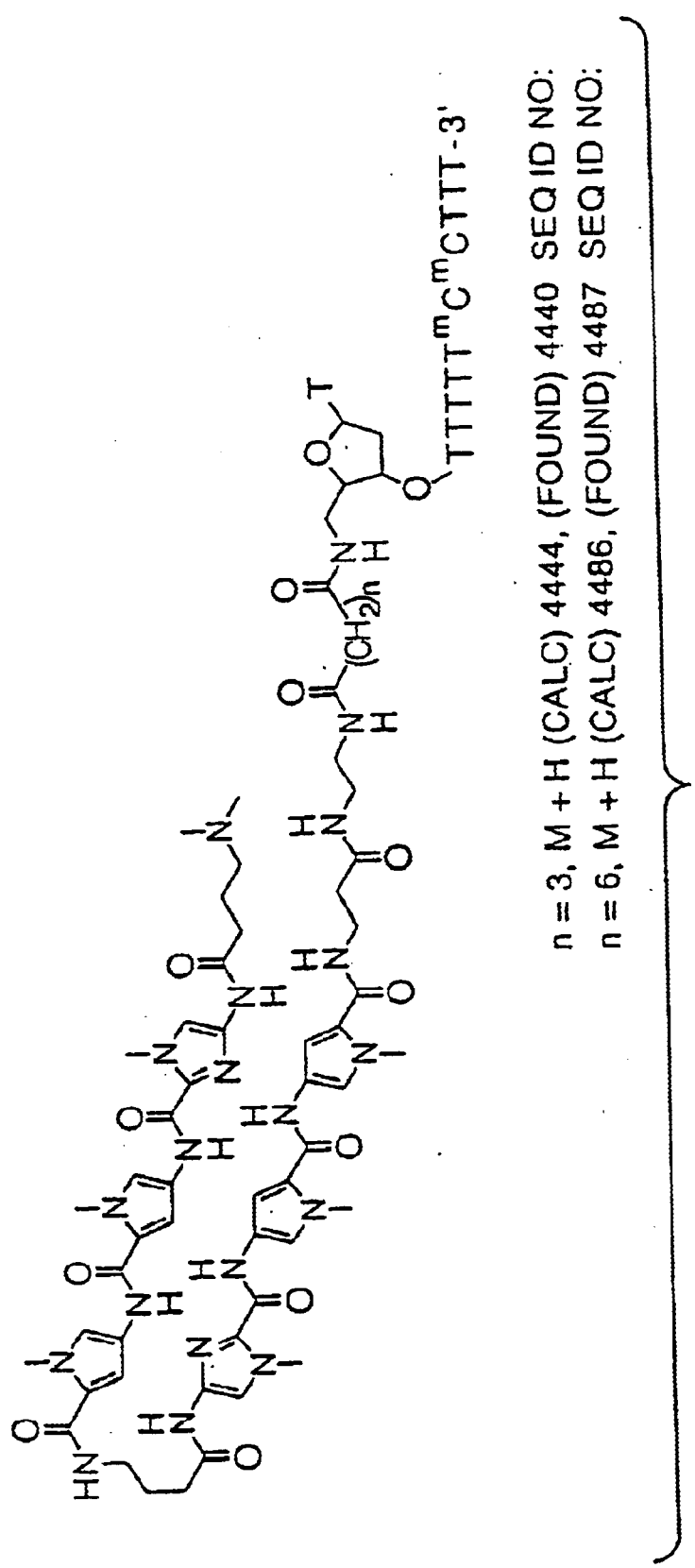
FIG. 17 depicts illustrative polyamide-oligonucleotide conjugates synthesized by the method of this invention. Included in the figure are the calculated and observed masses (MALDI-TOF).

Illustrative imidazole and pyrrole polyamides produced by the method of this invention are shown in FIG. 7 and Tables 1 and 4. Illustrative imidazole and pyrrole carboxamide polyamide-oligonucleotide conjugates produced by the method of this invention are shown in Table 5 and FIG. 17.

The present invention extends to all novel imidazole and pyrrole carboxamide polyamides, imidazole and pyrrole carboxamide polyamide-oligonucleotide conjugates and imidazole and pyrrole carboxamide polyamide-protein conjugates that can be prepared according to the methods of the present invention.

Further included in this invention is an improved method for the preparation of the Boc-pyrrole-OBt and Boc-imidazole-OBt activated amino acid monomers and a novel method for the preparation of the Fmoc-pyrrole-OBt and Fmoc-imidazole-OBt activated amino acid monomers. Also included in this invention are novel monomers in which the pyrrole is substituted at the N-methyl position and at the 3 position of the pyrrole ring. Also included is a novel method for the preparation of imidazole containing dimers.

Certain terms used to describe the invention herein are defined as follows:

The term "polyamide" is used to describe the polypeptides synthesized by the method of this invention. A polyamide is a polymer of amino acids chemically bound by amide linkages (CONH). A "amino acid" is defined as an organic molecule containing both an amino group (NH₂) and a carboxylic acid (COOH). The polyamides of this invention are comprised of imidazole carboxamides, pyrrole carboxamides, aliphatic amino acids, aromatic amino acids and any chemical modifications thereof.

The term "amino acid monomer" refers to a pyrrole or imidazole amino acid or an aliphatic or aromatic amino acid in which the amine has been protected with the Boc-protecting group, Fmoc-protecting group or allyl-protecting group and the carboxylic acid has been activated as the -OBt ester or the symmetric anhydride.

The activated "pyrrole amino acid monomers" of this invention, are generally depicted as follows:

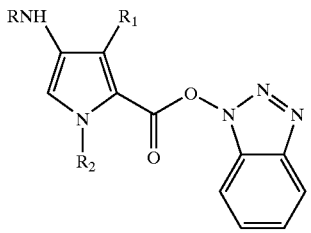

wherein R is a protecting group independently selected from the groups consisting of tert-butoxycarbonyl (Boc-), allyl (—CH₂CH═CH₂) or 9-fluorenylmethyl carbonyl (Fmoc-); $R_1$ is independently selected from the group consisting of H, CH₃, OH, NH₂, Cl or CF₃; and $R_2$ is independently selected from the group consisting of H, C1–C10 alkyl, such as methyl, ethyl or isopropyl, C1–C10 alkenyl, C1–C10 alkynyl, such as —C≡CCH₃, or a carboxylic acid, such as —CH₂COOH.

The activated "imidazole amino acid monomers" of this invention are generally depicted as follows:

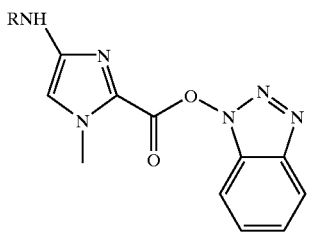

wherein R is a protecting group independently selected from the groups consisting of tert-butoxycarbonyl (Boc-), allyl (—CH₂CH═CH₂) or 9-fluorenylmethylcarbonyl (Fmoc-).

The -OBt activated "dimers" of this invention are generally depicted as follows:

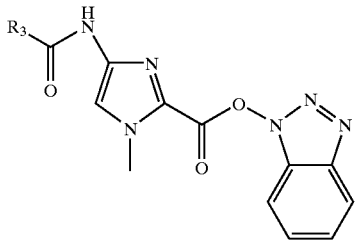

wherein $R_3$ is independently selected from the group consisting of an aliphatic or aromatic amino acid, an imidazole carboxamide or a pyrrole carboxamide or any chemical modification thereof.

"Oligonucleotide-polyamide conjugate" is a term used to describe a molecule which is comprised of an oligonucleotide chain and a polyamide chain joined by a covalent linkage.

"Protein-polyamide conjugate" is a term used to describe a molecule which is comprised of a protein chain and a polyamide chain joined by a covalent linkage.

"Nucleoside" means either a deoxyribonucleoside or a ribonucleoside or any chemical modifications thereof. Modifications of the nucleosides include, but are not limited to, 2'-position ribose modifications, 5-position pyrimidine modifications, 8-position purine modifications, modifications at cytosine exocyclic amines and the like.

A "failure sequence" refers to a polyamide chain which has not reacted with the pyrrole/imidazole monomer or dimer during a particular reaction cycle.

The solid phase polyamide synthesis protocols of this invention were modified from the in situ neutralization. Boc-chemistry recently reported by Kent and coworkers (Schnolzer et al. (1992) Int. J. Peptide Protein Res. 40:180–193; Milton et al. (1992) Science 252:1445–1448). In its most basic form the method of preparing imidazole and pyrrole carboxamide polyamides according to the present invention may be defined by the following series of steps: (1) The solid support, preferably a polystyrene resin, is prepared. The polystyrene resin is prepared by reaction with a linker molecule to enable facile attachment and removal of the polyamide. In one embodiment a spacer molecule is attached to the polyamide prior to attachment of the linker molecule. (2) The appropriate amino acid (aa) monomer or dimer is then protected at the amino (2) group and activated at the carboxylic acid (COOH) group. The amino ($NH_2$) group is protected with a Boc-group an Fmoc-group and the carboxylic acid is activated by the formation of the -OBt ester, to give, in the case of the pyrrole and imidazole amino acids Boc-pyrrole-OBt (9), Boc-imidazole-OBt (13), Fmoc-pyrrole-OBt (21a) and Fmoc-imidazole-OBt (21b). (3) The protected and activated amino acids are then sequentially added to the solid support beginning with the carboxy terminal amino acid. High concentrations of activated monomer results in fast coupling reactions and in situ neutralization chemistry assures that the unstable deprotonated amine is generated simultaneous with the initiation of a coupling reaction. Coupling times are rapid, generally 72 minutes per residue, and simple, requiring no special precautions beyond those required for ordinary solid phase peptide synthesis. (4) When the desired polyamide has been prepared the amino acids are deprotected and the peptide is cleaved from the resin and purified. The reactions are periodically monitored using picric acid titration and high pressure liquid chromatography (HPLC). Each of these steps are described in detail below. The synthesis of ImPyPyPyPyPy-G-ED (G=glycine, ED=ethylenediamine) 1a, ImPyPyPyPyPyPy-G-Dp (Dp=dimethylaminopropylamine) 1b, ImPyPyPyPyPyPy-G-Ta (Ta=3,3'-diamino-N-methylpropylamine) 1c. ImPyPyPyPyPyPy-G-Ta-EDTA (EDTA=ethylenediaminetetraacetic acid) 1d, ImPyPy-G-PyPyPy-G-ED 2a, ImPyPy-G-PyPyPy-Dp 2b, AcImPyPy-G-PyPyPy-G-Dp (Ac=acyl) 2c, AcImPyPy-G-PyPyPy-G-Ta-EDTA 2d, AcImPyPy-γ-PyPyPy-G-Dp 3a, AcImPyPy-γ-PyPyPy-G-Ta 3b, AcImPyPy-γ-PyPyPy-G-EDTA 3c, AcImImPy-γ-PyPyPy-G-Dp 4a, AcImImPy-γ-PyPyPy-G-Ta 4b, AcImImPy-γ-PyPyPy-G-EDTA 4c, AcPyPyPy-γ-ImImPy-G-Dp 5a, AcPyPyPy-γ-ImImPy-G-Ta 5b, and AcPyPyPy-γ-ImImPy-G-Ta-EDTA 5c (FIG. 7) is described herein. A complete list of illustrative polyamides synthesized by the methods of this invention is set forth in Table 1. All compounds listed in this table have been characterized by $^1$H NMR, HPLC, MALDI-TOF mass spectroscopy and in some cases $^{13}$C NMR.

The pyrrole and imidazole polyamides of this invention are contemplated for use as antiviral, antibacterial and antitumor compounds which recognize double stranded DNA by interaction with the minor groove of the DNA. Specifically, it is anticipated that the pyrrole and imidazole polyamides may be used to sequence DNA ligands which are able to specifically inhibit DNA binding proteins, such as transcription factors which are responsible for gene regulation, thus, providing a basis for rapid rational design of therapeutic compounds. The ethylenediaminetetraacetic acid (EDTA) derivatives of the polyamides synthesized by the method of this invention are also contemplated for use in the field of molecular biology. These molecules can be used to bind and cleave double stranded DNA at a specific site using iron (Fe) and EDTA.

It is further contemplated that the novel N-substituted pyrrole monomers of this invention will provide polyamides with novel DNA binding properties, with enhanced pharmacological properties, or provide, functionalized polyamides for synthesis of modified derivatives.

In its most basic form the method of preparing imidazole and pyrrole polyamide-oligonucleotide conjugates according to the present invention may be defined by the following series of steps: (1) The oligonucleotide is assembled on a solid support using standard methodology. (2) The appropriate amino acid monomer is then protected and activated. The amino group is protected with the Boc- or Fmoc-group and the aromatic acid is activated by the formation of the -OBt ester, to give, in the case of the pyrrole and imidazole amino acids. Boc-pyrrole-OBt (9) and Boc-imidazole-OBt (13) Fmoc-pyrrole-OBt (21a) and Fmoc-imidazole-OBt (21b). (3) The protected and activated amino acids are then sequentially added to the assembled oligonucleotide beginning with the carboxyterminal amino acid. As stated above, high concentrations of activated monomer results in fast coupling reactions and in situ neutralization chemistry assures that the unstable deprotonated amine is generated simultaneous with the initiation of a coupling reaction. Coupling times are rapid, generally 72, minutes per residue, and simple, requiring no special precautions beyond those required for ordinary solid phase peptide synthesis. (4) When the desired polyamide has been prepared the amino acids are deprotected and the polyamide-conjugate is cleaved from the resin.

The pyrrole and imidazole polyamide-oligonucleotide conjugates of this invention are contemplated for use as potential antiviral compounds which recognize double stranded DNA by triple helix formation. Many DNA-binding proteins bind in the major groove of DNA. It is anticipated that polyamide-oligonucleotide conjugates may be more effective inhibitors of sequence specific DNA binding proteins, since they will occlude both the major and minor grooves.

In its most basic form the method of preparing imidazole and pyrrole polyamide-protein conjugates according to the present invention may be defined by the following series of steps: (1) The protein is assembled using standard methodology; (2) The appropriate amino acid monomer is then protected and activated as discussed above. (3) The protected and activated amino acid monomers are then sequentially added to the assembled protein beginning with the carboxyterminal amino acid. (4) When the desired polyamide has been prepared the amino acids are deprotected and the polyamide-conjugate is cleaved from the resin.

The pyrrole and imidazole polyamide-protein conjugates of this invention are contemplated for use as potential antiviral, antibacterial and antitumor compounds which recognize double stranded DNA by interaction with the minor groove of DNA. Many DNA-binding proteins bind in the major groove of DNA. It is anticipated that the appended peptide moiety will provide a means for introducing the polyamide into the cell.

Synthesis of the Imidazole and Pyrrole Amino Acid Monomers. The Boc-pyrrole-OBt (Boc-Py-OBt) (9) and Boc-imidazole-OBt (Boc-Im-OBt) (13) monomers are synthesized using a modified procedure of Grehn and coworkers (Grehn and Ragnarsson (1991) J. Org. Chem. 46:3492–3497; Grehn et al. (1990) Acta. Chem. Scand. 44:67–74) (Example 1 and Scheme 9). The modification involves the use of the commercially available Boc-anhydride (di-t-butyl-dicarbonate) as the Bocing agent, rather than the highly reactive Bocing agent, tert-butyloxycarbonyl fluoride (Boc-fluoride) employed by Grehn. Boc-fluoride is dangerous to prepare in large quantities, requiring the use of chlorofluorophosgene which is very toxic. Additionally, Boc-fluoride is not stable for storage (Wackerle and Ugi (1975) Synthesis 598–599; Franzen and Ragnarsson (1979) Acta. Chem. Scand. 33:690–692; Dang and Olofson (1990) J. Org. Chem. 55:1847–1851). The reaction of Boc-anhydride with the pyrrole amino group has been reported by Bailey et al. (1989) J. Pharm. Sci. 78: 910–917. Overall yields starting from the nitro/methyl esters are reproducibly greater than 60% for both the pyrrole and imidazole -OBt esters, with simple purification requiring no column chromatography. Additionally, the Boc-imidazole-OBt ester prepared by this procedure is stable at room temperature.

The Fmoc-protected monomers are synthesized from the Boc-protected monomers as illustrated in Scheme 12 (Example 1). Fmoc- is an alternate protecting group commonly used for peptide synthesis. Fmoc- is removed with dilute base, whereas the Boc-group is removed under acidic conditions. The use of Fmoc- as a protecting group provides additional versatility to the method of this invention.

Boc-pyrrole monomers substituted at the N-methyl position having the following general formula:

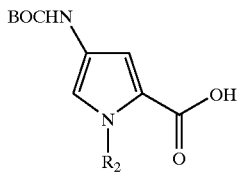

where $R_2$ is independently selected from the group consisting of H, C1–C10 alkyl, such as methyl, ethyl or isopentyl, a 1° or 2° amine, such as N, N, dimethylpropylamine, ethylamine, a carboxylic acid, such as —$CH_2$—COOH, an alkenyl, or an alkynyl, such as —≡—$CH_3$ are prepared as illustrated in Scheme 1. As stated above, it is believed that such compounds will provide polyamides with enhanced pharmacological properties. A general method for the preparation of these compounds is as follows:

Scheme 1

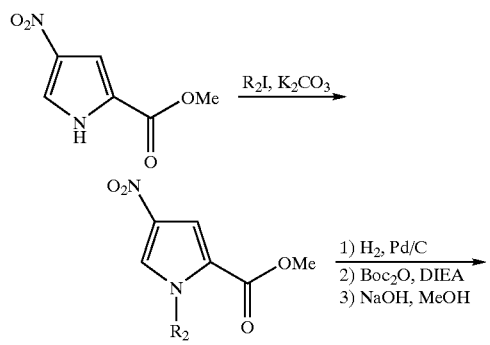

-continued

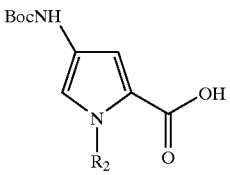

(See Example 1, Scheme 13).

Pyrrole monomers substituted at the 3 position of the pyrrole ring having the following general formula:

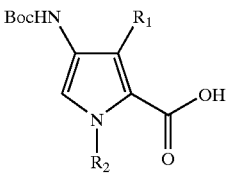

wherein $R_1$ is independently selected from the group consisting of a C1–C10 alkyl group, such as —$CH_3$, or an —OH, —$NH_2$, or —$OR_4$, wherein $R_1$ is a C1–C10 alkyl group, such as methyl or allyl and $R_2$ is independently selected from the group consisting of H, C1–C10 alkyl, such as methyl, ethyl or isopentyl, a 1° or 2° amine, such as N, N, dimethylpropylamine, ethylamine, a carboxylic acid, such as —$CH_2$—COOH, an alkenyl, or an alkynyl, such as —≡—$CH_3$, were synthesized as discussed in Example 1 (Schemes 14 and 15). Such compounds are of interest because they allow substitution of a proton which is known by structural studies to be tightly associated in the floor of the minor groove (see FIG. 4). As discussed below, monomers substituted at the 3 position of the pyrrole ring will likely provide polyamides with novel DNA binding properties.

While studying polyamide DNA complexes, it was discovered that the recognition of a GC base pair by the combination of a pyrrole carboxamide opposite a pyrrole carboxamide is a potential mismatch. (FIG. 4C) (Mirksich et al. (1994) J. Am. Chem. Soc. 116:6873–7988). A polyamide prepared using a pyrrole monomer substituted at the 3 position with an alkyl, group, therefore, will likely introduce a steric clash when pyrrole carboxamide pyrrole carboxamide binds opposite GC. (FIG. 4D). A,T recognition by the methyl derivative will not be greatly inhibited. (FIG. 4B). A general method for the preparation of a pyrrole with an alkyl substituent in the 3 position is set forth in Example 1 (Scheme 14).

Substituted monomers in which $R_1$ is —OH or —$NH_2$ may be used to introduce a specific hydrogen bond interaction between the —OH or —$NH_2$ group of the pyrrole and the carbonyl of thymine, which is capable of forming bifurcated hydrogen bonds, and should be able to hydrogen bond to both a pyrrole carboxamide and the substituted pyrrole. Adenine, on the other hand, will not be able to form this additional hydrogen bond, since it has only a single lone pair electron which is already hydrogen bonded to a Pyrrole carboxamide. (See FIGS. 5 and 6). A general method for the preparation of a pyrrole with a hydroxy or alkoxy substituent in the 3 position of the ring is set forth in Example 1 (Scheme 15).

Synthesis of Resin Linkage Agents. For solid phase synthesis, the growing polymer chain must be attached to the insoluble matrix by a linkage agent which is stable for the course of the synthesis, but cleaved in high yields under appropriate conditions to release the synthesized polymer. A number of resin linkages were investigated. Of these, Merrifield's PAM (tert-butyloxycarbonylaminoacyl-pyrrole-4-(oxymethyl)phenyl-acetamidomethyl resin (Boc-Py-PAM-resin), synthesized as described below, is the preferred solid support because it is stable to trifluoroacetic acid (TFA) and because it can be cleaved from the resin under a variety conditions including, liquid hydrogen fluoride, aminolysis, hydrolysis, hydrazinolysis, catalytic hydrogenation, or lithium borohydride to give a peptide acid, amide, hydrazide, or primary alcohol, as discussed above. Two resin linkage agents, compounds 39 and 40 were employed. These compounds were prepared in three steps according to the published procedures of Merrifield, using the Boc-protected pyrrole amino acid, Boc-Py-COOH (8) (Mitchell et al. (1978) J. Org. Chem. 43:2845–2852) (Example 3, Scheme 16).

reactions were preferably stopped at 0.2 to 0.3 mmol/gram substitution as determined by the quantitative ninhydrin test and by picric acid titration (Sarin et al. (1981) Anal. Biochem. 117:147–157; Gisin (1972) Anal. Chim. Acta. 58:248).

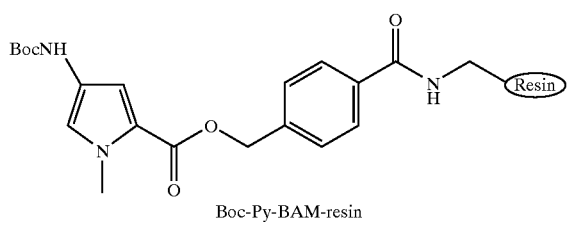

(41)

Boc-Py-BAM-resin

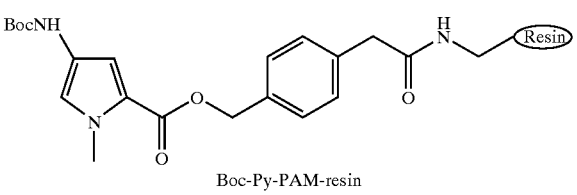

(42)

Boc-Py-PAM-resin

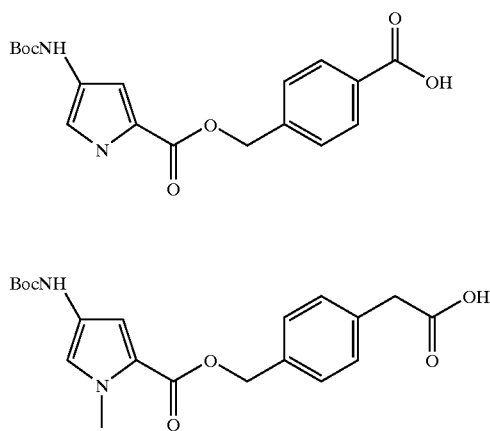

(39)

(40)

Activated resin linkage agents 39 and 40 were also reacted with the commercially available Boc-glycine-PAM-resin (Boc-G-PAM-resin) to give Boc-pyrrole-PAM-G-PAM-resin (Boc-Py-PAM-G-PAM-resin) and the corresponding BAM resin. Finally, the commercially available Boc-G-PAM-resin and Boc-β-alanine-PAM-resin (Boc-β-PAM-resin) were reacted with Boc-Pyrrole-OBt (9) to yield the Boc-pyrrole-G-PAM-resin (43) (see Scheme 2, step a) and the Boc-pyrrole-β-PAM-resin (44), respectively. Unreacted amino groups were capped by acetylation.

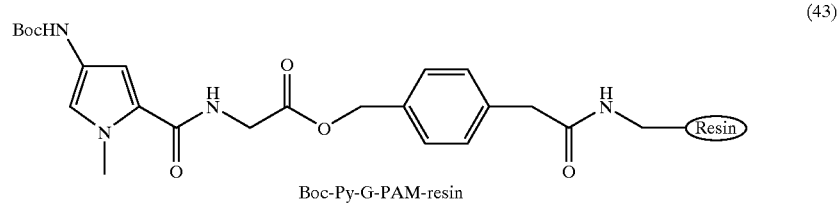

(43)

Boc-Py-G-PAM-resin

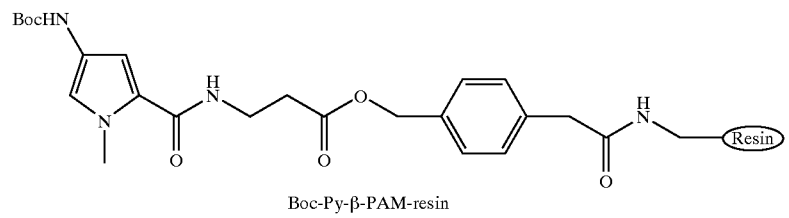

(44)

Boc-Py-β-PAM-resin

To attach the resin linkage agents to the resin, compounds 39 and 40 were activated with dicyclohexylcarbodiimide (DCC) followed by reaction with aminomethylated polystyrene for 24 hours to give Boc-pyrrole-BAM-resin 41 and Boc-pyrrole-PAM-resin 42, respectively (Example 3). The The corresponding Boc-imidazole-G-PAM and Boc-imidazole-β-PAM-resins were synthesized using the same procedure.

Solid Phase Polyamide Synthesis Protocols. The solid phase peptide synthesis (SPPS) methods of this invention were modified from the in sites neutralization chemistry described by Kent and coworkers. (Schnolzer et al. (1992) Int. J. Peptide Protein Res. 40:180–193; Milton et al. (1992) Science 252:1445–1448). One embodiment for the synthesis of polyamides according to the method of this invention is listed in Table 2 and shown schematically in FIG. 8. (See Example 4). The Boc-protected monomers are used in Example 4 for purposes of illustration. The methods illustrated are readily extendable to the Fmoc-protected monomers.

The method consists of washing either the Boc-pyrrole-PAM/BAM-resins (41 and 42), or the Boc-pyrrole-G-PAM (43)/Boc-pyrrole-β-PAM (44) resins or the corresponding Boc-imidazole resins with dichloromethane followed by the removal of the Boc-group with 65% trifluoroacetic acid (TFA)/35% dichloromethane/0.5M thiophenol for 20 minutes. The deprotected resin is then washed with dichloromethane followed by dimethylformamide (DMF). A sample of the resin can be analyzed at this time using the picric acid test, as described below. After deprotection of the resin, an -OBt activated amino acid monomer and diisopropylethylamine are added to the resin and the reaction is allowed to proceed for 45 minutes. After 45 minutes a sample is taken for analysis and the resin is washed with DMF. The overall stepwise assembly of a single residue takes approximately 72 minutes under the standard conditions.

The coupling of the -OBt ester of Boc-pyrrole to the imidazole amine on the solid support was found to be slow using the above procedure. In a preferred embodiment of the invention, the pyrrole monomer was activated as the symmetric anhydride, rather than the -OBt ester, using a modified procedure of Ding et al. (1963) Acta Chem. Scand. 23:751. Ding describes the solution phase coupling of pyrrole to pyrazole by formation of the symmetric anhydride of the pyrrole monomer (DCC and DMAP in dichloromethane) prior to coupling. This procedure was modified for use on a solid support and provides a rapid and effective method for the coupling of pyrrole to imidazole. This modified procedure, which is described in Example 5, provides a high yielding rapid reaction. Coupling yields were found to be greater than 98% for the synthesis of the polyamide AcPyImPy-G-Dp.

In developing a method for the solid phase synthesis of polyamides, it was anticipated that intermolecular chain aggregation could be a severe problem, with the adjacent extended aromatic polyamide providing excellent surface areas for stacking. To minimize the possibility of aggregation, a low substitution resin, 0.2 mmol or 0.3 mmol per gram, is used in combination with in situ neutralization. The high coupling yields (>99% in most cases), indicate that intermolecular interactions are not a problem under these conditions. In situ neutralization has also been found to increase the lifetime of the aromatic amines.

In situ neutralization involves the elimination of a separate neutralization step by adding diisopropylethylamine (DIEA) simultaneously with the activated monomer. In standard solid phase peptide synthesis it has been demonstrated by direct physical measurement that intermolecular aggregation of the growing peptide chain is disrupted by TFA, which is an excellent solvent for most peptides, the aggregates reform, however, during the subsequent neutralization of the amine trifluoroacetate (Larsen et al. (1990) Peptides 183–185; Woerkom and Nipsen (1991) Int. J. Pep. Prot. Res. 38: 103–113; Milton et al. (1990) J. Am. Chem. Soc. 112:6039–6046). By adding the monomer simultaneously with neutralizing agent, coupling is able to occur before an aggregate can form. In situ neutralization was adopted by Kent and coworkers to eliminate low coupling yields resulting from intermolecular aggregation in Boc-chemistry SPPS. (Larson et al. (1990) Peptides 183–185; Hudson (1988) J. Org. Chem. 53:617–624; Woerkom and Nipson (1991) Int. J. Pep. Prot. Res. 38:103–113).

In the standard in situ neutralization procedure DMF is used as the solvent, because it maximizes the solvation of the growing peptide chain. Because the mixing of DMF and TFA is very exothermic the standard procedure of Kent is modified by addition of the steps of washing the resin with dichloromethane both before and after treatment with TFA. Thiophenol is also added in the TFA deprotection step as a scavenger for the t-butyl cation. This is necessitated by the potential for side reactions between the t-butyl cation and the unprotected imidazole nitrogen, which has been reported to be nucleophilic in solution phase reactions. (Grehn and Ragnarsson (1981) J. Org. Chem. 46:3492–3497; Grehn et al. (1990) Acta. Chem. Scand. 44:67–74). Thiophenol, methyl ethyl sulfide, and ethanedithiol have all been reported to compete effectively as scavengers of t-butyl cation. (Lundt et al (1978) Int. J. Pep. Prot. Res. 12:258–268).

Monitoring the Progress of the Synthesis. In standard SPPS, the quantitative ninhydrin test is the preferred method of monitoring the coupling reactions and calculating yields. (Sarin et al. (1981) Anal. Biochem. 117:147–25 157; Gisin (1972) Anal. Chim. Acta. 58:248). The aromatic amines of pyrrole and imidazole, however, do not react in the quantitative ninhydrin test. In place of the ninhydrin test, picric acid titration and stepwise cleavage and monitoring by HPLC are used to estimate coupling yields and monitor the course of the reactions. In the few cases where it is possible to use the quantitative ninhydrin test, such as the coupling of Boc-Py-OBt to $N_2H$-γ or $H_2N$-G, all yields have been observed to be better than 99.8%.

Picric acid titration measures the amount of unreacted amine remaining. The method involves formation of the picrate salt of the amine, which is then quantitated from the reported extinction coefficients. The experimental procedure is set forth in Example 6. The picric acid test is inaccurate for low concentrations of amine, thus it is only possible to determine if a reaction is >90% complete using this measurement. Picric acid titration is useful for immediate monitoring of coupling reactions.

High pressure liquid chromatography (HPLC) is used for the stepwise monitoring of the polyamide synthesis. After each coupling reaction a small portion of resin is removed from the reaction mixture and the polyamide is cleaved from the resin and analyzed by analytical HPLC, as described in Example 7. The use of stepwise HPLC analysis is an effective way to obtain detailed information on the progress of a synthesis, allowing the exact step that results in a side reaction or deletion product to be readily identified and eliminated.

Cleavage of the Polyamide from the Boc-pyrrole-resin. Example 8 describes a general method for cleaving the polyamide from the Boc-Py-PAM/BAM-resins using Pd(OAc)$_2$. The successful cleavage of minor groove polyamides is achieved from PAM and BAM pyrrole resins with Pd(OAc)$_2$ in DMF under a pressurized atmosphere of hydrogen (100 psi, 8 hours). Scheme 17 (Example 8) illustrates this procedure with the acetylated tripyrrole AcPyPyPy-PAM-resin. Upon being cleaved from the resin the terminal pyrrole acid can be activated with DCC/hydroxybenzotriazole (HOBt) and reacted with a primary amine to yield the corresponding amide.

Cleavage from PAM and BAM resins by amminolysis was unsuccessful at 37° C. and 60° C. in 1:1 amine:DMF or neat amine for 24 hours.

Cleavage of the Polyamide from the Boc-G-PAM-Resin. Example 9 describes a general method for the cleavage of the polyamide from the Boc-G-PAM-resin using a 1:1 mixture of dimethylaminopropylamine:DMF. Scheme 18 (Example 9) illustrates this method with the acetylated tripyrrole AcPyPyPy-PAM-G-PAM-resin. After reaction with a 1:1 mixture of dimethylaminopropylamine:DMF at 37° C. for 12 hours, two products AcPyPyPy-PAM-G-Dp (98% of product) and the failure sequence AcPyPy-PAM-G-Dp (2%) were identified by $^1$H NMR. Recovery of the product was very high—almost 50% of the theoretical yield—indicating that the pyrrole-G-PAM-resin is cleaved with much higher recovery than the pyrrole-PAM-resin.

Based on the excellent recovery of acetylated tripyrrole under chemically mild conditions, the use of a glycine spacer is the preferred synthetic method. This method offers two advantages, high cleavage yields from the resin and commercial availability of highly pure Boc-G-PAM-resin with 0.2 mmol/gram substitution.

Purification and Characterization of Peptides. Reversed phase HPLC purification provides a convenient and efficient method for the purification of the solid phase peptide products (Fransson et al. (1983) J. Chrom. 268:347–351). Amminolysis reactions are filtered to remove the resin, diluted with water and immediately purified by reversed phase HPLC with a gradient of 0.15% CH$_3$CN/min. in 0.1% wt./v. TFA. A single preparatory run is sufficient to obtain purity greater than 98% as determined by a combination of HPLC, $^1$H NMR and mass spectroscopy. $^1$H NMR is carried out in the non-exchangeable solvent d$_6$-DMSO, making all amide hydrogens and the trifluoroacetamide protons clearly visible. 2-D COSY experiments are used to assist in the assignment of protons. MALDI-TOF mass spectroscopy provides an accurate and rapid method of confirming that full length product has been isolated.

Scheme 2 illustrates a representative solid phase synthetic scheme for the polyamide AcImImPy-γ-PyPyPy-G-Dp (Dp= dimethylaminopropylamine) (4a) starting from the commercially available Boc-G-PAM-resin. The polyamide was synthesized with 7 standard synthesis cycles and the final product was acetylated. The synthesis was monitored by analytical HPLC as illustrated in FIGS. 9A–9C. FIG. 9A, which depicts the spectrum of Boc-Py-γ-PyPyPy-G-Dp, shows that the synthesis has proceeded after five reaction cycles with a major peak eluting at 31.6 minutes observed. The Boc-group is removed under standard conditions to give upon cleavage of a small sample H$_2$N-Py-γ-PyPyPy-G-PAM-resin which elutes at 24.3 minutes (FIG. 9B). The pyrrole amine is reacted with 4 equivalents of Boc-Im-OBt under standard conditions, giving a quantitative conversion to Boc-ImPy-γ-PyPyPy-G-PAM-resin which is observed upon cleavage with dimethylaminopropylamine to elute at 31.8 minutes (FIG. 9C). All coupling reactions proceeded in greater than 90% yield as determined by picric acid titration. The coupling of pyrrole to γ-aminobutyric acid (γ) and glycine proceeded in 99.9% yield as determined by the quantitative ninhydrin test. All yields are established as >99% by HPLC analysis of each individual coupling step. Monitoring each individual step before and after deprotection assures that high yields are being obtained. Upon completion of the synthesis, the resin is cleaved by amminolysis with a 1:1 mixture of DMF and N,N-dimethylaminopropylamine at 37° C. for 12 hours. After 12 hours the reaction mixture is filtered to remove the resin, diluted with 4 volumes water and immediately purified by reversed phase HPLC with a gradient of 0.15% CH$_3$CN/min. in 0.1% wt/v TFA. A single preparatory scale separation is sufficient to obtain purity, greater than 98% as determined by a combination of HPLC, $^1$H NMR and mass spectroscopy.

The HPLC, MS and $^1$H NMR spectra of the purified product are shown in FIGS. 10A–10C respectively. As can be seen in the $^1$H NMR spectrum (FIG. 10C) only the expected protons are observed, from high field to low field, 2 imidazole, carboxamide protons, four pyrrole carboxamide protons, a trifluoroacetate proton (the tertiary amine is obtained as the trifluoroacetate salt after HPLC purification in 0.1% TFA. and the trifluoroacetate proton is identified by 2-D COSY experiments), the three amides corresponding to the aliphatic amines, two imidazole ring protons (singlets) and 8 pyrrole ring protons are observed as either doublets or multiplets. MALDI-TOF mass spectroscopy (FIG. 10B) provides an accurate and rapid method of confirming that full length product has been isolated and that side reactions such as alkylation or acylation of the unprotected imidazole nitrogen have not occurred. A combination of analyses ensures that pure full length peptide has been obtained in high purity.

SCHEME 2

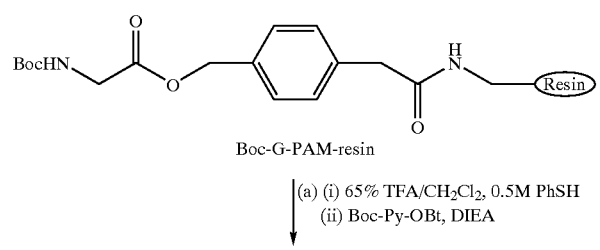

Boc-G-PAM-resin (a) (i) 65% TFA/CH$_2$Cl$_2$, 0.5M PhSH
    (ii) Boc-Py-OBt, DIEA -continued

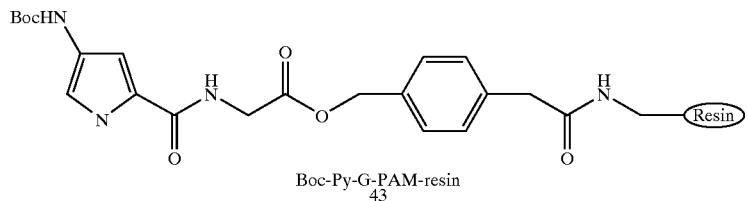

Boc-Py-G-PAM-resin
43

(b) (i) 65% TFA/CH$_2$Cl$_2$, 0.5M PhSH
 (ii) BocPy-OBt, DIEA
 (iii) 65% TFA/CH$_2$Cl$_2$, 0.5M PhSH
 (iv) BocPy-OBt, DIEA
 (v) 65% TFA/CH$_2$Cl$_2$, 0.5M PhSH
 (vi) Boc-γ-OBt(activated in situ), DIEA
 (vii) 65% TFA/CH$_2$Cl$_2$, 0.5M PhSH (viii) BocPy-OBt, DIEA
 (ix) 65% TFA/CH$_2$Cl$_2$, 0.5M PhSH
 (x) BocIm-OBt, DIEA
 (xi) 65% TFA/CH$_2$Cl$_2$, 0.5M PhSH
 (xii) BocIm-OBt, DIEA
 (xiii) 65% TFA/CH$_2$Cl$_2$, 0.5M PhSH
 (xiv) Ac$_2$O, DIEA

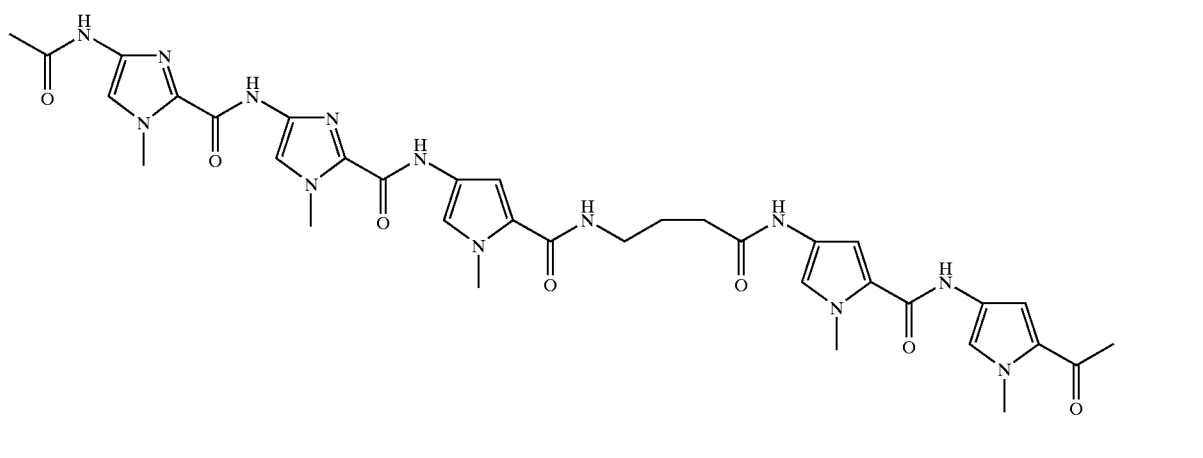

(c) (i) 1:1 N, N-dimethylaminopropylamine DMF
 (ii) HPLC purification

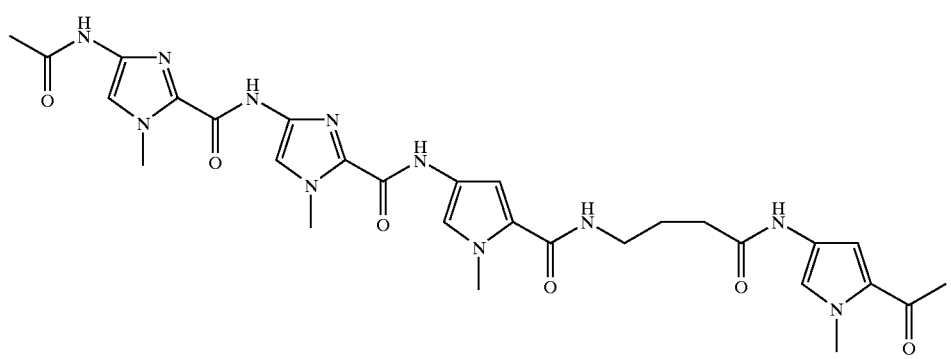

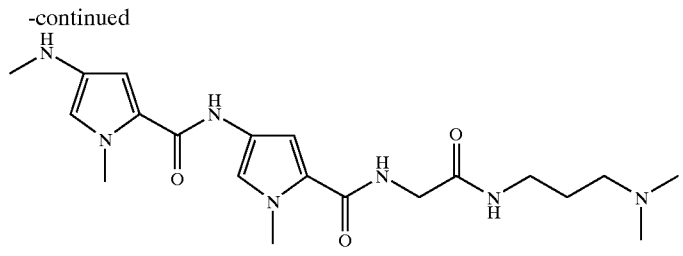

(4a)
AcImlmPy-γ-PyPyPy-G-Dp

Synthesis of Polyamide Derivatives. The methods for the synthesis of minor-groove polyamides can be readily extended to the synthesis of various derivatives. Scheme 3 illustrates the synthetic scheme for introduction of EDTA into the C-terminus of minor groove polyamides by cleavage from the resin with a symmetrical triamine followed by reaction with EDTA monoanhydride. (See Example 4).

SCHEME 3

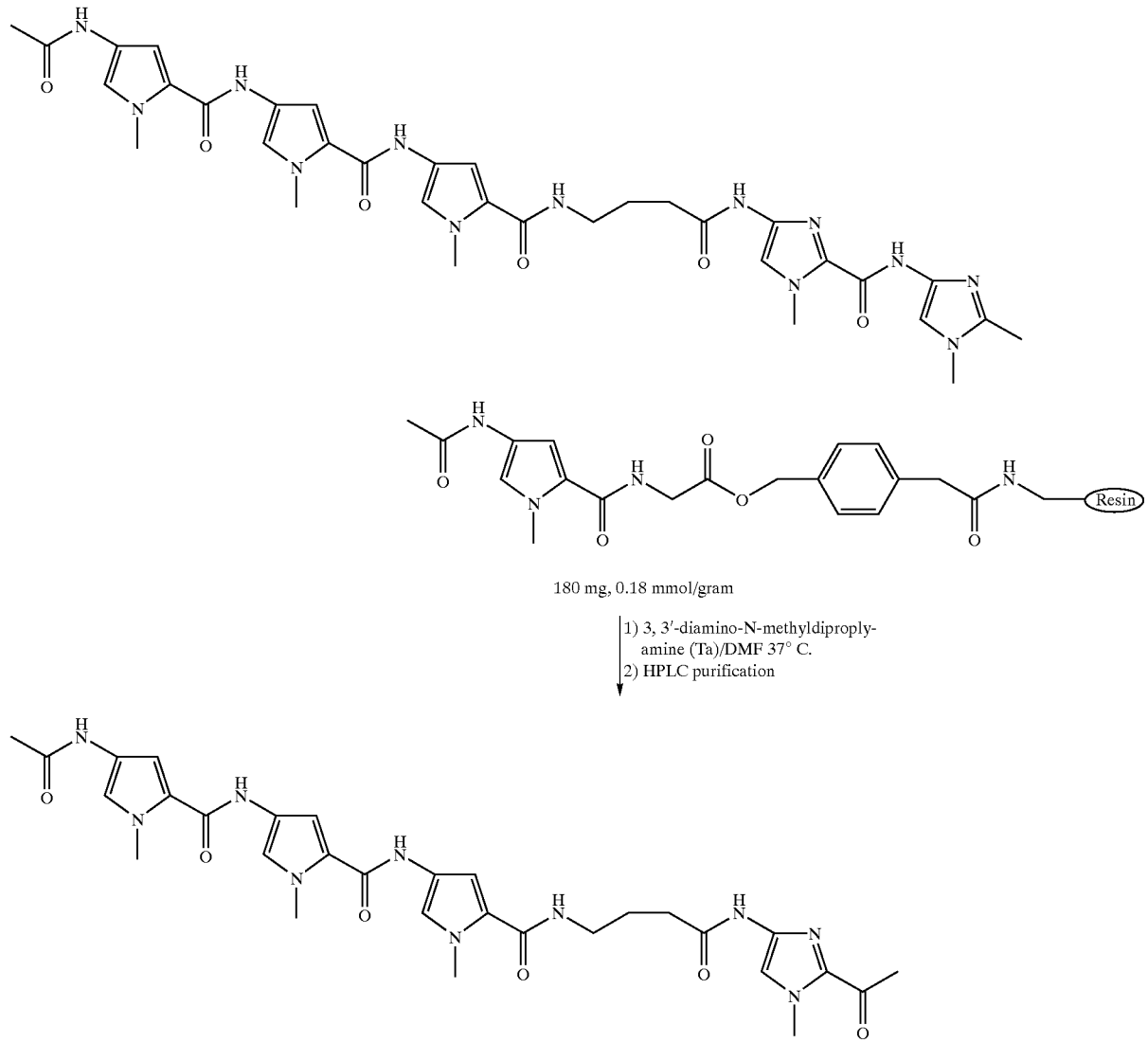

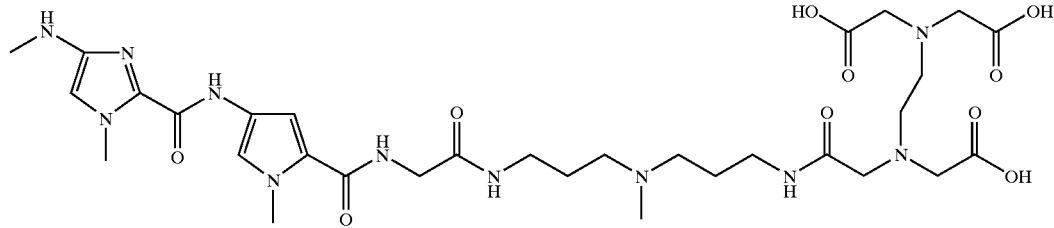

3.1 mg (37% yield)
AcPyPyPy-γ-ImImPy-G-Ta-EDTA
(5c)

C-terminus EDTA derivatized polyamides are typically recovered in approximately 30% yield after HPLC purification.

Example 4 further describes the synthesis of C-terminus dimethylaminopropylamine (Dp), ethylenediamine (ED), 3,3'-diamino-N-methylpropylamine (Ta) and β-alanine (β) derivatized polyamides. Finally, Example 4 also describes the synthesis of N-terminus EDTA derivatized polyamides using the synthesis of EDTA-γ-ImPyPy-β-PyPyPy-G-Dp as an example. Briefly, the polyamide $H_2N$-γ-ImPyPy-β-PyPyPy-G-Dp is prepared by cleavage of $H_2N$-γ-ImPyPy-β-PyPyPy-G-Resin with dimethylaminopropylamine (Dp). The primary amine is then derivatized with EDTA as described in Scheme III and isolated by preparatory HPLC.

The intermediates, containing a free primary amine, provide access to a wide number of modified minor-groove polyamides, including, but not limited to intercalators, polysaccharide conjugates, photoreactive agents and metal chelates. Furthermore, a polyamide containing a free primary amine can be reacted with an activated carboxylic acid to synthesize polyamides of increasing complexity, thiol modified polyamides, or bromoacetic acid modified polyamides. Amine modified polyamides are also useful for attachment to an appropriate support for making affinity chromatography columns. The synthetic methods outlined for Boc-protected monomers substituted at the N-methyl group, allows for the synthesis of amino modified pyrrole monomers for the addition of EDTA into any region of the polyamide.

Effect of C-terminal Glycine and C-terminal β-alanine on DNA Binding Properties: Specifically for "Slipped" Versus "Overlapped" Binding Modes.

The DNA-binding affinities of several polyamides having the core sequence ImPyPy-X-PyPyPy (X=G, β, γ, Py) to the targeted 13 bp site 5'-AAAAAGACAAAAA-3'(SEQ ID NO:2), and to the targeted 9 bp site 5'-TGTTAAACA-3' (SEQ ID NO:4) were examined by DNase I footprint titration (Galas and Schmitz (1978) Nucleic Acids Res. 5:3157–3170; Fox and Waring (1984) Nucleic Acids Res. 12:9271–9285; Brenowitz et al. (1986) Methods Enzymol. 130:132–181; Brenowitz et al. (1986) Proc. Natl. Acad Sci. U.S.A. 83:8462–8466; Senear et al. (1986) Biochemistry 25:7344–7354) (Example 10). The polyamide:DNA complexes predicted for the 13 bp and 9 bp target sites represent two distinct binding modes, referred to as "slipped" and "overlapped" (see FIG. 11). The "slipped" (13 bp) binding mode (FIG. 11A) integrates the 2:1 and 1:1 binding motifs at a single site. In this binding mode, the ImPyPy portion of two ImPyPy-X-PyPyPy polyamides bind the central 5'-AGACA-3' sequence in a 2:1 manner and the PyPyPy portion of the polyamides bind the A/T flanking sequences similar to the 1:1 complexes of Distamycin. In the "overlapped" (9 bp) binding mode (FIG. 11B), two ImPyPy-X-PyPyPy polyamides bind directly opposite one another, with the ImPyPy portion of one polyamide opposite the PyPyPy portion of the other polyamide recognizing the 5 bp subsides 5'-TGTTA-3' and 5'-AAACA-3' as in the ImPyPy-Dp/Distamycin (PyPyPy) heterodimer.

In the 13 bp "slipped" and 9 bp "overlapped" sites described above, the GC and CG base-pairs are separated by one and five A/T base-pairs, respectively. It should be noted that "partially slipped" sites of 10, 11 and 12 bp in which the GC and CG base-pairs are separated by two, three and four A/T base-pairs, respectively, are also potential binding sites of the polyamides studied here.

Affinities for polyamides differing only in the presence or absence of a C-terminal glycine residue reveals that C-terminal glycine dramatically affects the DNA-binding properties of polyamides. (See Table 3, FIG. 12.) Relative to the polyamide ImPyPy-G-PyPyPy-Dp, which binds the "slipped" site 5'-AAAAAGACAAAAA-3'(SEQ ID NO:2) and the "overlapped" site 5'-TGTTAAACA-3'(SEQ ID NO:4) (with similar affinities (approximately $1 \times 10^8$ $M^{-1}$) (FIG. 12A), polyamide ImPyPy-G-PyPyPy-G-Dp, which was previously prepared by solution methods and has a C-terminal glycine, binds these sites with approximately 1.5-fold ($7 \times 10^7$ $M^{-1}$) and 80-fold ($1.7 \times 10^6$ $M^{-1}$) lower affinities, respectively (FIG. 12B). Also, relative to ImPyPy-G-PyPyPy-Dp, ImPyPy-G-PyPyPy-G-Dp binds to the 11 bp site 5'-TGTGCTGCAAG-3'(SEQ ID NO:6) with >50-fold lower affinity (FIGS. 12A and 12B). Each data point is the average value obtained from three quantitative footprint titration experiments (Example 10). Similarly, relative to ImPyPy-β-PyPyPy-Dp, ImPyPy-β-PyPyPy-G-Dp binds 5'-AAAAAGACAAAAA-3'(SEQ ID NO:2) and 5'-TGTTAAACA-3'(SEQ ID NO:4) with approximately 1.5-fold and 10-fold lower affinities, respectively (FIGS. 12C and 12D). In both cases, C-terminal glycine confers specificity for "slipped" relative to "overlapped" complexes. In the case of ImPyPyPyPyPyPy-Dp and ImPyPyPyPyPyPy-G-Dp, the presence of a C-terminal glycine reduces the binding affinities at both the "slipped" and "overlapped" sites by factors of approximately 8 and 15, respectively (FIGS. 12G and 12H).

In contrast to ImPyPy-G-PyPyPy-Dp, ImPyPy-G-PyPyPy-β-Dp has DNA-binding affinities and specificities similar to ImPyPy-G-PyPyPy-Dp (Table 3, FIG. 12F). Modeling indicates that ImPyPy-G-PyPyPy-Dp and ImPyPy-G-PyPyPy-β-Dp have similar DNA-binding surfaces at the C-terminal end of the polyamides (FIG. 13). The disruption of "overlapped" 2:1 complexes by C-terminal glycine may result from a steric interaction between the glycine carbonyl group and the floor of the minor groove. In the "slipped" binding mode, the C-terminal part of the molecule is bound in a 1:1 manner, which is tolerant of C-terminal glycine (FIG. 14).

Rates and Efficiency of Coupling Reactions. Under the standard coupling conditions the efficiency of coupling reactions is as follows, (activated ester/free amine), Py/G≈Im/G>G/Py≈G/Im>Im/Py>Py/Py>Im/Im>Py/Im. All couplings except for Im/Im and Py/Im are >99.8% complete in 42 minutes. The faster couplings are more than 99.8% complete within 5 minutes. For the Im/Im and Py/Im couplings, extended reaction times are recommended in order to assure complete reaction. Fortunately, these couplings occur least frequently in the current synthesis of the minor groove polyamides. The Py/Py coupling is the most common and was used as the model around which the synthetic methodology was optimized. Coupling rates are estimated based on picric acid titration data and ninhydrin tests when possible. No correction was made for the change in substitution of the resin resulting from the addition of a monomer, because the effect is very small for the low substitution resins used for synthesis. The change in substitution during a specific coupling or for the entire synthesis can be calculated as $$L_{new}=L_{old}/(1+L_{old}(W_{new}-W_{old})\times 10^{-3}) \quad (1)$$

where L is the mmol of amine per gram of resin, and W is the weight (gmol$^{-1}$) of the growing polyamide attached to the resin. The subscript old, indicates a parameter before the coupling reaction, new indicates a parameter referring to the resin after a coupling reaction.

For the Py/Py, Im/Py, Py/G and G/Py couplings an attempt was made to measure rates using picric acid titration at 1 minute time intervals. The Im/Py, Py/G, and G/Py couplings all reached completion too rapidly to measure an accurate rate. For the Py/Py coupling, reasonably accurate data was obtained for monitoring the disappearance of amine. From the slope of a plot of ln (meq. amine) versus time, it is possible to estimate a rate of reaction of 0.18 h$^{-1}$ which corresponds to a 3.9 minute half life, and indicates that 25.6 minutes are required for 99% reaction, and 38.4 minutes for 99.9% reaction (FIG. 15). A 45 minute coupling time was chosen to ensure complete reaction.

Preparation of Dimeric Building Blocks. As discussed above the amine group of imidazole is less reactive than the amine group of pyrrole. When coupling aliphatic amino acids to an imidazole amine, extended coupling times or double couplings sometimes required. For the coupling of pyrrole to imidazole, a symmetrical anhydride protocol, in which, pyrrole is activated by formation of the symmetrical anhydride in the presence of DMAP (Example 5) was developed. The reaction of the activated imidazole acid is extremely rapid, with dilute solutions (<0.1 M) reacting to completion in the standard coupling time when coupling is imidazole amine, pyrrole amine and aliphatic amines. To avoid the reduced reactivity of the imidazole amine, while taking advantage of the increased reactivity of the imidazole acid a set of dimeric building blocks were prepared.

The dimeric building blocks were prepared with a series of reactions analogous to the preparation of the Boc-imidazole monomer and require no flash chromatography. Scheme 4 (Example 11) illustrates this general method with the synthesis of the Boc-γ-ImCOOH (47) and Boc-PyImCOOH (45) dimers. Both dimers can be prepared in multigram quantities without chromatography. The Boc-group is introduced to the imidazole amine with a Boc-protected -OBt activated amino acid. The resulting Boc-amino acid-imidazole-ethyl ester is isolated by precipitation from water, the ethyl group removed by alkaline hydrolysis, and the dimer is collected by filtration after acidification of the reaction mixture.

SCHEME 4

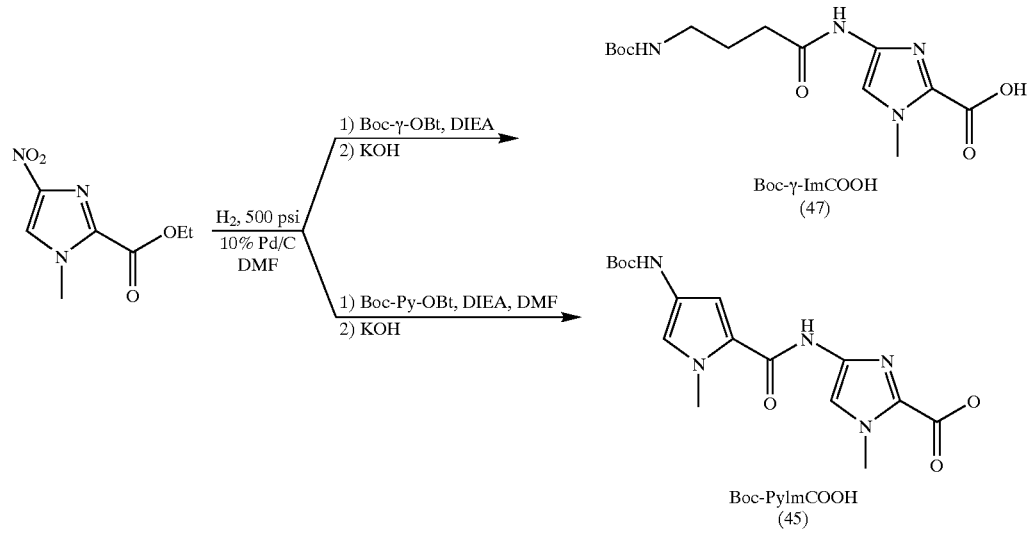

Solid Phase Synthesis of Cyclic Polyamides. Cyclic polyamides have also been found to bind to DNA. For example, the cyclic polyamide cyclo-(ImPyPy-γ-PyPyPy-γ-), which took more than a year to synthesize by solution phase methods, has been shown to bind the predicted target site 5'-WGWWW-3'(W=A or T) with high affinity and moderate specificity. (Cho et al. (1995) Proc. Natl. Ac ad. Sci. USA 92:10389). The outlined methods for the synthesis of straight chain polyamides are readily extendible to the synthesis of cyclic polyamides. Using the solid phase peptide synthesis method of this invention cyclic polyamides can be prepared in large quantities in a matter of days. A typical synthetic scheme is outlined in Scheme 5 (see Examples 12 and 13).

A key intermediate for the solid phase synthesis of cyclic polyamides is the Boc-protected allyl ester pyrrole monomer (52), in which the N-methyl group is substituted so as to allow attachment to the resin. The synthesis of this monomer is described in Example 12 (Scheme 19). Briefly, methyl 4-nitropyrrole-2-carboxylate (49) (Fanta (1966) Org. Syn. Coll. 4:844; Morgan and Morrey (1966) Tetrahedron 22:57) is reacted with benzyl-2-bromoacetate in the presence of potassium iodide and anhydrous potassium carbonate to give the nitro-diester (50) in 85% yield. The nitro group is reduced to the amine and the benzyl ester simultaneously reduced to the acid with Pd/C catalyst and $H_2$. The amine is immediately protected with boc-anhydride and purified by flash chromatography to give the Boc-protected monoacid (51). The methyl ester is then reacted with allyl alkoxide to give the desired monomer (52). The allyl group is stable to both Boc- or Fmoc-chemistry, but is easily removed on the solid support with a soluble palladium catalyst to which the benzyl ester resin linkage is stable.

Referring back to Scheme 5, a single equivalent of the Boc-protected allyl ester pyrrole monomer (52), is attached to the Glycine-PAM-resin, to provide Boc-Py(O-allyl)-G-PAM-resin (53), in high yield. Standard manual solid phase methods, as described above, are then used to assemble the polyamide, $H_2N$-γ-ImPyImPy-γ-ImPyImPy(O-allyl)-G-PAM-resin (54). The allyl group is removed with a soluble palladium catalyst to yield acid (55), which is cleaved from the resin with dimethylaminopropylamine. HPLC purification yields 105 mg of polyamide from cleavage of 0.25 mmol resin, a 45% yield. A small sample of precursor was then cyclized by treatment with diphenylphosphoryl azide (DPPA) in dilute DMF solution to yield the cyclized polyamide (57), which was purified by HPLC to yield 38% of the cyclic polyamide. Illustrative polyamides prepared by this method are set forth in Table 4.

SCHEME 5

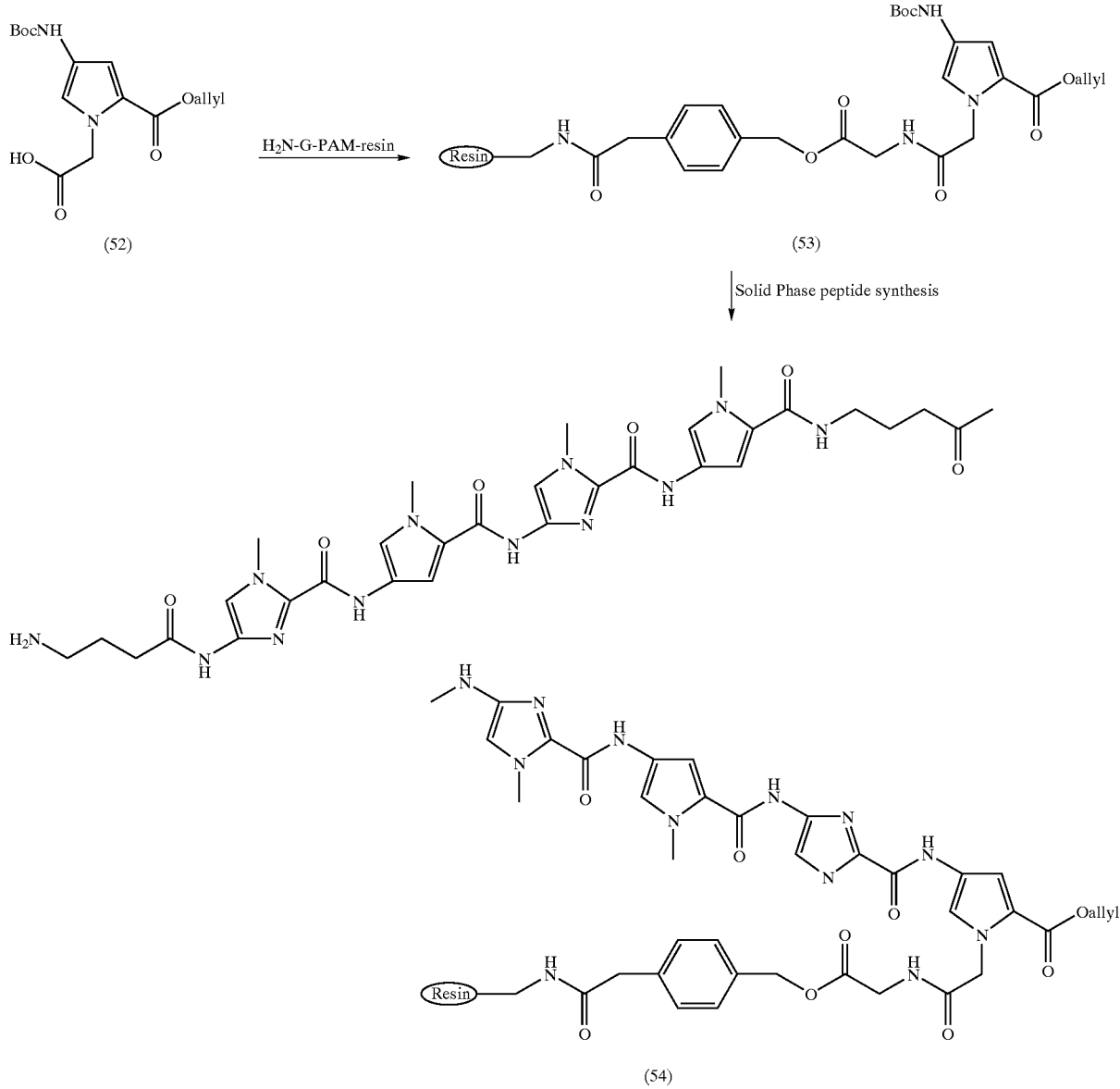

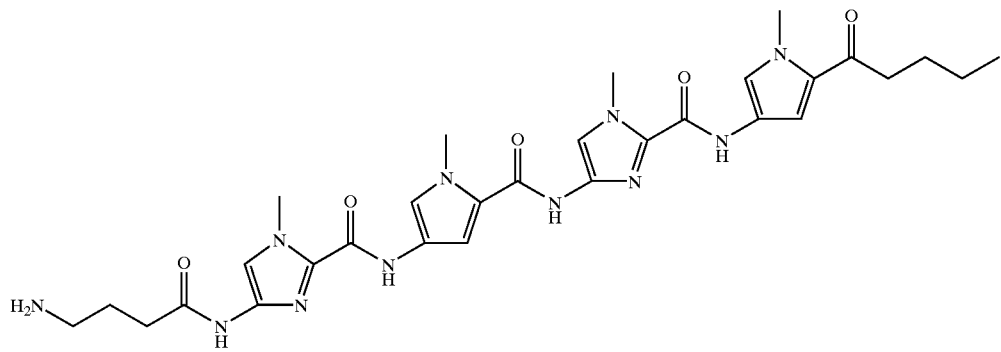
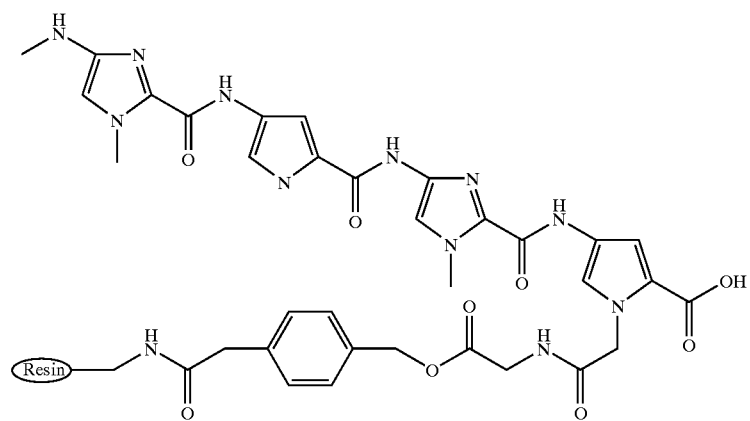
(55)
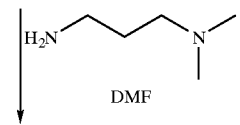
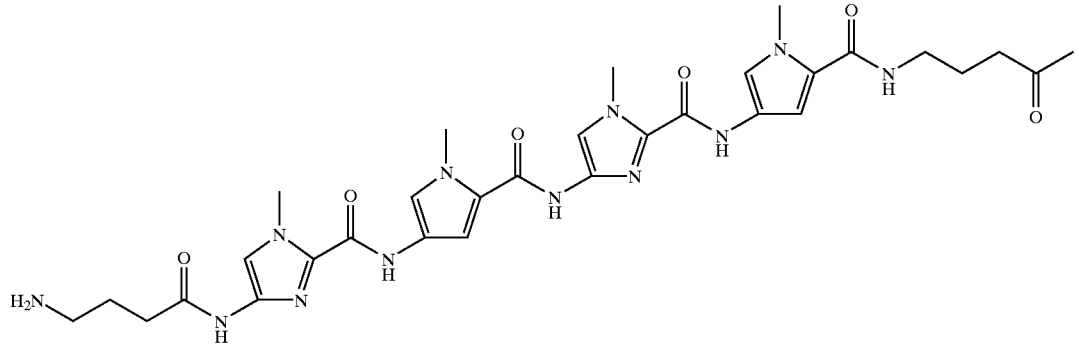

-continued

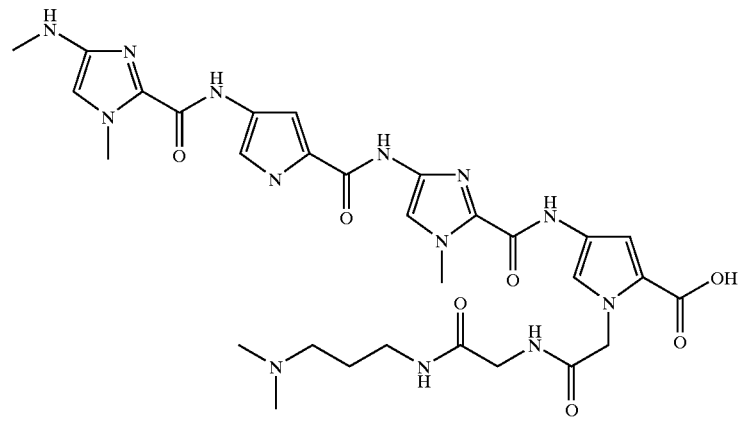

(56)

↓ DPPA, NaCO₃
  DMF

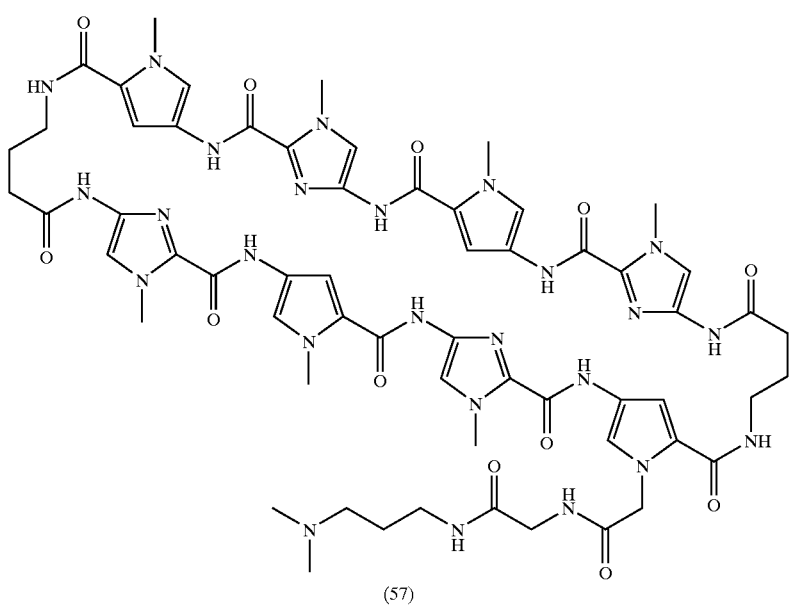

(57)

Synthesis of Oligonucleotide-minor Groove Polyamide Conjugates. The methods for the synthesis of minor-groove polyamides are also readily extendable to the synthesis of oligonucleotide-minor groove polyamide conjugates. A typical synthesis of an oligonucleotide minor-groove polyamide is outlined in Scheme 6 (see Example 13).

SCHEME 6

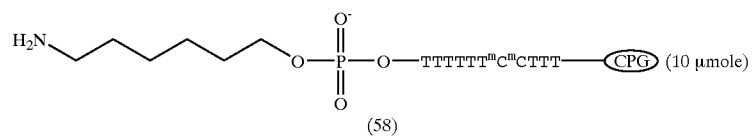

(58)

↓ Boc-Py-HOBt (0.2M), DIEA, DMF

-continued

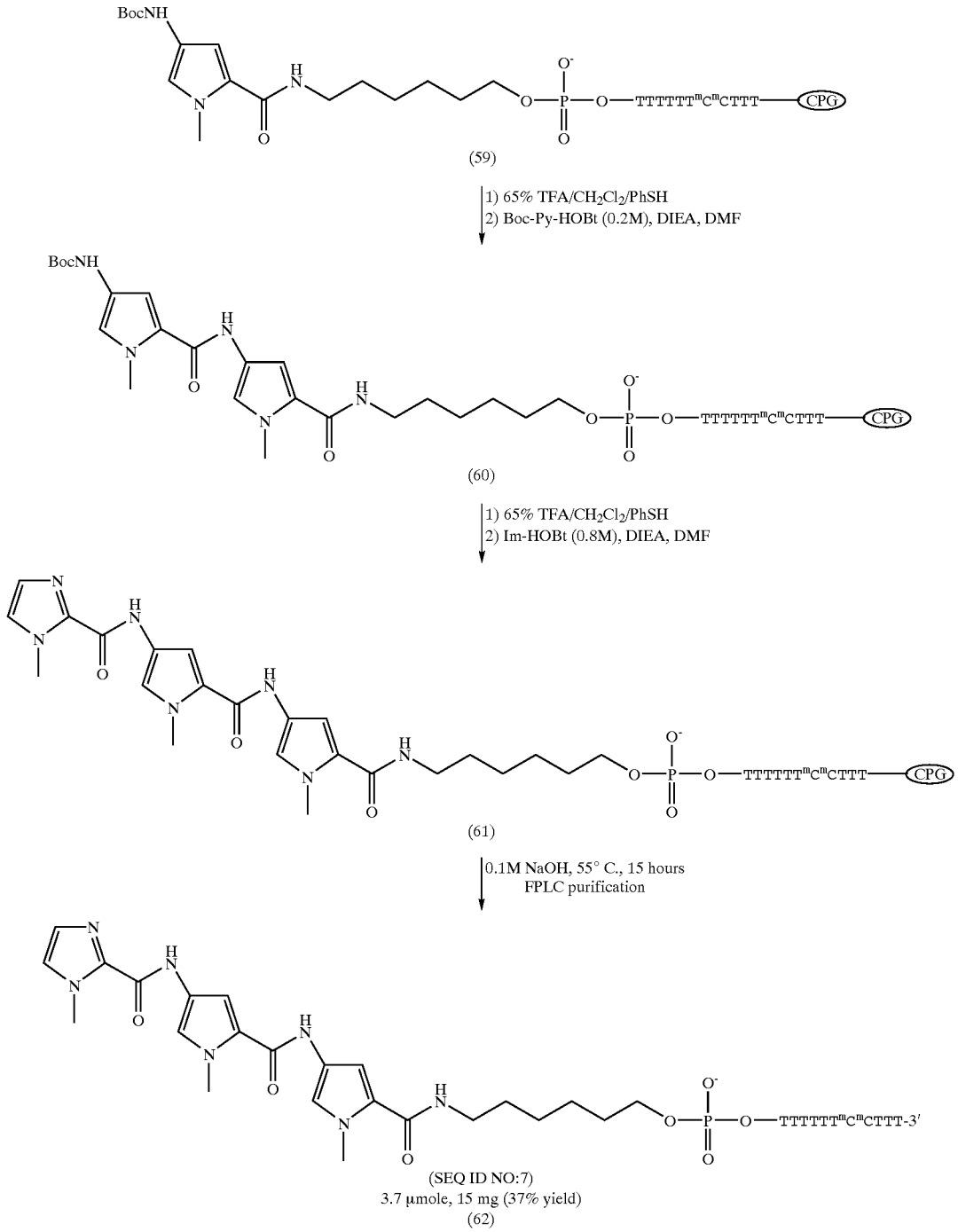

(SEQ ID NO:7)
3.7 μmole, 15 mg (37% yield)
(62)

The oligonucleotide portion of the molecule (10 μmol) was assembled on an automated DNA synthesizer using standard DNA cycles, a commercially available 5'-MMT-C6-amino modifier (MMT=monomethoxytrityl) was attached using an extended 10 minute synthesis cycle. (Connolly and Rider (1985) Nuc. Acid. Res. 13:4485 Sproat et al. (1987) Nuc. Acid. Res. 15:4837; Juby et al. (1991) Tet. Lett. 32:879–882). The MMT group was removed from the modified oligonucleotide by manual treatment with 3% trichloroacetic acid (TCA) in dichloromethane. The controlled pore glass support was then removed from the synthesis cartridge and transferred to a standard peptide synthesis reaction vessel. The oligonucleotide (58) was reacted with a 0.2 M solution of Boc-Py-OBt in DMF/0.4M DIEA for 45 minutes. The reaction was determined to be complete by the quantitative ninhydrin test, which showed a distinct blue color for the oligonucleotide-polyamide conjugate (59), consistent with a 0.05 mmol/gram loading, and a lack of a blue color after 1 hour of reaction time. The Boc-group was removed with 65% TFA $CH_2Cl_2$/0.5M PhSH for 20 minutes and a second Boc-protected pyrrole coupled to form the aromatic carboxamide (60). The Boc-group is removed with TFA and the polyamide capped with N-methylimidazole-2-carboxylic acid. The oligonucleotide-polyamide conjugate (61) was then simultaneously cleaved from the resin and deprotected by treatment with 0.1M NaOH at 55° C. for 15 hours and purified by FPLC chromatography.

A single reversed phase purification yields the polyamide conjugate, ImPyPy-CONH(CH$_2$)$_6$—P(O)$_4$TTTTTT$^m$C$^m$CTTT-3'(62)(SEQ ID NO:7) ($^m$C methylcytidine), in high purity. The product obtained is characterized by a number of techniques (data not shown). MALDI-time of flight mass spectroscopy shows a single peak corresponding to a molecular mass of 3813.5 (predicted mass of 3814.3), indicating that fill length product has been isolated. Reverse phase HPLC analysis of 10 nmoles of the conjugate, exhibits one major product, absorbing at both oligonucleotide wavelength (260) and polyamide wavelength (340). Enzymatic digestion and subsequent HPLC analysis of a 10 nmole sample of conjugate is consistent with the proposed composition of the oligonucleotide.

Ultraviolet spectroscopy indicates an additive spectra as might be expected for a conjugate of 2-imidazole Netropsin and an 11-mer thymidine rich oligonucleotide. From the extinction coefficient of the bases, 8,800 for thymidine (T) at 260 nm and 5,700 for methylcytidine (MeC) at 260 nm and the reported extinction coefficients for 2-ImN of 19,000 (255 nm) and 26,000 (302 nm), it is possible to predict the ratio of the extinction coefficients at 260 nm. (Colocci et al. (1993) J. Am. Chem. Soc. 115:4468–4473). Assuming a contribution from the oligo of 90,600 and from the polyamide of 19,000, a ratio of 4.2 is expected and a ratio of 3.7 is observed.

Finally, a 14 mg sample of the polyamide conjugate was dissolved in 700 µl of deuterium oxide and analyzed by $^1$H NMR spectroscopy at 300 MHz. Although most of the spectrum is complex, the aromatic region is readily interpreted. The protons expected in the aromatic region correspond to the polyamide ring protons, and the C$_6$ ring protons of thymidine and 5-methylcytidine. The observed spectrum is consistent with the predicted sequence ImPyPy-CONE (CH$_2$)$_6$—P(O)$_4$TTTTTT$^m$C$^m$CTTT-3', with the 2 protons observed at 7.7 corresponding to the cytidine, 9 protons at 7.6 corresponding to the thymidine contribution, 2 protons at 7.3 corresponding to the imidazole ring, four pyrrole doublets at 7.2, 7.1, 6.9, and 6.7 corresponding to four protons, and 11 anomeric protons at 6.2. The purity of the sample, as determined by NMR, is >98%. The ability to rapidly obtain NMR data (30 minutes of acquisition) on a molecule of this size (3 kD) warrants a synthesis scale such as the one chosen here. Table 5 sets forth illustrative oligonucleotide-polyamide conjugates synthesized by the method of this invention.

In another embodiment (Scheme 7), the oligonucleotide, prepared using standard phosphoramidite chemistry, is capped with a 2', 5'-dideoxy-5'-aminothimidine (Smith et al. (1985) Nucleic Acids Research 13:2399), prior to attachment of the polyamide (68).

The free amino group of the oligonucleotide is then reacted with the bis NHS ester of glutaric acid (DMF/DIEA) for 2 hours at room temperature to form activated acid (69). Excess NHS ester is removed by washing with a large excess of DMF. The activated acid is then treated with an equivalent of a polyamide containing a free amine prepared by the method of this invention. The coupling reaction (DMF/DIEA) is allowed to proceed for 12 hours, and any unreacted polyamide is removed by washing the resin. The oligonucleotide (70) is deprotected and simultaneously cleaved from the resin with a solution of 0.1 M NaOH at 55° C. for 12 hours. The polyamide-oligonucleotide conjugate (71) is then purified by a single reverse phase chromatography step (C18, TEAA, pH 7), to give a 10% yield. A list of illustrative polyamide-oligonucleotide conjugates which have been prepared by the method of this invention is set forth in FIG. 17 and Table 5. FIG. 18 depicts a ribbon graphic illustrating how the conjugate Dp-G-PyPyPy-G-PyPyIm-linker-TTTTTT$^m$C$^m$CTTT-3' might bind to the double helical DNA.

SCHEME 7

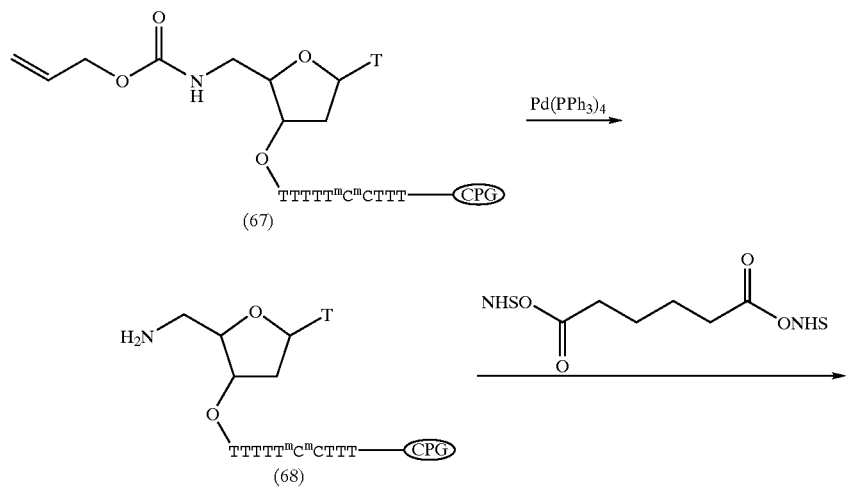

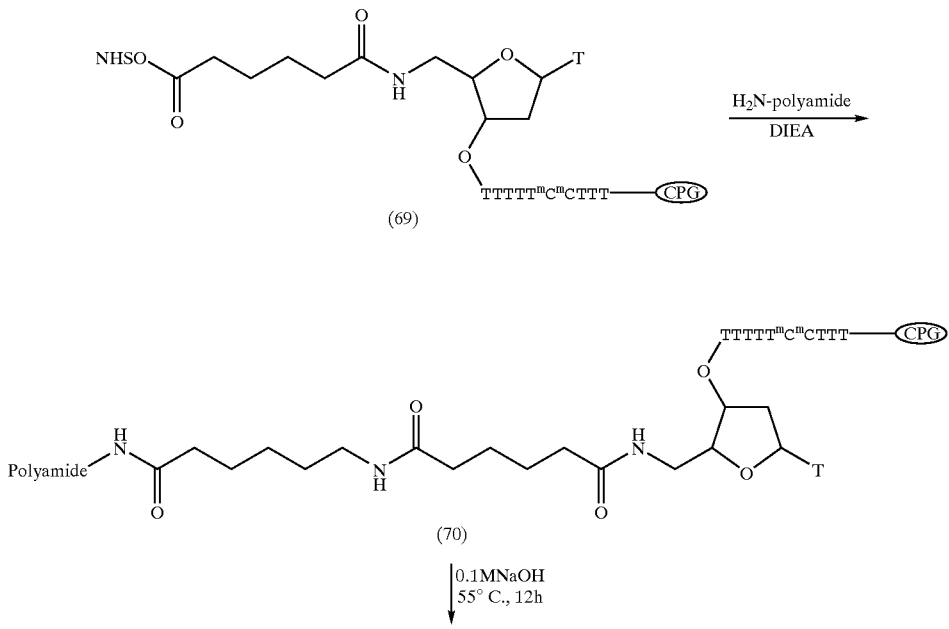

(69)

(70)

0.1M NaOH
55° C., 12h

Preparation of modified derivatives. In yet another embodiment of this invention, modified polyamide-oligonucleotide conjugates having terminal 1°, 2° and 3° amino groups are prepared. Modifications include, but are not limited to the formation of the dimethylaminopropylamine (Dp), the γ-aminobutyric acid (γ), the ethylenediamine (ED), the 3,3'-diamino-N-methylpropylamine (Ta) or the ethylenediaminetetraacetic acid (EDTA) derivatives.

Scheme 7 illustrates this method by the formation of the γ-aminobutyric derivative (75) which is then further modified by formation of the EDTA derivative (76).

SCHEME 8

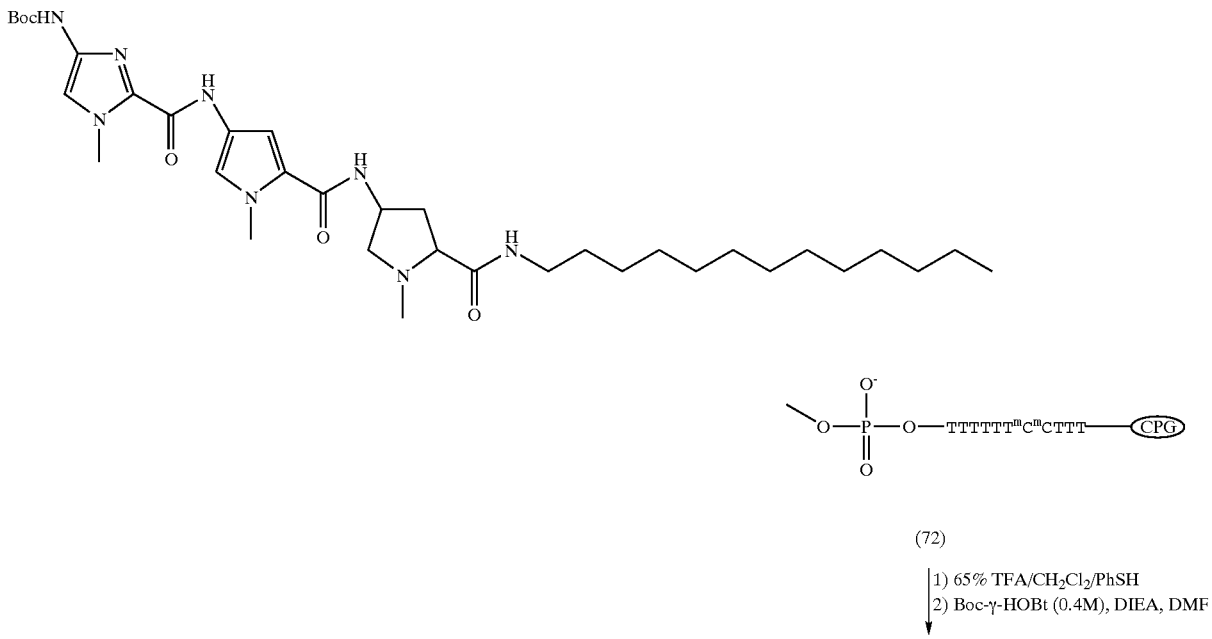

(72)

1) 65% TFA/CH$_2$Cl$_2$/PhSH
2) Boc-γ-HOBt (0.4M), DIEA, DMF

-continued
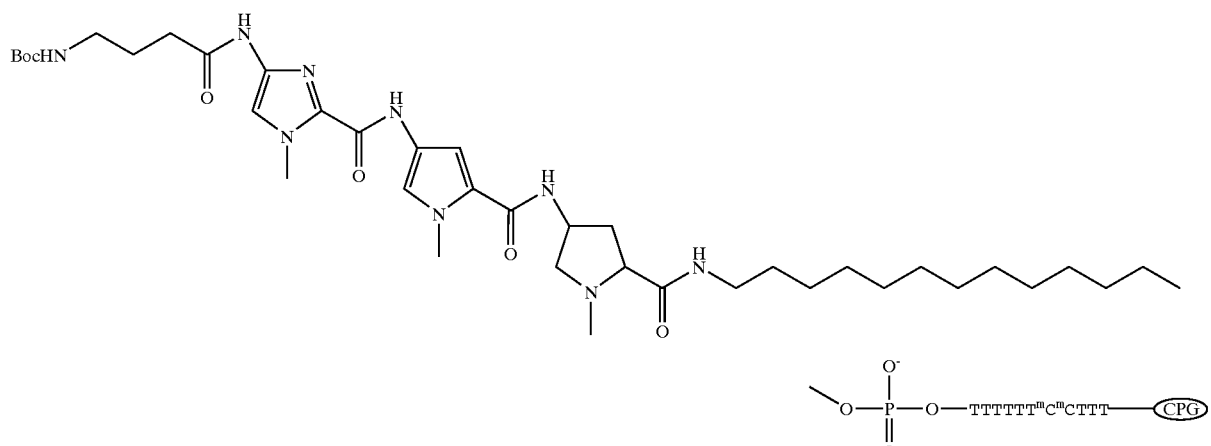
(73)
1) 0.1M NaOH, 55° C., 15 hours
2) FPLC purification
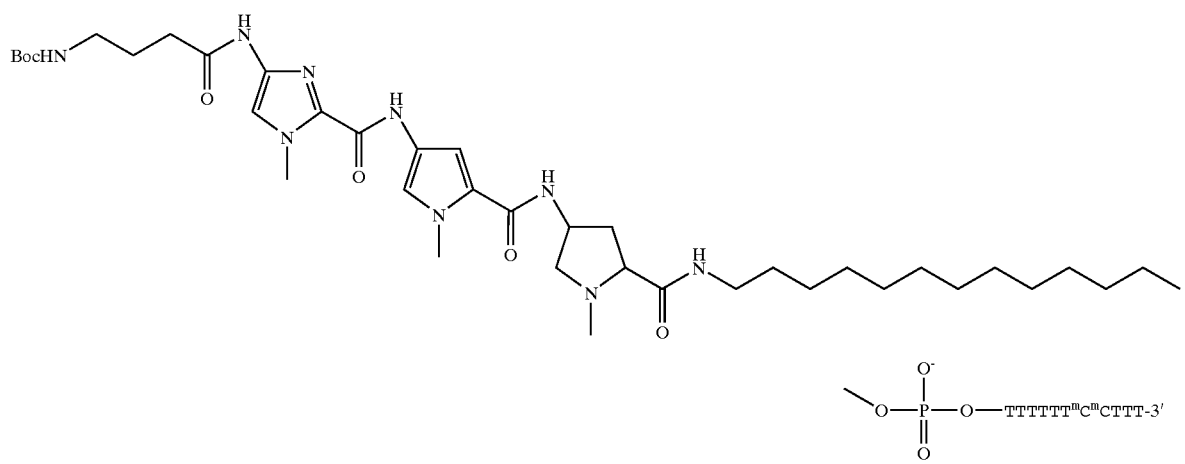
(SEQ ID NO:12)
(74)
1) 65% TFA/CH$_2$Cl$_2$/PhSH
2) FPLC purification
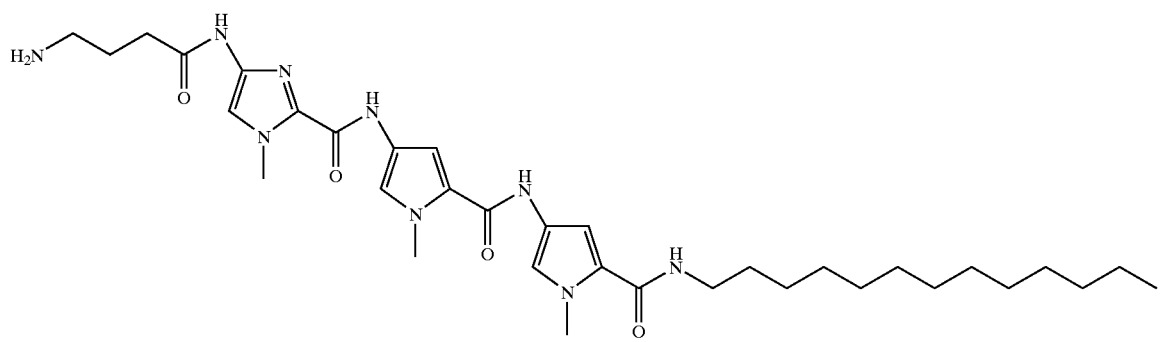

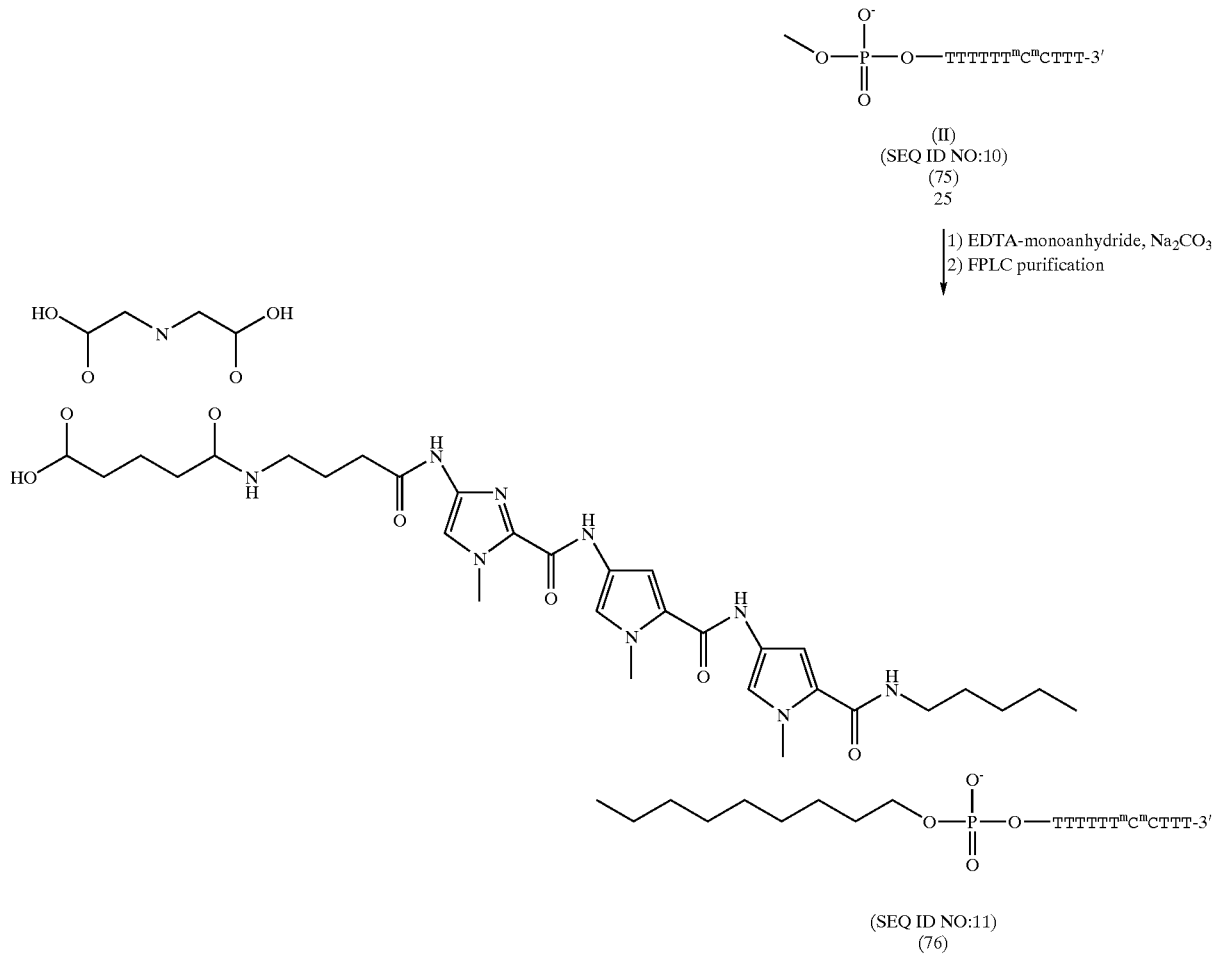

(II)
(SEQ ID NO:10)
(75)

1) EDTA-monoanhydride, Na₂CO₃
2) FPLC purification (SEQ ID NO:11)
(76)

Referring to Scheme 7, the conjugate Boc-ImPyPy-CONH (CH$_2$)$_{12}$—P(O)$_4$-TTTTTT$^m$C$^m$CTTT-CPG (72) is synthesized on solid support as described above. The Boc-group is removed with TFA under standard conditions and the product is reacted with the HOBt ester of Boc-γ (generated in situ). The product, Boc-γ-ImPyPy-CONH(CH$_2$)$_{12}$—P(O)$_4$-TTTTTT$^m$C$^m$CTTT-CPG (73) is simultaneously cleaved from the resin and the bases deprotected by treatment with 0.1M NaOH at 55° C. for 15 hours. The mixture is then purified by FPLC to give Boc-γ-ImPyPy-CONH(CH$_2$)$_{12}$—P(O)$_4$TTTTTT$^m$C$^m$CTTT-3'(SEQ ID NO:12)(74) which is characterized by HPLC, enzymatic degradation and mass spectroscopy. The Boc-group is then removed by treatment with TFA under standard conditions and the mixture purified by FPLC to give H$_2$N-γ-ImPyPy-CONH(CH$_2$)$_{12}$—P(O)$_4$-TTTTTT$^m$C$^m$CTTT-3'(75)(SEQ ID NO:10) which is characterized by mass spectroscopy. The oligonucleotide-polyamide conjugate is then reacted with the monoanhydride of EDTA in pH 9.5 carbonate buffer to yield the EDTA derivative (76)(SEQ ID NO:11).

Synthesis of Protein-minor Groove Polyamide Conjugates.

Figure 20:
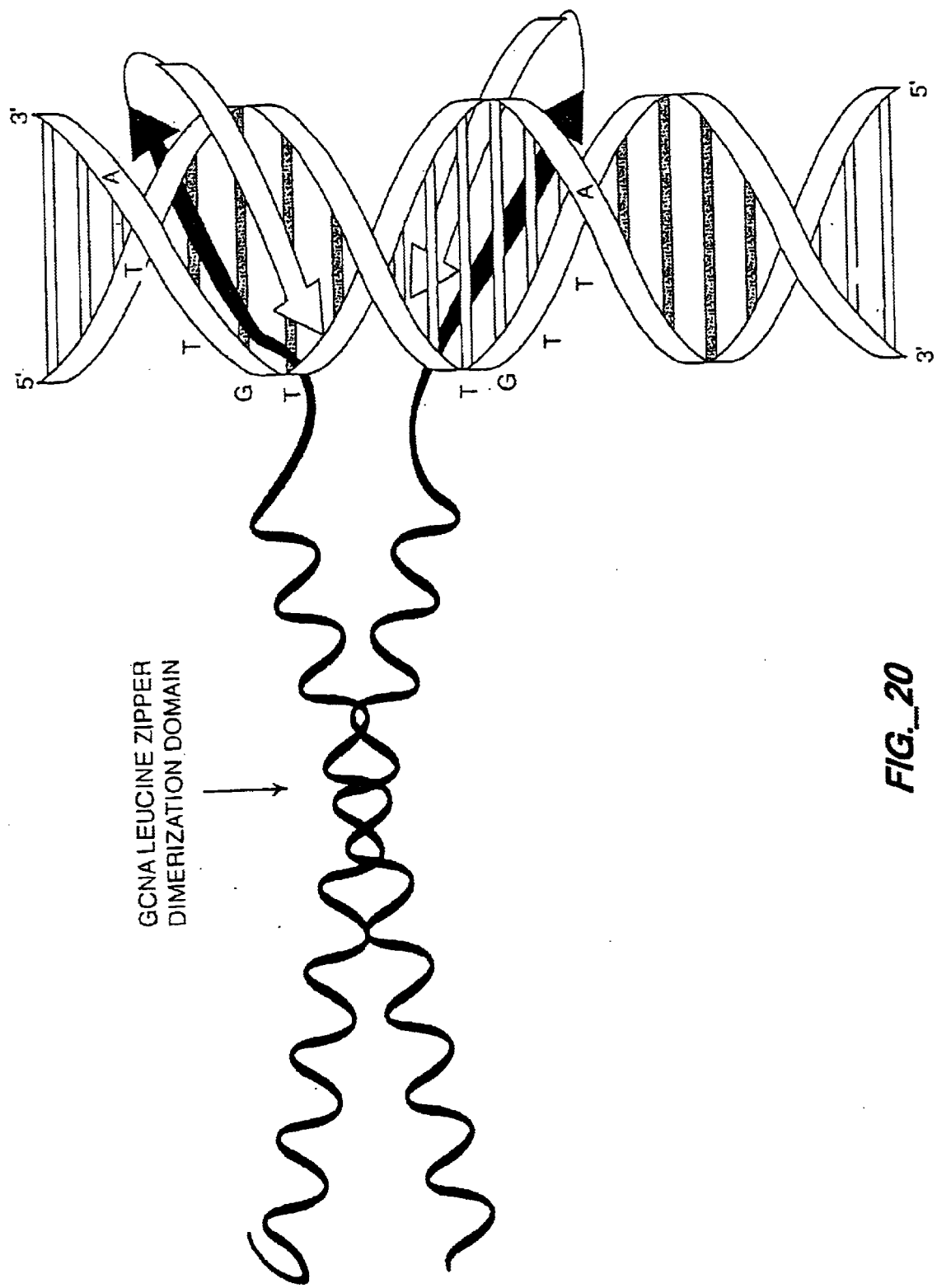
FIG. 20 depicts a ribbon model of the GCN-4-polyamide conjugate illustrating the binding region of the substituted polyamide to DNA.

In another embodiment of this invention the method of preparing polyamides is extended to the preparation of polyamides that are attached to a protein (referred to herein as a protein-polyamide conjugate). This method is illustrated by the replacement of the DNA binding domain of the major groove DNA binding protein GCN-4 (Oakley and Dervan (1989) Science 248:847) with the polyamide, NH$_2$-β-β-ImPyPy-γ-PyPyPy-γ-γ-, prepared as described above. A ribbon model of GCN-4 is depicted in FIG. 19. As illustrated in FIG. 19 the first 50 residues comprise an α-helix which has a DNA binding domain and a coiled coil dimerization region. The coiled-coil region—Lys Gln Leu Glu Asp Lys Val Glu Glu Leu Leu Ser Lys Asn Tyr His Leu Glu Asn Glu Val Ala Arg Leu Lys Lys Leu Val Gly Glu Arg-CO$_2$NH$_2$ (SEQ ID NO:24)—is prepared using standard NMP/HOBt methods for an ABI 430A peptide synthesizer. The polyamide domain is then appended in a stepwise fashion using the synthetic methods described above. The conjugate H$_2$N-β-β-ImPyPy-γ-γ-protein (SEQ ID NO:25) is then cleaved from the resin with anhydrous HF, and purified by reversed phase HPLC chromatography, to provide 1.1 mg of conjugate from cleavage of 100 mg of resin. The conjugate has been characterized by analytic HPLC and mass spectroscopy. FIG. 20 illustrates the DNA binding domain of the GCN-4-polyamide conjugate.

The ability to easily prepare polyamides with an appended peptide moiety is useful since peptide leader sequences often provide a means for delivering molecules into cells. (Soukchareun (1995) J. Bioconj Chem. 61:43–53)

Automated Synthesis of Polyamides.

Figure 21:
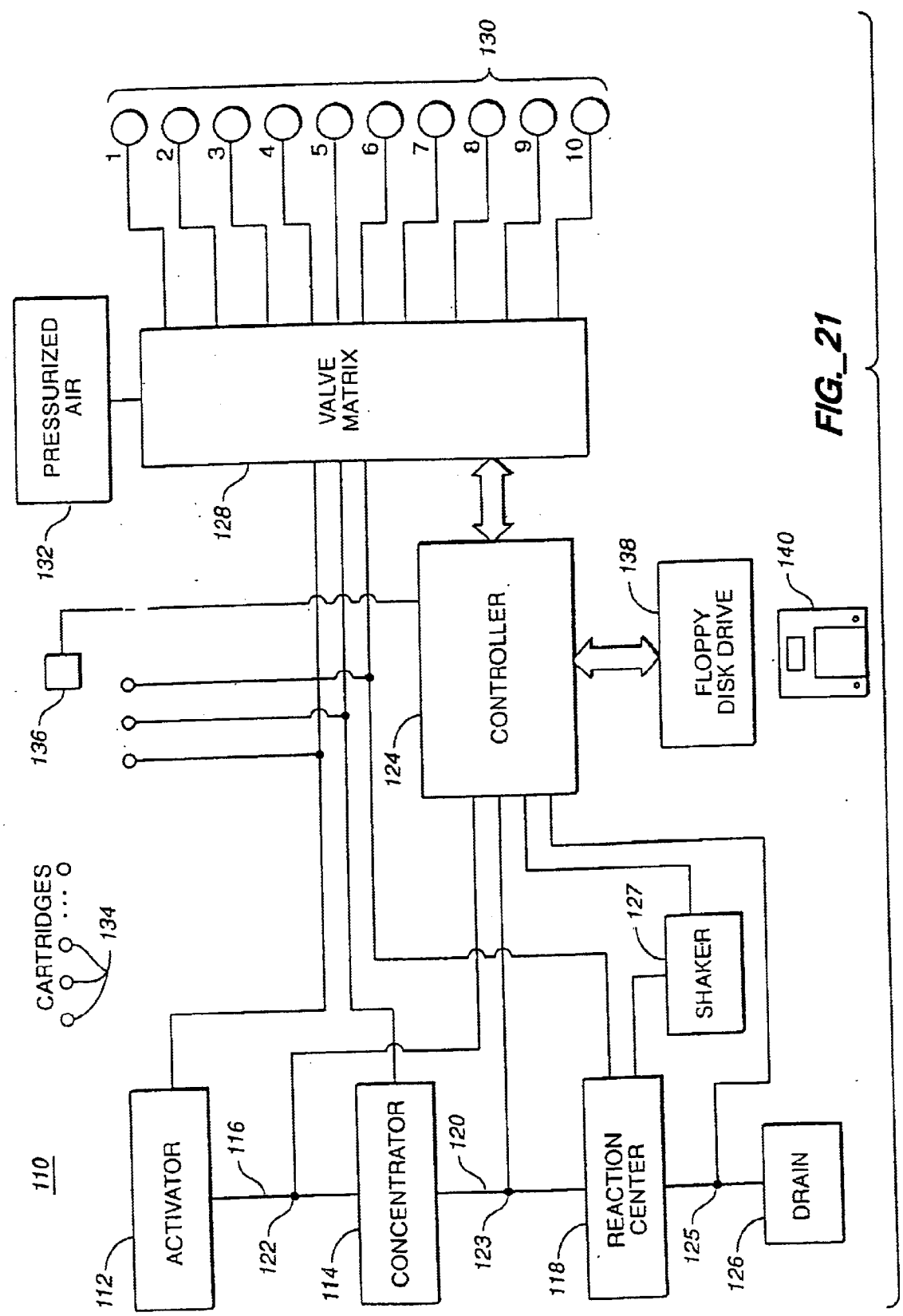
FIG. 21 depicts a schematic representation of a peptide synthesizer.

The methods of this invention for the syntheses of polyamides are suitable for automation. A peptide synthesizer 110, shown in FIG. 21 was modified to prepare polyamides containing imidazole and pyrrole carboxamides. The peptide synthesizer 110 has three chemistry centers where the reactions occur: an activator center 112, a concentrator center 114 and a reaction center 118. The activator center (first chemistry center) 112 is not used in preparing the polyamide. The concentrator center (second chemistry center) 114 is coupled to the activator center 112 by a tube 116. The reaction center (third chemistry center) 118 is coupled to the concentrator center 114 by a tube 120. A first valve 122 controls the flow of the contents from the activator center 112 to the concentrator center 114. A second valve 123 controls the flow of the contents from the concentrator center 114 to the reaction center 118. Both valves 122, 123 are coupled to a controller 124, that provides signals that control both valves 122, 123.

Another valve 125, operated by the controller 124, connects the reaction center 118 to a drain 126. A shaker 127, operated by the controller 124, shakes the reaction center 118. The three chemistry centers 112, 114 and 118 are coupled to a plurality of reagents by a valve matrix 128. The reagents are contained in a plurality of bottles 130 in one of ten reagent positions. The valve matrix allows any of the reagents in reagent positions 1–10 to flow into any of the three chemistry center 112, 114, 118. The valve matrix has programmable valves that are controlled by the controller 124. The pressurized air source 32 allows aeration of each of the three chemistry center 112, 114 and 118.

A plurality of cartridges 134 typically contains predissolved/preactivated monomer units. A programmable needle 36 transfers the contents of the cartridges 134 to one of the plurality of chemistry center 112, 114 and 118. The programmable needle 136 is directed by the controller 124.

Figure 22:
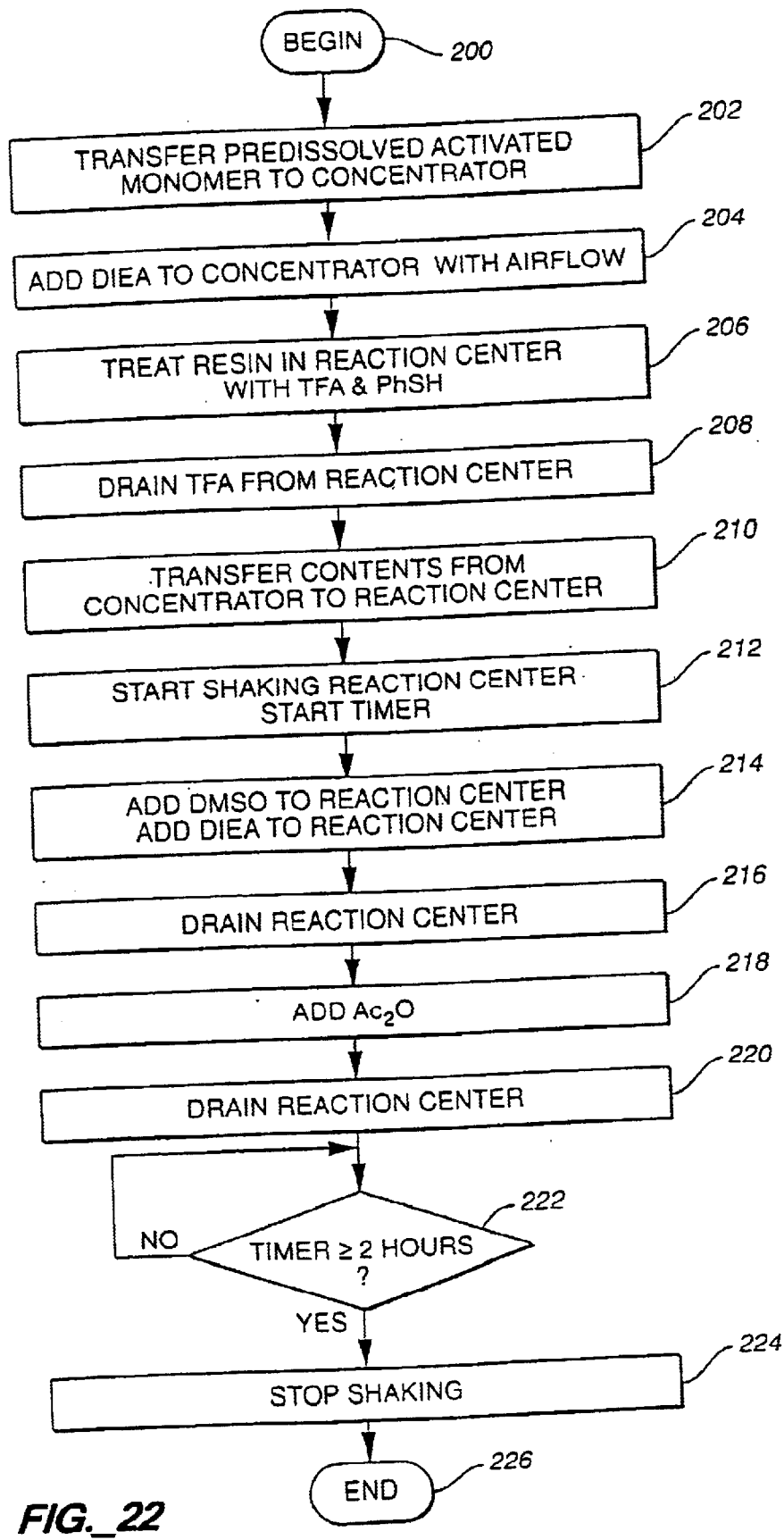
FIG. 22 depicts a flow chart of the computer program used to produce polyamides in the peptide synthesizer illustrated in FIG. 21.

The controller 124 is connected to a floppy disk drive 138. The floppy disk drive 138 accepts a floppy disk 140 having a storage medium encoded with a computer program to direct the operation of the peptide synthesizer 110. FIG. 22 is a flow chart of a computer program used to produce polyamides containing imidazole and pyrrole carboxamides the peptide synthesizer 110. The process begins at block 200. First, preactivated monomer is dissolved in DMF and transferred from one of the plurality of cartridges 134 to the concentrator 114, at block 202 bypassing the activator center 112. DIEA, from one of the plurality of reagent bottles 130, is transferred to the concentrator 114, at block 204. Simultaneously, a resin in the reaction center 118 is treated with TFA and PhSH, at block 206. The TFA and PhSH are contained in the reagent bottles 30. The resin is used to support the growing polyamide. Next, the TFA is drained for the reaction center 118, at block 208. Dichloromethane and TFA washes are performed before and after TFA/PhSH treatment. The dichloromethane and PhSH are contained in the plurality of reagent bottles 130. Following the dichloromethane/TFA wash, the contents of the concentrator 14 are transferred to the reaction center 118, at block 210. At block 212, a shaker starts shaking the reaction center 118 and a timer in the controller is started. At t=1800s DMSO from one of the plurality of reagent bottles is added to the reaction center and DIEA from one of the plurality of reagent bottles is added to the reaction center, at block 214. The reaction center 118 is then drained, at block 216. The reagent Ac$_2$O is added to the reaction center at block 218. The reaction center 118 is then drained again at block 220. At block 222, it is determined if a timer is greater than or equal to two hours. The process waits at block 222 until the timer equals or exceeds two hours. Then the shaking is stopped at block 224 and the process ends at block 226.

The machine assisted protocols are highly efficient as demonstrated by the synthesis of the 8 residue polyamide ImPyPy-γ-PyPyPy-β-Dp, with the crude reaction product containing >70% of the desired polyamide as determined by HPLC analysis. It is possible, however, to modify other commercially available peptide synthesizers and organic synthesis machines to accommodate the automated chemistry performed to synthesize the polyamides of this invention.

Figure 23:
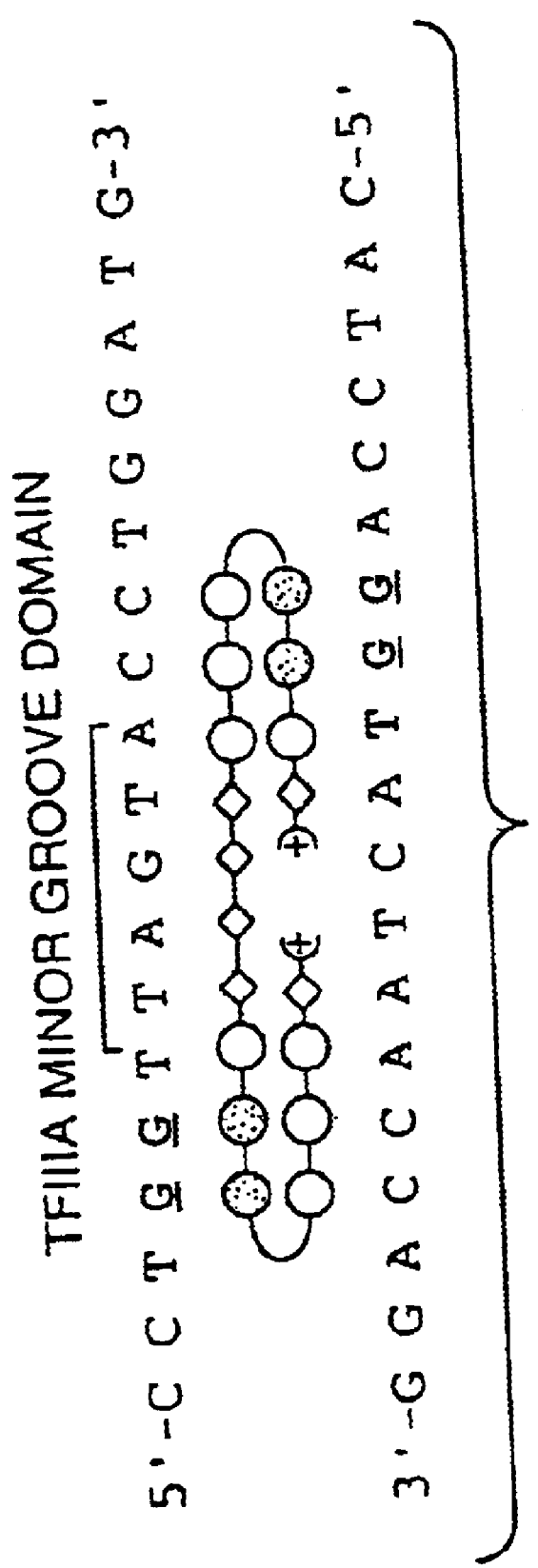
FIG. 23 depicts a ball and stick model of the projected binding mode of polyamide H₂N-β-PyPyPy-γ-ImImPy-β-β-β-β-PyPyPy-γ-ImImPy-β-Dp with the target DNA sequence 5'-TGGTTAGTACCT-3'(SEQ ID NO:5).

The versatility of the machine assisted protocols is demonstrated by the synthesis of polyamides H$_2$N-β-PyPyPy-γ-ImImPy-β-β-β-PyPyPy-γ-ImImPy-β-Dp and H$_2$N-β-PyPyPy-γ-ImImPyPy-β-β-PyPyPyPy-γ-ImImPy-β-Dp both of which were characterized by HPLC, $^1$H NMR, and MALDI-TOF mass spectroscopy. FIG. 23 depicts a ball and stick model of the projected binding mode of polyamide (#) with the target sequence 5'-TGGTTAGTACCT-3'(SEQ ID NO:5) on PXLO-wt. The binding affinity was determined to be approximately 1×10$^9$ M$^{-1}$. Introduction of a single base pair mismatch in the binding site lowers affinity by approximately a factor of 10-fold.

EXAMPLES

Materials. Di-t-butyldicarbonate (Boc-anhydride), Boc-G-(-4-carboxamidomethyl)-benzyl-ester-copoly(styrene-divinylbenzene) resin [Boc-G-PAM-resin] (0.2 mmol/gram), dicyclohexylcarbodiimide (DCC), hydroxybenzotriazole (HOBt) and aminomethylated polystyrene resin (0.7 mmol/gram) were purchased from Peptides International (Louisville, Ky.). N,N-diisopropylethylamine (DIEA), N,N-dimethylformamide (DMF), acetic anhydride, N-methylpyrrolidone (NMP), 0.0002M potassium cyanide/pyridine, dimethylsulfoxide (DMSO) and DMSO/NMP were purchased from Applied Biosystems. Boc-Glycine(Boc-G) was purchased from Peninsula, Boc-γ-aminobutyric acid (Boc-γ) from NOVA Biochem, dichloromethane from EM, thiophenol (PhSH) and picric acid from Aldrich, trifluoroacetic acid (TFA) from Halocarbon, phenol from Fisher, and ninhydrin from Pierce. Unless stated otherwise reagent-grade chemicals were used. Additionally, all reagents were used without further purification. Quick-Sep polypropylene disposable filters were purchased from Isolab Inc. and were used for filtration of dicyclohexylurea (DCU) for washing the resin for the ninhydrin and picric acid tests. A shaker for manual solid phase synthesis was obtained from Milligen. Screw-cap glass peptide synthesis reaction vessels (5 ml) with a=scintered glass frit were made at the California Institute of Technology glass shop as described by Kent. (Kent (1988) Ann. Rev. Biochem. 57:957).

DNA Reagents and Materials. Sterilized 0.1% DEPC-treated water (Sambrock et al. (1989) Molecular Cloning, 2nd ed.; Cold Spring Harbor, N.Y.) was either prepared or purchased from Gibco. Polyacrylamide gel electrophoresis was performed in a 1×TBE buffer. Autoradiography was carried out using Amersham Hyperfilm MP or Kodak X-Omat film. Gels were analyzed by storage phosphor technology. (Miyahara et al. (1986) Nuc. Inst. Meth. Phys. Res. A246:572–578; Johnston et al. (1990) Electrophoresis 11:355–360).

NMR were recorded on a GE 300 instrument operating at 300 MHz ($^1$H) and 75 MHz ($^{13}$C). Chemical shifts are reported in ppm relative to the solvent residual signal. UV spectra were measured on a Hewlett-Packard Model 8452A diode array spectrophotometer. Matrix-assisted, laser desorption/ionization time of flight mass spectrometry was carried out at the Protein and Peptide Microanalytical Facility at the California Institute of Technology. HPLC analysis was performed either on a HP 1090M analytical HPLC or a Beckman Gold system using a RAINEN C$_{18}$, Microsorb MV, 5 μm, 300×4.6 mm reversed phase column in 0.1%

(wt/v) TFA with acetonitrile as eluent and a flow rate of 1.0 ml/min, gradient elution 1.25% acetonitrile/min. Preparatory HPLC was carried out on a Beckman HPLC using a Waters DeltaPak 25×100 mm, 100 μm C$_{18}$ column equipped with a guard, 0.1% (wt/v) TFA. 0.25% acetonitrile/min. 18MΩ water was obtained from a Millipore MilliQ water purification system, all buffers were 0.2 μm filtered. Flash column chromatography was carried out using Silica Gel 60 (230–400 mesh, Merck). Thin layer chromatography (TLC) was performed on Silica Gel 60 F$_{254}$ precoated plates (Merck).

Example 1

Preparation of the Pyrrole and Imidazole Monomers

Preparation of Boc-Py-OBt (9) and Boc-Im-OBt (13).

The Boc-Py-OBt (9) and Boc-Im-OBt (13) monomers were synthesized starting from the known nitro-esters 6 and 10 (prepared as described in Schemes 10 and 11 (Bailey et al. Org. Syn. 101–102; Corwin and Quattlebaum (1936) J. Am. Chem. Soc. 58:1081–1085; Grehn (1978) Chim. Scripta 13:67–77; Morrey and Morrey (1966) Tetrahedron 22:57–62; Krowicki and Lown (1987) J. Ore. Chem. 52:3493–3501) as outlined in Scheme 8 below. Reduction of the nitro group gave amines 7 and 11, in 91% and 81% yield respectively. The amines were Boc-protected with Boc-anhydride (pyrrole amine 7 in aqueous carbonate/dioxane and imidazole amine 11 in DMF/DIEA) and the ester groups were hydrolyzed with aqueous sodium hydroxide to yield the Boc-protected acids 8 and 12 in 93% and 88% yields, respectively. The acids were then activated at high concentration (>0.2 M acid in DMF) with 1 equivalent of DCC and HOBt and the -OBt esters precipitated from water to give compounds 9 and 13. Overall yields starting from the nitro methyl esters are reproducibly greater than 60% for both the pyrrole and imidazole -OBt esters, with simple purification requiring no column chromatography. The Boc-imidazole acid has been reported to decarboxylate even at reduced temperature. The Boc-Im-OBt ester 13, however, has been found to be stable at room temperature, with HOBt effectively acting as a protecting group for the unstable imidazole carboxylic acid.

SCHEME 9

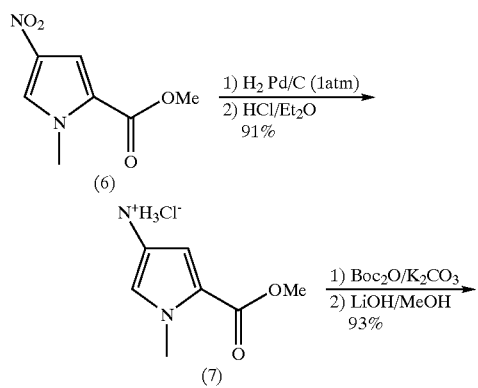

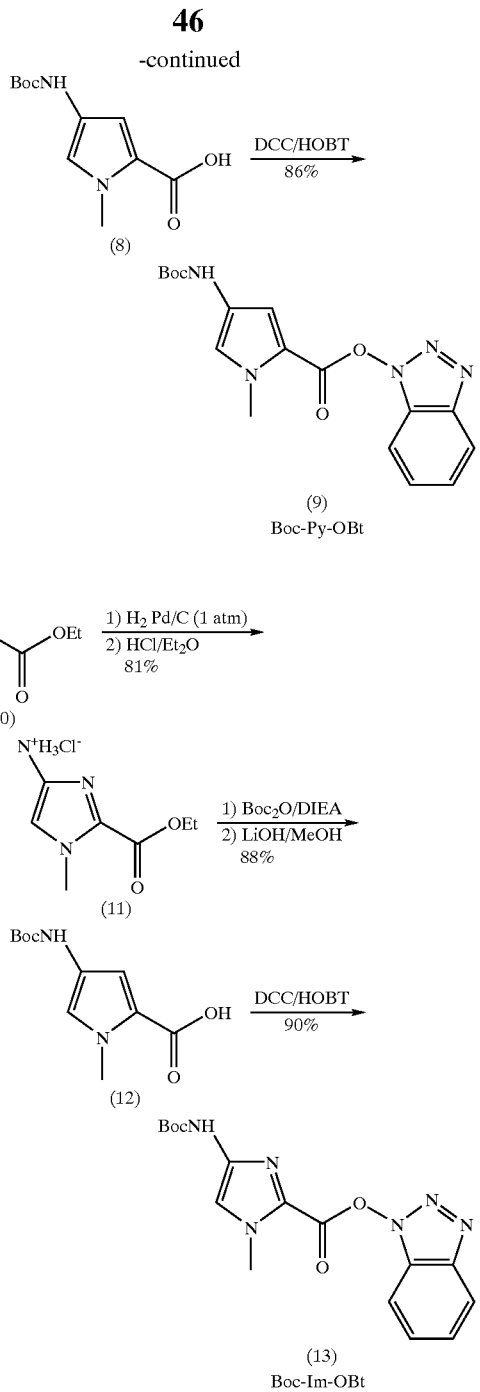

Preparation of Methyl 4-amino-1-methyl-pyrrole-2-carboxylate hydrochloride (7). Recrystallized methyl 1-methyl-4-nitropyrrole-2-carboxylate 6 (40 g, 0.22 mol) was dissolved in 900 ml ethyl acetate. A slurry of 10 g of 10% Pd/C in 100 ml ethyl acetate was added arid thee mixture stirred under a slight positive pressure of hydrogen (about 1.1 ATM) for 48 hours. The Pd/C was removed by filtration through Celite, washed with 50 ml ethyl acetate, and the volume of the mixture was reduced to about 200 ml. 700 ml of ethyl ether was added and HCl gas gently bubbled through the mixture while maintaining a temperature below 20° C. The precipitated amine hydrochloride was then collected after storage at −20° C. for 40 hours to yield (38 g, 91%) of a very white powder. TLC (ethyl acetate) Rf amine (0.6), Rf salt (0.0) $^1$H NMR (DMSO-d$_6$) δ 10.23 (br s, 3H), 7.24 (d, 1H, J=1.9 Hz), 6.79 (d, 1H, J=2.0 Hz), 3.83 (s, 3H), 3.72 (s, 3H); $^{13}$C NMR (DMSO-d$_6$) δ 160.8, 124.3, 121.2, 113.4, 112.0, 51.8, 37.1.

Preparation of 4-[[(tert-Butyloxy)carbonyl]-amino]-1-methylpyrrole-2-carboxylic acid (8). The hydrochloride salt of the pyrrole amine 7 (24 g, 146 mmol) was dissolved in 300 ml of 10% aqueous sodium carbonate and di-t-butyldicarbonate (40 g, 174 mmol) slurried in 75 ml of dioxane was added over a period of ten minutes at room temperature. The reaction was allowed to proceed at room temperature for two hours and then cooled to 5° C. for 2 hours. The resulting white precipitate was collected by vacuum filtration. The crude product was dissolved in 350 ml MeOH and 350 ml of 1M NaOH was added and the solution was heated at 60° C. for 6 hours. The reaction was then cooled to room temperature, washed with ethyl ether (2×500 ml). The pH of the aqueous layer was reduced to approximately 3 with aqueous citric acid and was extracted with ethyl acetate (4×500 ml). The combined ethyl acetate extracts were dried with sodium sulfate and concentrated in vacuo to give a tan foam. The foam was dissolved in 100 ml of dichloromethane and 400 ml petroleum ether was added and the resulting slurry was concentrated in vacuo. This step was repeated three times to give (31 g, 93% yield) of a fine white powder. TLC (7:2 benzene/ethyl acetate v/v) Rf (ester) 0.8, Rf (acid) 0.1, (ethyl acetate), Rf (acid) 0.6; $^1$H NMR (DMSO-d$_6$) δ 12.10 (s, 1H), 9.05 (s, 1H), 7.02 (s, 1H), 6.55 (s, 1H), 3.75 (s, 3H), 1.41 (s, 9H); $^{13}$C NMR (DMSO-d$_6$) δ 162.4, 153.2, 123.3, 120.1, 119.2, 107.9, 78.9, 36.6, 28.7.

Preparation of 1,2,3-Benzotriazol-1-yl 4[[(tert-Butyloxy)carbonyl]-amino]-1-methylimidazole-2-carboxylate (9). The Boc-pyrrole-acid 8 (31 g, 129 mmol) was dissolved in 500 ml DMF and hydroxybenzotriazole (17.4 g, 129 mmol) was added followed by DCC (34 g, 129 mmol). The reaction was allowed to stir for 24 hours and then filtered dropwise into a well stirred solution of 5 liters of water (0° C.). The precipitate was allowed to sit for 15 minutes at 0° C. and then collected by filtration. The wet cake was dissolved in 500 ml of dichloromethane, washed with 200 ml brine, and added slowly to a stirred solution of petroleum ether at −20° C. After 4 hours at −20° C. the precipitate was collected by vacuum filtration and dried in vacuo to give (39 g, 85% yield) of a finely divided white powder. (A yellowish impurity may be observed, which can be removed by flash chromatography (acetone:dichloromethane), followed by precipitation in petroleum ether). TLC (7:2 benzene/ethyl acetate v/v) Rf 0.6; $^1$H NMR (DMSO-d$_6$) δ 9.43 (s, 1H), 8.12 (d, 1H, J=8.4 Hz), 7.80 (d, 1H, J=8.2 Hz), 7.64 (t, 1H, J=7.0 Hz), 7.51 (m, 2H), 7.18 (s, 1H), 3.83 (s, 3H), 1.45 (s, 9H); $^{13}$C NMR (DMSO-d$_6$) δ 156.5, 153.3, 143.2, 129.6, 129.2, 125.7, 125.2, 124.6, 120.3, 112.8, 110.3, 109.8, 79.5, 36.8, 28.6.

Preparation of Ethyl 4-amino-1-methylimidazole-2-carboxylate hydrochloride (11). Nitro imidazole ethyl ester 10 (10 g, 50 mmol) was dissolved in 500 ml of 1:1 ethanol/ethyl acetate, 1 g 10% Pd/C slurried in 50 ml ethyl acetate was added and the mixture was stirred under a slight positive pressure of hydrogen (approximately 1.1 atm) for 48 hours. The reaction mixture was filtered, concentrated in vacuo and dissolved in 600 ml ether. HCl gas was bubbled through the ether solution at 0° C. to give a white precipitate. The solution was cooled at −20° C. for 4 hours and the precipitate was collected by vacuum filtration and dried in vacuo to give (8.1 g, 81% yield) of 11 as a fine white powder. $^1$H NMR (DMSO-d$_6$) δ 10.11 (br s, 3H), 7.43 (s, 1H), 4.28 (q, 2H, J=7.1 Hz), 3.92 (s, 1H), 1.28 (t, 3H, J=7.1 Hz); $^{13}$C NMR (DMSO-d$_6$) δ 157.6, 132.6, 117.4, 117.3, 61.8, 36.6, 14.5.

Preparation of 4-[[(tert-Butyloxy)carbonyl]-amino]-1-methylimidazole-2-carboxylic acid (12). The imidazole amine 11 (3 g, 14.5 mmol) was dissolved in 20 ml DMF and diisopropylethylamine (4.5 ml, 25 mmol) was added followed by di-t-butyldicarbonate (6 g, 27 mmol). The mixture as shaken at 40° C. for 18 hours, allowed to return to room temperature and then partitioned between 500 ml of brine and 500 ml of ethyl ether. The ether layer was extracted with (2×200 ml each) 10% citric acid, brine, saturated sodium bicarbonate and brine. The ether layer was dried over sodium sulfate and concentrated in vacuo to yield the Boc-ester. The crude Boc-ester was dissolved in 40 ml of MeOH and 40 ml of 1 M KOH was added. The reaction mixture was shaken at 40° C. for 4 hours, cooled to room temperature and partitioned between 200 ml of water and 300 ml ethyl ether. The aqueous layer was washed with 300 ml ethyl ether, the ether washes were discarded and the pH of the aqueous layer was brought down to approximately 3 with 10% aqueous sodium bisulfate. The aqueous layer was extracted (10×150 ml) with ethyl acetate and the organic layers were combined, dried over sodium sulfate and concentrated in vacuo to yield pure 12 as a white chalky powder (3.1 g, 88% yield). $^1$H NMR (DMSO-d$_6$) δ 9.61 (s, 1H), 7.23 (s, 1H), 3.85 (s, 3H), 1.41 (s, 9H).

Preparation of 1,2,3-Benzotriazol-1-yl 4[[(tert-butyloxy)carbonyl]-amino]-1-methylpyrrole-2-carboxylate (13). The Boc-imidazole-acid 12 (2 g, 8.3 mmol) was in dissolved in 10 ml of DMF and 1-hydroxybenzotriazole was added (1.2 g, 9 mmol) followed by DCC (2.4 g, 9 mmol). After 6 hours the precipitate was removed by filtration and washed with 4 ml of DMF. The DMF solution was added dropwise to 250 ml of well stirred ice water and the resulting precipitate was collected by vacuum filtration. The filter cake was ground and dried in vacuo over P$_2$O$_5$ to give (2.7 g, 89%) of 13 as a pale yellow power contaminated with a small amount of DCU (2.7 g, 89%). $^1$H NMR (DMSO-d$_6$) δ 9.62 (s, 1H), 7.96 (s, 1H), 7.68 (d, 1H), 7.52 (d, 1H), 7.38 (d, 1H), 7.23 (s, 1H), 3.85 (s, 3H), 1.33 (s, 9H).

Preparation of Methyl 1-methyl-4-nitropyrrole-2-carboxylate (6) and Ethyl 1-methyl-4-nitroimidazole-2-carboxylate (10). Nitroesters 6 and 10 were synthesized from the inexpensive N-methylpyrrole and N-methylimidazole as outlined in Schemes 10 and 11, respectively. Each of these compounds can be prepared economically on a large scale. Methyl 1-methyl-4-nitropyrrole-2-carboxylate (6) was prepared using a modification of the reported synthesis of pyrrole-2-trichloroketone. (Bailey et al. (1971) Org. Syn. 51:101). Briefly, reaction of the inexpensive N-methylpyrrole (14) with trichloroacetylchloride followed by nitration with nitric acid gave nitropyrrole trichloroketone (15), which was treated with sodium methoxide to yield nitropyrrole (6).

SCHEME 10

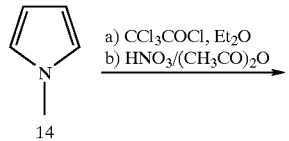

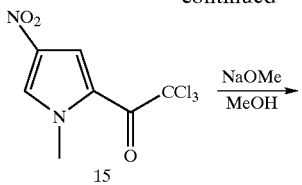
-continued

SCHEME 11

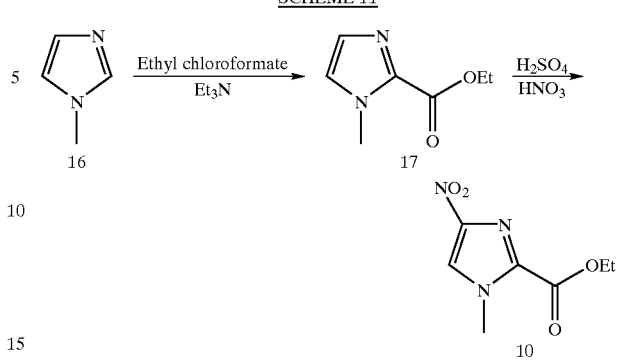

Preparation of 4-nitro-2-trichloroacetyl-1-methylpyrrole (15). To a well stirred solution of trichloroacetylchloride (1 kg, 5.5 mole) in 1.5 liters of ethyl ether was added dropwise over a period of 3 hours a solution of N-methylpyrrole (14) (0.45 kg, 5.5 mole) in 1.5 liters of anhydrous ethyl ether. The reaction was allowed to stir for an additional 3 hours and quenched by the dropwise addition of a solution of 400 g of potassium carbonate in 1.5 liters of water. The layers were separated and the ether layer was concentrated in vacuo to provide 2-trichloroacetyl pyrrole (1.2 kg, 5.1 mole) as a yellow crystalline solid, which can be purified by recrystallization from benzene, but is sufficiently pure to be used without further purification. To a cooled (−40° C.) solution of 2-trichloroacetyl pyrrole (1.2 kg, 5.1 mole) in acetic anhydride (6 liters) flask equipped with a mechanical stirrer was added 440 ml of fuming nitric acid over a period of 1 hour while maintaining a temperature of −40° C. The reaction was carefully allowed to warm to room temperature and stirred an additional 4 hours after which the mixture was cooled to −30° C. and isopropyl alcohol (6 liters) was added. The solution was stirred at −20° C. for 30 minutes during which time a white precipitate formed. The solution was allowed to stand for 15 minutes and the resulting precipitate collected by vacuum filtration to provide (15) (0.8 kg, 54% yield). TLC (7:2 benzene/ethyl acetate) Rf 0.7; $^1$H NMR (DMSO-$d_6$) δ 8.55 (d, 1H, J=1.7 Hz), 7.77 (d, 1H, J=1.7 Hz), 3.98 (s, 3H); $^{13}$C NMR (DMSO-$d_6$) δ 173.3, 134.7, 133.2, 121.1, 116.9, 95.0, 51.5; IR (KBr) 1694, 1516, 1423, 1314, 1183, 1113, 998, 750; FABMS m/e 269.936 (M−H 269.9937 calc. for $C_7H_5N_2O_3Cl_3$).

Preparation of Methyl 1-methyl-4-nitropyrrole-2-carboxylate (6). To a solution of (15) (800 g, 2.9 mol) in 2.5 liters of methanol in a flask equipped with a mechanical stirrer was added dropwise a solution of NaH (60% dispersion in oil) (10 g, 0.25 mole) in 500 ml of methanol. The reaction was allowed to stir for 2 hours at room temperature, and quenched by the addition of concentrated sulfuric acid (25 ml). The reaction was then heated to reflux, until a clear light yellow solution formed. The reaction was slowly cooled to room temperature as (6) crystallizes as white needles, which are collected by vacuum filtration and dried in vacuo to provide 450 g (47% yield). TLC (ethyl acetate) Rf 0.8; $^1$H NMR (DMSO-$d_6$) δ 8.22 (d, 1H, J=1.7 Hz), 7.22 (d, 1H, J=1.6 Hz), 3.88 (s, 3H), 3.75; $^{13}$C NMR (DMSO-$d_6$) δ 37.8, 52.2, 112.0, 123.0, 129.9, 134.6, 160.3; IR (KBr) 3148, 1718, 1541, 1425, 1317, 1226, 1195, 1116, 753; FABMS m/e 183.048 (M+H 184.048 calc. for $C_7H_8N_2O_4$).

Ethyl 1-methyl-4-nitroimidazole-2-carboxylate (10) was prepared by treatment of N-methylimidazole (16) with ethylchloroformate and triethylamine followed by nitration with nitric acid.

Preparation of Ethyl 1-methyl-imidazole-2-carboxylate (17). N-methylimidazole (16) (320 g, 3.9 mol) was combined with 2 liters of acetonitrile and 1 liter of triethylamine in a flask equipped with a mechanical stirrer and the solution was cooled to −20° C. Ethylcloroformate (1000 g, 9.2 mol) was added with stirring, keeping the temperature between −20° C. and −25° C. The reaction was allowed to slowly warm to room temperature and stir for 36 hours. Precipitated triethylamine hydrochloride was removed by filtration and the solution was concentrated in vacuo at 65° C. The resulting oil was purified by distillation under reduced pressure (2 torr, 102° C.) to provide (17) as a white solid (360 g, 82% yield). TLC (7:2 benzene/ethyl acetate) Rf 0.2; $^1$H NMR (DMSO-$d_6$) δ 7.44 (d, 1H, J=2.8 Hz), 7.04 (d, 1H, J=2.8 Hz), 4.26 (q, 2H, J=3.5 Hz) 3.91 (s, 3H), 1.26 (t, 3H, J=3.5 Hz); $^{13}$C NMR (DMSO-$d_6$) δ 159.3, 129.1, 127.7, 61.0, 36.0, 14.5; IR (KBr) 3403, 3111, 2983, 1713, 1480, 1422, 1262, 1134, 1052, 922, 782, 666; FABMS m/e 155.083 (M+H 155.083 calc. for $C_7H_{11}N_2O$).

Preparation of Ethyl 4-nitro-1-methylimidazole-2-carboxylate (10). Compound (17) was carefully dissolved in 1000 ml of concentrated sulfuric acid cooled to 0° C. 90% nitric acid (1 liter) was slowly added maintaining a temperature of 0° C. The reaction was then refluxed with an efficient condenser (−20° C.) in a well ventilated hood for 50 minutes. The reaction was cooled with an ice bath, and quenched by pouring onto 10 liters of ice. The resulting blue solution was then extracted with 20 liters of dichloromethane and the combined extracts were dried and concentrated in vacuo to yield a tan solid which was recrystallized from 22 liters of 21:1 carbon tetrachloride/ethanol. The resulting white crystals were collected by vacuum filtration to provide pure (10). (103 g, 22% yield). TLC (7:2 benzene/ethyl acetate) Rf 0.5, $^1$H NMR (DMSO-$d_6$) δ 8.61 (s, 1H), 4.33 (1, 2H, J=6.4 Hz), 3.97 (s, 3H), 1.29 (t, 3H, J=6.0 Hz); $^{13}$C NMR (DMSO-$d_6$) δ 158.2, 145.4, 135.3, 127.4, 62.2, 37.3, 14.5; IR (KBr) 3139, 1719, 1541, 1508, 1498, 1381, 1310, 1260, 1147, 1112, 995, 860, 827, 656; FABMS m/e 200.066 (M+H 200.067 calc. for $C_7H_{10}N_3O_4$).

Synthesis of Fmoc-Py-OBt (21a) and Fmoc-Im-OBt (21b). The Fmoc-monomers were synthesized from the Boc-monomers as set forth in Scheme 12. Briefly, the Boc-protected monomer is converted to the cesium salt followed by treatment with benzyl bromide to yield the benzyl esters (18). The Boc-protecting group is then removed with trifluoroacetic acid in the presence of thiophenol and the product precipitated by the addition of HCl saturated ethyl ether. The amine hydrochloride is then treated with Fmoc-chloroformate in potassium carbonate, and the benzyl ester removed by hydrogenation to provide the Fmoc-protected monomers (21a and 21b). This method is illustrated using the synthesis of the Fmoc-protected pyrrole (21a) as an example.

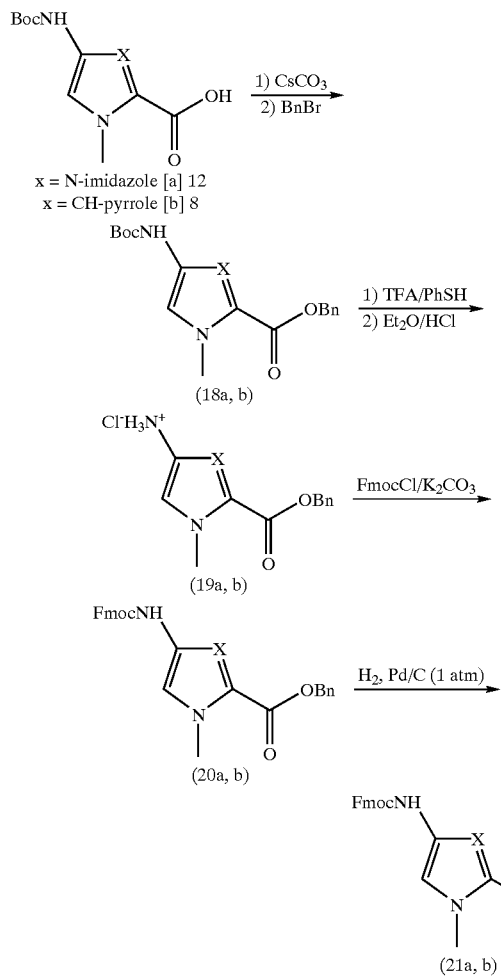

SCHEME 12

Preparation of Benzyl 4-[[tert-butyloxy)carbonyl]amino]-1-methylpyrrole-2-carboxylate (18a, b). To a solution of Boc-acid (8) (5 g) in 100 ml of 66% ethanol was added cesium carbonate (3.3 g in 25 ml of water). The solution was stirred for 20 minutes, filtered through glass wool, and concentrated in vacuo to yield the cesium salt as a solid. The solid was dissolved in 75 ml of ethanol and concentrated to dryness three times. The cesium salt was then dissolved in 500 ml of DMF and 2.6 ml of benzyl bromide was immediately added dropwise. The resulting solution was stirred at 40° C. for 10 hours. After 10 hours the solution was poured into 300 ml of ice water and allowed to stand at 4° C. for 1 hour. The resulting precipitate was collected by vacuum filtration to yield 6.59 (93%) of the Boc protected benzyl ester (18a). $^1$H NMR (DMSO-$d_6$) δ 9.1 (s, 1H), 7.4 (m, 5H), 7.1 (d, 1H), 6.8 (d, 1H), 5.2 (s, 2H), 3.8 (s, 3H), 1.4 (2, 9H).

Preparation of Benzyl 4-amino-1-methylpyrrole-2-carboxylate (19a). To a solution of the Boc-benzyl ester (18a) (5 g) in 20 ml of dichloromethane was added 20 ml of 65% TFA/CH$_2$Cl$_2$/0.5 M PhSH. The reaction was allowed to stir for 1 hour, and then partitioned between 100 ml of 1M LiOH and 100 ml of ethyl ether. The layers were separated and the aqueous layer was extracted with ethyl ether (5×20 ml). HCl (g) was bubbled through the combined organics and the product collected by vacuum filtration to yield 3.2 g (76%) of benzylamine (19a). $^1$H NMR (DMSO-$d_6$) δ 10.1 (br s, 3H), 7.4 (m, 5H), 7.2 (d, 1H), 6.8 (d, 1H), 5.2 (s, 2H), 3.8 (s, 3H).

Preparation of 4-[[(9-fluorenylmethyl)carbonyl]amino]-1-methylpyrrole-2-carboxylate (20a). To a solution of the benzylamine (19a) (1 gram) in dichloromethane cooled at 0° C. was added DIEA (1.4 ml) and 9-fluorenylmethylchloroformate (973 mg). The reaction was allowed to stir for 30 minutes. The reaction was worked up using standard methods to yield 1.8 g (88%) of benzylester (21a). $^1$H NMR (DMSO-$d_6$) δ 9.5 (s, 1H), 7.9 (d, 2H), 7.7 (d, 2H), 7.3 (m, 9H), 7.1 (s, 1H), 6.7 (s, 1H), 5.2 (s, 2H), 4.4 (d, 2H), 4.2 (t, 1H), 3.8 (s, 3H).

Preparation of 4-[[(9-fluorenylmethyl)carbonyl]amino]-1-methylpyrrole-2-carboxylic acid (21a). To a solution of the benzylester (20a) (900 mg) dissolved in THF (10 ml) was added 10% Pd/C (100 mg). The solution was hydrogenated (1 atm) for 19 hours and worked up using standard methods to yield 580 mg (80%) of compound (21a). $^1$H NMR (DMSO-$d_6$) δ 9.4 (s, 1H), 8.0 (m, 2H), 7.8 (m, 2H), 7.3 (m, 4H), 7.1 (s, 1H), 6.8 (s, 1H), 4.6 (m, 2H), 4.3 (m, 1H), 3.8 (s, 3H).

Preparation of N-substituted Monomers.

Preparation of N-2-methyl-butyl-4-[[(tert-butyloxy) carbonyl]amino]-2-carboxylic acid (24). N-2-methyl-propyl-4-[[(tert-butyloxy)carbonyl]amino]-2-carboxylic acid 24 was synthesized as outlined in Scheme 13. Briefly, methyl 4-nitropyrrole-2-carboxylate 22, prepared as described below, was alkylated by refluxing with the appropriate alkyl halide in acetone in the presence of potassium carbonate. The ester was then hydrogenated and hydrolyzed to provide the modified monomer 24 which is ready for use in, solid phase synthesis.

SCHEME 13

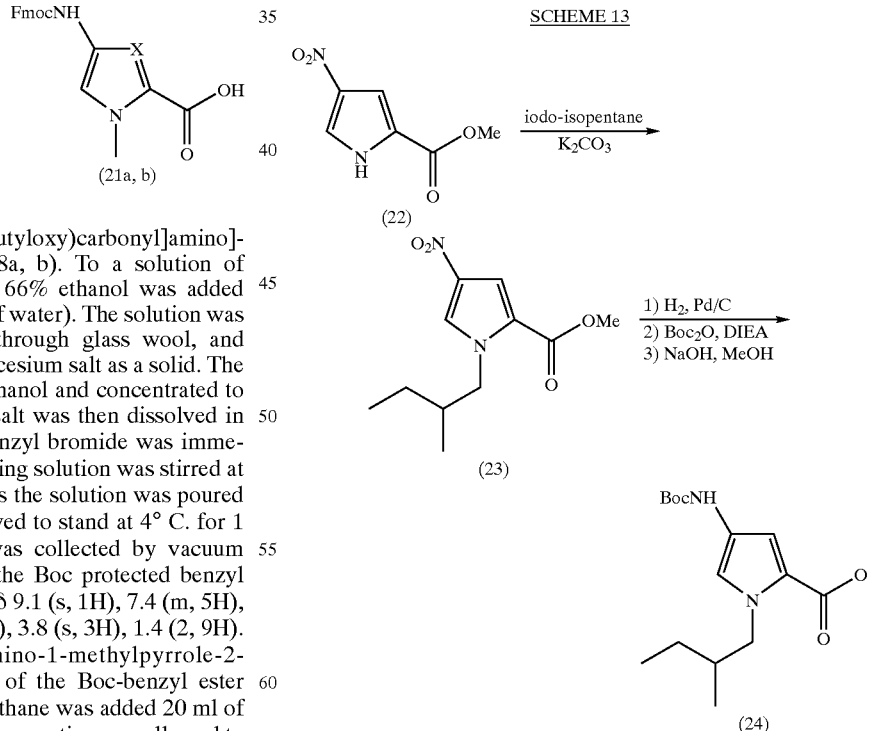

Preparation of Methyl N-2-methyl-butyl-4-nitropyrrole-2-carboxylate (23). Methyl 3-nitropyrrole-2-carboxylate (22) (2.7 g, 15.9 mmol), potassium, carbonate (6.5 g), and iodo-2-methylbutane (5.2 ml) were dissolved in 100 ml of acetone and refluxed for 10 hours. The reaction mixture was then cooled to room temperature, concentrated in vacuo, partitioned between 200 ml of dichloromethane and 200 ml of water and extracted with dichloromethane (2×200 ml). The combined organic layers were dried (sodium sulfate) and concentrated in vacuo. The resulting yellow oil was purified by flash chromatography to provide the substituted nitro pyrrole 23 (2.5 g, 70% yield). $^1$H NMR (DMSO-$d_6$) δ 8.30 (d, 1H, J=2.0 Hz), 7.33 (d, 1H, J=1.9 Hz), 4.15 (d, 2H, J=7.4 Hz), 3.77 (s, 3H), 2.03 (m, 1H, J=3.1 Hz), 0.80 (d, 6H, J=6.7 Hz); $^{13}$C NMR (DMSO-$d_6$) δ 160.30, 134.79, 129.80, 122.40, 112.76, 105.00, 56.63, 52.41, 29.72, 19.73; FABMS, 226.096 calcd, 226.095 found.

Preparation of N-2-methylbutyl-4-[[(tert-butyloxy) carbonyl]amino]-2-carboxylic acid (24). A solution of methyl N-2-methylbutyl-4-nitropyrrole-2-carboxylate 23 (2.3 g, 0.98 mmol) in 20 ml of DMF was treated with a Pd/C catalyst (10%, 500 mg) and the mixture was hydrogenated in a Parr bom apparatus (500 psi $H_2$) for 7 hours. After 7 hours, Boc-anhydride (2.95 g, 13.5 mmol) was added followed by DIEA (5 ml) and the reaction was stirred overnight. The reaction mixture was then partitioned between 200 ml of water and 200 ml of ethyl ether and extracted with ethyl ether (2×200 ml). The combined organics were dried over sodium sulfate and concentrated in vacuo to yield a yellow oil. The resulting yellow oil was dissolved in 30 ml of methanol and 30 ml of 1M NaOH was added. The solution was heated at 50° C. for 6 hours, cooled to room temperature, extracted with ethyl ether (2×200 ml), acidified to pH 0 with sodium bisulfate, and extracted with ethyl ether (3×200 ml). The combined acidic extracts were dried (sodium sulfate) and concentrated in vacuo to yield a white solid. (1.2 g, 41% yield). $^1$H NMR (DMSO-$d_6$) δ 12.1 (br s, 1H), 9.09 (s, 1H), 7.05 (s, 1H), 6.59 (s, 1H), 4.10 (d, 2H, J=7.1 Hz), 3.35 (s, 2H), 1.92 (m, 1H), 1.44 (s, 9H), 1.70 (d, 6H, J=6.4 Hz); $^{13}$C NMR (DMSO-$d_6$) 175.0, 161.9, 112.9, 119.4, 118.5, 108.3, 108.2, 55.0, 30.1, 28.4, 19.7.

Preparation of Monomers Substituted at the 3-Position of the Pyrrole.

Preparation of 3-methyl substituted pyrroles. Scheme 14 outlines a general synthesis of a 3-methyl substituted pyrrole. In this example the amine is protected with an allyloxycarbonyl group. Briefly, diethylester (25) is methylated and hydrolyzed to yield monoacid 27. Monoacid 27 is reacted with allyl alcohol/DPPA to yield allyl ester (28) which is hydrolyzed to form compound 29.

SCHEME 14

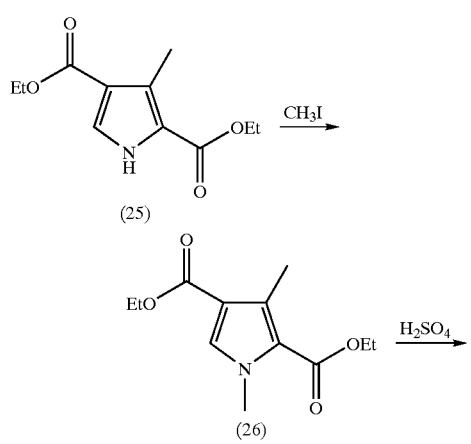

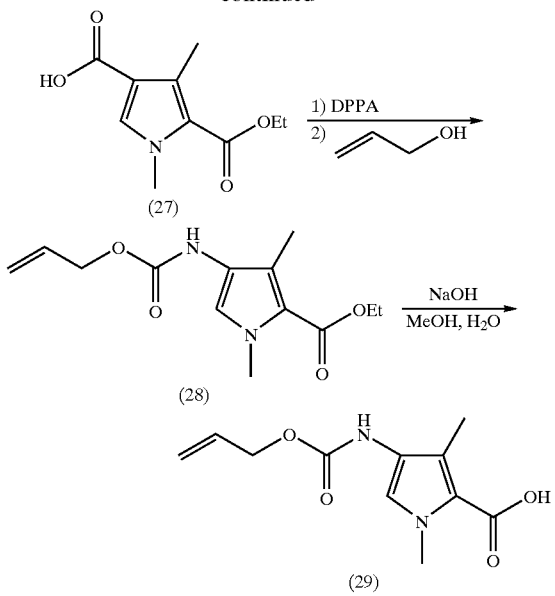

2,4-Dicarbethoxy-1,3-dimethylpyrrole (26). A solution of 2,4-dicarbethoxy-3 methylpyrrole (25) (2.44 g, 10.9 mmol), $K_2CO_3$ (9.9 g), and iodomethane (55 ml) in 750 ml acetone was refluxed at 50° C. for 15 hours. The solution was concentrated in vacuo, partitioned between 450 ml of dichloromethane and 600 ml of water. The aqueous layer was extracted with $CH_2Cl_2$ (2×500 ml), dried (sodium sulfate), and concentrated in vacuo to yield a brown oil that solidified upon standing at room temperature for several minutes and was used without further purification. (2.37 g, 91% yield). TLC (benzene) Rf 0.3; $^1$H NMR ($CD_2Cl_2$) δ 7.31 (s, 1H), 4,23 (m, 4H), 3,84 (s, 3H), 2.54 (2, 3H), 1.33 (m, 6H).

1,3-Dimethyl-4-carboxyl-2-carbethoxypyrrole (27). 2,4-Dicarbethoxy-1,3-dimethyl pyrrole (26) (9.24 g, 38.6 mmol) was suspended in 120 ml of concentrated sulfuric acid and vigorously stirred for 32 minutes at room temperature. The mixture was then precipitated by pouring into 2 liters of ice. The product was collected by vacuum filtration, washed with water (5×250 ml), and dried in vacuo to provide a white sand, (7.38 g, 91% yield). $^1$H NMR ($CDCl_3$) δ 7.42 (s, 1H), 4.35 (m, 2H), 3.89 (s, 3H), 2.59 (s, 3H), 1.39 (t, 3H, J=7.1 Hz); $^{13}$C NMR ($CDCl_3$) δ 237.1, 188.9, 184.4, 163.4, 161.6, 160.8, 159.9, 105.0, 46.6, 15.6.

Preparation of Ethyl 4-[(Allyloxycarbonyl)amino]-1,3-dimethylpyrrole-2-carboxylate (28). 1,3-dimethyl-4-carboxyl-2-carbethoxypyrrole (27) (2.19 g, 10.4 mmol), triethylamine (1.45 ml, 10.4 mmol) and diphenylphosphorylazide (DPPA) (Rappnport) (2.234 ml, 10.4 mmol) were dissolved in 31 ml of DNA synthesis grade $CH_3CN$ (Fisher). The solution was refluxed for 4.5 hours under argon, after which allyl alcohol (31 ml) was added. The solution was refluxed for an additional 22 hours under argon. After 22 hours, the solution was concentrated in vacuo, partitioned between 250 ml water and 250 ml diethyl ether, washed several times with 10% $Na_2CO_3$, 1M HCl, and water. The organic layer separated, dried (sodium sulfate), and concentrated to provide yellow crystals 28 (1.59 g, 58% yield). TLC (ethyl acetate) Rf 0.9; $^1$H NMR (DMSO) δ 8.77 (br, 1H), 7.05 (s, 1H) 5.95 (m, 1H), 5.36 (d, 1H, J=17.1 Hz), 5.22 (d, 1H, J=10.4 Hz), 4.54 (d, 2H, J=5.04 Hz), 4.19 (1, 2H, J=7.1 Hz), 3,75 (s, 3H), 2.10 (s, 3H), 1.27 (t, 3H, J=7.1 Hz); $^{13}$C NMR (DMSO) δ 161.3, 154.6, 133.8, 123.0, 121.1, 117.4, 64.8, 59.4, 37.1, 14.5, 10.5.

Preparation of 4-[(Allyloxycarbonyl)amino]-2-carboxyl-1,3-dimethylpyrrole (29). Ethyl 4-[(allyloxycarbonyl)amino]-1,3-dimethylpyrrole-2-carboxylate (28) (1.00 g, 3.75 mmol) was suspended in 6 ml water. Methanol was added with vigorous stirring until all starting material dissolved. 8 M NaOH (8 ml) was added, and the solution was stirred for five hours at 50° C. The reaction mixture was allowed to cool to room temperature, and 1M HCl added to approximately pH 2 while solution cooled in ice bath to precipitate out product. The product was collected by vacuum filtration, washed once with water, and dried in vacuo to yield 0.800 g (90% yield) of compound 29. TLC (ethyl acetate) Rf 0.8; $^1$H NMR (DMSO) δ 12.23 (br, 1H), 8.73 (s, 1H), 7.01 (s, 1H), 5.93 (m, 1H), 5.33 (d, 1H, J=17.1 Hz), 5.19 (d, 1H, J=10.5 Hz), 4.53 (d, 2H, J=5.5 Hz) 3.74 (s, 3H), 2.09 (s, 3H); mass. spec. Calc. 238.0954 Found 238.0952.

Scheme 15 illustrates two syntheses of 3-hydroxy substituted pyrrole monomers. Both syntheses utilize the previously described ethyl N-methyl-2,4-carboxy-3-hydroxypyrrole (30) as a starting material (Momose et al. (1978) Chem. Pharm. Bull. 26:2224). In the first approach, the acid is converted to the allyl carbamate (31) using DPPA and allyl alcohol in a modified Curtius reaction. The hydroxy group is then protected as a methyl ester with DMS, and the ethyl ester subsequently hydrolyzed with sodium hydroxide to yield compound (33).

The second approach produces a 3-substituted monomer which is appropriate as an N-terminal capping reagent. In this approach, ethyl N-methyl-2,4-carboxy-3-hydroxypyrrole (30) is first decarboxylated under acidic conditions. The hydroxy group is then protected as the allyl ether, and the ethyl ester subsequently hydrolyzed to yield compound (36).

SCHEME 15

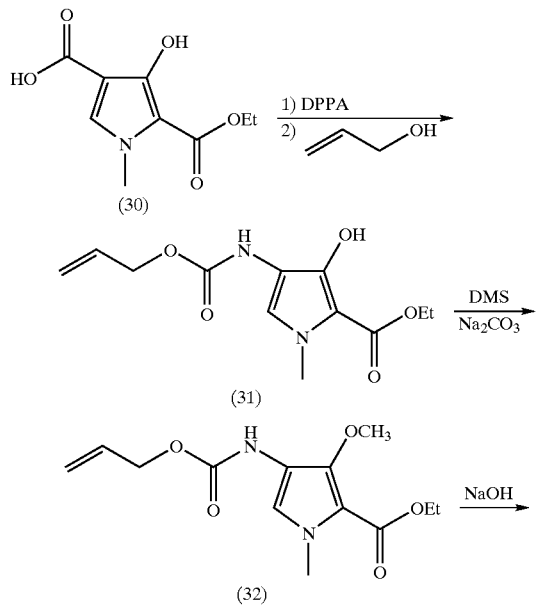

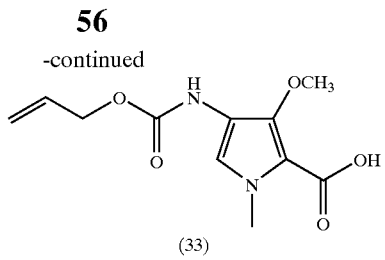

SCHEME 16

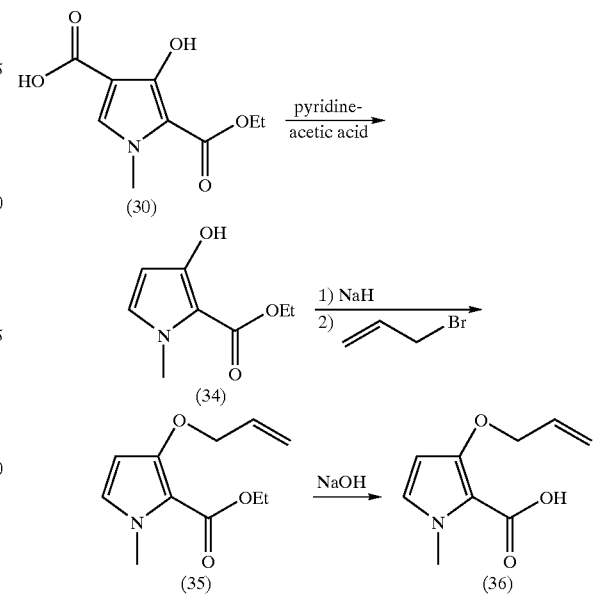

Preparation of Ethyl 4-allyloxycarbonyl-3-hydroxy pyrrole-2-carboxylate (31). Ethyl N-methyl-2,4-carboxy-3-hydroxypyrrole (30) (500 mg, 2.36 mmol) was dissolved in 7 ml of acetonitrile. Triethylamine (329 μl) was added to this solution followed by DPPA, (508 μl). The mixture was refluxed for 1.5 hours, after which allyl alcohol was added (7.1 ml) and the mixture was refluxed for an additional 17 hours. The reaction mixture was worked up using standard methods and the product was purified by flash chromatography (2% MeOH/CHCl$_3$/AcOH) to yield 250 mg, (39%) of compound (31). FABMS (low res. 268 found, 268 calc.)

Preparation of 4-allyloxycarbonyl-3-methoxy pyrrole-2-carboxylic acid (33). Compound 32 was prepared from Compound 31, using standard means (Dms, Na$_2$CO$_3$) (Greene (1991) in Protecting Groups in Organic Synthesis, John Wiley & Sons 2nd Ed., NY, N.Y.) To a solution of ethyl 4-allyloxycarbonyl-3-methoxy pyrrole-2-carboxylate (32) (190 mg, 675 μmol) in 12 ml of ethanol was added 0.1 sodium hydroxide (6.8 ml). The solution was refluxed for 3 days and worked up using standard methods.

Preparation of Ethyl 3-hydroxy pyrrole-2-carboxylate (34). To a solution of ethyl N-methyl-2,4-carboxy-3-hydroxypyrrole (30) (1000 mg, 4.7 mmol) in pyridine (8 ml) was added acetic acid (8 ml) and the solution was refluxed for 6 hours. The reaction mixture was concentrated onto silica gel and purified by flash chromatography (25%) to yield 580 mg (73%) of compound (34).

Preparation of Ethyl 3-allyloxy pyrrole-2-carboxylate (35). To a solution of ethyl 3-hydroxypyrrole-2-carboxylate (34) (580 mg) in benzene (12 ml) was added sodium hydride (387 mg). The suspension was heated at 60–70° C. for 1 hour. A solution of allyl bromide in benzene was then added and the mixture heated at 70–80° C. for ??hour. The reaction was concentrated onto silica gel and purified by flash chromatography (25% EtOAc/hexane) to yield 300 mg (50%) of compound (35).

Example 2

Activation of Amino Acids

To activate the various amino acids 1.0 mmol of the appropriate amino acid was dissolved in 2 ml DMF. HOBt (135 mg, 1.0 mmol) was added followed by DCC (263 mg, 1 mmol) and the solution lightly shaken for at least 30 minutes. The precipitated DCU by product was filtered before addition to the coupling reaction.

Example 3

Preparation of Boc-Pyrrole-PAM and Boc Pyrrole-BAM-Resins (24) and (25)

Preparation of Resin Linkage Agents 39 and 40. Resin linkage agents 39 and 40 were prepared in three steps according to the published procedures of Merrifield, using Boc-Py-COOH as the amino acid (Mitchell et al. (1978) J. Org. Chem. 43:2845–2852) as outlined in Scheme 16.

SCHEME 16

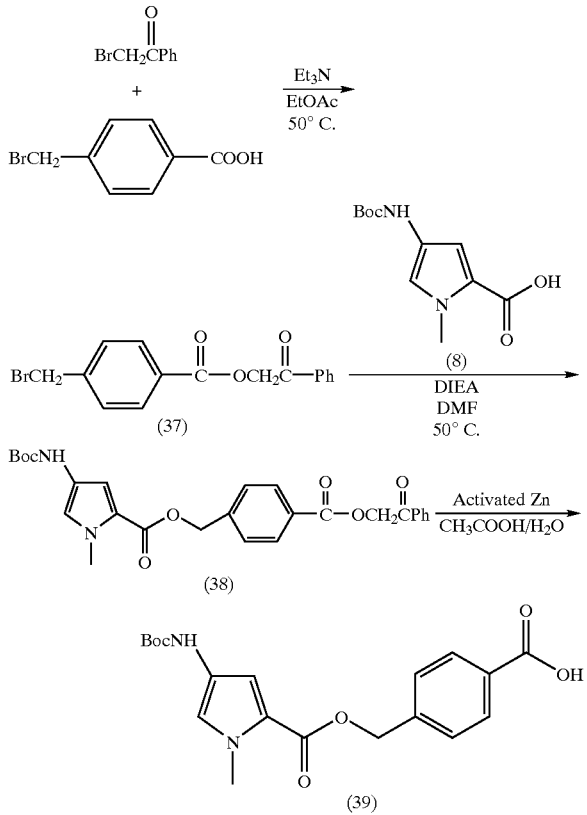

Preparation of 4-(Bromomethyl)benzoic acid phenacyl ester (37). Triethylamine (16 ml, 115 mmol) and bromoacetophenone (22.9 g, 115 mmol) were dissolved in 450 ml of ethyl acetate. The solution was stirred at 50° C. and 4-(bromomethyl)benzoic acid (17.5 g, 155 mmol) was added in seven equal portions over a three hour period. Stirring was continued for an additional 8 hours at 50° C. Precipitated triethylaminehydrobromide was removed by filtration and the ethyl acetate solution was washed with (3×150 ml each) of 10% citric acid, brine saturated sodium bicarbonate and brine. The organic phase was dried with sodium sulfate and concentrated in vacuo. The residue was recrystallized from dichloromethane-petroleum ether to give fine white crystals (10.2 g, 27% yield). $^1$H NMR (DMSO-$d_6$) δ 7.99 (m, 4H), 7.69–7.54 (m, 5H), 5.74 (s, 2H), 4.77 (s, 2H); $^{13}$C NMR (DMSO-$d_6$) δ 193.7, 165.9, 144.6, 134.9, 131.2, 131.0, 130.7, 130.6, 130.2, 129.9, 128.8, 128.6, 68.2, 34.0.

Preparation of Boc-pyrrolyl-4-(oxymethyl)benzoic acid phenacyl ester (38). A solution of Boc-pyrrole-OH (8) (2.9 g 12 mmol), 4-(bromomethyl)benzoic acid phenacyl ester (22) (4 g, 12 mmol) and diisopropylethylamine (3.0 ml, 16.8 mmol) in 60 ml of DMF were stirred at 50° C. for 6 hours. The solution was cooled and partitioned between 400 ml of water and 400 ml of ethyl ether. The ether layer was washed with (2×200 ml each) of 10% citric acid, brine, saturated sodium bicarbonate and brine. The organic phase was dried with sodium sulfate and concentrated in vacuo to yield compound 38 as light white foam which was used without further purification (5.4 g, 97% yield). TLC (2:3 hexane/ethyl acetate) Rf 0.6; $^1$H NMR (DMSO-$d_6$) δ 9.14 (s, 1H), 8.03 (m, 4H), 7.67 (m, 4H), 7.5 (m, 4H), 7.13 (s, 1H), 6.72 (d, 1H, J=1.5 Hz), 5.74 (s, 1H), 5.32 (s, 1H), 3.79 (s, 3H), 1.42 (s, 9H); $^{13}$C NMR (DMSO-$d_6$) δ 193.2, 165.5, 160.4, 153.2, 143.1, 134.5, 130.1, 129.5, 128.3, 128.2, 123.8, 120.3, 118.8, 108.2, 79.1, 67.7, 64.6, 36.7, 28.6.

Preparation of Boc-pyrrolyl-4-(oxymethyl)phenylacetic acid phenacyl ester. This compound was prepared by the method described above for Boc-pyrrolyl-4-(oxymethyl) benzoic acid phenacyl ester. The product was purified by crystallization with hexane:ethyl acetate (3:1) as long needles (6.1 g, 44.5%). TLC (3:1 hexane/ethyl acetate) Rf 0.2; $^1$H NMR (DMSO-$d_6$) δ 9.11 (s, 1H), 7.93 (d, 2H, J=8.2), 7.67 (t, 1H, J=7.0), 7.52 (t, 2H, J=7.9), 7.35 (m, 4H), 7.10 (s, 1H), 6.67 (s, 1H), 5.50 (s, 2H), 5.22 (s, 2H), 5.19 (s 2H), 3.83 (s, 3H), 1.42 (s, 9H); $^{13}$C NMR (DMSO-$d_6$) δ 193.1, 171.2, 160.6, 153.2, 135.7, 134.4, 130.1, 129.4, 128.5, 128.3, 123.7, 120.0, 119.0, 108.0, 79.0, 67.4, 65.1, 36.7, 28.6.

Preparation of Boc-pyrrolyl-4-(oxymethyl)benzoic acid (39). Boc-pyrrolyl-4-(oxymethyl)benzoic acid phenacyl ester (38) (3 g, 5.9 mmol) was dissolved in 90 ml of acetic acid and water (80:20). Activated zinc dust (9.6 g, 147 mmol) was added and the reaction was stirred for 18 hours at room, temperature. The zinc was removed by filtration and the reaction mixture was partitioned between 200 ml of ethyl ether and 200 ml of water. The layers were separated and the aqueous layer was extracted with another 200 ml ethyl ether. The ether layers were combined and washed with (5×100 ml) of water. The combined organics were dried with sodium sulfate, concentrated in vacuo, and azeotroped with (6×100 ml) of benzene. The product was purified by flash chromatography with a gradient of 2:1 hexane:ethyl acetate to ethyl acetate to give a yellow oil (1.9 g, 54%) of compound 39. TLC (ethyl acetate) Rf 0.7.

Preparation of Boc-pyrrolyl-4-(oxymethyl)phenylacetic acid (40). Prepared in a manner analogous to 39, yielding 40 as a yellow oil in 78% yield.

Preparation of Boc-aminoacyl-pyrrolyl-4-(oxymethyl)-BAM-resin (41). BAM linker acid (39) (1 g, 2.6 mmol) was dissolved in 6.5 ml of DMF/HOBt (382 mg, 2.8 mmol). DCC (735 mg, 2.8 mmol) was added and the reaction mixture was shaken at room temperature. After 4 hours the precipitated DCU byproduct was filtered and the reaction mixture was added to 3 grams aminomethyl-polystyreneresin (0.7 mmol/gram substitution) previously swollen for 30 minutes in DMF. Diisopropylethylamine (913 μl, 5.3 mmol) was added and the reaction was shaken for 12 hours. After 12 hours the resin was determined by the ninhydrin test to be approximately 0.3 mmol/gram substituted. At this time the resin was washed with DMF and the remaining amine groups were capped by acetylation (2×) with excess acetic anhydride capping solution. The resin was washed with DMF, dichloromethane and MeOH and dried in vacuo.

Preparation of Boc-aminoacyl-pyrrolyl-4-(oxymethyl)-PAM-resin (42). Boc-Py-PAM-resin (42) (0.3 mmol/g substitution) was prepared using PAM linker acid 40 as described above for the BAM resin.

Example 4

Solid Phase Polyamide Synthesis

Preparation of Boc-PyPy-G-PyPyPy-G-PAM-resin Boc-G-PAM-resin (1.25 g, 0.25 mmol amine) was shaken in DMF for 15 minutes and drained. The N-boc group was removed by washing with dichloromethane for 1 minute, followed by washing with 65% TFA/$CH_2Cl_2$/0.5M PhSH for 30 seconds, shaking in 65% TFA/$CH_2Cl_2$/0.5 PhSH for 60 seconds, washing with 65% TFA/$CH_2Cl_2$/PhSH for 30 seconds, and shaking in 65% TFA/$CH_2Cl_2$/PhSH for 20 minutes. The trifluoroacetic acid deprotection mixture (65% TFA/$CH_2Cl_2$/0.5M PhSH) was prepared by combining and shaking a mixture of trifluoroacetic acid (TFA) (290 ml), dichloromethane (150 ml), and thiophenol (23 ml, 225 mmol). The resin was washed for 1 minute with dichloromethane, 30 seconds with DMF, and shaken for 1 minute in DMF. The resin was then drained completely and activated acid, Boc-Py-OBt, (1 mmol, 4 eq., prepared as described in Example 2) in 2 ml DMF was added followed by DIEA (355 μl, 8 eq.) and the resin shaken vigorously to make a slurry. After shaking the reaction was allowed to proceed for 45 minutes after which the reaction vessel was washed with DMF for 30 seconds completing a single reaction cycle. Five additional cycles were performed adding, Boc-Py-OBt, Boc-Py-OBt, Boc-G-OBt, Boc-Py-OBt and Boc-Py-OBt to give Boc-PyPy-G-PyPyPy-G-PAM-Resin. The resin was washed with DMF (1 minute), dichloromethane (1 minute) and methanol (1 minute) and dried in vacuo. This compound was then used to synthesize ImPyPy-G-PyPyPy-G-Ed (2a). ImPyPy-G-PyPyPy-G-Dp (2b), AcImPyPy-G-PyPyPy-G-Dp (2c), ImPyPy-G-PyPyPy-G-Ta-EDTA, ImPyPy-G-PyPyPy-G-Ta, and AcImPyPy-G-PyPyPy-G-Ta (2d) as described below.

Preparation of AcImPyPy-G-PyPyPy-G-Dp (2c). A sample of Boc-PyPy-G-PyPyPy-G-PAM-resin (600 mg, about 100 μmole) was placed in a reaction vessel and shaken in DMF for 20 minutes. The resin was subsequently drained and subjected to an additional coupling cycle with Boc-Im-OBt, as described above, to add an N-terminal Boc imidazole. The N-Boc group was removed as described above and the resin was washed with dichloromethane (30 seconds) and DMF (1 minute). The resin was then treated with 4 ml of an acetylation mixture (acetylation mixture: DMF (4 ml). DIEA (710 μl, 4.0 mmol), and acetic anhydride (380 μl, 4.0 mmol) combined immediately before use) for 1 hour. The reaction vessel was then washed with DMF (1 minute), dichloromethane (1 minute) and methanol (1 minute) and dried in vacuo to yield AcImPyPy-G-PyPyPy-G-PAM-Resin. The resin (180 mg, 29 μmol) was weighed into a glass scintillation vial and treated with 1.5 ml of DMF, after 10 minutes, 1.5 ml of dimethylaminopropylamine (Dp) was added and the mixture was shaken at 37° C. for 12 hours.

The resin was removed by filtration through an ISOLAB polypropylene filter and washed with 11 ml of water. The DMF solution and the water washes were combined. Seven milliliters of the combined solution was loaded on a $C_{18}$ preparatory HPLC column, the column was washed for 2 minutes in 0.1% TFA at 8 ml/min. to remove the DMF, followed by addition of a second 7 ml portion, which was also washed free of DMF with 0.1% TFA for 2 minutes at 8 ml/min. No flushing of the polyamide occurs so long as the injection solution is less than 20% v/v DMF. The polyamide was then eluted in 100 minutes with a gradient of 0.25% $CH_3CN$ per minute. The polyamide was collected in 4–5 separate 8 ml fractions, the purity of the individual fractions was verified by HPLC and $^1$H NMR, to give AcImPyPy-G-PyPyPy-G-Dp (2c) (11.8 mg, 39%).

Characterization of 2c. HPLC, r.t. 26.9; UV($H_2O$/DMSO) $\lambda_{max}(\epsilon)$, 246 (45,200), 304 (50,200) (Extinction coefficients ($\epsilon$) were determined by taking a 5 μl aliquot from two separate NMR samples, diluting to 1 ml with water and measuring the UV spectrum. The presence of 0.5% DMSO does not result in a significant change in the measured extinction coefficient.); $^1$H NMR (DMSO-$d_6$) δ 10.24 (s, 1H), 9.98 (s, 1H), 9.96 (s, 1H), 9.94 (s, 1H), 9.92 (s, 1H), 9.90 (s, 1H), 9.2 (br s, 1H, $CF_3COOH$), 8.29 (m, 2H, G-NH and G-NH), 8.02 (t, 1H, J=6.6 Hz, PyCONH-G), 7.41 (s, 1H), 7.26, (d, 1H, J=1.7 Hz), 7.23 (m, H), 7.16 (d, 1H, J=1.8 Hz), 7.14 (d, 1H, J=1.7 Hz), 7.05 (d, 1H, J=1.8 Hz), 6.94 (m, 3H), 3.93 (s, 3H), 3.89 (d, 2H, J=3.9 Hz, Gly $CH_2$), 3.84 (s, 3H), 3.84 (s, 3H), 3.83 (s, 3H), 3.80 (s, 3H), 3.79 (s, 3H), 3.72 (d, 2H, J=4.9 Hz, Gly$CH_2$), 3.14 (q, 2H, J=5.0 Hz), 3.03 (q, 2H, J=6.0 Hz), 2.74 (d, 6H, J=6.0 Hz, $CH_2N(CH_3)_2$), 2.00 (s, 3H, $CH_3CONH$), 1.77 (quintet, 2H, J=4.6 Hz, $CH_2CH_2N(CH_3)_2$); MALDI-TOF MS, calcd M$^+$H 993.1, found 993.8.

Preparation of ImPyPy-G-PyPyPy-G-Dp (2b). A sample of Boc-PyPy-G-PyPyPy-G-PAM-Resin (600 mg, about 100 μmole) was placed in a reaction vessel and shaken in DMF for 15 minutes. The N-Boc group was removed with TFA as described above and the resin was washed with dichloromethane (30 seconds) and DMF (1 minute) and was treated with the HOBt ester of N-methyl imidazole-2-carboxylic acid (about 16 equivalents, prepared as described below) and DIEA (155 μl, 16 eq.) for 2 hours. The resin was washed with DMF, dichloromethane and MeOH (1 minute each) and dried in vacuo to yield ImPyPy-G-PyPyPy-G-PAM-Resin. It should be noted that polyamides capped with N-methyl imidazole-2-carboxylic acid tend to give false positives for the picric acid test even when reactions are >99% complete as determined by stepwise HPLC analysis. The crude product was cleaved from the resin (180 mg, 29 μmole) with dimethylaminopropylamine and purified as described for (2c) to yield ImPyPy-G-PyPyPy-G-Dp (2b) (12 mg, 40% recovery).

Characterization of 2b. HPLC, r.t. 26.9; UV($H_2O$/DMSO) $\lambda_{max}(\epsilon)$, 246 (41,100), 304 (48,400); $^1$H NMR (DMSO-$d_6$) δ 10.49 (s, 1H), 9.98 (s, 1H), 9.95 (s, 1H), 9.92 (s, 1H), 9.89 (s, 1H), 9.2 (br s, 1H, $CF_3COOH$), 8.30 (m, 2H, Gly-NH and Gly-NH), 8.06 (t, 1H, J=5.8 Hz, PyCONH-Gly), 7.40 (s, 1H), 7.24 (d, 1H, J=1.7 Hz), 7.23 (m, 3H) 7.17 (m, 2H), 7.06 (m, 2H), 6.94 (m, 3H) 3.99 (s, 3H), 3.89 (d, 2H, Gly$CH_2$), 3.84 (s, 3H), 3.84 (s, 3H), 3.83 (s, 3H), 3.81 (s, 3H), 3.80 (s, 3H), 3.72 (d, 2H, J=4.3 Hz, Gly$CH_2$), 3.13 (q, 2H, J=5.7 Hz), 3.01 (q, 2H, J=5.2 Hz), 2.76 (d, 6H, J=4.3 Hz, $CH_2N(CH_3)_2$), 1.77 (quintet, 2H, J=7.4 Hz, $CH_2CH_2N(CH_3)_2$); MALDI-TOF MS, calc. for (M$^+$H$^+$) 936.0, found 935.7.

Preparation of ImPyPy-G-PyPyPy-G-Ed (2a). ImPyPy-G-PyPyPy-G-PAM-Resin (180 mg, 29 μmole, synthesized as described for 2b was shaken in 1.5 ml of DMF. After 20 minutes, ethylenediamine (Ed) (1.5 ml) was added and the mixture was shaken at 37° C. for 12 hours. The crude product was purified as described for 2c to yield ImPyPy-G-PyPyPy-G-Ed (2a) (9 mg, 39%).

Characterization of 2a. HPLC, r.t. 24.2; UV($H_2O$/DMSO) $\lambda_{max}(\epsilon)$, 246 (44,400), 304 (51,300); $^1$H NMR (DMSO-$d_6$) δ 10.49 (s, 1H), 9.97 (s, 1H), 9.94 (s, 1H), 9.92 (s, 1H), 9.88 (s, 1H), 8.30 (t, 1H, J=2.6 Hz), 8.23 (t, 1H, J=5.6 Hz), 8.04 (t, 1H, J=3.1 Hz), 7.73 (br s, 1H), 7.40 (s, 1H), 7.28 (d, 1H, J=1.7 Hz), 7.23 (d, 1H, J=1.7 Hz), 7.22 (m, 2H), 7.15 (m, 2H), 7.05 (m, 2H), 6.95 (m, 3H), 3.98 (s, 3H), 3.88 (d, 2, J=4.1), 3.83 (s, 3H), 3.82 (m, 6H), 3.80 (s, 3H), 3.79, (s, 3H), 3.76 (m, 2H), 3.29 (m, 2H), 2.84 (m, 2H); MALDI-TOF MS, calc. for ($M^+H^+$) 893.9, found 894.9.

Preparation of AcImPyPy-G-PyPyPy-G-Ta (2d). AcImPyPy-G-PyPyPy-G-PAM-Resin (180 mg, 29 μmole, synthesized as described for 2c) was treated with 1.5 ml of DMF. After 20 minutes, 1.5 ml of 3,3'-diamino-N-methylpropylamine (Ta) was added and the mixture was shaken at 37° C. for 12 hours and purified as described for (2c) to yield AcImPyPy-G-PyPyPy-G-Ta (2d) (6.7 mg, 23% yield).

Characterization of 2d. HPLC, r.t. 25.9; UV($H_2O$/DMSO) $\lambda_{max}(\epsilon)$, 246 (43,600), 304 (51,800); $^1$H NMR (DMSO-$d_6$) δ 10.23 (s, 1H), 9.99 (s, 1H), 9.96 (s, 1H), 9.94 (s, 1H), 9.91 (s, 1H), 9.89 (s, 1H) 9.53 (br s, 1H, $CF_3COOH$), 8.28 (m, 2H, J=6.1 Hz, Gly-NH and Gly-NH), 8.04 (t, 1H, J=5.3 Hz, PyCONH-Gly), 7.79–7.82 (br s, 3H, $CH_2NH_3$), 7.41, (s, 1H), 7.25 (d, 1H, J=1.7 Hz), 7.23 (d, 1H, J=1.7 Hz), 7.22 (d, 1H, J=1.7 Hz), 7.20 (d, 2H, J=1.7 Hz), 7.15 (d, 1H, J=1.7 Hz), 7.13 (d, 1H, J=1.7 Hz), 7.05 (d, 1H, J=1.7 Hz), 6.94 (m, 2H), 6.92 (d, 1H, J=1.7 Hz), 3.89 (s, 3H), 3.88 (d, 2H, $GlyCH_2$), 3.85 (s, 3H), 3.84 (s, 3H), 3.82 (s, 3H), 3.80 (s, 3H), 3.79 (s, 3H), 3.71 (d, 2H, J=5.5 Hz, $GlyCH_2$), 3.37 (m, 2H), 3.13 (m, 4H), 2.80 (m, 2H), 2.73 (d, 3H, J=3.3 Hz, $NCH_3$), 2.01 (s, 3H, $CH_3CO$), 1.89 (m, 2H), 1.77 (m, 2H); MALDI-TOF MS, calc. for ($M^+H^+$) 1036.2, found 1036.2.

AcImPyPy-G-PyPyPy-G-Ta-EDTA (2e). To a solution of AcImPyPy-G-PyPyPy-G-PAM-resin (synthesized as described for 2c) (3.0 mg, 2.5 μmole) in 750 μl of DMSO was added 750 μl NMP, followed by EDTA monoanhydride (30 mg, 118 μmole) and the solution was heated at 37° C. After 2 hours, 13 ml of water was added and the reaction was purified by preparatory HPLC as described above. The EDTA derivative eluted at 120 minutes to give AcImPyPy-G-PyPyPy-G-Ta-EDTA (2e) (1.1 mg, 32% yield).

Characterization of 2e. HPLC, r.t. 27.8; UV($H_2O$/DMSO) $\lambda_{max}$, 246, 304; $^1$H NMR (DMSO-$d_6$) δ 10.23 (s, 1H), 9.99 (s, 1H), 9.96(s, 1H), 9.94 (s, 1H), 9.91 (s, 1H), 9.89 (s, 1H) 9.25 (br s), 8.43 (t, 1H), 8.3 (m, 2H), 8.06 (t, 1H) 7.41, (s, 1H), 7.26 (d, 1H, J=1.7 Hz), 7.22 (d, 1H, J=1.7 Hz), 7.21 (d, 1H, J=1.7 Hz), 7.20 (d, 2H, J=1.7 Hz), 7.15 (d, 1H, J=1.7 Hz), 7.13 (d, 1H, J=1.7 Hz), 7.07 (d, 1H, J=1.7 Hz), 6.94 (m, 2H), 6.92 (d, 1H, J=1.7), 3.93 (s, 3H), 3.88 (d, 2H), 3.85 (s, 3H), 3.84 (s, 3H), 3.82 (s, 3H), 3.80 (s, 3H), 3.79 (s, 3H), 3.71 (d, 2H), 3.65 (m 4H), 3.26 (m, 10H), 3.13 (m, 4H), 2.71 (d, 3H), 2.00 (s, 3H) 1.78 (m, 6H), 1.21 (m, 2H); MALDI-TOF MS, calc. for ($M^+H^+$) 1310.4, found 1311.7.

Preparation of ImPyPyPyPyPyPy-G-Ed (1a). This compound was synthesized and purified by the general procedures described above to yield 6.7 mg (19%) of ImPyPyPyPyPyPy-G-Ed (1a) which was 97% pure. A portion of this material was purified a second time by preparatory HPLC to give pure 1a (0.8 mg).

Characterization of 1a. HPLC, r.t. 28.3; UV($H_2O$/DMSO) $\lambda_{max}(\epsilon)$, 246 (35,600), 312 (57,000); $^1$H NMR (DMSO-$d_6$) δ 10.48 (s, 1H), 9.99 (s, 1H, PyNH), 9.96 (m, 4H, PyNH), 8.26 (t, 1H, J=6.3 Hz, G-NH), 8.04 (t, 1H, J=5.3 Hz, PyCONH-Gly), 7.75–7.67 (br s, 3H, $NH_3$), 7.40 (s, 1H), 7.28 (d, 1H, J=1.7 Hz), 7.3 (m 5H), 7.17 (d, 1H, J=1.7 Hz), 7.08 (m, 4H), 7.05 (d, 1H, J=1.7 Hz), 6 95 (d, 1H, J=1.7 Hz), 3.98 (s, 3H), 3.85 (m, 15H), 3.79 (s, 3H), 3.74 (d, 2H, J=6.4 Hz, $GlyCH_2$), 3.31 (q, 2H, J=6.1 Hz, Gly-NE-$CH_2$), 2.85 (m, 2H, J=3.0 Hz, $CH_2NH_2$); MALDI-TOF MS, calc. for $M^+H^+$ 959.0, found 959.3.

Preparation of ImPyPyPyPyPyPy-G-Dp (1b). This compound was synthesized by the general procedures described above to give 8 mg, 24% yield of ImPyPyPyPyPyPy-G-Dp (1b). A portion of this material was purified a second time by preparatory HPLC to give pure 1b (1.2 mg).

Characterization of 1b. HPLC, r.t. 28.5; UV($H_2O$/DMSO) $\lambda_{max}(\epsilon)$ 246 (34,600), 312 (55,300); $^1$H NMR (DMSO-$d_6$) δ 10.55 (s, 1H, PyNH), 10.02 (s, 1H, PyNH), 10.00 (m, 4H, PyNH), 9.3 (br s, 1H, $CF_3COOH$), 8.32 (t, 1H, J=6.2 Hz, Gly-NH), 8.06 (t, 1H, J=5.9 Hz, PyCONH-Gly), 7.44 (d, 1H, J=0.6 Hz), 7.31 (d, 1H, J=1.7 Hz), 7.26 (m, 5H), 7.19 (d, 1H, J=1.8 Hz), 7.10 (m, 5H), 6.97 (d, 1H, J=1.7 Hz), 4.01 (s, 3H), 3.87 (m, 15H), 3.82 (s, 3H), 3.73 (d, 2H, J=5.5Hz, $GlyCH_2$), 3.16 (q, 2H, J=6.2 Hz, Gly-NH-$CH_2$), 3.03 (q, 2H, J=5.2 Hz, $CH_2N(CH_3)_2$), 2.74 (d, 6H, J=4.9 Hz, $CH_2N(CH_3)_2$), 1.77 (quintet, 2H, J=6.7 Hz, $CH_2CH_2N(CH_3)_2$); MALDI-TOF MS, calc. for 1001.1, found 1000.5.

Preparation of ImPyPyPyPyPyPy-G-Ta (1c). This compound was synthesized by the general procedures described above to yield 9.2 mg, (28%) of product 1c.

Characterization of 1c. HPLC, r.t. 29.3; UV($H_2O$/DMSO) $\lambda_{max}(\epsilon)$, 246 (33,400), 312 (53,500); $^1$H NMR (DMSO-$d_6$) δ 10.47 (s, 1H, PyNH), 9.95 (m, 5H PyNH), 9.4 (br s, 1H, $CF_3COOH$), 8.28 (t, 1H, J=6.1 Hz, Gly-NH), 8.04 (t, 1H, J=5.1 Hz, PyCONH-Gly), 7.8 (br s, 3H, $CH_2NH_3$), 7.39 (d, 1H, J=0.6 Hz), 7.28 (d, 1H, J=1.2 Hz), 7.23 (m, 5H), 7,17 (d, 1H, J=1.8 Hz), 7.09 (m, 4H), 7.04 (d, 1H, J=1.7 Hz), 6.96 (d, 1H, J=1.6 Hz), 3.98 (s, 3H), 3.85 (m, 15H), 3.79 (s, 3H), 3.72 (d, 2H, J=5.2 Hz, $GlyCH_2$), 3.15 (q, 2H, J=5.0 Hz), 3.11 (m, 4H), 2.80 (m, 2H), 2.74 (d, 3H, J=2.9 Hz, $NCH_3$), 1.89 (quintet, 2H, J=7.4 Hz), 1.77, (quintet, 2H, J=6.8 Hz); MALDI-TOF MS, calc. for $M^+H^+$ 1044.2, found 1044.1.

Preparation of ImPyPyPyPyPyPy-G-Ta-EDTA (1d). Synthesized by the general procedures described above to yield 1.1 mg, 32% yield of compound 1d.

Characterization of 1d. HPLC, r.t. 30.6; UV($H_2O$/DMSO) $\lambda_{max}$, 246, 312; $^1$H NMR (DMSO-$d_6$) δ 10.47 (s, 1H), 9.46 (m, 4H), 7.39 (s, 1H), 7.28 (d, 1H, J=1.7 Hz), 7.28 (d, 1H, J=1.6 Hz), 7.24 (d, 1H, J=1.6 Hz), 7.23 (m, 4H), 7.17 (d, 1H, J=1.7 Hz), 7.08 (m, 5H), 7.04 (d, 1H, J=1.6 Hz), 6.95 (d, 1H, J=1.5 Hz), 3.98 (s, 3H), 3.84 (m, 15H), 3.79 (s, 3H), 3.71 (d, 2H), 3.66 (m, 4H), 3.26 (m, 8H), 3.13 (m, 4H), 2.73 (d, 3H), 2.27 (t, 2H), 1.78 (m, 6H), 1.21 (m, 2H); MALDI-TOF MS, calc. for $M^+H^+$ 1317.4, found 1318.1.

Preparation of AcImPyPy-γ-PyPyPy-G-Dp (3a). This compound was synthesized by the general procedures set forth above to yield 13.1 mg (30%) of compound 3a. The only variation was that Boc-γ is activated in situ.

Characterization of 3a. HPLC, r.t. 24.0; UV($H_2O$/DMSO) $\lambda_{max}(\epsilon)$, 246 (35,900), 312 (48,800); $^1$H NMR (DMSO-$d_6$) δ 10.23 (s, 1H), 9.98 (s, 1H), 9.32 (s, 1H), 9.90 (m, 2H), 9.84 (s, 1H), 9.2 (br s, 1H), 8.27 (t, 1H, J=5.0 Hz), 8.05 (m, 2H), 7.41 (s, 1H), 7.25 (d, 1H, J=1.2 Hz), 7.22 (m, 2H), 7.16 (m, 2H), 7.12 (d, 1H, J=1.7), 7.05 (d, 1H, J=1.5 Hz), 6.94 (d, 1H, J=1.6 Hz), 6.89 (d, 1H, J=1.7 Hz) 6.87 (d, 1H, J=1.6 Hz), 3.93 (s, 3H), 3.83 (s, 3H), 3.82 (m, 6H), 3.81 (s, 3H), 3.79 (s, 3H), 3.71 (d, 2H, J=5.1 Hz), 3.19 (m, 2H, J=5.8), 3.12 (m, 2H, J=5.0 Hz), 3.01 (m, 2H, J=4.2 Hz), 2.74 (d, 6H, J=4.6

Hz), 2.26 (m 2H, J=4.6 Hz), 2.00 (s, 3H), 1.75 (m, 4H); MALDI-TOF MS, calc. for M+H+ 1021.1, found 1021.6.

Preparation of AcImPyPy-γ-PyPyPy-G-Ta (3b). This compound was synthesized by the general procedures set forth above to yield 9.2 mg (31%) of product 3b.

Characterization of 3b. HPLC, r.t. 24.9; UV(H$_2$O/DMSO) $\lambda_{max}$(ε), 246 (37,400), 312 (50,500); $^1$H NMR (DMSO-d$_6$) δ 10.24 (s, 1H), 9.98 (s, 1H), 9.94 (s, 1H), 9.91 (m, 2H), 9.85 (s, 1H), 9.7 (br s, 1H), 8.28 (t, 1H, J=5.2 Hz), 8.05 (m, 2H), 7.86 (br s, 3H), 7.42 (d, 1H, J=1.6 Hz), 7.26 (d, 1H, J=1.7 Hz), 7.22 (m, 2H), 7.17 (m, 2H), 7.13 (d, 1H, J=1.7 Hz), 7.06 (d, 1H, J=1.7 Hz), 6.95 (d, 1H, J=1.7 Hz), 6.90 (d, 1H, J=1.7 Hz), 6.88 (d, 1H, J=1.7 Hz), 3.94 (s, 3H), 3.84 (s, 6H), 3.82 (s, 3H), 3.80 (s, 6H), 3.72 (s, 3H), 3.14 (m, 6H), 3.08 (m, 2H), 2.85 (m, 2H), 2.75 (d, 3H, J=4.2 Hz), 2.72 (t, 2H, J=6.8 Hz), 2.01 (s, 3H), 1.90 (m, 2H), 1.75 (m, 4H); MALDI-TOF-MS, calc. for M+H+ 1064.2, found 1064.5.

Preparation of AcImPyPy-γ-PyPyPy-G-Ta-EDTA (3c). Synthesized by the general procedures described above to yield 3.2 mg (41%) of compound 3c.

Characterization of 3c. HPLC, r.t. 24.3; UV(H$_2$O DMSO) $\lambda_{max}$, 246, 312; $^1$H NM (DMSO-d$_6$) δ 10.32 (s, 1H), 9.97 (s, 1H), 9.93 (s, 1H), 9.90 (m, 2H), 9.84 (s, 1H), 8.40 (t, 1H), 8.27 (t, 1H), 8.05 (m, 2H), 7.41 (s, 1H), 7.25 (d, 1H, J=1.6 Hz), 7.20 (m, 2H), 7.16 (m, 2H), 7.11 (d, 1H, J=1.6 Hz), 7.05 (d, 1H, J=1.7 Hz), 6.94 (d, 1H, J=1.7 Hz), 6.86 (d, 1H, J=1.7 Hz), 3.92 (s, 3H), 3.83 (s, 3H), 3.82 (s, 3H), 3.81 (s, 3H), 3.78 (m, 6H), 3.72 (d, 2H, J=5.5 Hz), 3.66 (m, 4H), 3.40 (m, 10H), 3.15 (m, 6H), 2.73 (d, 3H, J=4.2 Hz), 2.27 (t, 2H, J=6.9 Hz), 2.03 (s, 3H), 1.78 (m, 6H), 1.23 (m, 2H); MALDI-TOF-MS, calc. for M+H+ 1339.4, found 1340.

Preparation of ImImPy-γ-PyPyPy-G-Dp (4d). Synthesized by the general procedures described above to yield 8.9 mg (3.0%) ImImPy-γ-PyPyPy-G-Dp (4d).

Characterization of 4d. HPLC, r.t. 24.6; UV(H$_2$O/DMSO) $\lambda_{max}$(ε), 246 (37,600), 312 (50,700); $^1$H NMR (DMSO-d$_6$) δ 10.30 (s, 1H), 10.28 (s, 1H), 9.93 (s, 1H), 9.90 (s, 1H), 9.84 (s, 1H), 9.33 (s, 1H), 9.28 (br s, 1H), 8.05 (t, 1H, J=5.1), 8.08 (t, 1H), 8.02 (t, 1H), 7.56 (s, 1H), 7.50 (s, 1H), 7.21 (m, 3H), 7.16 (d, 1H, J=1.2 Hz), 7.05 (d, 1H, J=1.1 Hz), 7.00 (d, 1H, J=1.4 Hz), 6.94 (d, 1H, J=1.4 Hz), 6.87 (d, 1H, J=1.2 Hz), 3.99 (s, 3H), 3.97 (s, 3H), 3.83 (s, 3H), 3.82 (s, 3H), 3.80 (s, 3H), 3.79 (s, 3H), 3.71 (d, 2H, J=4.2 Hz), 3.20 (m, 2H), 3.14 (m, 2H), 3.01 (m, 2H), 2.75 (d, 6H, J=3.2 Hz), 2.27 (t, 2H, J=7.2 Hz), 2.03 (s, 3H), 1.76 (m, 4H); IR (neat) 3260 (m), 2927 (w) 2332 (w), 1666 (s), 1531 (s), 1449 (m), 1396 (w), 1196 (w), 1126(w); MALDI-TOF-MS, calc. for C$_{47}$H$_{60}$N$_{18}$O$_9$M+H+ 1022.1, found 1022.4.

AcImImPy-γ-PyPyPy-G-Dp (4a). Synthesized by the general procedures described above to yield 8.9 mg (30%) of compound 4a.

Characterization of 4a. HPLC, r.t. 24.1; UV(H$_2$O/DMSO) $\lambda_{max}$(ε), 246 (37,600), 312 (50,700); $^1$H NMR (DMSO-d$_6$) δ 10.30 (s, 1H) 10.28 (s, 1H), 9.93 (s, 1H), 9.90 (s, 1H), 9.84 (s, 1H), 9.33 (s, 1H), 9.28 (br s, 1H), 8.05 (t, 1H, J=5.1 Hz), 8.08 (t, 1H), 8.02 (t, 1H), 7.56 (s, 1H), 7.50 (s, 1H), 7.21 (m, 3H), 7.16 (d, 1H, J=1.2 Hz), 7.05 (d, 1H, J=1.1 Hz), 7.00 (d, 1H, J=1.4 Hz), 6.94 (d, 1H, J=1.4 Hz), 6.87 (d, 1H, J=1.2 Hz), 3.99 (s, 3H), 3.97 (s, 3H), 3.83 (s, 3H), 3.82 (s, 3H), 3.80 (s, 3H), 3.79 (s, 3H), 3.71 (d, 2H, J=4.2 Hz), 3.20 (m, 2H), 3.14 (m, 2H), 3.01 (m, 2H, J=6.2 Hz), 2.75 (d, 6H, J=3.2 Hz), 2.27 (t, 2H, J=7.2 Hz), 2.03 (s, 3H), 1.76 (m, 4H); MALDI-TOF-MS, calc. for M+H+ 1022.1, found 1022.7.

AcImImPy-γ-PyPyPy-G-Ta (4b). Synthesized by the general procedures described above to yield 7.4 mg (25%) of compound 4b.

Characterization of 4b. HPLC, r.t. 23.8; UV(H$_2$O/DMSO) $\lambda_{max}$(ε), 246 (37,000), 312 (50000); $^1$H NMR (DMSO-d$_6$) δ 10.31 (s, 1H), 10.29 (s, 1H), 9.93 (s, 1H), 9.90 (s, 1H), 9.84 (s, 1H), 9.34 (s, 1H), 8.31 (t, 1H, J=5.0 Hz), 8.08 (m, 2H), 7.80 (br s, 3H), 7.56 (s, 1H), 7.50 (s, 1H), 7.20 (m, 3H), 7.15 (d, 1H, J=1.2 Hz), 7.06 (d, 1H, J=1.2 Hz), 7.00 (d, 1H, J=1.3 Hz), 6.95 (d, 1H, J=1.2 Hz), 6.88 (d, 1H, J=1.3 Hz), 3.98 (s, 3H), 3.96 (s, 3H), 3.82 (s, 3H), 3.82 (s, 3H), 3.79 (m, 6H), 3.71 (d, 2H, J=4.9 Hz), 3.15 (m, 6H), 3.06 (m, 2H, J=4.7 Hz), 2.84 (m, 2H, J=4.9 Hz), 2.74 (d, 3H, J=4.2 Hz), 2.27 (t, 2H), 2.02 (s, 3H), 1.89 (m, 2H), 1.75 (m, 4H); MALDI-TOF-MS, calc. for M+H+ 1065.2, found 1065.2.

Preparation of AcImImPy-γ-PyPyPy-G-Ta-EDTA (4c). Synthesized by the general procedures described above to yield 2.1 mg (35%) of product 4c.

Characterization of 4e. HPLC, r.t. 23.8; UV(H$_2$O/DMSO) $\lambda_{max}$, 246, 312; $^1$H NMR (DMSO-d$_6$) δ 10.31 (s, 1H), 10.29 (s, 1H), 9.93 (s, 1H), 9.90 (s, 1H), 9.84 (s, 1H), 9.33 (s, 1H), 9.21 (br s, 1H), 8.37 (t, 2H, J=4.6 Hz), 8.28 (t, 1H, J=5.2 Hz), 8.09 (t, 1H, J=5.2 Hz), 8.03 (t, 1H, J=5.4 Hz), 7.6 (s, 1H), 7.5 (s, 1H), 7.21 (m, 3H), 7.15 (d, 1H, J=0.8 Hz), 7.06 (d, 1H, J=1.0 Hz), 7.00 (d, 1H, J=1.2 Hz), 6.95 (d, 1H, J=1.1 Hz), 6.88 (d, 1H, J=1.2 Hz), 3.99 (s, 3H), 3.96 (s, 3H), 3.83 (s, 3H), 3.82 (s, 3H), 3.79 (m, 6H), 3.71 (d, 2H, J=5.0 Hz), 3.66 (m, 4H), 3.25 (m, 10H), 3.15 (m, 6H), 2.72 (d, 3H, J=4.4 Hz), 2.47 (t, 2H), 2.00 (s, 3H), 1.77 (m, 6H), 1.27 (m, 2H); MALDI-TOF-MS, calc. for M+H+ 1338.4, found 1338.6.

Preparation of AcPyPyPy-γ-ImImPy-Gly-Dp (5a). Synthesized by the general procedures described above to yield 9.9 mg (37%) of compound 5a.

Characterization of 5a. HPLC, r.t. 23.8; UV(H$_2$O/DMSO) $\lambda_{max}$(ε), 246 (41,800), 312 (56,400); $^1$H NMR (DMSO-d$_6$) δ 10.34 (s, 1H), 10.33 (s, 1H), 9.90 (m, 1H), 9.83 (s, 1H), 9.35 (s, 1H), 9.29 (br s, 1H), 8.29 (t, 1H, J=5.3 Hz), 8.03 (m, 2H), 7.56 (s, 1H), 7.53 (s, 1H), 7.27 (d, 1H, J=1.0 Hz), 7.22 (d, 1H, J=7.16 Hz), 7.16 (d, 1H, J=0.9 Hz), 7.13 (d, 1H, J=1.0 Hz), 7.03 (m, 2H), 6.88 (d, 1H, J=1.1 Hz), 6.84 (d, 1H, J=1.0 Hz), 3.98 (s, 3H), 3.97 (s, 3H), 3.92 (s, 3H), 3.83 (s, 3H), 3.81 (s, 3H), 3.79 (s, 3H), 3.72 (s, 3H), Gly CH$_2$ was covered by water, 3.20 (m, 2H, J=5.6 Hz), 3.12 (m, 2H, J=5.9 Hz), 3.02 (quintet, 2H, J=4.1 Hz), 2.74 (d, 6H, J=4.4 Hz), 2.36 (t, 2H, J=7.0 Hz), 1.95 (s, 3H), 1.77 (m, 4H); MALDI-TOF-MS, calc. for M+H+ 1022.1, found 1022.4.

Preparation of AcPyPyPy-γ-ImImPy-G-Ta (5b). Synthesized by the general procedures described above to yield 8.2 mg (27%) of compound 5b.

Characterization of 5b. HPLC, r.t. 23.6; UV(H$_2$O/DMSO) $\lambda_{max}$(ε), 246 (39,300), 312 (53,100); $^1$H NMR (DMSO-d$_6$) δ 10.38 (s, 1H), 10.34 (s, 1H), 9.92 (m, 2H), 9.85 (s, 1H), 9.35 (s, 1H), 8.33 (t, 1H), 8.07 (m, 2H), 7.82 (br s, 1H), 7.57 (s, 1H), 7.54 (s, 1H), 7.28 (d, 1H, J=1 Hz), 7.23 (d, 1H, J=1 Hz), 7.17 (d, 1H, J=1 Hz), 7.14 (d, 1H, J=1 Hz), 7.14 (d, 1H, J=1.3 Hz), 7.04 (m, 2H), 6.89 (d, 1H, J=1 Hz), 6.84 (d, 1H, J=1 Hz), 3.99 (s, 3H), 3.97 (s, 3H), 3.83 (s, 3H), 3.82 (s, 3H), 3.81 (s, 3H), 3.79 (s, 3H), 3.71 (d, 2H, J=5.2 Hz), 3.26 (m, 2H), 3.14 (d, 2H, J=5.1 Hz), 3.05 (m, 2H), 2.83 (q, 2H, J=5.6 Hz), 2.74 (d, 3H, J=4.3 Hz), 2.39 (m, 2H), 1.96 (s, 3H), 1.88 (q, 2H, J=6.6 Hz), 1.78 (m, 2H); MALDI-TOF-MS, calc. for M+H+ 1065.2, found 1065.9.

Preparation of AcPyPyPy-γ-ImImPy-G-Ta-EDTA (5c). Synthesized by the general procedures described above to yield 3.1 mg (37%) of 5c.

Characterization of 5c. HPLC, r.t. 24.0; UV(H$_2$O/DMSO) $\lambda_{max}$(ε), 246. 312; $^1$H NMR (DMSO-d$_6$) δ 10.37 (s, 1H), 10.34 (s, 1H), 9.91 (m, 2H), 9.84 (s, 1H), 9.37 (s, 1H), 8.38 (t, 1H), 8.32 (t, 1H), 8.06 (m, 24H), 7.57 (s, 1H), 7.53 (s, 1H), 7.27 (s, 1H), 7.22 (s, 1H), 7.17 (s, 1H), 7.14 (s, 1H), 7.04 (m, 2H), 6.88 (s, 1H), 6.85 (s, 1H), 3.99 (s, 3H), 3.96 (s, 3H), 3.83 (s, 3H), 3.82 (s, 3H), 3.79 (m, 6H), 3.71 (d, 2H), 3.64 (m, 4H), 3.25 (m, 10H), 3.15 (m, 6H), 2.72 (d, 3H), 2.50 (t, 2H), 1.95 (s, 3H), 1.79 (m, 6H), 1.22 (m, 2H); MALDI-TOF-MS, calc. for M+H+ 1338.4, found 1339.1.

Preparation of EDTA-γ-ImPyPy-β-PyPyPy-G-Dp. The polyamide ImPyPy-β-PyPyPy-G-Dp, synthesized by the general procedures described above, was modified with the dianhydride of EDTA in DMSO/NMP at 55° C. for 10 minutes, the anhydride was then opened with 0.1M NaOH (20 minutes), and the reaction mixture purified by reverse phase preparatory HPLC to provide the EDTA modified polyamide.

Preparation of ImPyPy-G-PyPyPy-β-Dp. The polyamide was prepared as described above to yield a white powder. (12.3 mg, 42% recovery). HPLC, r.t. 25.5; UV(H$_2$O/DMSO) $\lambda_{max}$(ε), 246 (39,500), 312 (52,000) nm; $^1$H NMR (DMSO-d$_6$) δ 10.46 (s, 1H), 9.96 (s, 1H), 9.90 (s, 1H), 9.88 (m, 2H), 9.21 (br s, 1H), 8.27 (t, 1H, J=452.5 Hz), 8.06 (m, 2H), 7.39 (s, 1H), 7.28 (d, 1H, J=1.6 Hz), 7.23 (d, 1H, J=1.7 Hz), 7.20 (d, 1H, J=1.5 Hz), 7.15 (m, 3H), 7.04, (m, 2H), 7.03 (d, 1H, J=1.6 Hz), 6.94 (d, 1H, J=1.7 Hz), 6.92 (d, 1H, J=1.4 Hz), 3.98 (s, 3H), 3.88 (d, 2H), 3.83 (s, 3H), 3.82 (m, 6H), 3.79 (s, 3H), 3.78 (s, 3H), 3.36 (q, 2H, J=5.3 Hz), 3.09 (q, 2H, J=6.0 Hz), 2.99 (m, 2H), 2.75 (t, 2H, J=5.2 Hz), 2.72 (d, 6H, J=4.8 Hz), 2.30 (t, 2H, J=6.3 Hz), 1.72 (quintet, 2H, J=5.7 Hz); MALDI-TOF MS 950.06; FABMS m/e 949.462 (M+H 949.455 calc. for C$_{45}$H$_{57}$N$_{16}$O$_8$).

Example 5

Symmetric Anhydride Activation of Pyrrole

In a typical symmetric anhydride procedure (0.25 mmol synthesis cycle), the resin was washed with 5% DIEA/CH$_2$Cl$_2$. No DIEA should be present, however, at the start of the coupling reaction Boc-pyrrole-COOH (514 mg, 2 mmol) was slurried in 3 ml dichloromethane, DCC (406 mg, 2 mmol) was then added upon which time the white slurry turned clear. After three minutes, dimethylaminopyridine (DMAP) (101 mg, 1 mmol) was added and the solution was stirred, filtered and added to the reaction vessel containing the resin. The coupling was allowed to proceed for 2 hours, 355 µl DIEA was then added and the reaction allowed to proceed for an additional hour.

Example 6

Picric Acid Test

In order to monitor the progress of the reactions 8–10 mg samples were periodically removed from the deprotection reaction mixtures and evaluated using picric acid titration. The 10 mg sample was washed with dichloromethane, 5% TEA/CH$_2$Cl$_2$, and dichloromethane, and dried either at 50° C. or by aspiration. A sample of about 5 mg of the dried resin was weighed into a disposable polypropylene filter, successively washed using gravity filtration with approximately: 5 ml dichloromethane, 5 ml 0.1M picric acid/dichloromethane and 50 ml dichloromethane to carefully remove any excess picric acid, the picric acid salt eluted with 5% DIEA/CH$_2$Cl$_2$ (3×500 µl). The DIEA/CH$_2$Cl$_2$ wash was collected and diluted with 4 ml MeOH and the absorbance measured at 358 nm.

Example 7

Stepwise HPLC Analysis

Approximately 2 mg of a resin sample was placed in a 1.5 ml polypropylene tube, 40 µl of DMF was added and the resin was allowed to stand for 10 minutes, 40 µl of dimethylaminopropylamine was then added and the mixture was vortexed, briefly centrifuged, and heated at 37° C. for 12 hours. After 12 hours the solutions were again vortexed, centrifuged, and a 10 µl aliquot was taken, diluted with 90 µl water and analyzed by analytical HPLC under standard conditions at 254 nm.

Example 8

Cleavage of the Polyamide From the Resin Using Pd(OAc)$_2$

Scheme 17 illustrates a general method for cleaving the synthesized polyamide from the resin. The acetylated tripyrrole AcPyPyPy-PAM-resin is used for purposes of illustration.

SCHEME 17

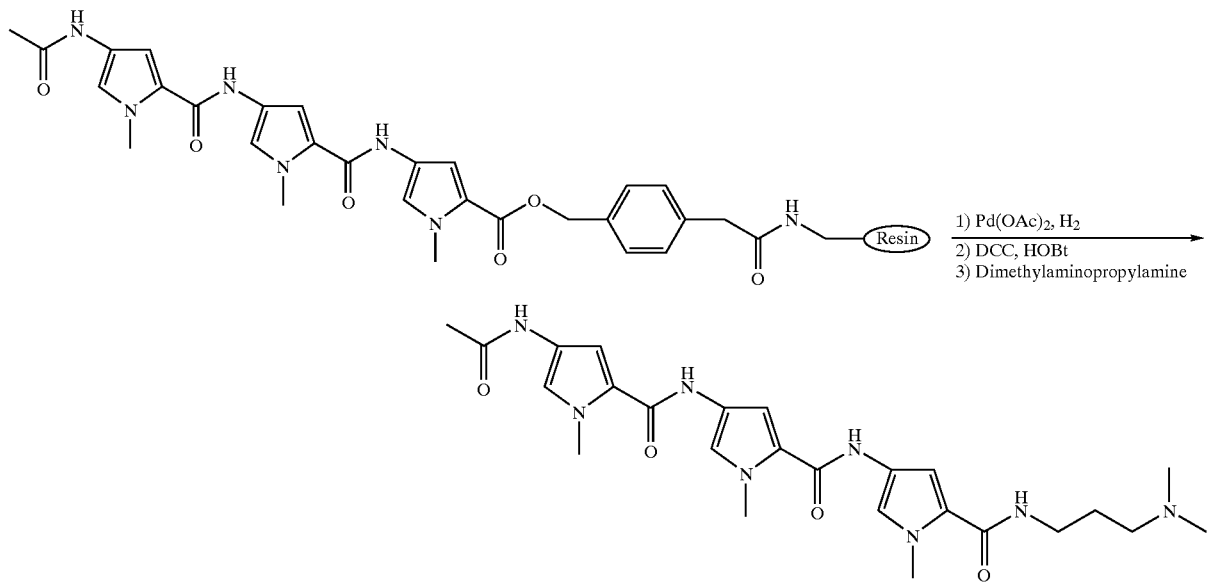

The PAM or BAM pyrrole resin was treated with Pd(OAc)$_2$ in DMF under a pressurized atmosphere of hydrogen (100 psi, 8 hours). The palladium black was filtered and the pyrrole acid activated with DCC/HOBt and reacted with a large excess of dimethylaminopropylamine to give the HPLC purified acetylated tripyrrole in 5% overall yield. HPLC and NMR are consistent with that of an authentic standard synthesized by solution phase methods by Wade et al. (1992) J. Am. Chem. Soc. 144:8783–8794.

Example 9

Cleavage of the Polyamide from the G-PAM-resin

Scheme 18 illustrates a general method for cleaving the synthesized polyamide from the G-PAM-resin. The acetylated tripyrrole AcPyPyPy-PAM-G-PAM-resin is used for purposes of illustration.

SCHEME 18

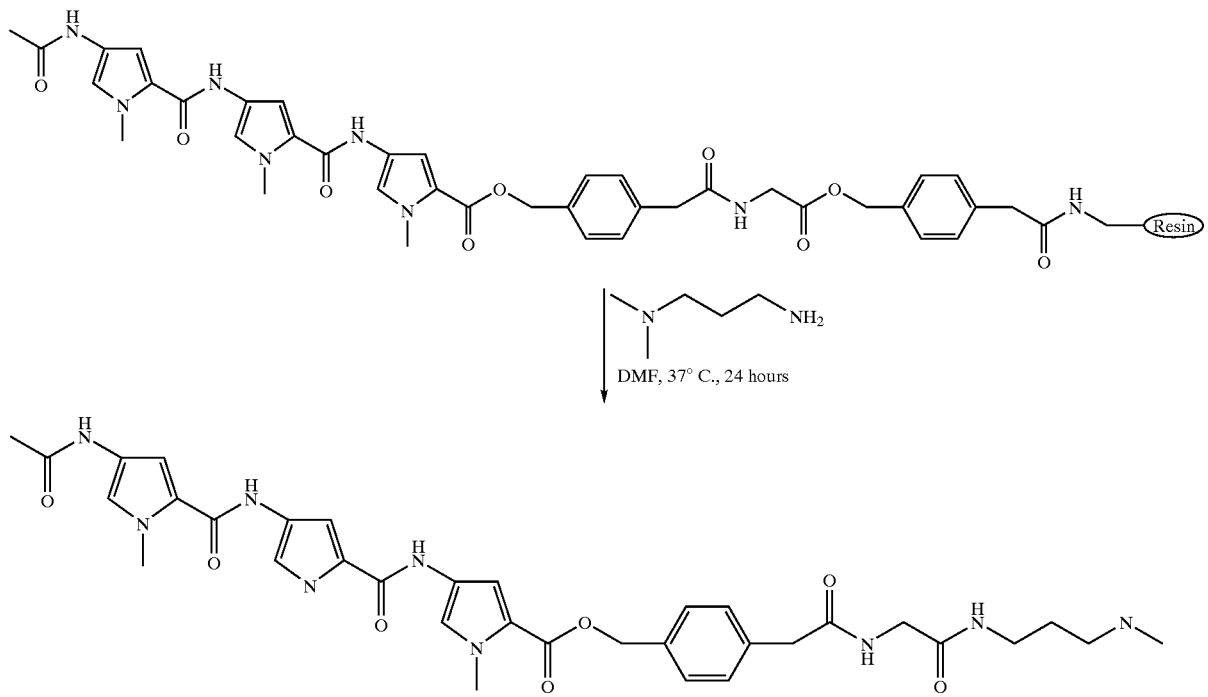

180 mg (29 μmole) of AcPyPyPy-PAM-G-PAM-resin was treated with 1.5 ml DMF followed by 1.5 ml dimethylaminopropylamine and the reaction mixture shaken for 12 hours, and purified by preparatory HPLC to give AcPyPyPy-PAM-G-Dp in 49% yield. $^1$H NMR (DMSO-d$_6$) δ9.90 (m, 2H), 9.83 (s, 1H), 9.3 (br s, 1H), 8.37 (t, 1H, J=5.7 Hz), 8.05 (t, 1H, J=5.8 Hz), 7.44 (d, 1H, J=1.7 Hz), 7.32 (q, 4H, J=8.2 Hz), 7.20 (d, 1H, J=1.7 Hz), 7.13 (d, 1H, J=1.7 Hz), 7.04 (d, 1H, J=1.7 Hz), 6.95 (d, 1H, J=1.9 Hz), 6.83 (d, 1H, J=1.8 Hz), 5.19 (s, 2H), 3.82 (s, 3H), 3.82 (s, 3H), 3.81 (s, 3H), 3.63 (d, 2H, J=6.1 Hz), 3.48 (s, 2H), 3.11 (q, 2H, J=6.1 Hz), 2.96 (m, 2H), 2.67 (d, 6H, J=4.8 Hz), 1.95 (s, 3H), 1.71 (quintet, 2H, J=7.4 Hz). A failure a sequence was also isolated from the reaction mixture in 25% yield. $^1$H NMR (DMSO-d$_6$) δ 9.91 (m, 2H), 9.80 (s, 1H), 9.3 (br s, 1H), 8.40 (t, 1H, J=5.7 Hz), 8.08 (t, 1H, J=5.8 Hz), 7.44 (d, 1H, J=1.7 Hz), 7.38 (q, 4H, J=8.4 Hz), 7.15 (d, 1H, J=1.7 Hz), 6.96 (d, 1H, J=1.8 Hz), 6.85 (d, 1H, J=1.7 Hz), 5.15 (s, 2H), 3.84 (s, 3H), 3.82 (s, 3H), 3.69 (d, 2H, J=5.4 Hz), 3.51 (s, 2H), 3.19 (m, 2H), 3.04 (m, 2H), 2.74 (d, 6H, J=4.2 Hz), 1.97 (s, 3H), 1.77 (m, 2H).

Example 10

Quantitative DNase I Footprint Titrations

All reactions were executed in a total volume of 40 μL. A polyamide stock solution (H$_2$O containing no polyamide was used for reference reactions) was added to an assay buffer containing radio labeled restriction fragment (15,000 cpm), affording final solution conditions of 10 mM Tris HCl, 10 mM KCl, 10 mM MgCl$_2$, 5 mM CaCl$_2$, pH 7.0 and (i) 0.1 nM–1 μM polyamide, for all polyamides except ImPyPy-β-PyPyPy-Dp and ImPyPy-β-PyPyPy-G-Dp, (ii). 0.01 nM–0.1 μM polyamide for ImPyPy-β-PyPyPy-Dp and ImPyPy-β-PyPyPy-G-Dp. The solutions were allowed to equilibrate for 5 hours at 22° C. Footprinting reactions were initiated by the addition of 4 μL of DNase I stock solution (at the appropriate concentration to give 55% intact labeled DNA) containing 1 mM dithiothreitol. The reactions were allowed to proceed for approximately seven minutes at 22° C. After seven minutes the reactions were by the addition of 10 μL of a solution containing 1.25 M NaCl, 100 mM EDTA, and 0.2 mg/ml glycogen, and ethanol precipitated. The reactions were resuspended in 1×TBE/80% formamide loading buffer, denatured at 85° C. for 10 minutes, placed on ice, and loaded onto an 8% polyacrylamide gel (5% cross-link, 7 M urea). The reaction products were separated by electrophoresis in 1×TBE at 2000 V. Gels were dried and exposed to a storage phosphor screen (Molecular Dynamics).

Data from the footprint titration gels were obtained using a Molecular Dynamics 400S PhosphorImager followed by quantitation using ImageQuant software (molecular Dynamics).

Background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($q_{app}$) of the sites were calculated using the equation:

$$\theta_{app} = 1 - \frac{I_{site}/I_{ref}}{I^o_{site}/I^o_{ref}} \quad (1)$$

where $I^o_{site}$ and $I^o_{ref}$ are the site and reference intensities, respectively, from a control lane to which no polyamide was added.

The ($[L]_{tot}$, $\theta_{app}$) data points were fit to a general Hill equation (eq) by minimizing the difference between $\theta_{app}$ and $\theta_{fit}$:

$$\theta_{fit} = \theta_{min} + \theta_{max} + \theta_{min})\frac{Ka^n[L]^n_{tot}}{1 + Ka^n[L]^n_{tot}} \quad (2)$$

where $[L]_{tot}$ is the total polyamide concentration, $K_a$ is the apparent first-order association constant, and $\theta_{min}$ and $\theta_{max}$ are the experimentally determined site saturation values when the site is unoccupied or saturated, respectively. The data were fit using a nonlinear least-squares fitting procedure with $K_a$, n, $\theta_{min}$ as the adjustable parameters. In cases for which the best-fit value of n was ≧1.5, the data were fit with n=2, with $K_a$, $\theta_{max}$, and $\theta_{min}$ as the adjustable parameters. The binding isotherms were normalized using the following equation:

$$\theta_{norm} = \frac{\theta_{app} - \theta_{min}}{\theta_{max} - \theta_{min}} \quad (3)$$

Three sets of data were used in determining each association constant.

At higher concentrations of polyamide (>~0.1 μM for ImPyPy-β-PyPyPy-Dp and ImPyPy-β-PyPyPy-Dp, and >1 μM for the other six polyamides), the reference sites become partially protected due to non-specific DNA-binding, resulting in low $\theta_{app}$ values. For this reason, higher concentrations were not used. As a consequence, association constants for sites that are not saturated or nearly saturated at the highest concentration of polyamide used can be determined only approximately. The method for determining association constants used here involved the assumption that $[L]_{tot}=[L]_{free}$ where $[L]_{free}$ is the concentration of polyamide free in solution (unbound). For very high association constants this assumption becomes invalid, resulting in underestimated association constants. In these experiments, the concentration of DNA is estimated to be 50 pM. As a consequence, association constants of $2 \times 10^9$ M$^{-1}$ and $5 \times 10^9$ M$^{-1}$ will be underestimated by approximately 90% and 80%, respectively.

Example 11

Preparation of Dimers

Preparation of Ethyl 4-[[(tert-butyloxy)carbonyl]amino]-1-methylpyrrole-2-(4-carboxamido-1-methyl-imidazole)-2-carboxylate (44). To a solution of 4-[[(tert-butyloxy)carbonyl]amino]-1-methylpyrrole-2-carboxylic acid (8 g, 33 mmol) in 20 ml DMF was added 1.2 eq HOBt (5.3 g, 39 mmol) followed by 1.2 eq DCC (8 g, 39 mmol). The solution was stirred for 24 hours, after which the DCU byproduct was removed by filtration. Separately, to a solution of ethyl 4-nitro-1-methylimidazole-2-carboxylate (8 g, 40 mmol) in 20 ml DMF was added Pd/C catalyst (10%, 1 g), and the mixture hydrogenated in a Parr bom apparatus (500 psi H$_2$) for 2 hours. The catalyst was removed by filtration through celite, and the filtrate immediately added to the -OBt ester solution, an excess of DIEA (10 ml, 110 mmol) added, and the mixture stirred at 37° C. for 48 hours. The reaction mixture was added dropwise to a stirred solution of ice water and the resulting precipitate collected by vacuum filtration and dried, in vacuo to yield a brown powder. (12.3 g, 94% yield). $^1$H NMR (DMSO-d$_6$) δ 10.7 (s, 1H), 9.2 (s, 1H), 7.6 (s, 1H), 6.8 (d, 1H), 4.3 (q, 2H), 3.9 (s, 3H), 3.7 (s, 3H), 1.5 (s, 9H), 1.3 (t 3H).

Preparation of 4-[[(tert-butyloxy)carbonyl]amino]-1-methylpyrrole-2-(4-carboxamido-1-methylimidazole)-2-carboxylic acid (45). To a solution of ethyl 4[[tert-butyloxy)carbonyl]amino]-1-methylpyrrole-2-(4-carboxamido-1-methylimidazole)-2-carboxylate (44) (5 g, 12.7 mmol) in 50 ml methanol was added 50 ml 1M KOH and the reaction was allowed to stir for 6 hours at 37° C. Excess methanol was removed in vacuo and the resulting solution acidified by the addition of 10% potassium bisulfate. The resulting precipitate was collected by vacuum filtration and dried in vacuo to yield a brown powder. (4.4 g, 89% yield). $^1$H NMR (DMSO-d$_6$) δ 10.9 (s, 1H), 8.9 (s, 1H), 7.6 (s, 1H), 7.3 (d, 1H), 6.9 (d, 1H), 4.1 (s, 3H), 3.9 (s, 3H), 1.4 (s, 9H).

Preparation of Ethyl γ-[[tert-butyloxy)carbonyl]amino]-butyric acid-(4-carboxamido-1-methylimidazole)-2-carboxylate (46). To a solution of Boc-γ-aminobutyric acid (10 g, 49 mmol) in 40 ml DMF was added 1.2 eq HOBt (7.9 g, 59 mmol) followed by 1.2 eq DCC (11.9 g 59 mmol). The solution was stirred for 24 hours, and the DCU byproduct was removed by filtration. Separately, to a solution of ethyl 4-nitro-1-methylimidazole-2-carboxylate (9.8 g, 49 mmol) in 20 ml DMF was added Pd/C catalyst (10%, 1 g), and the mixture was hydrogenated in a Parr bom apparatus (500 psi H$_2$) for 2 hours. The catalyst was removed by filtration through celite and the filtrate was immediately added to the -OBt ester solution. An excess of DIEA (15 ml) was then added and the reaction was stirred at 37° C. After 48 hours the reaction mixture was added dropwise to a stirred solution of ice water and the resulting precipitate collected by vacuum filtration and dried in vacuo to yield a brown powder. (9.4 g, 54% yield). $^1$H NMR (DMSO-d$_6$) δ 10.6 (s, 1H), 7.6 (s, 1H), 6.9 (t, 1H), 4.2 (q, 2H), 3.9 (s, 3H), 2.9 (q, 2H), 2.3 (t, 2H), 1.4 (s, 9H), 1.3(t, 3H).

Preparation of γ-[[(tert-butyloxy)carbonyl]amino]-butyric acid-(-4-carboxamido-1-methyl-pyrrole)-2-carboxylate (47). To a solution of ethyl γ-[[(tert-butyloxy)carbonyl]amino]-butyric acid-(4-carboxamido-1-methyl)-2-carboxylate (5 g, 14.1 mmol) in 50 ml methanol was added 50 ml 1M KOH and the resulting mixture was allowed to stir for 6 hours at 37° C. Excess methanol was removed in vacuo and the resulting solution acidified by the addition of 10% potassium bisulfate. The resulting precipitate was collected by vacuum filtration and dried in vacuo to yield a brown powder. (4.1 g, 91% yield). $^1$H NMR (DMSO-d$_6$) δ 10.6 (s, 1H), 7.6 (s, 1H), 6.8 (t, 1H), 3.9 (s, 3H), 2.8 (q, 2H), 2.3 (q, 2H), 1.7 (t, 2H), 1.5 (s, 9H).

Activation of Boc-X-Im-COOH. Boc-γ-Im-COOH or Boc-Py-Im-COOH (100 mg, about 0.3 mmol) and HBTU (2-(1H-Benzotriazole-1-yl)-1,1,3,3-tetramethyl uronium hexafluoro phosphate) (118 mg, 0.3 mmol) were dissolved in 500 μl DMF, 100 μl DIEA was added and the solution allowed to stand for 3 minutes.

Example 12

Preparation of Allyl Protected Monomers

Scheme 19 illustrates a general method for the preparation of allyl protected monomers for use in preparation of cyclic polyamides.

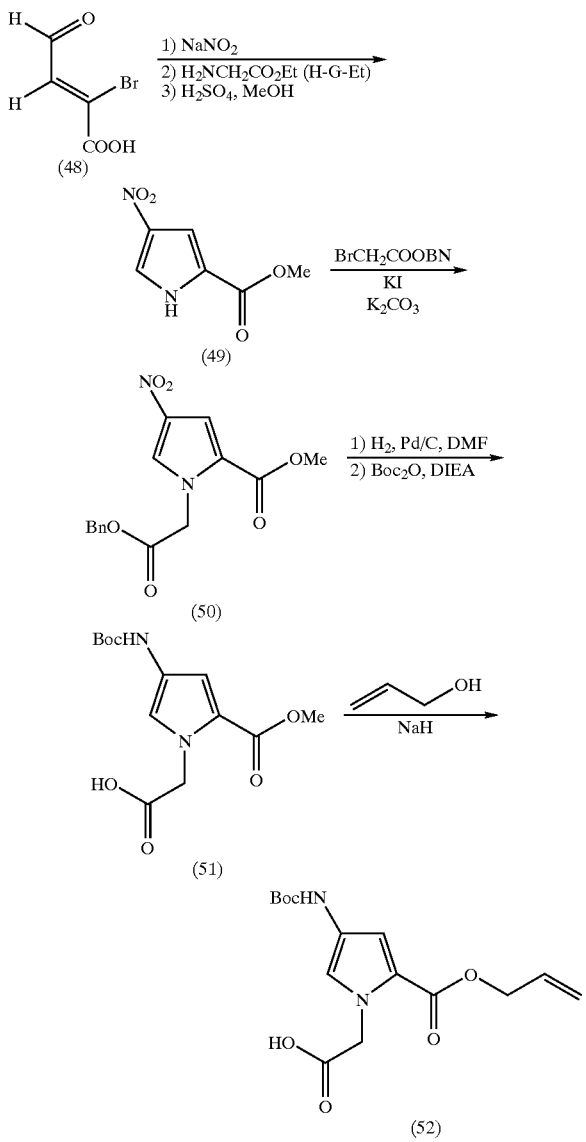

Methyl-4-nitropyrrole-2-carboxylic acid (49). To a solution of sodium nitrite (714 g, 10.2 mol) in 700 ml of water at 50° C.±5° C. was added over a period of 3 hours a solution of mucobromic acid (48) (700 g, 2.7 mol) in 700 ml of warm ethanol. The reaction was stirred for 15 minutes, cooled to 0° C., and 700 ml of ethanol was added. The resulting orange precipitate was collected by vacuum filtration and dried in vacuo to yield sodium nitromalondialdehyde monohydrate (305 g, 1.9 mol) which was used in the next step without further purification. Glycine ethyl ester (300 g, 2.9 mol) and nitromalondialdehyde monohydrate (305 g, 1.9 mol) were placed in a 12 l round bottom flask and slurried with a mechanical stirrer in 560 ml of methanol and 280 ml of water. Sodium hydroxide (800 g, 20 mol) dissolved in 1.6 l water was added to the solution at a rate which maintained the temperature at 50° C. The reaction was cooled to 0° C. with an ice bath and neutralized to pH. 0 with 1.7 1 HCl (conc.) while maintaining the temperature below 10° C. A black precipitate was removed by filtration through Celite and the product was extracted with 20 liters of ethyl acetate. The organic layer was dried with sodium sulfate and concentrated in vacuo to provide 4-nitropyrrole-2-carboxylic acid (140 g, 0.9 mol) as a brown solid which was used without further purification. To a solution of 4-nitropyrrole-2-carboxylic acid (140 g, 0.9 mol) dissolved in 180 ml of methanol was added 8 ml of concentrated sulfuric acid. The solution was refluxed for 15 hours, cooled to 0° C. and 90 ml of water was added. The solution was then allowed to stand at −20° C. for 2 days. The resulting light brown crystals were collected by vacuum filtration to yield pure methyl-4-nitropyrrole-2-carboxylate (49) (10 g, 0.62 mol) in 23% overall yield. $^1$H NMR (DMSO-$d_6$) δ 14.2 (br s, 1H), 7.74 (d, 1H, J=1.6 Hz), 7.35 (d, 1H, J=1.7 Hz), 3.73 (s, 3H).

Preparation of 1-(Benzyloxycarbonylmethyl)-2-carboxy-4-nitropyrrole methyl ester (50). To a solution of methyl 4-nitropyrrole-2-carboxylate (49) (8.1 g 48 mmol) dissolved in 100 ml of acetone was added potassium carbonate (19.5 g, 141 mmol) and potassium iodide (7.2 g, 43.4 mmol), followed by 2-benzylbromoacetate (18.9 ml). The solution was refluxed for 2 hours, an additional 5 ml of 2-benzylbromoacetate was added and the solution was refluxed for an additional 2 hours. The reaction mixture was concentrated in vacuo partitioned between 300 ml of water and 300 ml of dichloromethane and extracted with dichloromethane (2×100 ml). The extracts were combined, dried over sodium sulfate and concentrated in vacuo. The resulting oil was purified by flash chromatography (4:1 hexane:ethyl acetate) to yield 910.4 g (32.7 mmol, 68%) of the diester (50). $^1$H NMR (DMSO-$d_6$) δ 8.30 (d, 1H, J=1.9 Hz), 7.35 (d, 1H, J=1.9 Hz), 7.35 (s, 5H), 5.27 (s, 2H), 5.19 (s, 2H), 3.17 (s, 3H); $^{13}$C NMR (DMSO-$d_6$) δ 168.1, 160.3, 135.2, 130.2, 129.0, 128.8, 128.6, 123.1, 112.1, 67.1, 52.5, 51.5; FABMS, found 318.085, calc. 318.085.

Preparation of methyl 1-(carboxymethyl)-4-[[tert-butyloxy)carbonyl]amino]-2-carboxylate (51). To a solution of diester (50) (4.3 g, 13.5 mmol) in 80 ml of DMF was added Pd/C catalyst (10%, 1 g) and the mixture was hydrogenated in a Parr bom apparatus (500 psi $H_2$) for 7 hours. Boc-anhydride (2.95 g, 13.5 mmol) was then added followed by DIEA (6 ml, 66 mmol) and the reaction was stirred for 2 hours. The Pd/C catalyst was removed by filtration through Celite and the reaction mixture was partitioned between 500 ml of bicarbonate and 500 ml of dichloromethane and extracted with dichloromethane (2×200 ml). The pH was then reduced to three with 10% citric acid and the mixture was extracted with dichloromethane (4×200 ml.) The combined acidic extracts were dried (sodium sulfate) and concentrated in vacuo to yield a brown oil. The crude mixture was purified by flash chromatography (10% MeOH/dichloromethane) to yield a white solid. (2.8 g, 69.5% yield). $^1$H NMR (DMSO-$d_6$) δ 12.75 (br s, 1H), 9.15 (s, 1H), 7.14 (s, 1H), 6.64 (2, 1H), 4.90 (s, 2H), 3.68 (s, 3H), 1.46 (s, 9H).

Preparation of allyl 1-(carboxymethyl)-4-[[(tert-Butyloxy)carbonyl]amino]-2-carboxylate (52). To a solution of the Boc-methyl ester (51) (500 mg, 1.6 mmol) in 5 ml of dry allyl alcohol was added a solution of 60% sodium hydride (640 mg) dissolved in 10 ml of allyl alcohol. The gel-like mixture was refluxed for 30 minutes and cooled to room temperature. 100 ml of 10% citric acid was added and the reaction mixture was extracted with dichloromethane (3×200 ml). The combined organics were dried and concentrated in vacuo to yield the pure Boc allyl ester (31) as a brown oil. (408 mg, 82% yield). $^1$H NMR (DMSO-d$_6$) δ 9.18 (s, 1H), 7.18 (s, 1H), 6.68 (s, 1H), 5.91–6.01 (m, 1H), 5.21–5.34 (dd, 2H), 4.96 (s, 2H), 4.3 (d, 2H, J=5.2 Hz), 1.45 (s, 9H); $^{13}$C NMR (DMSO-d$_6$) δ 170.4, 160.0, 152.9, 133.1, 123.4, 119.7, 117.8, 107.9, 78.8, 64.0, 50.0, 28.3; FABMS found 313.140, calc. 313.140.

Example 13

Preparation of Cyclo-(-γ-ImPyImPy-γ-ImPyImPy(-G-Dp)-) (57)

Synthesis of the linear precursor H$_2$N-γ-ImPyImPy-γ-ImPyImPy(-G-Dp)-COOH (56). Boc-G-PAM resin (1.25 g, 0.25 mmol) was deprotected under standard conditions. Boc allyl monomer 52 (101 mg, 0.325 mmol) and HOBt (88 mg, 0.65 mmol) were dissolved in 400 µl DMF and DCC (66 mg, 0.325 mmol) was added. After 15 minutes DCU was removed by filtration and the activated ester was added to the reaction vessel, followed by 1.5 ml DMF and 355 µl DIEA. The reaction was allowed to proceed for 12 hours providing Boc-Py(O-allyl)-G-resin (53). The remaining polyamide was synthesized by standard solid phase methods of this invention to provide H$_2$N-γ-ImPyImPy-γ-ImPyImPy(O-allyl)-G-resin (54). To remove the allyl protecting group, the resin was then treated with THF (2×200 ?? ml) and 10 ml of a solution of 593 µl n-butylamine and 250 µl formic acid in 25 ml THF was then added, followed by 280 mg Pd$_2$(dba)$_3$—CHCl$_3$ and 980 mg triphenylphosphine. The reaction mixture was shaken for 3 hours at room temperature, drained, rinsed with acetone (200 ml), 0.1M sodium N,N-diethyl-dithiocarbamate in water (50 ml, 2×1 min), acetone (200 ml), water (200 ml), 0.1M sodium N,N-diethyl-dithiocarbamate in water (50 ml, 2×1 min), acetone (200 ml), water (200 ml), methanol (200 ml), dichloromethane (200 ml), methanol (200 ml), and the resin was dried in vacuo. The polyamide was then cleaved and purified under standard conditions to yield the linear precursor (56) as a fluffy white solid. (105 mg, 45% yield). HPLC, r.t. 27.0 min.; $^1$H NMR (DMSO-d$_6$) δ 10.37 (s, 1H), 10.29 (s, 1H), 10.23 (s, 1H), 10.22 (s, 1H), 10.18 (s, 1H), 9.96 (s, 1H), 9.92 (s, 1H), 9.86 (s, 1H), 9.31 (br s, 1H), 8.31 (t, 1H), 8.06 (t, 1H), 7.85 (t, 1H), 7.71 (br s, 3H), 7.53 (m, 2H), 7.44 (s, 1H), 7.36 (s, 1H), 7.189 (d, 1H, J=1.5 Hz), 7.12 (d, 1H, J=1.7 Hz), 6.97 (d, 1H, J=1.6 Hz), 6.94 (d, 1H, J=1.5 Hz), 4.97 (s, 2H), 3.96 (m, 6H), 3.94 (m, 9H), 3.85 (m, 6H), 3.79 (s, 3H), 3.66 (d, 1H, J=5.7 Hz), 3.23 (m, 4H), 2.98 (m, 2H), 2.79 (m, 2H), 2.71 (d, 6H, J=4.4 Hz), 2.33 (m, 4 Hz), 1.77 (m, 6H); MALDI-TOF MS, 1355.4, found 1355.7 calc.

Removal of the allyl group yielded no undesirable side products as determined by HPLC.

Synthesis of cyclo-(-γ-ImPyImPy-γ-ImPyImPy(-G-Dp)-) (57). The linear precursor (56) (16 mg) was dissolved in 7 ml of DMF, DPPA (28 mg) was added followed by potassium carbonate (45 mg) and the reaction mixture rapidly shaken for 3 hours, upon which time the reaction was determined to be complete by HPLC analysis r.t. 29 min. The cyclic peptide was purified by preparatory HPLC. MALDI-TOF MS 1355.4 calc., 1355.7 found (FIG. 18).

Example 14

Preparation of Oligonucleotide-polyamide Conjugates Materials

The following additional materials are needed for synthesis of oligonucleotide-polyamide conjugates. 6-(4-monomethoxytritylamino)propyl-(2-cyanoethyl)-(N,N-diisopropyl)-phosphoramidite, 5'-amino-modifier C6, 12-(4-monomethoxytritylamino)propyl-(2-cyanoethyl)-(N,N-diisopropyl)-phosphoramidite, 5'-amino-modifier C12, dT CE (2-cyanoethyl)phosphoramidite, 0.45 M sublimed tetrazole in acetonitrile, THF/lutidine/Ac$_2$O (8:1:1), 10% MeIm in THF, 0.1M I$_2$ in THF/Pyridine/H$_2$O, 3% TCA/CH$_2$Cl$_2$, 5-methylcytidine CE (2-cyanoethyl)phosphoramidite, and bulk 500 Å dT-Icaa-CPG were purchased from Glen Research. All 10 µmole preparation columns were packed manually from bulk support. 1,2,3-benzotriazol-1-yl-4[[(tert-butyloxy)carbonyl]-amino]-1-methylpyrrole-2-carboxylate and 1,2,3-benzotriazol-1-yl-4[[(tert-butyloxy)carbonyl]-amino]-1-methylimidazole-2-carboxylate were prepared as previously described. (Baird and Dervan Manuscript in Preparation; Schnozler et al. (1992) Int. J. Pep. Prot. Res. 40:180–193; Grehn and Ragnarsson (1981 J. Org. Chem. 46:3492–3497; Grehn et al. (1990) Acta. Chem. Scand. 44:67–74.). 0.0002M potassium cyanide/pyridine, and acetic anhydride (Ac$_2$O) were purchased from Applied Biosystems. HPLC analysis was performed either on a HP 1090 M analytical HPLC or a Beckman Gold system using a RAINEN C18, Microsorb MV, 5 µm, 300×4.6 mm reversed phase column in 100 mM ammonium acetate, pH 4.9 with acetonitrile as eluent and a flow rate of 1.0 ml/min, gradient elution 1.0% acetonitrile/min. Oligonucleotide conjugates were purified by FPLC (Pharmacia) on a ProRPC HR 10/10 reversed phase column using a linear gradient from 0 to 40% acetonitrile in 55 minutes, 100 mM triethylammonium acetate, pH 7.0.

Preparation of ImPyPy-CONH(CH$_2$)$_6$—P(O)$_4$TTTTT$^m$C$^m$CTTT-3'(62) (SEQ ID NO:7). The oligonucleotide DMT-TTTTTT$^m$C$^m$CTTT-CPG was prepared on an Applied Biosystems Model 394B DNA synthesizer using a manually prepared 10 µmole synthesis column and a standard 10 µmole synthesis cycle. C$_6$-Aminomodifier-MMT (100 µmole) was dissolved in 1,100 µl of anhydrous acetonitrile, vortexed vigorously, and placed on the synthesizer. The amino modifier was added by machine synthesis using a modified 10 µmole synthesis cycle with an extended 10 minute coupling time and the MMT group left on. The column was manually washed with 50 ml of 3% trichloroacetic acid/dichloromethane until a yellow color was no longer observed in the wash (approximately 12 minutes). The column was then washed with 15 ml dichloromethane and dried in vacuo. The CPG was transferred to a 5 ml glass manual peptide reaction vessel and washed with DMF (30 seconds). A sample was taken for ninhydrin test and an absorbance consistent with 50 µmole/gram substitution was found.

Boc-pyrrole-OBt ester (9) (70 mg, 200 µmole) was dissolved in DMF (600 µl) and DIEA (68 µl) was added. The coupling mixture was added to the reaction vessel and the mixture was shaken for 60 minutes. The resin was washed with DMF (30 seconds), dichloromethane (30 seconds) and 65% TFA/CH$_2$Cl$_2$/0.5M PhSH (30 seconds). The resin was shaken in 65% TFA/CH$_2$Cl$_2$/0.5M PhSH for 20 minutes, drained, washed with dichloromethane (30 seconds) followed by DMF (30 seconds). A second equivalent of Boc-pyrrole-OBt was added under identical conditions to the first, and the reaction shaken for 1 hour, washed with DMF (30 seconds), dichloromethane (30 seconds) and treated with 65% TFA/CH$_2$Cl$_2$/0.5M PhSH as described for the first deprotection. N-methylimidazole-2-carboxylic acid (133 mg) was activated in 1 ml of DMF with HOBt/DCC as described above and added to the reaction vessel with DIEA (200 µl) and the reaction was shaken to shake for 2 hours. The CPG was washed with DMF (30 seconds), dichloromethane (30 seconds) and dried in vacuo. The entire CPG (approximately 210 mg) was placed in 2 ml of 0.1M NaOH and heated at 55° C. for 15 hours. The CPG was removed by filtration through a polypropylene filter, and 1 ml of 1M triethylammonium acetate, pH 7, was added and the reaction diluted to 10 ml total volume with water. The mixture was purified in two separate portions by FPLC. In each run the conjugate was triple injected in 1.5 ml volume portions. Collected fractions were lyophilized, and relyophilized from water to yield the desired conjugate ImPyPy-CONH(CH$_2$)$_6$P(O)$_4$-TTTTTT$^m$C$^m$CTTT-3'(62) (SEQ ID NO:7) (15 mg, 37% yield).

Characterization of ImPyPy-CONH(CH$_2$)$_6$P(O)$_4$-TTTTTT$^m$C$^m$CTTT-3'(62). Analytic HPLC (10 nmole), r.t., 14.8 min.; UV(H$_2$O/DMSO)$\lambda_{max}$($\epsilon$), 260 (118,000), 304 (33,000); 18,800u, Enzymatic digestion (10 nmole), 7.8 min. (mC, 2441u), 9.0 min. (T, 15,235u) 26.2 min. (peptide, 4257u (260), 1843u 340); $^1$H NMR (D$_2$O) $\delta$ 7.71 (s, 1H), 7.69 (s, 1H), 7.50 (m, 9H), 7.19 (s, 1H), 7.18 (s, 1H), 7.12 (d, 1H, J=1.2 Hz), 7.05 (d, 1H, J=1.3 Hz), 6.89 (d, 1H, J=1.3 Hz), 6.67 (d, 1H, J=1.3 Hz), 6.11 (m, 11H), 4.89, 4.76, 4.70, 4.22, 4.01, 3.91, 3.88, 3.75, 3.42, 3.11, 2.40, 2.25, 2.20, 1.80, 1.75, 1.41, 1.23; MALDI-TOF MS, calc. M-1 3814.3, found 3813.5.

Synthesis of AcImPyPy-CONH(CH$_2$)$_{12}$P(O)$_4$-TTTTTT$^m$C$^m$CTTT-3'(63) (SEQ ID NO:8). Boc-PyPy-CONH(CH$_2$)$_{12}$P(O)$_4$-TTTTTT$^m$C$^m$CTTT-CPG was assembled as described above for compound 62. The N-boc group was removed with 65% TFA/CH$_2$Cl$_2$/0.5M PhSH and the resin was treated with a solution of Boc-Im-OBt (13) (70 mg), DIEA (68 $\mu$l) and DMF (600 $\mu$l), and shaken for 1 hour. The CPG was washed with DMF (30 seconds), dichloromethane (30 seconds) and dried in vacuo. One third of the CPG, 70 mg, was removed from the synthesis and placed in a 10 $\mu$mole DNA synthesis column. Two syringes were used simultaneously to manipulate reagents into and out of the column. The column was washed with dichloromethane and carefully treated with 65% TFA/CH$_2$Cl$_2$/0.5M PhSH to remove the N-Boc, group. The column was carefully washed with dichloromethane (20 ml) and DMF (20 ml) and then treated with acetylation mixture for 1 hour, washed with DMF (20 ml) and CH$_2$Cl$_2$ (20 ml) and the cartridge dried in vacuo. The resin was removed from the column and placed in 1 ml 0.1M NaOH at 55° C. for 15 hours. The CPG was removed by filtration, 1 ml of 1 M pH 7 triethylammonium acetate was added and the mixture purified by FPLC. The appropriate fractions were collected and concentrated in vacuo to give AcImPyPy-CONH(CH$_2$)$_{12}$P(O)$_4$-TTTTTT$^m$C$^m$CTTT-3'(63) (SEQ ID NO:8) (336 nmole, 10% yield).

Characterization of AcImPyPy-CONH(CH$_2$)$_{12}$P(O)$_4$-TTTTTT$^m$C$^m$CTTT-3'(63). Analytic HPLC (10 nmole), r.t., 19.7 min.; UV(H$_2$O/DMSO)$\lambda_{max}$($\epsilon$), 260 (110,000), 304 (36,000); 13,000 u, Enzymatic digestion (10 nmole), 7.7 min. (mC, 1551u), 8.9 min. (T, 11374u), 33.2 min. (peptide, 1646u (260), 1281u 340); MALDI-TOF MS, calc. M-1 3953.5, found 3952.9.

Preparation of Boc-$\gamma$-ImPyPy-CONH(CH$_2$)$_{12}$P(O)$_4$-TTTTTT$^m$C$^m$CTTT-3'(64) (SEQ ID NO:9). A sample of Boc-ImPyPy-CONH(CH$_2$)$_{12}$P(O)$_4$-TTTTTT$^m$C$^m$CTTT-CPG (140 mg), prepared by the general procedures described above was placed in a 10 $\mu$mole DNA synthesis column. The column was washed with dichloromethane and carefully treated with 65% TFA/CH$_2$Cl$_2$/0.5M PhSH to remove the N-Boc group. The column was then carefully washed with dichloromethane (20 ml) and DMF (20 ml) and then treated with the HOBt ester of Boc-$\gamma$ prepared in situ (1 mmol, 200 $\mu$l DIEA, 1 ml DMF) and allowed to react for 1 hour. The CPG was washed with DMF (20 ml), dichloromethane (20 ml), and dried in vacuo. The resin was removed from the column and placed in 1 ml 0.1M NaOH at 55° C. for 15 hours. The CPG was removed by filtration, 1 ml of 1M pH 7 triethylammonium acetate was added and the mixture purified by FPLC. The appropriate fractions were collected and concentrated in vacuo to give Boc-$\gamma$-ImPyPy-CONH(CH$_2$)$_{12}$P(O)$_4$-TTTTTT$^m$C$^m$CTTT-3'(64) (SEQ ID NO:9) (3.43 nmole, 5% yield).

Characterization of Boc-$\gamma$-ImPyPy-CONH(CH$_2$)$_{12}$P(O)$_4$-TTTTTT$^m$C$^m$CTTT-3'(64). UV(H$_2$O/DMSO)$\lambda_{max}$($\epsilon$) 260 (120,000), 304 (34,000); Analytic HPLC (5 nmole), r.t., 23.0 min., 6,000u, Enzymatic digestion (5 nmole), 7.7 min. (mC, 779u), 8.9 min. (T, 5873u) 42.1 min. (peptide, 767u (260), 597u 340) MALDI-TOF MS, calc. M-1 4094.7, found 4096.8.

Preparation of H$_2$N-$\gamma$-ImPyPy-CONH(CH$_2$)$_{12}$P(O)$_4$-TTTTTT$^m$C$^m$CTTT-3'(65) (SEQ ID NO:10). Boc-$\gamma$-ImPyPy-CONH(CH$_2$)$_{12}$P(O)$_4$-TTTTTT$^m$C$^m$CTTT-3'(64) (330 nmole) was treated with 400 $\mu$l of 65% TFA/CH$_2$Cl$_2$/0.5M PhSH for 30 minutes. 2 ml of 1M pH 7 triethylammonium acetate and 5 ml of water was added and the reaction mixture was vortexed, frozen, and lyophilized. The reaction mixture was then dissolved in 5 ml of 100 mM triethylammonium acetate and purified by FPLC, appropriate fractions were collected and concentrated in vacuo to give H$_2$N-$\gamma$-ImPyPy-CONH(CH$_2$)$_{12}$P(O)$_4$-TTTTTT$^m$C$^m$CTTT-3'(65) (240 nmole, 70% yield). MALDI-TOF MS, calc. M-1 3995.5, found 3999.7.

Preparation of EDTA-$\gamma$-ImPyPy-CONH(CH$_2$)$_{12}$P(O)$_4$-TTTTTT$^m$C$^m$CTTT-3'(66) (SEQ ID NO:11). H$_2$N-$\gamma$-ImPyPy-CONH(CH$_2$)$_{12}$P(O)$_4$-TTTTTT$^m$C$^m$CTTT-3'(65) (SEQ ID NO:10) was dissolved in 500 $\mu$l 500 mM carbonate buffer (pH 9.5). 10 mg of the monoanhydride of EDTA was added and the reaction allowed to proceed for 15 minutes. After 15 minutes 1 ml of triethylammonium acetate, pH 7.0 was added with 4 ml of water and the reaction immediately purified by FPLC. The appropriate fractions were collected and concentrated in vacuo to give EDTA-$\gamma$-ImPyPy-CONH (CH$_2$)$_{12}$P(O)$_4$-TTTTTT$^m$C$^m$CTTT-3'(66) (70 nmole, 41% yield).

Example 15

Automated Synthesis of Polyamides

The manual solid phase method for synthesis of pyrrole and imidazole polyamides was adapted for use on an ABI 430A peptide synthesizer. Machine-assisted synthesis was performed on a 0.18 mmol scale (900 mg resin at 0.2 mmol/gram). Each cycle of amino acid addition involved: deprotection with approximately 80% TFA and 0.4 M thiophenol in dichloromethane for 3 minutes, draining the reaction vessel, and then deprotection for 17 minutes; 2 dichloromethane flow washes; an-NMP flow wash; draining the reaction vessel; coupling for 1 hour with in situ neutralization, addition of DMSO/NMP, coupling for 30 minutes, addition of DIEA, coupling for 30 minutes; draining the reaction vessel; washing with dichloromethane, taking a resin sample for evaluation of the progress of the synthesis by HPLC analysis; capping with acetic anhydride/DIEA in dichloromethane for 6 minutes; and washing with dichloromethane.

The synthesizer was left in the standard hardware configuration for NMP-HOBt protocols. Reagent positions 1 and 7 (FIG. 20) were DIEA, reagent position 2 was TFA/0.5M thiophenol, reagent position 3 as 70% ethanolamine/methanol, reagent position 4 was acetic anhydride, reagent position 5 was DMSO/NMP, reagent position 6 was methanol and reagent position 8 was 0.48 M HBTU. All pyrrole and imidazole monomers were preactivated, predissolved and filtered through an ISOLAB filter (cat. #QS-Q) before placing in a synthesis cartridge. Boc-Py-OBt ester (357 mg, 1 mmol) was dissolved in 2 ml of DMF and filtered into a synthesis cartridge. Boc-imidazole monomer (125 mg, 0.5 mmol) and HOBT (135 mg, 1.0 mmol) were dissolved in 500 $\mu$l of DMF, DCC (102 mg, 0.5 mmol) was added, and the mixture allowed to stand for 15 minutes. DMF (1.5 ml)

was then added, DCU removed by filtration and the activated monomer placed in a synthesis cartridge. Boc-γ-Im-COOH or Boc-PyIm-COOH (100 mg, approximately 0.3 mmol) and HBTU (118 mg, 0.3 mmol) were dissolved in 500 μl DMF, 100 μl DIEA was added and the solution allowed to stand for 3 minutes. 1.5 ml of DMF was added and the solution filtered into a synthesis cartridge. For capping with imidazole-2-carboxylic acid, no activation conditions were compatible with the delivery-line filters. Im-COOH (800 mg, approximately 6 mmol) and HBTU (1 g, 3 mmol) were combined in 2.5 ml DMF, 1 ml DIEA was added and the mixture allowed to stand for 15 minutes. At the initiation of the coupling cycle, the synthesis was interrupted, the reaction vessel vented with toggle switches 0 and 2, the activated monomer filtered through a 0.2μ nylon filter and added directly to the reaction vessel via syringe. Temporary attachment of the resin sampling tube to a syringe, provides an easy method for direct manual addition of regents to the reaction vessel. For coupling pyrrole to imidazole, Boc-Py-COOH (514 mg, 2 mmol) was dissolved in 2 ml dichloromethane, DCC (420 mg, 2 mmol) was added, and the solution allowed to stand for 10 minutes. DMAP (101 mg, 1 mmol) was then added and the solution allowed to stand for an additional 1 minute. The solution was filtered and manually added to the reaction vessel at the initiation of coupling via syringe. For both coupling procedures where manual addition was necessary, the standard pyrrole-imidazole polyamide activator cycle was used in conjunction with an empty synthesis cartridge. Aliphatic amino acids (2 mmol) in 2 ml DMF were activated with HBTU (718 mg, 1.9 mmol), filtered and placed in a synthesis cartridge. Alternatively, the amino acid (1.5 mmol) was placed dry in a cartridge and 0.48 M HBTU (3 ml, 1.4 mmol) added using a calibrated delivery loop from reagent bottle eight, followed by the addition of 1 ml DIEA from reagent bottle 7 using a calibrated delivery loop, 3 minute mixing of the cartridge, direct transfer to the concentrator without rinse, and subsequent transfer to the reaction vessel without rinse.

Preparation of ImPyPy-β-PyPyPy-G-Dp. The Polyamide ImPyPy-β-PyPyPy-G-Dp was prepared by the general automated solid phase methods described above to yield a white powder. (17.2 mg, 57% recovery). HPLC, r.t. 26.5; UV($H_2O$/DMSO)$\lambda_{max}(\epsilon)$, 246 (46,500), 312 (54,800); $^1$H NMR (DMSO-$d_6$) δ 10.54 (s, 1H), 9.92 (s, 1H), 9.90 (m, 3H), 9.23 (br s, 1H), 8.27 (t, 1H, J=5.5 Hz), 8.06 (t, 1H, J=6.3 Hz), 8.03 (t, 1H, J=6.2 Hz), 7.39 (s, 1H), 7.26 (d, 1H, J=1.7 Hz), 7.20 (m, 2H), 7.17 (m, 2H), 7.13 (m, 2H), 7.04 (d, 1H, J=1.5 Hz), 6.87 (d, 1H, J=1.8 Hz), 6.83 (d, 1H, J=1.8 Hz), 3.97 (s, 3H), 3.82 (m, 15H), 3.78 (d, 2H, J=3.4 Hz), 3.27 (m, 4H), 3.15 (m, 2H), 3,79 (m, 2H), 2,76 (d, 6H, J=4.9 Hz), 1.78 (quintet, 2H, J=6.6 Hz); MALDI-TOF MS 950.2; FABMS m/e 949.458 ($M^+H^+$ 949.455, calc. for $C_{45}H_{57}N_{16}O_8$).

TABLE 1

Polyamides synthesized by the solid phase method of this invention

ImPyPy-G-PyPyPy-G-Dp
AcImPyPy-γ-PyPyPy-G-Ta
AcImPyPy-γ-PyPyPy-G-Ta-EDTA
AcPyPyPy-γ-ImImPy-G-Dp
ImPyPy-γ-PyPyPy-β-Dp
ImPyPy-β-PyPyPy-γ-ImPyPy-β-PyPyPy-β-Dp
AcImPyPy-γ-PyPyPy-β-Dp
$H_2$N-γ-ImPyPy-β-PyPyPy-G-Dp

TABLE 1-continued

Polyamides synthesized by the solid phase method of this invention

HOOC-Suc-ImPyPy-γ-PyPyPy-G-Dp
AcPyImPy-G-Dp
$H_2$N-PyPyPy-G-Dp
ImPyPy-Dala-PyPyPy-G-Dp
ImPyPy-γ-PyPyPy-G-Dp
ImPyPy-Lala-PyPyPy-G-Dp
ImPyPy-AIB-PyPyPy-G-Dp
ImPyImPy-β-Dp
ImPyPy-β-PyPyPy-G-Dp
ImImPy-γ-PyPyPy-β-Dp
AcImPyPy-G-PyPyPy-G-Dp
ImPyPy-G-PyPyPy-β-Dp
ImPyPy-β-PyPyPy-γ-ImPyPy-β-PyPyPy-β-Ta
ImPyPy-γ-ImPyPy-β-PyPyPy-G-Dp
ImPyPy-β-PyPyPy-G-Ta
ImPyPy-G-PyPyPy-G-Ta
AcPyPyPyPyPy-G-Ta
AcImPyPy-γ-PyPyPy-Dp
ImPyPyPyPyPy-G-Ta-EDTA
ImPyPy-Lglu-PyPyPy-G-Dp
ImPyPyPyPyPy-G-Dp
ImPyPyPyPyPy-G-Ed
AcImPyPy-G-PyPyPy-G-Ta-EDTA
AcImImPy-γ-PyPyPy-G-Ta
AcPyPyPy-γ-ImImPy-G-Ta
AcPyPyPy-γ-ImImPy-β-Dp
AcPyPyPy-γ-ImImPy-G-Dp
$H_2$N-ImPyPy-G-PyPyPy-G-Dp
EDTA-γ-ImPyPy-β-PyPyPy-G-Dp
ImPyPy-γ-ImPyPy-G-PyPyPy-G-Dp
$H_2$N-γ-ImPyPy-β-PyPyPy-G-Ta
AcImImPy-γ-PyPyPy-G-Dp
AcImPyPy-γ-PyPyPy-G-Dp
ImPy-G-Py-γ-ImPy-G-Py-β-Dp
ImImPy-γ-ImPyPy-β-PyPyPy-G-Dp
ImPyImPy-γ-ImPyImPy-β-Dp
ImPyImPy-γ-PyPyPy-β-Dp
ImImPyPy-γ-PyPyPy-β-Dp
ImPyPy-β-PyPyPy-G-Ta-EDTA
ImPyPy-G-PyPyPy-G-Ta-EDTA
AcImImPy-γ-PyPyPy-β-Dp
AcImPyPy-G-PyPyPy-G-Ta
ImPyPy-G-PyPyPy-G-Ed
ImPyPy-γ-ImPyPy-β-Dp
AcImPyPyPyPyPy-G-Ta-EDTA
AcPyPyPy-γ-ImImPy-G-Ta-EDTA
ImPyPy-transcyclopropyl-PyPyPy-β-Dp
AcImPyPy-G-PyPyPy-G-Ta
PyPyPy-γ-ImImPy-G-Dp
ImImIm-β-PyPyPy-β-Dp
AcPyPyImPy-γ-PyPyPyPy-β-Dp
AcImImPy-γ-PyPyPy-G-Dp
$H_2$N-β-PyPyPy-γ-ImImPy-β-β-β-β-PyPyPy-γ-ImImPy-β-Dp (automated synthesis)
ImPyPyPy-γ-ImPyPyPy-β-Dp
PyPyPy-γ-ImImPy-β-Dp
PyPyPy-γ-ImImPy-G-Dp
DM-γ-ImPyPy-β-PyPyPy-β-Dp
ImPyPy-β-ImImPyPy-γ-ImImPyPy-β-Dp
ImPyPy-β-PyPyPy-β-Dp
ImImPyPy-γ-ImImPyPy-β-Dp
ImPyPy-γ-β-β-β-Dp
ImPyPy-γ-β-PyPy-β-Dp
ImPyPy-γ-ImPyPy-β-PyPyPy-G-Ta-EDTA
$H_2$N-γ-ImPyPyPy-γ-PyPyPyPy(G-Dp)-COOH
ImImImIm-γ-PyPyPyPy-β-Dp
ImPyPyPy-β-ImImPyPy-γ- ImImPyPy-β-Ta-EDTA
ImPyPyPy-γ-PyPyPyPy-β-Dp
$H_2$N-ε-ImPyPy-G-PyPyPy-G-Dp
DMγ-ImPyPy-γ-ImPyPy-β-ED
ImPyPyPy-γ-PyPyPyPy-Ta
ImPyPyPy-γ-PyPyPyPy-Ta-EDTA
ImPyPyPy-γ-ImPyPyPy-β-Ta
ImPyPyPy-γ-ImPyPyPy-β-Ta-EDTA

TABLE 1-continued

Polyamides synthesized by the solid phase method of this invention

ImPyPyPy-γ-ImImImPy-β-Ta
ImPyPyPy-γ-ImImImPy-β-PyPyPyPy-β-Ta
ImPyPy-Dala-PyPyPy-β-Dp
ImPyPy-Lala-PyPyPy-β-Dp
ImPyPy-β-PyPyPy-Dala-Dp
ImPyPy-β-PyPyPy-Lala-Dp
ImPyPy-γ-$^m$PyPyPy-β-Dp
Im$^m$Py-γ-PyPyPy-β-Dp
ImPyPy-β-Py$^m$PyPy-β-Dp
Im$^m$PyPy-β-PyPyPy-β-Dp
EDTA-γ-ImPyPy-G-PyPyPy-G-Dp
EDTA-γ-ImPyPy-G-PyPyPy-G-Ta-EDTA
EDTA-γ-ImPyPy-β-PyPyPy-G-Ta-EDTA

*All compounds listed have be characterized by HPLC, $^1$HNMR, MALDI-TOF mass spectroscopy and in some cases $^{13}$C NMR.
Abbreviations.
Im = Imidazole
EDTA-ethylenediaminetetraacetic acid
Py = Pyrrole
ED = ethylenediamine
G = Glycine
Ta = 3,3-diamino-N-methylpropylamine
Dp = Dimethylaminopropylamine
Lala = L-alanine
Ac = Acetyl
β = β-alanine
γ = γ-aminobutyric acid
Suc = Succinic acid
Dala = D-alanine
Lglu = L-Glutamic acid
AIB = alpha-isobutyric acid
ε = ε-aminohexanoic acid
DM-γ = N,N-dimethyl-γ-aminobutyric acid

TABLE 2

Standard protocol for manual synthesis of minor groove binding polyamides.

| SYNTHESIS CYCLE | REAGENTS | TIME/MODE |
| --- | --- | --- |
| 1) Deprotect | 65% TFA/CH$_2$Cl$_2$/PhSH | 1 × 30 s flow |
|  |  | 1 × 1 min shake |
|  |  | 1 × 30 s flow |
|  |  | 1 × 20 min shake |
| 2) Wash | CH$_2$Cl$_2$ | 1 × 1 min flow |
|  | DMF | 1 × 30 s flow |
|  |  | 1 × 1 min shake |
|  |  | (take sample for picric acid test) |
| 3) Couple | HOBt acid, DIEA | 45 min shake |
|  |  | (take sample for picric acid test) |
| 4) Wash | DMF | 1 × 30 s flow |
|  | CH$_2$Cl$_2$ | 1 × 30 s flow |

TABLE 3

Apparent First-Order Association Constants (M$^{-1}$) for selected polyamides.[a]

|  | Polyamide | | | |
| --- | --- | --- | --- | --- |
| Binding Site | ImPyPy-G-PyPyPy-Dp | ImPyPy-G-PyPyPy-G-Dp | ImPyPy-G-PyPyPy-β-Dp | SEQ ID NO: |
| 5'-AAAAAGACAAAAA-3' | 1.1 (±0.1) × 10$^8$ | 7.0 (±1.2) × 10$^7$ | 1.0 (±0.2) × 10$^8$ | 2 |
| 5'-ATATAGACATATA-3' | 6.6 (±0.4) × 10$^6$ | ≈3.5 (±1.4) × 10$^6$ | 1.0 (±0.2) × 10$^7$ | 3 |
| 5'-TGTTAAACA-3' | 1.4 (±0.1) × 10$^8$ | ≈1.7 (±0.7) × 10$^6$ | 3.4 (±0.5) × 10$^7$ | 4 |
| 5'-TGTAAAACG-3 | 5.5 (±0.3) × 10$^7$ | ≈3.0 (±1.5) × 10$^6$ | 4.0 (±1.3) × 10$^7$ | ? |
| 5'-TGTGCTGCAAG-3' | 5.4 (±0.2) × 10$^7$ | <1 × 10$^6$ | 3.7 (±1.0) × 10$^7$ | 6 |

[a]Values reported are the mean values obtained from three DNase 1 footprint titration experiments. The standard deviation for each value is indicated in parentheses.

TABLE 4*

Illustrative Cyclic Polyamides.

cyclo-(ImPyImPy-γ-ImPyImPy-(G-Dp)-γ-)
cyclo(ImPyImPy-γ-ImPyImPy(G-Dp))
cyclo(ImPyPyPy-γ-PyPyPyPy(G-Dp))
H$_2$N-γ-ImPyImPy-γ-ImPyImPy(G-Dp)-COOH
H$_2$N-γ-ImPyImPy-γ-ImPyImPy(G-Dp)-COOH

* Abbreviations.
Im = Imidazole
Py = Pyrrole
G = Glycine
Dp = Dimethylaminopropylamine
γ = γ-aminobutyric acid

TABLE 5

Oligonucleotide-polyamide conjugates.

| OLIGONUCLEOTIDE-POLYAMIDE CONJUGATE* | SEQ ID NO: |
| --- | --- |
| ImPyPy-C$_6$-P(O)$_4$TTTTTT$^m$C$^m$CTTT-3' | 7 |
| AcImPyPy-C$_{12}$-P(O)$_4$TTTTTT$^m$C$^m$CTTT-3' | 8 |
| Boc-γ-ImPyPy-C$_{12}$-P(O)$_4$TTTTTT$^m$C$^m$CTTT-3' | 9 |
| H$_2$N-γ-ImPyPy-C$_{12}$-P(O)$_4$TTTTTT$^m$C$^m$CTTT-3' | 10 |
| EDTA-γ-ImPyPy-C$_{12}$-P(O)$_4$TTTTTT$^m$C$^m$CTTT-3' | 11 |
| ImPyPy-C$_6$-P(O)$_4$TTT$^m$C$^m$CTTTTTT-3' | 12 |
| AcImPyPy-C$_{12}$-P(O)$_4$-TTT$^m$C$^m$CTTTTTT-3' | 13 |
| H$_2$N-γ-ImPyPy-C$_6$-P(O)$_4$-TTT$^m$C$^m$CTTTTTT-3' | 14 |
| H$_2$N-γ-ImPyPy-C$_8$-P(O)$_4$-TTT$^m$C$^m$CTTTTTT-3' | 15 |
| H$_2$N-γ-ImPyPy-C$_{10}$-P(O)$_4$-TTT$^m$C$^m$CTTTTTT-3' | 16 |
| H$_2$N-γ-ImPyPy-C$_{12}$-P(O)$_4$-TTT$^m$C$^m$CTTTTTT-3' | 17 |
| H$_2$N-γ-ImPyPy-C$_6$-P(O)$_4$(CH$_2$)$_8$(NH)TTT$^m$C$^m$CTTTTTT-3' | 18 |
| Dp-G-PyPyPy-G-PyPyIm-ε-DSA-(NH)TTT$^m$C$^m$CTTTTTT-3' | 19 |
| Dp-G-PyPyPy-G-PyPyIm-ε-DSG-(NH)TTT$^m$C$^m$CTTTTTT-3' | 20 |
| Dp-G-PyPyPy-G-PyPyIm-ε-DSS-(NH)TTT$^m$C$^m$CTTTTTT-3' | 21 |
| Dm-γ-ImPyPy-γ-ImPyPy-β-ED-DSG-(NH)TTT$^m$C$^m$CTTTTTT-3' | 22 |
| DMγ-ImPyPy-γ-ImPyPy-β-ED-DSA-(NH)TTT$^m$C$^m$CTTTTTT-3' | 23 |

*Abbreviations.
C$_6$ represents CONH(CH$_2$)$_6$
C$_{12}$ represents CONH(CH$_2$)$_{12}$
$^m$C = 5-methylcytidine
ETDA = ethylenediaminetetraacetic acid
γ = γ-aminobutyric acid
DSA = Adipic acid
DSG = Glutaric acid
DSS = Suberic acid
(NH)T = 2',5'-dideoxy-5'-aminothymidine
Im = Imidazole
Py = Pyrrole
G = Glycine
Dp = Dimethylaminopropylamine
ε = ε-aminohexanoic acid
β = β-alanine
ED = ethylenediamine
C$_8$ – CONH(CH2)$_8$
C$_{10}$ – CONH(CH2)$_{10}$

What is claimed is:

1. A polyamide of the formula:

$$R_3\text{—}A\text{—}(Y\text{—}A)_n\text{—}R_4$$

or a pharmaceutically acceptable salt thereof, wherein:

each A is independently

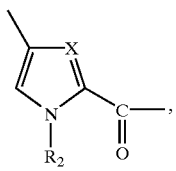

wherein each X is independently selected from the group consisting of N and C—$R_1$, each $R_1$ is independently selected from the group consisting of H, $CH_3$, OH, $NH_2$, Cl, and $CF_3$, and each $R_2$ is independently selected from the group consisting of H, $C_{1-10}$ alkyl, $C_{1-10}$ alkenyl, and $C_{1-10}$ alkynyl, wherein at least one X is C—OH or C—$NH_2$;

n is 1–11;

each Y is independently selected from the group consisting of:

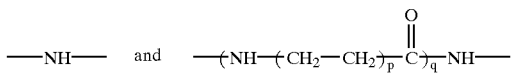

wherein each p is independently 0 to 3, and each q is independently 1–5;

$R_3$ is selected from the group consisting of: H, or NH—$R_6$, wherein $R_6$ is selected from the group consisting of H, $C(O)CH_3$, γ-aminobutyric acid, β-alanine, glycine, ethylenediamine, 3,3'-diamino-N-methylpropylamine, tert-butoxycarbonyl (Boc), dimethylaminopropylamine (Dp), and ethylenediaminetetraacetic acid, wherein if $R_6$ is γ-aminobutyric acid, β-alanine, or glycine, $R_6$ is optionally substituted at its amino terminus with γ-aminobutyric acid, β-alanine, glycine, ethylenediamine, 3,3'-diamino-N-methylpropylamine, tert-butoxycarbonyl (Boc), dimethylaminopropylamine (Dp), or ethylenediaminetetraacetic acid; and $R_4$ is selected from the group consisting of H, OH, $CH_3$, $NH_2$, γ-aminobutyric acid, L-alanine, β-alanine, glycine, ethylenediamine, 3,3'-diamino-N-methylpropylamine, tert-butoxycarbonyl (Boc), dimethylaminopropylamine (Dp), ethylenediaminetetraacetic acid, and 3,3'-diamino-N-methylpropylamine-ethylenediaminetetraacetic acid, wherein if $R_4$ is γ-aminobutyric acid, L-alanine, β-alanine, or glycine, $R_4$ is optionally substituted at its carboxyl terminus with γ-aminobutyric acid, β-alanine, glycine, ethylenediamine, 3,3'-diamino-N-methylpropylamine, tert-butoxycarbonyl (Boc), dimethylaminopropylamine (Dp), ethylenediaminetetraacetic acid, or 3,3'-diamino-N-methylpropylamine-ethylenediaminetetraacetic acid.

2. A polyamide according to claim 1, wherein the polyamide forms a hairpin structure that binds to a minor groove of a double-stranded DNA molecule.

3. A polyamide according to claim 1, wherein the polyamide binds to a minor groove of a double-stranded DNA molecule in a slipped binding mode.

4. A polyamide according to claim 1, wherein the polyamide binds to a minor groove of a double-stranded DNA molecule in an overlapped binding mode.

5. A polyamide according to claim 1, wherein the polyamide contains at least one γ-aminobutyric acid moiety.

6. A polyamide according to claim 1, wherein the polyamide contains at least one aliphatic or aromatic amino acid.

7. A polyamide according to claim 1, wherein the polyamide contains at least one amino acid selected from the group consisting of a glycine and β-alanine.

8. A polyamide according to claim 1, wherein at least 1 $R_1$ is OH.

9. A polyamide according to claim 1, wherein at least 1 $R_1$ is $NH_2$.

10. A polyamide of the formula:

$$R_3\text{—}A\text{—}(Y\text{—}A)_n\text{—}R_4$$

or a pharmaceutically acceptable salt thereof, wherein:

each A is independently

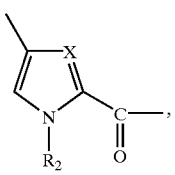

wherein each X is independently selected from the group consisting of N and C—$R_1$, each $R_1$ is independently selected from the group consisting of H, $CH_3$, OH, $NH_2$, Cl, and $CF_3$, and each $R_2$ is independently selected from the group consisting of H, $C_{1-10}$ alkyl, $C_{1-10}$ alkeneyl, and $C_{1-10}$ alkynyl, wherein at least one X is C—OH or C—NH$_2$;

n is 1–11;

each Y is independently selected from the group consisting of:

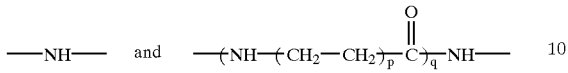

wherein each p is independently 0 to 3, and each q is independently 1–5; and $R_3$ and $R_4$ together form a covalent linkage to form a cyclic molecule.

11. A polyamide according to claim 10, wherein the polyamide forms a hairpin structure that binds to a minor groove of a double-stranded DNA molecule.

12. A polyamide according to claim 10, wherein the polyamide contains at least one γ-aminobutyric acid moiety.

13. A polyamide according to claim 10, wherein the polyamide contains at least one aliphatic or aromatic amino acid.

14. A polyamide according to claim 10, wherein the polyamide contains at least one amino acid selected from the group consisting of a glycine and β-alanine.

15. A polyamide according to claim 10, wherein at least 1 $R_1$ is OH.

16. A polyamide according to claim 10, wherein at least 1 $R_1$ is NH$_2$.

17. A polyamide comprising:

at least two carboxamide residues selected from the group consisting of pyrrole carboxamide residues and imidazole carboxamide residues, wherein said pyrrole carboxamide residues have the structure

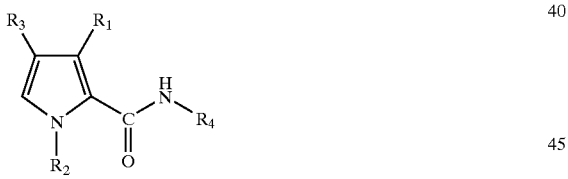

wherein $R_1$ is selected from the group consisting of H, CH$_3$, Cl, CF$_3$, OH and NH$_2$;

$R_2$ is selected from the group consisting of H, $C_1$–$C_{10}$ alkyl, $C_1$–$C_{10}$ alkenyl, and $C_1$–$C_{10}$ alkynyl;

$R_3$ is selected from the group consisting of H and a covalent bond; and $R_4$ is a covalent bond;

wherein said imidazole carboxamide residues have the structure

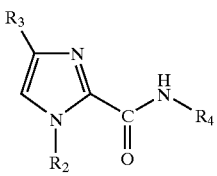

wherein $R_2$ is selected from the group consisting of $C_1$–$C_{10}$ alkyl, $C_1$–$C_{10}$ alkenyl, and $C_1$–$C_{10}$ alkynyl;

$R_3$ is selected from the group consisting of H and a covalent bond; and $R_4$ is a covalent bond; and wherein at least one carboxamide residue of said polyamide is a pyrrole carboxamide residue having the structure

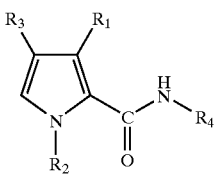

wherein $R_1$ is selected from the group consisting of OH and NH$_2$;

$R_2$ is selected from the group consisting of $C_1$–$C_{10}$ alkyl, $C_1$–$C_{10}$ alkenyl, and $C_1$–$C_{10}$ alkynyl;

$R_3$ is selected from the group consisting of H and a covalent bond; and $R_4$ is a covalent bond.

18. A polyamide according to claim 17, wherein the polyamide forms a hairpin structure that binds to a minor groove of a double-stranded DNA molecule.

19. A polyamide according to claim 17, wherein the polyamide binds to a minor groove of a double-stranded DNA molecule in a slipped binding mode.

20. A polyamide according to claim 17, wherein the polyamide binds to a minor groove of a double-stranded DNA molecule in an overlapped binding mode.

21. A polyamide according to claim 17, wherein the polyamide further comprises a γ-aminobutyric acid moiety.

22. A polyamide according to claim 17, wherein the polyamide further comprises an aliphatic or aromatic amino acid.

23. A polyamide according to claim 17, wherein the polyamide further comprises an amino acid selected from the group consisting of a glycine and β-alanine.

24. A polyamide according to claim 17, wherein $R_1$ is OH.

25. A polyamide according to claim 17, wherein $R_1$ is NH$_2$.

* * * * *

UNITED STATES PATENT AND TRADEMARK OFFICE
CERTIFICATE OF CORRECTION

PATENT NO.     : 6,683,189 B1
DATED          : January 27, 2004
INVENTOR(S)    : Peter B. Dervan and Eldon Baird It is certified that error appears in the above-identified patent and that said Letters Patent is hereby corrected as shown below:

Title page,
Item [75], Inventors "Peter B. Deryan" should read -- Peter B. Dervan --.

Signed and Sealed this

First Day of June, 2004

JON W. DUDAS
*Acting Director of the United States Patent and Trademark Office*